United States Patent
Miyauchi et al.

(10) Patent No.: US 8,114,886 B2
(45) Date of Patent: Feb. 14, 2012

(54) PYRIDYLMETHYLSULFONE DERIVATIVE

(75) Inventors: Satoru Miyauchi, Edogawa-ku (JP);
Hideki Kubota, Edogawa-ku (JP);
Kayoko Motoki, Edogawa-ku (JP);
Masayuki Ito, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 1163 days.

(21) Appl. No.: 11/910,500

(22) PCT Filed: Apr. 7, 2006

(86) PCT No.: PCT/JP2006/307464
§ 371 (c)(1),
(2), (4) Date: Oct. 2, 2007

(87) PCT Pub. No.: WO2006/109729
PCT Pub. Date: Oct. 19, 2006

(65) Prior Publication Data
US 2009/0149439 A1    Jun. 11, 2009

(30) Foreign Application Priority Data

Apr. 8, 2005  (JP) .................. 2005-112802
Dec. 21, 2005 (JP) .................. 2005-367976

(51) Int. Cl.
*A01N 43/40* (2006.01)
*A01N 43/42* (2006.01)
*A61K 31/435* (2006.01)
*A61K 31/44* (2006.01)

(52) U.S. Cl. ...................... 514/277; 514/290

(58) Field of Classification Search .............. 514/277, 514/290
See application file for complete search history.

(56) References Cited

FOREIGN PATENT DOCUMENTS

| | | |
|---|---|---|
| JP | 9-95444 | 4/1997 |
| WO | 00/50391 | 8/2000 |
| WO | 01/70677 | 9/2001 |
| WO | WO 02/40451 A2 | 5/2002 |
| WO | WO 02/40508 A2 | 5/2002 |
| WO | WO 02/47671 A2 | 6/2002 |
| WO | 02/081435 | 10/2002 |
| WO | WO 02/081433 A1 | 10/2002 |
| WO | WO 03/018543 A1 | 3/2003 |
| WO | 03/055850 | 7/2003 |
| WO | 2005/000798 | 1/2005 |

OTHER PUBLICATIONS

Gravina, S.A. et al., "Amyloyd beta Protein in Alzheimer's Disease Brain", The Journal of Biological Chemistry, vol. 270, No. 3, pp. 7013-7016, 1995.
Xiao-Dan Cai, et al., "Release of Excess Amyloid β Protein from a Mutant Amyloid β Protein Precursor", Science, vol. 259, Jan. 22, 1993, pp. 514-516.
Stephen A. Gravina, et al., "Amyloid β Protein (Aβ) in Alzheimer's Disease Brain", The Journal of Biological Chemistry, vol. 270, No. 13, 1995, pp. 7013-7016.
Robert Vassar, et al., "β-Secretase Clevage of Alzheimer's Amyloid Precursor Protein by the Transmembrane Aspartic Protease BACE", Science, vol. 286, Oct. 22, 1999, pp. 735-741.
I. Hussain, et al., "ASP1 (BACE2) Cleaves the Amyloid Precursor Protein at the β-Secretase Site", Molecular and Cellular Neuroscience, vol. 16, 2000, pp. 609-619.
Michael S. Wolfe, "Secretase Targets for Alzheimer's Disease: Identification and Therapeutic Potential", Journal of Medicinal Chemistry, vol. 44, No. 3, Jun. 21, 2001, pp. 2039-2060.

*Primary Examiner* — Yong Chong
(74) *Attorney, Agent, or Firm* — Oblon, Spivak, McClelland, Maier & Neustadt, L.L.P.

(57) ABSTRACT

The present invention relates to a novel compound having an effect of inhibiting production/secretion of β-amyloid protein. The present invention provides a compound represented by the general formula (1):

$$\text{(1)}$$

or a salt thereof, or a solvate of the compound or the salt; and a medicament comprising thereof.

6 Claims, No Drawings

PYRIDYLMETHYLSULFONE DERIVATIVE

TECHNICAL FIELD

The present invention relates to a novel compound having an effect of inhibiting production/secretion of a β-amyloid protein, and a therapeutic agent for various diseases caused by abnormal production/secretion of the β-amyloid protein, for example, Alzheimer's disease, Down syndrome and other diseases associated with amyloid deposition.

BACKGROUND ART

Alzheimer's disease is a neurodegenerative disease which is pathologically characterized by formation of senile plaques and neurofibrillary tangles, together with neuronal degeneration and dropout. Alzheimer's disease causes symptoms of dementia in which memory, recognition, thinking, judgment and the like are progressively lost, thus finally leading to death. To the present, no method which is effective for prevention and treatment of this disease has been known.

A protein playing a major role in constituting senile plaques deposited in the brain is β-amyloid protein (amyloid β protein, Aβ), which consists of 39 to 43 amino acids. β-Amyloid protein has cytotoxicity, which is thought to cause Alzheimer's disease (Non-Patent Document 1). The β-amyloid protein which is secreted from cells is a polypeptide mostly consisting of 40 to 42 amino acids, and in particular, the β-amyloid protein consisting of 42 amino acids is known to be deposited in the brain in an early stage with stronger aggregability, and to have strong cytotoxicity (Non-Patent Document 2). Although the β-amyloid protein is ubiquitously produced in the body, the original function thereof has not been clarified.

β-amyloid protein is produced by processing of an amyloid precursor protein (APP), which is a transmembrane protein. Among the patients suffering from familial Alzheimer's disease, there are cases where mutation is recognized in the APP gene. Furthermore, it is known that in the cells transfected with this mutated APP gene, the amount of production/secretion of the β-amyloid protein is increased. From these, it is conceived that a medicament inhibiting the production/secretion of β-amyloid protein would be effective for the prevention or treatment of Alzheimer's disease.

With regard to the process for the cleavage of APP to β-amyloid protein, an aspartic protease such as BACE (β-site APP cleaving enzyme) (Non-Patent Document 3) or Asp1 (Non-Patent Document 4) is reported as the β-secretase associated with the N-terminal cleavage of the β-amyloid protein. Meanwhile, with regard to the γ-secretase which is responsible for the C-terminal cleavage, it is strongly suggested that Presenilin constitutes a part thereof (Non-Patent Document 5). There has been a report on the inhibitors of these β-secretases or γ-secretase (Non-Patent Document 6), and many of them are peptidic compounds.

Smith et al. disclose a compound in Patent Document 1, which has a sulfonamide skeleton, and regulates the production of β-amyloid protein. Belanger et al. also disclose a compound in Patent Document 2, which has a bicycloalkylsulfonamide skeleton, and inhibits γ-secretase. Furthermore, Patent Documents 3, 4 and 5 disclose compounds having an activity for inhibiting the production of β-amyloid protein. Patent Documents 6, 7 and 8 also disclose diarylsulfone compounds which inhibit γ-secretase. In addition, Patent Documents 9 and 10 also disclose compounds inhibiting the production of β-amyloid protein. Meanwhile, Patent Document 11 discloses a thionaphthalene derivative which inhibits the aggregation of amyloid proteins.

[Patent Document 1] International Publication No. WO 00/50391

[Patent Document 2] International Publication No. WO 01/70677

[Patent Document 3] International Publication No. WO 02/40451

[Patent Document 4] International Publication No. WO 02/40508

[Patent Document 5] International Publication No. WO 02/47671

[Patent Document 6] International Publication No. WO 02/081433

[Patent Document 7] International Publication No. WO 02/081435

[Patent Document 8] International Publication No. WO 03/018543

[Patent Document 9] International Publication No. WO 03/055850

[Patent Document 10] International Publication No. WO 05/000798

[Patent Document 11] Japanese Patent Application Laid-open No. 9-95444

[Non-Patent Document 1] Science, Vol. 259, p. 514 (1993)

[Non-Patent Document 2] Journal of Biological Chemistry, Vol. 270, p. 7013 (1995)

[Non-Patent Document 3] Science, Vol. 286, p. 735 (1999)

[Non-Patent Document 4] Molecular and Cellular Neuroscience, Vol. 16, p. 609 (2000)

[Non-Patent Document 5] Journal of Medicinal Chemistry, Vol. 44, p. 2039 (2001)

DISCLOSURE OF THE INVENTION

Problems to be Solved by the Invention

It is an object of the invention to provide a compound which has a potent inhibitory effect on the production/secretion of a β-amyloid protein, and thus is effective for the prevention and/or treatment of various diseases based on abnormal production/secretion of the β-amyloid protein.

Means for Solving the Problems

The inventors of the present invention conducted extensive examinations, and as a result, found that pyridylmethylthio compounds, pyridylmethylsulfin compounds and pyridylmethylsulfone compounds, all represented by the following general formula (1), inhibit the production/secretion of a β-amyloid protein by strongly inhibiting β-secretase, and therefore are useful as therapeutic agents for various diseases caused by abnormal production/secretion of β-amyloid protein, thus completing the present invention.

Thus, the present invention provides a compound represented by the following general formula (1):

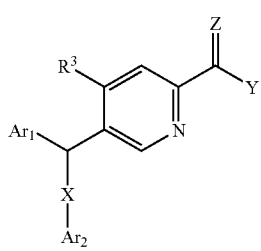

(1)

wherein Ar₁ represents a substituted phenyl group;

Ar₂ represents a phenyl group which may be substituted, or a heterocyclic group which may be substituted;

X represents —S—, —SO— or —SO₂—;

Y represents a hydrogen atom, —NR¹R² (wherein R¹ represents a hydrogen atom, a lower alkyl group, or a hydroxy group; and R² represents a hydrogen atom, a lower alkyl group which may be substituted, a lower alkanoyl group, an alkoxycarbonyl group which may be substituted, a lower alkoxy group which may be substituted, an amino group which may be substituted, a phosphono group, a phenyl group which may be substituted, or an aromatic heterocyclic group which may be substituted; or R¹ and R², together with the nitrogen atom to which they are bound, form a saturated heterocyclic group, with the saturated heterocyclic group representing one which may be substituted), or —OR¹' (wherein R¹' represents a hydrogen atom, or a lower alkyl group which may be substituted);

Z represents an oxygen atom or a sulfur atom; and

R³ represents a hydrogen atom, a lower alkyl group, or a halogen atom;

or a salt thereof, or a solvate of the compound or the salt.

Furthermore, the present invention is to provide a medicament containing the compound represented by the general formula (1), a salt thereof, or a solvate of the compound or the salt as an active ingredient.

The present invention is also to provide a pharmaceutical composition containing the compound represented by the general formula (1), a salt thereof, or a solvate of the compound or the salt, and a pharmaceutically acceptable carrier.

Furthermore, the present invention is to provide the use of the compound represented by the general formula (1), a salt thereof, or a solvate of the compound or the salt, for the manufacture of a medicament.

Moreover, the present invention is to provide a method for treating a disease caused by abnormal production/secretion of β-amyloid protein, the method including administering an effective amount of the compound represented by the general formula (1), a salt thereof, or a solvate of the compound or the salt.

Effects of the Invention

The present invention can provide a means for pharmaceutically preventing and/or treating various diseases, for example, Alzheimer's disease, Down syndrome or other diseases associated with amyloid deposition.

BEST MODE FOR CARRYING OUT THE INVENTION

Hereinafter, the compound represented by general formula (1) will be described.

Ar₁ represents a substituted phenyl group.

Here, the aforementioned phenyl group has, as substituents, 1 to 3 atoms or groups selected from the group consisting of a halogen atom, and a lower alkyl group which may be substituted with a halogen atom or a hydroxy group. The number of the substituents is preferably 2 or 3. In the case where a plurality of substituents are to be used as substituents, these substituents may be identical atoms or groups, or part of the substituents may be different atoms and/or groups, or all of the substituents may be different atoms and/or groups.

If there are two substituents, the positions of substitution are preferably the 2-position and 5-position; while if there are three substituents, the positions of substitution are preferably the 2-position, 3-position and 6-position.

Next, the atom and substituent which are substituted on the phenyl group represented by Ar₁ will be described below.

The term "halogen atom" means a chlorine atom, a fluorine atom, a bromine atom or an iodine atom. Among these, a chlorine atom and a fluorine atom are preferred, and particularly a fluorine atom is preferred.

The term "lower alkyl group which may be substituted with a halogen atom or a hydroxy group" means an unsubstituted lower alkyl group, as well as a lower alkyl group substituted with the above-described halogen atom or a hydroxy group.

The term "lower alkyl group" means a straight-chained, branched or cyclic alkyl group having 1 to 6 carbon atoms. Therefore, specific examples of the lower alkyl group include a methyl group, an ethyl group, a n-propyl group, an isopropyl group, a n-butyl group, an isobutyl group, a sec-butyl group, a tert-butyl group, a n-pentyl group, a 2-methylbutyl group, a 2,2-dimethylbutyl group, a 2-methylpentyl group, a n-hexyl group, a cyclopropyl group, a cyclopropylmethyl group, a cyclobutylmethyl group, a cyclopropylethyl group, a cyclopentyl group, a cyclohexyl group, and the like.

For the lower alkyl group substituted with a halogen atom or a hydroxy group, the number of substitution with a halogen atom or a hydroxy group is not limited as long as substitution can be carried out, but the number is preferably 1 to 3. Furthermore, in the case where a plurality of atoms or groups are to be used as substituents, identical atoms or groups may be used for the substitutions, or different atoms or groups may be used for the substitutions, but it is preferable that identical atoms are used for the substitutions. Therefore, the lower alkyl group substituted with a halogen atom or a hydroxy group includes a chloromethyl group, a dichloromethyl group, a trichloromethyl group, a fluoromethyl group, a difluoromethyl group, a trifluoromethyl group, a 2-fluoroethyl group, a 2-difluoroethyl group, a 2-trifluoroethyl group, a 1-fluoroethyl group, a 1-difluoroethyl group, a 1,2-difluoroethyl group, a hydroxymethyl group, a 2-hydroxyethyl group, a 1-hydroxyethyl group, and the like.

Thus, specific examples of Ar₁ include a 2-chlorophenyl group, a 3-chlorophenyl group, a 4-chlorophenyl group, a 2-fluorophenyl group, a 3-fluorophenyl group, a 4-fluorophenyl group, a 2,5-dichlorophenyl group, a 2,6-dichlorophenyl group, a 2,3,6-trichlorophenyl group, a 2,3-difluorophenyl group, a 2,4-difluorophenyl group, a 2,5-difluorophenyl group, a 2,6-difluorophenyl group, a 3,5-difluorophenyl group, a 2,3,5-trifluorophenyl group, a 2,3,6-trifluorophenyl group, a 2-methylphenyl group, a 3-methylphenyl group, a 4-methylphenyl group, a 2,5-dimethylphenyl group, a 3-chloro-2-methylphenyl group, a 3-fluoro-2-methylphenyl group, a 5-chloro-2-methylphenyl group, a 5-fluoro-2-methylphenyl group, a 2-chloro-5-methylphenyl group, a 2-fluoro-3-methylphenyl group, a 2-chloro-5-methylphenyl group, a 2-fluoro-5-methylphenyl group, a 2-chloromethylphenyl group, a 3-chloromethylphenyl group, a 2-dichloromethylphenyl group, a 3-dichloromethylphenyl group, a 2-trichloromethylphenyl group, a 3-trichloromethylphenyl group, a 2-fluoromethylphenyl group, a 3-fluoromethylphenyl group, a 4-fluoromethylphenyl group, a 2-difluoromethylphenyl group, a 3-difluoromethylphenyl group, a 2-trifluoromethylphenyl group, a 3-trifluoromethylphenyl group, a 2-chloro-5-chloromethylphenyl group, a 2-chloro-5-dichloromethylphenyl group, a 2-chloro-5-trichloromethylphenyl group, a 2-chloro-5-fluoromethylphenyl group, a 2-chloro-5-difluoromethylphenyl group, a 2-chloro-5-trifluoromethylphenyl group, a 5-chloro-2-chloromethylphenyl group, a 5-chloro-2-fluoromethylphenyl group, a 5-chloro-2-difluoromethylphenyl group, a 5-chloro-2-trifluoromethylphenyl group, a 2-fluoro-5-chloromethylphenyl group, a 2-fluoro-5-fluoromethylphenyl group, a 2-fluoro-5-difluoromethylphenyl group, a 2-fluoro-5-trifluoromethylphenyl group, a 5-fluoro-2-chloromethylphenyl group, a 5-fluoro-2-fluoromethylphenyl group, a 5-fluoro-2-difluoromethylphenyl group, a 5-fluoro-2-trifluoromethylphenyl group, a 2-methyl-5-chloromethylphenyl group, a 2-methyl-5-fluoromethylphenyl group, a 2-methyl-5-difluoromethylphenyl group, a 2-methyl-5-trifluoromethylphenyl group, a 2-chloromethyl-5-methylphenyl group, a 2-fluoromethyl-5-methylphenyl group, a 2-difluoromethyl-5-methylphenyl group, a 2-trifluoromethyl-5-methylphenyl group, a 5-chloro-2-fluorophenyl group, a 2-chloro-5-fluorophenyl group, a 5-chloro-2-hydroxymethylphenyl group, a 5-fluoro-2-hydroxymethylphenyl group, a 2-chloro-5-hydroxymethylphenyl group, a 2-fluoro-5-hydroxymethylphenyl group, a 2,3-difluoro-5-hydroxymethylphenyl group, a 2,6-difluoro-5-hydroxymethylphenyl group, and the like. Among these, a 2,5-difluorophenyl group and a 2,3,6-trifluorophenyl group are preferred.

Next, $Ar_2$ will be described in the following.

$Ar_2$ represents a phenyl group which may be substituted, or a heterocyclic group which may be substituted.

Here, the term "phenyl group which may be substituted" means an unsubstituted phenyl group, as well as a phenyl group which is substituted with one substituent, or two identical or different substituents selected from the group consisting of a lower alkyl group which may be substituted with a halogen atom, a hydroxy group, a lower alkoxy group which may be substituted, and a halogen atom. In the case where there is one substituent, the substitution position is preferably the 4-position, while in the case where there are two substituents, substitutions at the 3-position and 4-position or substitutions at the 3-position and 5-position are preferred.

The lower alkyl group which may be substituted with a halogen atom, which is a substituent for the above-mentioned phenyl group, means the same group as the lower alkyl group which may be substituted with a halogen atom described hereinbefore as a substituent for the $Ar_1$.

For the lower alkoxy group which may be substituted, which is used as a substituent for the above-mentioned phenyl group, the term "lower alkoxy group" means an alkoxy group having the above-described lower alkyl group as a constituent, and these lower alkoxy groups may be further substituted with a halogen atom. Thus, the lower alkoxy group which may be substituted may include a methoxy group, an ethoxy group, a propoxy group, an isopropoxy group, a butoxy group, an isobutoxy group, a tert-butoxy group, a pentoxy group, a hexyl group, a cyclopropyloxy group, a trifluoromethoxy group, a trichloromethoxy group, and the like. Among these, a methoxy group and a trifluoromethoxy group are preferred.

The halogen atom as a substituent for the above-mentioned phenyl group may be exemplified by the same ones as the halogen atoms described as substituents for the $Ar_1$, and a chlorine atom and a fluorine atom are preferred, with a fluorine atom being particularly preferred.

The heterocyclic group as in the heterocyclic group which may be substituted means a monocyclic or bicyclic heterocyclic group, and specifically means a pyridin-2-yl group, a pyridin-3-yl group, a thiophen-2-yl group, a benzofuran-6-yl group, a dihydrobenzofuran-6-yl group, a pyrimidin-5-yl group, or the like. These heterocyclic groups may be substituted with one group or atom, or two identical or different groups or atoms selected from the group consisting of a lower alkyl group which may be substituted with a halogen atom, a hydroxy group, a lower alkoxy group which may be substituted, and a halogen atom, as described in the case where $Ar_2$ is a phenyl group which may be substituted. That is, if a plurality of groups or atoms are present as substituents, these groups or atoms may be identical, or may be different from each other.

When $Ar_2$ is a substituted pyridin-2-yl group, a substituted pyridin-3-yl group or pyrimidin-5-yl group, the groups preferably have a substituent at a position para to the bond with the sulfur atom. That is, when $Ar_2$ is a substituted pyridin-2-yl group, it is preferable that substitution with a group or an atom occurs at the 5-position, while when $Ar_2$ is a substituted pyridin-3-yl group, it is preferable that substitution with a group or an atom occurs at the 6-position. When $Ar_2$ is a substituted pyrimidin-5-yl group, it is preferable That substitution with a group or an atom occurs at the 2-position.

Therefore, specific examples of $Ar_2$ include a phenyl group, a 2-methylphenyl group, a 3-methylphenyl group, a 4-methylphenyl group, a 2-ethylphenyl group, a 3-ethylphenyl group, a 4-ethylphenyl group, a 4-propylphenyl group, a 4-isopropylphenyl group, a 4-cyclopropylphenyl group, a 4-butylphenyl group, a 4-tert-butylphenyl group, a 4-cyclobutylphenyl group, a 4-cyclopentylphenyl group, a 4-cyclohexylphenyl group, a 2,3-dimethylphenyl group, a 2,4-dimethylphenyl group, a 3,4-dimethylphenyl group, a 3,5-dimethylphenyl group, a 2-methyl-4-ethylphenyl group, a 3-methyl-4-ethylphenyl group, a 3-ethyl-4-methylphenyl group, a 4-chloromethylphenyl group, a 4-dichloromethylphenyl group, a 4-trichloromethylphenyl group, a 2-fluoromethylphenyl group, a 2-difluoromethylphenyl group, a 2-trifluoromethylphenyl group, a 3-fluoromethylphenyl group, a 3-difluoromethylphenyl group, a 3-trifluoromethylphenyl group, a 4-fluoromethylphenyl group, a 4-difluoromethylphenyl group, a 4-trifluoromethylphenyl group, a 4-trichloromethyl-3-methylphenyl group, a 4-trifluoromethyl-3-methylphenyl group, a 5-trichloromethyl-3-methylphenyl group, a 5-trifluoromethyl-3-methylphenyl group, a 2-hydroxyphenyl group, a 3-hydroxyphenyl group, a 4-hydroxyphenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 4-(trifluoromethoxy)phenyl group, a 2-chlorophenyl group, a 3-chlorophenyl group, a 4-chlorophenyl group, a 2,3-dichlorophenyl group, a 2,4-dichlorophenyl group, a 3,4-dichlorophenyl group, a 3,5-dichlorophenyl group, a 2-fluorophenyl group, a 3-fluorophenyl group, a 4-fluorophenyl group, a 2,3-difluorophenyl group, a 2,4-difluorophenyl group, a 3,4-difluorophenyl group, a 3,5-difluorophenyl group, a 4-chloro-3-methylphenyl group, a 4-fluoro-3-methylphenyl group, a 3-chloro-4-methylphenyl group, a 3-fluoro-4-methylphenyl group, a 3-fluoro-4-fluoromethylphenyl group, a 3-fluoro-4-difluoromethylphenyl group, a 5-chloro-3-methylphenyl group, a 5-fluoro-3-methylphenyl group, a 3-fluoro-4-trifluoromethylphenyl group, a 3-fluoro-5-trifluoromethylphenyl group, a 3-fluoro-4-methoxyphenyl group, a 3-chloro-4-methoxyphenyl group, a 3-fluoro-4-ethoxyphenyl group, a 3-chloro-4-ethoxyphenyl group, a 4-fluoro-3-methoxyphenyl group, a 4-chloro-3-methoxyphenyl group, a 4-fluoro-3-ethoxyphenyl group, a 4-chloro-3-ethoxyphenyl group; a pyridin-2-yl group, a 3-methylpyridin-2-yl group, a 4-methylpyridin-2-yl group, a 5-methylpyridin-2-yl group, a 6-methylpyridin-2-yl group, a 5-(chloromethyl)pyridin-2-yl group, a 5-(dichloromethyl)pyridin-2-yl group, a 5-(trichloromethyl)pyridin-2-yl group, a 5-(fluoromethyl)pyridin-2-yl group, a 5-(difluoromethyl)pyridin-2-yl group, a 5-(trifluoromethyl)pyridin-2-yl group, a 5-hydroxypyridin-2-yl group, a 5-methoxypyridin-2-yl group, a 5-ethoxypyridin-2-yl group, a 3-chloropyridin-2-yl group, a 3-fluoropyridin-2-yl group, a 4-chloropyridin-2-yl group, a 4-fluoropyridin-2-yl group, a 5-chloropyridin-2-yl group, a 5-fluoropyridin-2-yl group, a 6-chloropyridin-2-yl group, a 6-fluoropyridin-2-yl group, a 5-chloro-3-methylpyridin-2-yl group, a 5-fluoro-3-methylpyridin-2-yl group, a 5-chloro-4-methylpyridin-2-yl group, a 5-fluoro-4-methylpyridin-2-yl group, a 5-chloro-6-methylpyridin-2-yl group, a 5-fluoro-6-methylpyridin-2-yl group, a 5-trifluoromethyl-4-methylpyridin-2-yl group; a pyridin-3-yl group, a 2-methylpyridin-3-yl group, a 4-methylpyridin-3-yl group, a 5-methylpyridin-3-yl group, a 6-methylpyridin-3-yl group, a 6-(chloromethyl)pyridin-3-yl group, a 6-(dichloromethyl)pyridin-3-yl group, a 6-(trichloromethyl)pyridin-3-yl group, a 2-(fluoromethyl)pyridin-3-yl group, a 2-(difluoromethyl)pyridin-3-yl group, a 2-(trifluoromethyl)pyridin-3-yl group, a 4-(fluoromethyl)pyridin-3-yl group, a 4-(difluoromethyl)pyridin-3-yl group, a 4-(trifluoromethyl)pyridin-3-yl group, a 5-(fluoromethyl)pyridin-3-yl group, a 5-(difluoromethyl)pyridin-3-yl group, a 5-(trifluoromethyl)pyridin-3-yl group, a 6-(fluoromethyl)pyridin-3-yl group, a 6-(difluoromethyl)pyridin-3-yl group, a 6-(trifluoromethyl)pyridin-3-yl group, a 6-methoxypyridin-3-yl group, a 2-chloropyridin-3-yl group, a 2-fluoropyridin-3-yl group, a 4-chloropyridin-3-yl group, a 4-fluoropyridin-3-yl group, a 5-chloropyridin-3-yl group, a 5-fluoropyridin-3-yl group, a 6-chloropyridin-3-yl group, a 6-fluoropyridin-3-yl group, a 6-chloro-4-methylpyridin-3-yl group, a 6-fluoro-4-methylpyridin-3-yl group, a 6-chloro-5-methylpyridin-3-yl group, a 6-fluoro-5-methylpyridin-3-yl group, a 5-methyl-6-trifluoromethylpyridin-3-yl group; a thiophen-2-yl group, a 3-methylthiophen-2-yl group, a 4-methylthiophen-2-yl group, a 5-methylthiophen-2-yl group, a 5-trichloromethylthiophen-2-yl group, a 5-trifluoromethylthiophen-2-yl group, a 5-hydroxythiophen-2-yl group, a 5-chlorothiophen-2-yl group, a 5-fluorothiophen-2-yl group; a benzofuran-6-yl group, a 3-methylbenzofuran-6-yl group, a 5-methylbenzofuran-6-yl group; a 2,3-dihydrobenzofuran-6-yl group, a 3-methyl-2,3-dihydrobenzofuran-6-yl group, a 5-methyl-2,3-dihydrobenzofuran-6-yl group; a pyrimidin-5-yl group, a 2-methylpyrimidin-5-yl group, a 2-chloropyrimidin-5-yl group, a 2-fluoropyrimidin-5-yl group, a 2-trichloromethylpyrimidin-5-yl group, a 2-trifluoromethylpyrimidin-5-yl group, and the like.

Among these, a phenyl group, a 4-methylphenyl group, a 4-chlorophenyl group, a 4-fluorophenyl group, a 4-trichloromethylphenyl group, a 4-trifluoromethylphenyl group, a 4-methoxyphenyl group, a 4-(trifluoromethoxy)phenyl group, a 3,4-difluorophenyl group, a 3,5-difluorophenyl group, a 4-chloro-3-methylphenyl group, a 4-fluoro-3-methylphenyl group, a 5-chloropyridin-2-yl group, a 5-fluoropyridin-2-yl group, a 5-methylpyridin-2-yl group, a 5-(fluoromethyl)pyridin-2-yl group, a 5-(difluoromethyl)pyridin-2-yl group, a 5-(trifluoromethyl)pyridin-2-yl group, a 6-chloropyridin-3-yl group, a 6-fluoropyridin-3-yl group, a 6-methylpyridin-3-yl group, a 6-(fluoromethyl)pyridin-3-yl group, a 6-(difluoromethyl)pyridin-3-yl group, a 6-(trifluoromethyl) pyridin-3-yl group, a 2-(trifluoromethyl)pyrimidin-5-yl group, a 5-chlorothiophen-2-yl group, a 5-fluorothiophen-2-yl group, a benzofuran-6-yl group, a 2,3-dihydrobenzofuran-6-yl group, and the like are preferred, and a phenyl group, a 4-methylphenyl group, a 4-trifluoromethylphenyl group, a 4-chlorophenyl group, a 4-fluorophenyl group, a 4-methoxyphenyl group, a 4-(trifluoromethoxy)phenyl group, a 3,4-difluorophenyl group, a 4-chloro-3-methylphenyl group, a 4-fluoro-3-methylphenyl group, a 3,5-difluorophenyl group, a 5-(trifluoromethyl)pyridin-2-yl group, a 6-(trifluoromethyl)pyridin-3-yl group, and a benzofuran-6-yl group are more preferred.

X represents —S—, —SO— or —SO$_2$—. The compound which is a compound represented by general formula (1), and in which X is —SO— or —SO$_2$—, may exhibit a desired effect, particularly in vivo situations.

Y represents a hydrogen atom, —NR$^1$R$^2$, or —OR$^{1'}$.

When Y is —NR$^1$R$^2$, R$^1$ and R$^2$ may be specifically exemplified by the groups described in the following, but is not particularly limited as long as the group can be metabolized in the body to generate —NH$_2$ as Y.

R$^1$ means a hydrogen atom, a lower alkyl group, or a hydroxy group. As described above, the lower alkyl group means a straight-chained, branched or cyclic alkyl group having 1 to 6 carbon atoms, and a methyl group and an ethyl group are preferred. For R$^1$, a hydrogen atom or a methyl group is particularly preferred.

R$^2$ is a hydrogen atom, a lower alkyl group which may be substituted, a lower alkanoyl group, an alkoxycarbonyl group which may be substituted, a lower alkoxy group which may be substituted, an amino group which may be substituted, a phosphono group, a phenyl group which may be substituted, or an aromatic heterocyclic group which may be substituted.

The term "lower alkyl group which may be substituted" in the case where R$^2$ is a lower alkyl group which may be substituted, means an unsubstituted lower alkyl group, as well as a lower alkyl group having, as substituents, 1 to 3 groups selected from the group consisting of a lower alkanoyl group, a carboxyl group, a lower alkoxycarbonyl group, a hydroxy group, a lower alkoxy group which may be substituted, a mercapto group, a lower alkylthio group, a lower alkylsulfinyl group, a lower alkylsulfonyl group, an amino group which may be substituted, a halogen atom, a phenyl group which may be substituted, and an aromatic heterocyclic group which may be substituted. When a plurality of groups are present as substituents, the groups may be identical, part of the groups may be identical, or all of the groups may be different.

Here, the lower alkyl group as in the lower alkyl group which may be substituted, includes the same groups as those described above, but a methyl group, an ethyl group, a propyl group and a tert-butyl group are preferred, with a methyl group or an ethyl group being more preferred.

Next, the substituents for the lower alkyl group in the case where R$^2$ is a lower alkyl group which may be substituted, will be described.

The term "lower alkanoyl group" means a straight-chained and branched alkanoyl group having 2 to 6 carbon atoms, and examples thereof include an acetyl group, a propionyl group, a butyryl group, a valeryl group, a hexanoyl group and the like.

The term "lower alkoxycarbonyl group" means a lower alkoxycarbonyl group having the above-described lower alkyl group as a constituent, and means a methoxycarbonyl group, an ethoxycarbonyl group, a propoxycarbonyl group or the like.

The lower alkoxy group as in the lower alkoxy group which may be substituted means the same group as the lower alkoxy group described as a substituent for Ar$_1$, and examples thereof include a methoxy group, an ethoxy group, a propoxy group, an isopropoxy group, a butoxy group, an isobutoxy group, a pentoxy group, a cyclopropyloxy group, a cyclopentyloxy group, a cyclopropylmethyloxy group, and the like. Among these, a methoxy group and an ethoxy group are preferred. These lower alkoxy groups may be further substituted with a carboxyl group, an alkoxycarbonyl group, a hydroxy group, or a heterocyclic group such as a pyridyl group. Therefore, the preferable lower alkoxy group which may be substituted includes a methoxy group, an ethoxy group, a carboxymethoxy group, a methoxycarbonylmethoxy group, an ethoxycarbonylmethoxy group, a 2-hydroxyethoxy group, a pyridin-3-ylmethoxy group and the like, while a methoxy group, an ethoxy group, a carboxymethoxy group, an ethoxycarbonylmethoxy group, a 2-hydroxyethoxy group, a pyridin-3-ylmethoxy group and the like may be mentioned as more preferred groups.

The term "lower alkylthio group" means a lower alkylthio group having the above-described lower alkyl group as a constituent, and examples thereof include a methylthio group, an ethylthio group, a propylthio group, a tert-butylthio group, a cyclopropylthio group, and the like.

The term "lower alkylsulfinyl group" means a lower alkylsulfinyl group having the above-described lower alkyl group as a constituent, and examples thereof include a methylsulfinyl group, an ethylsulfinyl group, a propylsulfinyl group, a tert-butylsulfinyl group, a cyclopropylsulfinyl group, and the like.

The term "lower alkylsulfonyl group" means a lower alkylsulfonyl group having the above-described lower alkyl group as a constituent, and examples thereof include a methylsulfonyl group, an ethylsulfonyl group, a propylsulfonyl group, a tert-butylsulfonyl group, a cyclopropylsulfonyl group, and the like.

The term "amino group which may be substituted" means an unsubstituted amino group, as well as an amino group substituted with one substituent selected from the group consisting of a lower alkyl group, a lower alkanoyl group, a lower alkoxycarbonyl group, and a nitrogen-containing heterocyclic group, and examples thereof include an amino group, a methylamino group, a dimethylamino group, an acetylamino group, a propionylamino group, a butyrylamino group, a methoxycarbonylamino group, an ethoxycarbonylamino group, a tert-butoxycarbonylamino group, and the like. Among these, a dimethylamino group is preferred.

The halogen atom means, as described above, a chlorine atom, a fluorine atom, a bromine atom or an iodine atom.

The term "phenyl group which may be substituted" means an unsubstituted phenyl group, as well as a phenyl group substituted with one to three of hydroxy groups or lower alkoxy groups. There is no limitation on the position of substitution for the substituents. Furthermore, when the phenyl group has a plurality of substituents, the phenyl group may be substituted with identical substituents, or part of the substituents may be identical, or all of the substituents may be different groups. Thus, specific examples of the phenyl group which may be substituted include a phenyl group, a 3-hydroxyphenyl group, a 3,4-dihydroxyphenyl group, a 3-hydroxy-4-methoxyphenyl group, a 3,5-dihydroxyphenyl group, a 3-methoxyphenyl group, a 3,4-dimethoxyphenyl group, a 3,4,5-trimethoxyphenyl group, and the like.

The term "aromatic heterocyclic group which may be substituted" means a nitrogen-containing aromatic heterocyclic group which may be substituted with the above-described lower alkyl group, and means a pyridyl group, a pyridazinyl group, a pyrimidinyl group, a pyrazinyl group, a pyrazolyl group, an imidazolyl group or a triazolyl group, each being unsubstituted, as well as a methylpyridyl group, a methylpyridazinyl group, a methylpyrimidinyl group, a methylpyrazinyl group or the like.

Moreover, in the case where $R^2$ is a lower alkyl group substituted with a hydroxy group, the aforementioned hydroxy group may be further substituted with a substituent which can be hydrolyzed in the body to generate the aforementioned hydroxy group. The type of the substituent is not particularly limited, and those substituents that are generally known to have such property can be used. For example, a substituent which results in an ester bond or the like, such as a substituted carbonyl group or phosphono group, may be mentioned. The substituted carbonyl group may be specifically exemplified by an alkanoyl group, a benzoyl group, an aromatic heterocyclic carbonyl group or the like. These groups may be further substituted with a hydroxy group, amino group, carboxy group or the like. Therefore, the substituent for the lower alkyl group which may be substituted may include an acetoxy group, a propionyloxy group, a butyryloxy group, a hydroxyacetoxy group, an aminoacetoxy group, an oxalyloxy group, a carboxyacetoxy group, a carboxypropionyloxy group, a carboxybutyryloxy group, a benzoyloxy group, a carboxybenzoyloxy group, a pyridylcarbonyloxy group, a carboxypyridylcarbonyloxy group, a phosphonooxy group, and the like.

Thus, examples of the lower alkyl group which may be substituted as for $R^2$ include a methyl group, an ethyl group, an n-propyl group, an isopropyl group, an n-butyl group, an isobutyl group, a sec-butyl group, a tert-butyl group, an n-pentyl group, a 2-methylpentyl group, an n-hexyl group, a cyclopropyl group, a cyclobutyl group, a cyclopentyl group, a cyclohexyl group; an acetylmethyl group, a 1-acetylethyl group, a 2-acetylethyl group, a 3-acetylpropyl group; a carboxymethyl group, a 2-carboxyethyl group, a 3-carboxypropyl group, a 2-carboxypropyl group; a methoxycarbonylmethyl group, an ethoxycarbonylmethyl group, a propoxycarbonylmethyl group, a butoxycarbonylmethyl group, a tert-butoxycarbonylmethyl group, a 2-methoxycarbonylethyl group, a 2-ethoxycarbonylethyl group, a 2-propoxycarbonylethyl group, a 2-butoxycarbonylethyl group, a 2-tert-butoxycarbonylethyl group; a hydroxymethyl group, a 2-hydroxyethyl group, a 1-hydroxyethyl group, a 1,2-dihydroxyethyl group, a 1-hydroxymethyl-2-hydroxyethyl group, a 1-hydroxypropyl group, a 3-hydroxypropyl group, a 2-hydroxy-1-hydroxymethylethyl group, a 1-hydroxybutyl group, a 2-hydroxybutyl group, a 3-hydroxybutyl group, a 2-hydroxycyclopropyl group, a 2-hydroxycyclobutyl group, a 4-hydroxycyclohexyl group; an acetoxymethyl group, a propionyloxymethyl group, a butyryloxymethyl group, a hydroxyacetoxymethyl group, an aminoacetoxymethyl group, an oxalyloxy group, a carboxylacetoxymethyl group, a carboxypropionyloxymethyl group, a benzoyloxymethyl group, a carboxybenzoyloxymethyl group, a pyridylcarbonyloxymethyl group, a carboxypyridylcarbonyloxymethyl group, a phosphonooxymethyl group; a methoxymethyl group, an ethoxymethyl group, a carboxymethoxymethyl group, a methoxycarbonylmethoxymethyl group, an ethoxycarbonylmethoxymethyl group, a 2-hydroxyethoxymethyl group, a (pyridin-3-ylmethoxy)methyl group, a methoxyethyl group, an ethoxyethyl group, a methoxypropyl group, a methoxyisopropyl group, a methoxybutyl group; a mercaptomethyl group; a methylthiomethyl group, an ethylthiomethyl group, a 2-methylthioethyl group, a 2-ethylthioethyl group, a 3-methylthiopropyl group, a 2-methylthiopropyl group, a 3-ethylthiopropyl group; a methylsulfinylmethyl group, an ethylsulfinylmethyl group, a 2-methylsulfinylethyl group, a 2-ethylsulfinylethyl group, a 3-methylsulfinylpropyl group, a 3-ethylsulfinylpropyl group; a methylsulfonylmethyl group, an ethylsulfonylmethyl group, a 2-methylsulfonylethyl group, a 2-ethylsulfonylethyl group, a 3-methylsulfonylpropyl group, a 2-methylsulfonylpropyl group, a 3-ethylsulfonylpropyl group; an aminomethyl group, a dimethylaminomethyl group, an acetylaminomethyl group, a propionylaminomethyl group, a butyrylaminomethyl group, a 2-aminoethyl group, a 2-acetylaminoethyl group, a 2-propionylaminoethyl group, a 2-butyrylaminoethyl group, a 1-acetylaminoethyl group, a 1-propionylaminoethyl group, a 1-butyrylaminoethyl group, a methoxycarbonylaminomethyl group, an ethoxycarbonylaminomethyl group, a tert-butoxycarbonylaminomethyl group, a 2-methoxycarbonylaminoethyl group, a 2-ethoxycarbonylaminomethyl group, a 2-tert-butoxycarbonylaminoethyl group; a chloromethyl group, a fluoromethyl group, a 2-chloroethyl group, a 2-fluoroethyl group; a phenylmethyl group, a 3-hydroxyphenylmethyl group, a 3,4-dihydroxyphenylmethyl group, a 3-hydroxy-4-methoxyphenylmethyl group, a 3,5-dihydroxyphenylmethyl group, a 3-methoxyphenylmethyl group, a 3,4-dimethoxyphenylmethyl group, a 3,4,5-trimethoxyphenylmethyl group; a 2-pyridylmethyl group, a 3-pyridylmethyl group, a 4-pyridylmethyl group, a 3-methyl-4-pyridylmethyl group, a 2-pyridazinylmethyl group, a 2-pyrimidinylmethyl group, a 4-pyrimidinylmethyl group, a 2-pyrazinylmethyl group, a 1H-imidazol-2-yl-methyl group, a 1H-pyrazol-5-yl-methyl group, a 1H-triazol-5-yl-methyl group, and the like.

The term "lower alkanoyl group" as in the case where $R^2$ is a lower alkanoyl group, means a straight-chained or branched alkanoyl group having 2 to 6 carbon atoms, and examples thereof include an acetyl group, a propionyl group, a butyryl group, a valeryl group, a hexanoyl group, and the like.

The term "lower alkoxycarbonyl group which may be substituted" as in the case where $R^2$ is a lower alkoxycarbonyl group which may be substituted, means the above-described lower alkoxy group which may be substituted with a hydroxy group or an aromatic heterocyclic group, and examples thereof include a carboxyl group, a methoxycarbonyl group, an ethoxycarbonyl group, a 2-hydroxyethoxycarbonyl group, a pyridyloxycarbonyl group, and the like.

The term "lower alkoxy group which may be substituted" as in the case where $R^2$ is a lower alkoxy group which may be substituted, means the above-described lower alkoxy group which may be substituted with a hydroxy group or an aromatic heterocyclic group, and examples thereof include a methoxy group, an ethoxy group, a 2-hydroxyethoxy group, a 2-pyridylmethoxy group, and the like.

The term "amino group which may be substituted" as in the case where $R^2$ is an amino group which may be substituted, means an unsubstituted amino group, as well as a methylamino group, a dimethylamino group, an ethylamino group, a 2-hydroxyethylamino group, a 2-pyridylamino group, an acetylamino group, and the like. Furthermore, the amino group which may be substituted may be a substituted aliphatic heterocyclic group containing, as a constituent, the nitrogen atom which constitutes the aforementioned amino group, and examples thereof include a morpholin-4-yl group, a piperidino group, a piperazino group, a 4-methylpiperazino group, and the like.

The term "phenyl group which may be substituted" as in the case where $R^2$ is a phenyl group which may be substituted, means an unsubstituted phenyl group, as well as a phenyl group which may be substituted with one substituent selected from the group consisting of a lower alkyl group, a hydroxy-lower alkyl group, a hydroxy group, an aminocarbonyl group, a methylaminocarbonyl group, and a dimethylaminocarbonyl group. It is preferable that these substituents are present on the para-position with respect to the bond between the aforementioned phenyl group and the amino group. Thus, examples of the phenyl group which may be substituted include a phenyl group, a 2-methylphenyl group, a 3-methylphenyl group, a 4-methylphenyl group, a 4-hydroxymethylphenyl group, a 4-hydroxyphenyl group, a 4-aminocarbonylphenyl group, a 4-methylaminocarbonylphenyl group, a 4-dimethylaminocarbonylphenyl group, and the like.

The aromatic heterocyclic group as in the case where $R^2$ is a heterocyclic group, may include a 5- or 6-membered nitrogen-containing aromatic heterocyclic group, for example, a 2-pyridyl group, a 3-pyridyl group, a 2-pyrimidinyl group, a 4-pyrimidinyl group, a 2-pyridazinyl group, a 1H-imidazol-2-yl group, a 1H-pyrazol-5-yl group, a 1H-triazol-5-yl group, and the like.

Among these, as for $R^2$, a hydrogen atom, a methyl group, an ethyl group, a tert-butyl group, a cyclopropyl group, a carboxymethyl group, a 2-carboxyethyl group, a 2-(ethoxycarbonyl)ethyl group, a hydroxymethyl group, a 2-hydroxyethyl group, a 4-hydroxycyclohexyl group, a 2-hydroxy-1-hydroxymethylethyl group, an acetoxymethyl group, a methylthiopropyl group, a methylsulfinylpropyl group, a methylsulfonylpropyl group, a methylcarbonylaminoethyl group, a methoxycarbonylaminoethyl group, a tert-butoxycarbonylaminoethyl group, a 2-chloroethyl group, a hydroxyacetoxymethyl group, a dimethylaminomethyl group, a carboxymethoxymethyl group, a methoxycarbonylmethoxymethyl group, an ethoxycarbonylmethoxymethyl group, a 2-hydroxyethoxymethyl group, a (pyridin-3-ylmethoxy)methyl group, a mercaptomethyl group, an acetyl group, and a methoxy group may be included as preferred groups; and a hydrogen atom, a methyl group, an ethyl group, a cyclopropyl group, a carboxymethyl group, a 2-carboxyethyl group, a hydroxymethyl group, a 2-hydroxyethyl group, an acetoxymethyl group, a methylsulfinylpropyl group, a methylsulfonylpropyl group, a methoxycarbonylaminoethyl group, a hydroxyacetoxymethyl group, a dimethylaminomethyl group, a carboxymethoxymethyl group, an ethoxycarbonylmethoxymethyl group, a 2-hydroxyethoxymethyl group, a (pyridin-3-ylmethoxy)methyl group, a mercaptomethyl group, an acetyl group, and a methoxy group may be included as more preferred groups. As even more preferred groups, a hydrogen atom, a methyl group, an ethyl group, a hydroxymethyl group, a 2-hydroxyethyl group, a dimethylaminomethyl group, and a methoxy group may be included.

As the substituent represented by $-NR^1R^2$, an amino group, a methylamino group, a dimethylamino group, a (hydroxymethyl)amino group, an N-methyl-N-(hydroxymethyl) amino group, a (2-hydroxyethyl)amino group, and an N-methyl-N-(2-hydroxyethyl)amino group may be included in preferred groups.

Furthermore, $R^1$ and $R^2$ may, together with the nitrogen atom to which these groups are bound, form a saturated heterocyclic group. The saturated heterocyclic group in this case means a 4- to 7-membered saturated heterocyclic group which may have, as a constituent, 1 to 3 identical or different atoms selected from a nitrogen atom, an oxygen atom and a sulfur atom in addition to the aforementioned nitrogen atom. Specific examples thereof include an azetidinyl group, a pyrrolidinyl group, a pyrazolidinyl group, an imidazolidinyl group, a thiazolidinyl group, an isothiazolidinyl group, an oxazolidinyl group, an isooxazolidinyl group, a piperidinyl group, a piperazinyl group, a morpholinyl group, a thiomorpholinyl group, a hexahydropyrimidinyl group, a tetrahydropyridazinyl group, a homopiperazinyl group, a homopiperidinyl group, a homomorpholinyl group, and the like.

Among these, an azetidinyl group, a pyrrolidinyl group, a pyrazolidinyl group, an imidazolidinyl group, a piperidinyl group, a piperazinyl group, a hexahydropyridazinyl group, a hexahydropyrimidinyl group, a morpholinyl group, a thiomorpholinyl group and a homopiperazinyl group are preferred, and a piperidinyl group, a piperazinyl group, a morpholinyl group and a thiomorpholinyl group are more preferred.

These 4- to 7-membered saturated heterocyclic groups may be substituted with one, or two to three identical or different groups selected from the group consisting of a lower alkyl group, a hydroxy-lower alkyl group, a hydroxy group, an oxo group, an amino group and a halogen atom. As long as substitution can be achieved, these substituents may be substituted on the same atom, or may be substituted on different atoms. The lower alkyl group and halogen atom that can be used for the substitution of the aforementioned saturated heterocyclic group may be exemplified by the same ones as those described above.

When the 4- to 7-membered saturated heterocyclic group is a thiomorpholinyl group, it is preferable that one or two oxo groups are substituted on the sulfur atom.

Thus, in the case where $R^1$ and $R^2$, together with the nitrogen atom to which these are bound, forms a 4- to 7-membered saturated heterocyclic group which may be substituted, specific examples thereof include an azetidin-1-yl group, a 3-methylazetidin-1-yl group, a 2,2-dimethylazetidin-1-yl group, a 3,3-dimethylazetidin-1-yl group, a 3-hydroxyazetidin-1-yl group, a 2-oxoazetidin-1-yl group, a 3-oxoazetidin-1-yl group, a 3-fluoroazetidin-1-yl group, a 3,3-difluoroazetidin-1-yl group; a pyrrolidin-1-yl group, a 2,2-dimethylpyrrolidin-1-yl group, a 3,3-dimethylpyrrolidin-1-yl group, a 2-hydroxypyrrolidin-1-yl group, a 3-hydroxypyrrolidin-1-yl group, a 3,4-dihydroxymethylpyrrolidin-1-yl group, a 2-oxopyrrolidin-1-yl group, a 3-oxopyrrolidin-1-yl group, a 2,5-dioxopyrrolidin-1-yl group, a 3-aminopyrrolidin-1-yl group; a pyrazolidin-1-yl group, a 2-methylpyrazolidin-1-yl group, a 2-hydroxypyrazolidin-1-yl group, a 3-oxopyrazolidin-1-yl group, a 3,5-dioxopyrazolidin-1-yl group; an imidazolidin-1-yl group, a 3-methylimidazolidin-1-yl group, a 2-oxoimidazolidin-1-yl group, a 4-oxoimidazolidin-1-yl group, a 3-methyl-2-oxoimidazolidin-1-yl group, a 3-methyl-4-oxoimidazolidin-1-yl group, a 2,2-dimethylimidazolin-1-yl group; a piperidin-1-yl group, a 4-methylpiperidin-1-yl group, a 2,2-dimethylpiperidin-1-yl group, a 3,3-dimethylpiperidin-1-yl group, a 4,4-dimethylpiperidin-1-yl group, a 4-hydroxymethylpiperidin-1-yl group, a 4-hydroxypiperidin-1-yl group, a 2-oxopiperidin-1-yl group, a 3-oxopiperidin-1-yl group, a 4-oxopiperidin-1-yl group, a 4-aminopiperidin-1-yl group, a 4-fluoropiperidin-1-yl group, a 4-chloropiperidin-1-yl group, a 3,3-difluoropiperidin-1-yl group, a 4,4-difluoropiperidin-1-yl group, a 3,3-dichloropiperidin-1-yl group, a 4,4-dichloropiperidin-1-yl group; a piperazin-1-yl group, a 4-methylpiperazin-1-yl group, a 4-ethylpiperazin-1-yl group, a 4-isopropylpiperazin-1-yl group, a 2-cyclopropylpiperazin-1-yl group, a 3-cyclopropylpiperazin-1-yl group, a 4-cyclopropylpiperazin-1-yl group, a 4-cyclobutylpiperazin-1-yl group, a 2,2-dimethylpiperazin-1-yl group, a 3,3-dimethylpiperazin-1-yl group, a 2,6-dimethylpiperazin-1-yl group, a 2-cyclopropyl-4-methylpiperazin-1-yl group, a 3-cyclopropyl-4-methylpiperazin-1-yl group, a 3,4,5-trimethylpiperazin-1-yl group, a 2,2,4-trimethylpiperazin-1-yl group, a 3,3,4-trimethylpiperazin-1-yl group, a 4-hydroxymethylpiperazin-1-yl group, a 4-hydroxypiperazin-1-yl group, a 2-oxopiperazin-1-yl group, a 3-oxopiperazin-1-yl group, a 2-oxo-4-methylpiperazin-1-yl group, a 3-oxo-4-methylpiperazin-1-yl group, a 2,3-dioxopiperazin-1-yl group, a 3,5-dioxopiperazin-1-yl group, a 2,6-dioxopiperazin-1-yl group, a 2,3-dioxo-4-methylpiperazin-1-yl group, a 3,5-dioxo-4-methylpiperazin-1-yl group, a 3,3,4-trimethyl-5-oxopiperazin-1-yl group, a 2,2,4-trimethyl-3-oxopiperazin-1-yl group; a hexahydropyridazin-1-yl group, a 2-methylhexahydropyridazin-1-yl group, a 3,3-dimethylhexahydropyridazin-1-yl group, a 4,4-dimethylhexahydropyridazin-1-yl group, a 6-hydroxyhexahydropyridazin-1-yl group, a 3-oxohexahydropyridazin-1-yl group, a 6-oxohexahydropyridazin-1-yl group; a hexahydropyrimidin-1-yl group, a 2-methylhexahydropyrimidin-1-yl group, a 3-methylhexahydropyrimidin-1-yl group, a 2,2-dimethylhexahydropyrimidin-1-yl group, a 4,4-dimethylhexahydropyrimidin-1-yl group, a 5,5-dimethylhexahydropyrimidin-1-yl group, a 6,6-dimethylhexahydropyrimidin-1-yl group, a 2-oxohexahydropyrimidin-1-yl group, a 4-oxohexahydropyrimidin-1-yl group, a 5-oxohexahydropyrimidin-1-yl group, a 6-oxohexahydropyrimidin-1-yl group; a morpholin-4-yl group, a 2,2-dimethylmorpholin-4-yl group, a 3,3-dimethylmorpholin-4-yl group; a thiomorpholin-4-yl group, a 2,2-dimethylthiomorpholin-4-yl group, a 3,3-dimethylthiomorpholin-4-yl group, a 2-oxothiomorpholin-4-yl group, a 1,1-dioxothiomorpholin-4-yl group; a homopiperazin-1-yl group, a 2-methylhomopiperazin-1-yl group, a 4-methylhomopiperazin-1-yl group, a 4-cyclopropylhomopiperazin-1-yl group, a 2,2-dimethylhomopiperazin-1-yl group, a 3,3-dimethylhomopiperazin-1-yl group, a 5,5-dimethylhomopiperazin-1-yl group, a 6,6-dimethylhomopiperazin-1-yl group, a 7,7-dimethylhomopiperazin-1-yl group, a 3,4,5-trimethylhomopiperazin-1-yl group, a 2-oxohomopiperazin-1-yl group, a 3-oxohomopiperazin-1-yl group, a 5-oxohomopiperazin-1-yl group, a 6-oxohomopiperazin-1-yl group, a 7-oxohomopiperazin-1-yl group, a 2-oxo-4-methylhomopiperazin-1-yl group, a 3-oxo-4-methylhomopiperazin-1-yl group, a 5-oxo-4-methylhomopiperazin-1-yl group, a 6-oxo-4-methylhomopiperazin-1-yl group, a 7-oxo-4-methylhomopiperazin-1-yl group, a 2,3-dioxohomopiperazin-1-yl group, a 2,3-dioxo-4-methylhomopiperazin-1-yl group, and the like. Among these, a 4-hydroxypiperidin-1-yl group, a 3-oxopiperazin-1-yl group, and a morpholin-1-yl group are preferred.

When Y is —$OR^{1'}$, $R^{1'}$ represents a lower alkyl group which may be substituted with a hydrogen atom or a hydroxy group. The lower alkyl group means, as described above, a straight-chained, branched or cyclic alkyl group having 1 to 6-carbon atoms. These may be substituted with one or two hydroxy groups. The position of substitution of the hydroxy group is not particularly limited as long as substitution can be achieved. Therefore, examples of $R^{1'}$ may include a hydrogen atom, a methyl group, an ethyl group, a hydroxymethyl group, a hydroxyethyl group, and the like. Among these, a hydrogen atom, a methyl group and an ethyl group are preferred.

Z represents an oxygen atom or a sulfur atom.

$R^3$ represents a hydrogen atom, a lower alkyl group, or a halogen atom. The lower alkyl group means, as described above, a straight-chained, branched or cyclic group having 1 to 6 carbon atoms. The halogen atom also represents the same groups as those described above. Among these, a hydrogen atom, a methyl group and a chlorine atom are preferred.

The combination of the respective substituents in general formula (1) is not particularly limited, but an exemplary combination of preferred substituents includes a 2,5-difluorophenyl group for $Ar_1$; a 4-fluorophenyl group for $Ar_2$; —SO— for X; a dimethylamino group for Y; an oxygen atom for Z; and a methyl group for R.

Moreover, another exemplary combination of preferred substituents includes a 2,5-difluorophenyl group or a 2,3,6-trifluorophenyl group for $Ar_1$; a phenyl group, a 4-fluorophenyl group or a 6-(trifluoromethyl)pyridin-3-yl group for $Ar_2$; —$SO_2$— for X; a (hydroxymethyl)amino group or an amino group for Y; an oxygen atom for Z; and a methyl group for $R^3$.

As such exemplary combinations of preferred substituents, for example, a combination of a 2,5-difluorophenyl group for $Ar_1$, a 4-fluorophenyl group for $Ar_2$, —$SO_2$— for X, a (hydroxymethyl)amino group for Y, an oxygen atom for Z, and a methyl group for R; or a combination of a 2,3,6-trifluorophenyl group for $Ar_1$, a 4-fluorophenyl group for $Ar_2$, —$SO_2$— for X, a (hydroxymethyl)amino group for Y, an oxygen atom for Z, and a methyl group for $R^3$; a combination of a 2,3,6-trifluorophenyl group for $Ar_1$, a phenyl group for $Ar_2$, —$SO_2$— for X, a (hydroxymethyl)amino group for Y, an oxygen atom for Z, and a methyl group for $R^3$; and a combination of a 2,3,6-trifluorophenyl group for $Ar_1$, a 6-(trifluoromethyl)pyridin-3-yl group for $Ar_2$, —$SO_2$— for X, a (hydroxymethyl)amino group for Y, an oxygen atom for Z, and a methyl group for $R^3$, may be mentioned.

The compound represented by general formula (1) of the present invention may exist in the form of stereoisomers, or optical isomers derived from asymmetric carbon atoms, and these stereoisomers, optical isomers and mixtures thereof are all included in the present invention.

The salt of the compound represented by general formula (1) of the present invention is not particularly limited as long as it is a pharmaceutically acceptable salt, and specific examples thereof include mineral acid salts such as hydrochlorides, hydrobromides, hydroiodides, phosphates, nitrates and sulfates; benzoates; organic sulfonic acid salts such as methanesulfonates, 2-hydroxyethanesulfonates and p-toluenesulfonates; and organic carboxylic acid salts such as acetates, propanoates, oxalates, malonates, succinates, glutarates, adipates, tartrates, maleates, malates and mandelates.

Also, when the compound represented by general formula (1) has an acidic group, the compound may be a salt of an alkali metal ion or of an alkaline earth metal ion. The solvate thereof is not particularly limited as long as it is pharmaceutically acceptable, and specifically, hydrates, ethanolates and the like may be mentioned.

Hereinafter, the method for producing the compound represented by general formula (1) of the present invention will be described.

The compound represented by general formula (1) of the present invention, a salt thereof, and a solvate of the compound or the salt can be produced by combinations of the known production methods used in general chemistry, and representative synthesis methods will be described in the following.

Hereinafter, a representative method for producing a pyridine compound of general formula (1) of the present invention, wherein Z is an oxygen atom (1:Z=O), will be described.

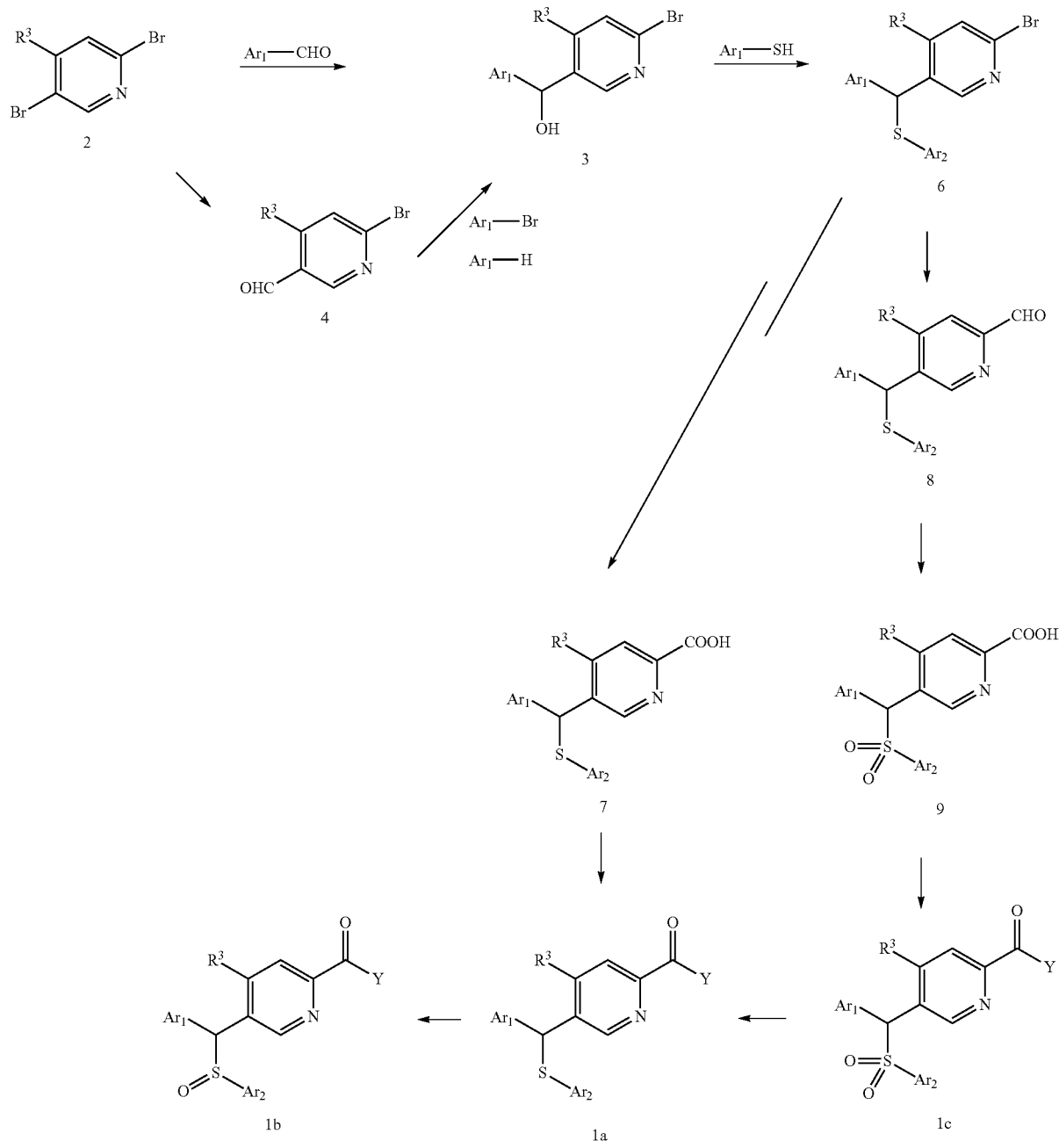

Y = —NR$^1$R$^2$ or —OR$^{1'}$ wherein $Ar_1$, $Ar_2$, $R^1$, $R^2$, $R^3$, $R^{1'}$ and Y are the same as described above.

1) Method for Producing Alcohol Derivative (3)

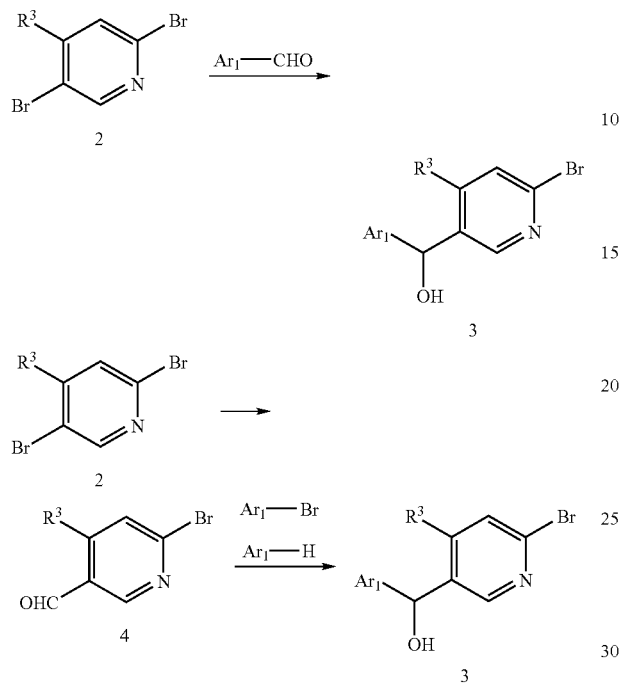

wherein $Ar_1$ and $R^3$ have are the same as described above.

In a solvent such as toluene or diethyl ether, a 2,5-dibromopyridine derivative (2) can be reacted with an equivalent of an organometallic reagent (as representatives, an organolithium reagent, or a Grignard reagent), to thereby selectively lithiate the 5-position of the pyridine. By adding an aldehyde represented by $Ar_1$—CHO as an electrophilic reagent to the resulting solution, an alcohol derivative (3) can be obtained.

In another method, when dimethylformamide or ethyl formate is added as the electrophilic reagent in the above-described reaction, an aldehyde derivative (4) can be obtained. The alcohol derivative can also be synthesized by adding $Ar_1$—Li thereto which is prepared with $Ar_1$—Br or $Ar_1$—H, and an equivalent to two equivalents of an organometallic reagent (as a representative, an organolithium reagent), in a solvent such as tetrahydrofuran or diethyl ether.

In addition, the arylcarbaldehyde ($Ar_1$—CHO), aryl bromide ($Ar_1$—Br) or aryl ($Ar_1$—H), or the 2,5-dibromopyridine derivative (2) used in the production process described above may be known compounds, or can be produced by a combination of methods that are well known to those ordinarily skilled in the art.

2) Method for Producing Sulfide Derivative (6)

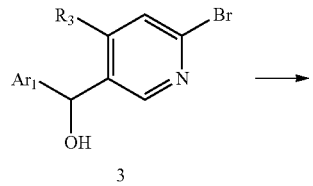

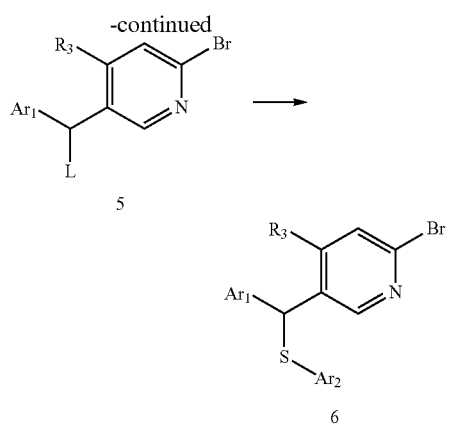

wherein L represents a leaving group; and $Ar_1$, $Ar_2$, and $R_3$ are the same as described above.

A compound (5) can be obtained from the alcohol derivative (3). The sulfide compound (6) can be produced by reacting the obtained compound (5) with a thiol compound ($Ar_2$—SH) in the presence of a base. In this case, the thiol compound may be used in the form of an alkali metal salt or an alkaline earth metal salt (for example, lithium, sodium, potassium).

In the reaction between the compound (5) and the thiol compound ($Ar_2$—SH), the temperature is usually from $-20$ to $200°$ C., and preferably from room temperature to $60°$ C. Depending on the type of the compound (5) or the thiol compound ($Ar_2$—SH), higher reaction temperature may be preferred, and also, it may be sometimes preferable to perform the reaction in a sealed tube. The reaction time is usually from 0.5 hour to 1 day.

Examples of the base include: inorganic bases such as hydrides of alkali metals or alkaline earth metals (for example, lithium hydride, sodium hydride, potassium hydride, calcium hydride); amides of alkali metals or alkaline earth metals (for example, lithium amide, sodium amide, lithium diisopropylamide, lithium dicyclohexylamide, lithium hexamethyldisilazide, sodium hexamethyldisilazide, potassium hexamethyldisilazide); lower alkoxides of alkali metals or alkaline earth metals (for example, sodium methoxide, sodium ethoxide, potassium t-butoxide); alkali metals, alkaline earth metals (for example, sodium hydroxide, potassium hydroxide, lithium hydroxide, barium hydroxide); carbonates of alkali metals, alkaline earth metals or silver (for example, sodium carbonate, potassium carbonate, cesium carbonate, silver carbonate); hydrogencarbonates of alkali metals (for example, sodium hydrogencarbonate, potassium hydrogencarbonate); alkyllithiums (for example, n-butyllithium) or alkyl Grignard (for example, methyl magnesium bromide); and silver oxide, and organic bases such as amines (for example, triethylamine, diisopropylethylamine, N-methylmorpholine); and basic heterocyclic compounds (for example, dimethylamino pyridine pyridine, imidazole, 2,6-lutidine, collidine, 1,8-diazabicyclo[5,4,0]undec-7-ene, 1,5-diazabicyclo[4,3,0]non-5-ene, 1,4-diazabicyclo[2,2,2]octane).

Examples of the solvent include alcohol solvents, ether solvents, halogen solvents, aromatic solvents, nitrile solvents, amide solvents, ketone solvents, sulfoxide solvents, and water, and mixtures of two or more of these may also be used. Among these, methylene chloride, tetrahydrofuran, diethyl ether and the like are preferred.

The compound (5) having a leaving group L can be produced from the alcohol derivative (3) by converting the hydroxy group to the leaving group according to a known method. Examples of the leaving group represented by L include a halogen atom (chlorine, bromine, iodine, etc.), a $C_{1-6}$ alkylsulfonyloxy group which may be halogenated (methanesulfonyloxy, ethanesulfonyloxy, trifluoromethanesulfonyloxy, etc.), a $C_{6-10}$-aromatic hydrocarbon sulfonyloxy which may be substituted, and the like. The substituent for the aromatic hydrocarbon sulfonyloxy group may include one to three of halogen atoms, $C_{1-6}$ alkyl groups which may be halogenated, $C_{1-6}$ alkoxy groups, and the like. Preferred examples of the leaving group include a benzenesulfonyloxy group, a p-toluenesulfonyloxy group, a 1-naphthalenesulfonyloxy group, a 2-naphthalenesulfonyloxy group, and the like.

In addition, the thiol compound ($Ar_2$—SH) used in the production process described above may be a known compound, or can be produced by a combination of methods that are well known to those ordinarily skilled in the art.

3) Method for Producing Pyridine-2-Carboxylic Acid Derivative (7)

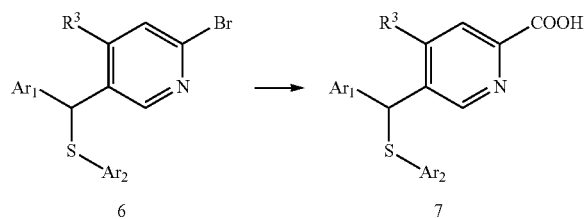

wherein $Ar_1$, $Ar_2$ and $R^3$ are the same as described above.

A pyridine-2-carboxylic acid derivative (7) can be produced by adding an organometallic reagent to a 2-bromopyridine derivative (6) followed by stirring, and then adding carbon dioxide as an electrophilic reagent.

The organic solvent may be exemplified by an ether solvent such as tetrahydrofuran or diethyl ether, a hydrocarbon solvent such as toluene, or hexamethylphosphoramide (HMPA), or a combination thereof. As the organometallic reagent, an equivalent to excess amount, preferably an equivalent amount of alkyllithium (for example, n-butyllithium, sec-butyllithium, t-butyllithium, phenyllithium, etc.) is subjected to the reaction. The temperature for the reaction is usually from $-100$ to $50°$ C., and preferably from $-78$ to $0°$ C. The stirring time is usually from 0.1 hour to 1 day.

Into this reaction solution, carbon dioxide in a gaseous or solid form is added as an electrophilic reagent. The temperature for the reaction is usually from $-100$ to $50°$ C., and preferably from $-78$ to $0°$ C. The reaction time is usually from 0.1 hour to 1 day.

4) Method for Producing Pyridine-2-Carboxylic Acid Derivative (9)

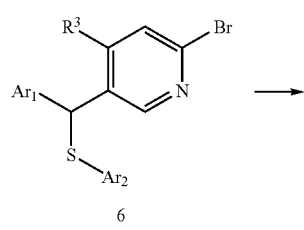

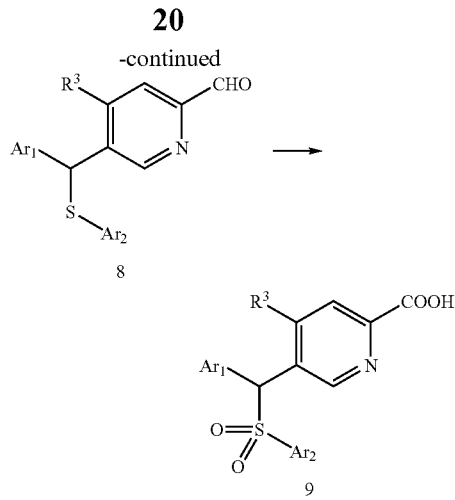

wherein $Ar_1$, $Ar_2$ and $R^3$ are the same as described above.

A pyridine-2-carbaldehyde derivative (8) can be produced by adding an organometallic reagent to a 2-bromopyridine derivative (6) followed by stirring, and then adding dimethylformamide or a formic acid ester such as ethyl formate as an electrophilic reagent.

The organic solvent may be exemplified by an ether solvent such as tetrahydrofuran or diethyl ether, a hydrocarbon solvent such as toluene, or hexamethylphosphoramide (HMPA), or a combination thereof. As the organometallic reagent, an equivalent to excess amount, preferably an equivalent amount of alkyllithium (for example, n-butyllithium, sec-butyllithium, t-butyllithium, phenyllithium, etc.) is subjected to the reaction. The temperature for the reaction is usually from $-100$ to $50°$ C., and preferably from $-78$ to $0°$ C. The stirring time is usually from 0.1 hour to 3 days.

Into this reaction solution, dimethylformamide or a formic acid ester such as ethyl formate is added.

The temperature for the reaction is usually from $-100$ to $50°$ C., and preferably from $-78$ to $0°$ C. The reaction time is usually from 0.1 hour to 3 days. The resulting pyridine-2-carbaldehyde derivative (8) can be oxidized with an oxidizing agent in a solvent, to produce a pyridine-2-carboxylic acid derivative (9).

The reaction temperature is usually from $-20$ to $200°$ C., and preferably from 0 to $100°$ C., and the reaction time is from 0.5 hours to 3 days. The solvent may be exemplified by an organic acid (for example, formic acid, acetic acid), an alcohol solvent, an ether solvent, a halogen solvent, an aromatic solvent, a nitrile solvent, an amide solvent, a ketone solvent, a sulfoxide solvent, or water, and a mixture of two or more of these may also be used. Among these, formic acid, methylene chloride, chloroform, methanol, ethanol and the like are preferred.

Examples of the oxidizing agent include hydrogen peroxide, organic peracid compounds (for example, performic acid, peracetic acid, meta-chloroperbenzoic acid), metaperiodate (for example, sodium metaperiodate), acyl nitrate, dinitrogen tetraoxide, halogens, N-halogen compounds (for example, N-chlorosuccinimide, N-bromosuccinimide), hydroperoxides (for example, t-butyl hydroperoxide), iodobenzene diacetate, iodobenzene dichloride, t-butyl hypochlorite, sulfuryl chloride, singlet oxygen, ozone, selenium oxide, selenic acid, and the like.

To mention specific examples of the reaction conditions, one to two equivalent amount of hydrogen peroxide is added to the pyridine-2-carbaldehyde derivative (8) in a formic acid solvent, and the mixture can be treated at room temperature for about 1 hour to 2 days, thus to produce the pyridine-2-carboxylic acid derivative (9).

5) Method for Producing Pyridine-2-Carboxamide Derivatives (1aN) and (1cN)

With regard to the pyridine derivatives in the present invention, a pyridine-2-carboxamide derivative (1aN) or (1cN) can be produced by combining a pyridine-2-carboxylic acid derivative (7) or (9), a primary or secondary amine ($HNR_1R_2$) or a salt thereof, and a condensing agent in a solvent as follows.

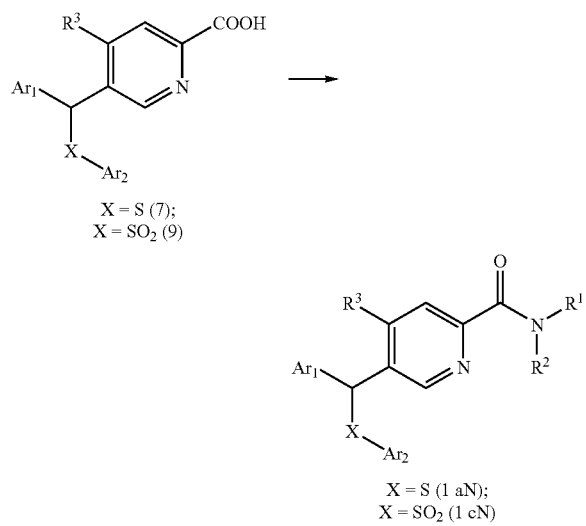

wherein $Ar_1$, $Ar_2$, $R^1$, $R^2$ and $R^3$ are the same as described above.

The reaction temperature is usually from −20 to 200° C., and preferably from 0 to 50° C. The reaction time is usually from 0.5 hours to 3 days. The solvent may be exemplified by ether solvents, halogenated solvents, aromatic solvents, alcohol solvents, nitrile solvents, amide solvents, ketone solvents, sulfoxide solvents, or water, and a mixture of two or more of these may also be used. Among these, tetrahydrofuran, methylene chloride, chloroform and the like are preferred.

As the condensing agent, 1,3-dicyclohexylcarbodiimide, 1-ethyl-3-(3'-dimethylaminopropyl)carbodiimide, (benzotriazol-1-yloxy)tripyrrolidinophosphonium hexafluorophosphate and the like may be mentioned, and a tertiary amine such as 1-hydroxybenzotriazole and/or N-ethyldiisopropylamine may also be added thereto.

In another method, the pyridine-2-carboxamide derivative (1aN) or (1cN) can also be produced by converting the pyridine-2-carboxylic acid derivative (7) or (9) to an acid chloride, and then adding a primary or secondary amine thereto in a solvent.

To mention a specific example of the reaction, thionyl chloride is added in excess to the pyridine-2-carboxylic acid derivative (7) or (9) at room temperature. It is preferable that a very small amount of dimethylformamide is co-present, and in the case of using a solvent, methylene chloride, chloroform or the like is preferably used. By concentrating this mixture, subsequently diluting with a solvent, and adding an equivalent to excess amount of amine, the pyridine-2-carboxamide derivative (1aN) or (1cN) can be produced. The solvent is preferably tetrahydrofuran, methylene chloride, chloroform, dimethylformamide or the like, and at this time, a tertiary amine such as triethylamine, or an aromatic amine such as pyridine may be present as a base.

In addition, the amine ($HNR^1R^2$) used in the production process described above may be a known compound, or can be produced by a combination of methods that are well known to those ordinarily skilled in the art.

6) Method for Producing Pyridine-2-Carboxylate Derivative (1aO) or (1cO)

With regard to the pyridine derivatives in the present invention, a pyridine-2-carboxylate derivative (1aO) or (1cO) can be produced by combining the pyridine-2-carboxylic acid derivative (7) or (9), an alcohol and a condensing agent in a solvent.

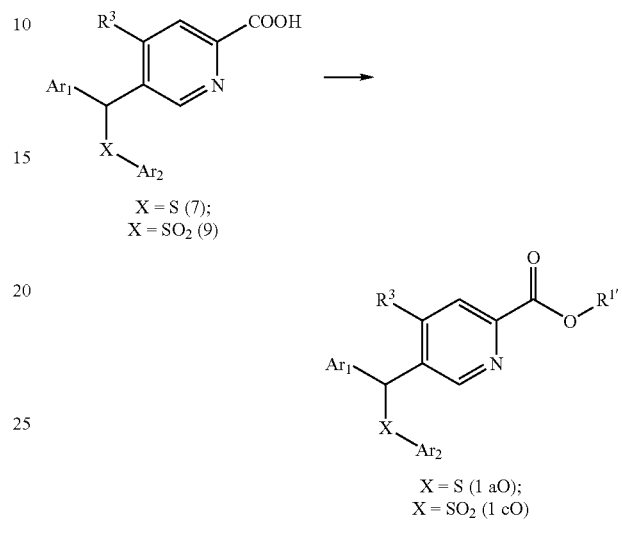

wherein $Ar_1$, $Ar_2$, $R^{1'}$ and $R^3$ are the same as described above.

The reaction temperature is usually from −20 to 200° C., and preferably from 0 to 50° C., and the reaction time is usually from 0.5 hours to 3 days. The solvent may be exemplified by an ether solvent, a halogen solvent, an aromatic solvent, a nitrile solvent, an amide solvent, a ketone solvent, or a sulfoxide solvent, and a mixture of two or more of these can also be used. Among these, toluene, tetrahydrofuran, methylene chloride and the like are preferred.

As the condensing agent, 1,3-dicyclohexylcarbodiimide, 1-ethyl-3-(3'-dimethylaminopropyl)carbodiimide and the like may be mentioned, and 0.1 to 2 equivalent amount of an amine such as 4-dimethylaminopyridine may be co-present.

In another method, the pyridine-2-carboxylate derivative (1aO) or (1cO) can also be produced by converting the pyridine-2-carboxylic acid derivative (7) or (9) to an acid chloride, and then adding an alcohol in a solvent in the co-presence of a base.

To mention a specific example of the reaction, thionyl chloride is added in excess to the pyridine-2-carboxylic acid derivative (7) or (9) at room temperature. It is preferable that a very small amount of dimethylformamide is co-present, and in the case of using a solvent, methylene chloride, chloroform or the like is preferably used. By concentrating this mixture, subsequently diluting with a solvent, and adding an equivalent to excess amount of alcohol and a base, the pyridine-2-carboxylate derivative (1aO) or (1cO) can be produced The solvent is preferably tetrahydrofuran, methylene chloride, chloroform, dimethylformamide or the like, and at this time, a tertiary amine or an aromatic amine, such as triethylamine or pyridine, may be present as a base.

In addition, the alcohol ($HOR^{1'}$) used in the production process described above may be a known compound, or can be produced by a combination of methods that are well known to those ordinarily skilled in the art.

7) Method for Producing Pyridine Derivative (1b) or (1c)

With regard to the pyridine derivatives in the present invention, the sulfinyl compound (1b) or the sulfonyl compound (1c) can be produced by oxidizing a sulfide compound (1a) with an oxidizing agent in a solvent as follows.

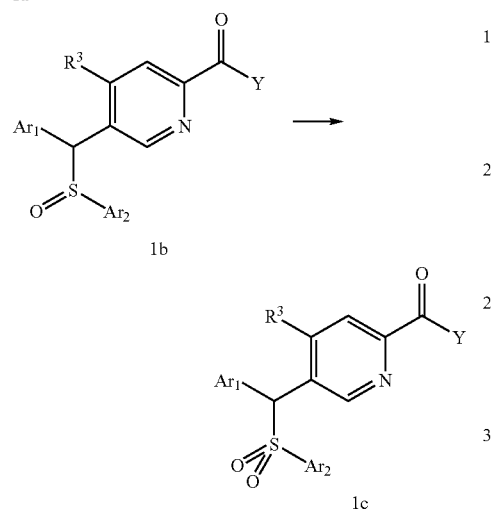

wherein $Ar_1$, $Ar_2$, $R^3$ and Y are the same as described above.

The reaction temperature is usually from −20 to 150° C., and preferably from 0 to 50° C., and the reaction time is usually from 0.5 hours to 3 days.

The solvent may be exemplified by an alcohol solvent, an ether solvent, a halogen solvent, an aromatic solvent, a carboxylic acid solvent, a nitrile solvent, an amide solvent, a ketone solvent, a sulfoxide solvent, or water, and a mixture of two or more of these can also be used. Among these, methylene chloride, chloroform, methanol, ethanol, acetic acid and the like are preferred.

As the oxidizing agent, hydrogen peroxide, organic peracid compounds (for example, peracetic acid, meta-chloroperbenzoic acid), metaperiodates (for example, sodium metaperiodate), acyl nitrate, dinitrogen tetraoxide, halogens, N-halogen compounds (for example, N-chlorosuccinimide, N-bromosuccinimide), hydroperoxides (for example, t-butyl hydroperoxide), iodobenzene diacetate, iodobenzene dichloride, t-butyl hypochlorite, sulfuryl chloride, singlet oxygen, ozone, selenium oxide, selenic acid, and the like, may be mentioned.

To mention a specific example of the reaction, the sulfinyl compound (1b) can be produced by adding a sulfide compound (1a) and 1 to 2 equivalent amount of meta-chloroperbenzoic acid or sodium periodate in a solvent such as methylene chloride, tetrahydrofuran-water or methanol, and treating the mixture at 0 to 100° C. for about 1 hour to 2 days. Alternatively, the sulfonyl compound (1c) can be produced by reacting the sulfide compound (1a) with 2 to 5 equivalent amount of an oxidizing agent (for example, meta-chloroperbenzoic acid, sodium periodate, hydrogen peroxide, hydrogen peroxide-ammonium molybdate, etc.) in methylene chloride, tetrahydrofuran-water, formic acid or methanol at 0 to 100° C. for about 1 hour to 3 days.

Furthermore, in the case of producing an optically active sulfoxide (1b), titanium tetraisopropoxide/optically pure diethyl tartrate/t-butyl hydroperoxide, titanium tetraisopropoxide/optically pure diethyl tartrate/peracetic acid, or the like may be used as the oxidizing agent.

With regard to the compound (1) of the present invention, in the case where Z is a sulfur atom, the pyridine derivative of the present invention can be produced by the following method.

8) Method for Producing Pyridyl-2-Thioamide Derivative $(1:Y=NR^1R^2, Z=S)$ or Pyridyl-2-Thiocarboxylate Derivative $(1:Y=OR^{1'}, Z=S)$

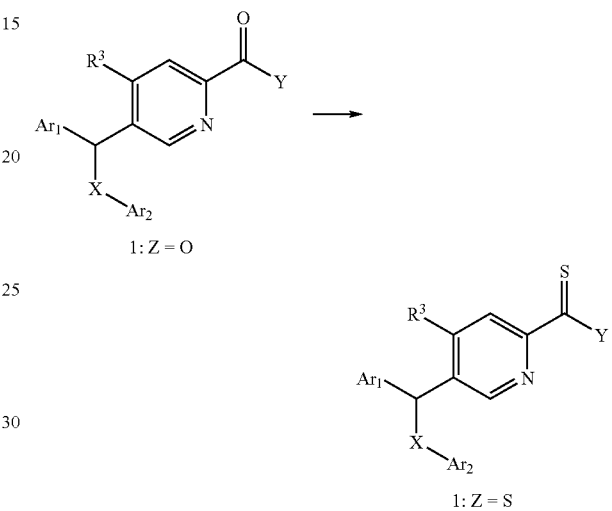

wherein $Ar_1$, $Ar_2$, $R^3$, X and Y are the same as described above.

A pyridyl-2-carboxamide derivative $(1:Y=NR^1R^2, Z=O)$ or a pyridyl-2-carboxylate derivative $(1:Y=OR^1, Z=O)$ can be converted to a pyridyl-2-thioamide derivative $(1:Y=NR^1R^2, Z=S)$ or a pyridyl-2-thiocarboxylate derivative $(1:Y=OR^{1'}, Z=S)$ by known methods. For instance, 1 to 5 equivalent amount of Lawesson's Reagent (2,4-bis(4-methoxyphenyl)-1,3-dithia-2,4-diphosphetane-2,4-disulfide) may be added to the pyridyl-2-carboxamide derivative $(1:Y=NR^1R^2, Z=O)$ or the pyridyl-2-carboxylate derivative $(1:Y=OR^{1'}, Z=O)$ in a solvent. As the solvent, toluene, xylene, tetrahydrofuran, dioxane, methylene chloride and the like are preferred. The reaction temperature is from 0° C. to 200° C., and preferably from room temperature to 130° C., and the reaction time is usually from 0.5 hours to 3 days.

With regard to the methods for producing the pyridine derivatives (1) of the compound of the present invention illustrated in the above, it may be sometimes necessary to protect such substituent as a nitrogen atom, a hydroxy group or a carboxyl group, and in that case, a commonly known protective group which can be appropriately removed may be used. Such protective group can be removed, when necessary, by a general method that is known in the field of organic synthetic chemistry.

Furthermore, with regard to Y ($—NR^1R^2$) of the pyridine derivative (1) of the compound of the present invention, in the case where the group for $R^1$ and/or $R^2$ is a hydrogen atom, further structural modification is possible. For instance, in the case of carboxamide (R1, R2=H), this can be converted to N-(hydroxymethyl) carboxamide (R1=H, R2=CH2OH) by reacting with an aqueous solution of formaldehyde and aqueous sodium hydroxide in ethylene glycol dimethyl ether.

Also, in the case of having one or plural functional groups among the groups for $R^1$ and/or $R^2$, further structural modification is also possible. For example, a compound having a hydroxy group among the groups for $R^1$ and/or $R^2$ can be converted to a group such as ester, carbamate or halogen, by known methods. Furthermore, such group can be converted to a group such as alkoxy, amine, amide or sulfide. Such conversion is also possible for various functional groups other than a hydroxy group, and the conversion can be performed using known techniques. The reagents, solvents and reaction conditions used in these conversion processes may be those well known to those ordinarily skilled in the art.

The compound represented by general formula (1) of the present invention strongly inhibited production/secretion of a β-amyloid protein in vitro. Furthermore, the compound represented by general formula (1) of the present invention also strongly inhibited production/secretion of β-amyloid protein in vivo by oral administration. From these results, it is believed that the compound represented by general formula (1) of the present invention is extremely useful as a prophylactic and therapeutic drug for diseases caused by abnormal production/secretion of β-amyloid protein, for example, Alzheimer's disease, Down syndrome and other diseases associated with amyloid deposition.

In particular, a compound represented by the following formula (1-1), wherein for the general formula (1), $Ar_1$ is a 2,5-difluorophenyl group, $Ar_2$ is a 4-fluorophenyl group, X is —SO—, Y is a dimethylamino group, Z is an oxygen atom, and $R^3$ is a methyl group:

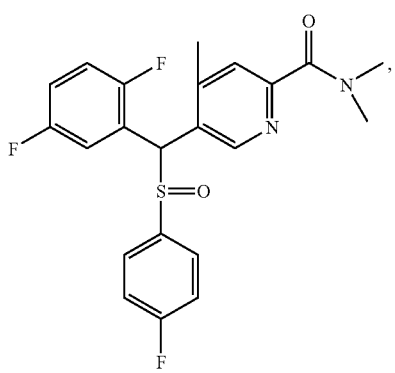

(1-1)

namely, 5-[(2,5-difluoro phenyl)[(4-fluorophenyl)sulfinyl]methyl]-N,N,4-trimethylpyridine-2-carboxamide, was recognized to have a sufficient difference between the dose for exhibiting an effect by oral administration and the dose for inducing an immunosuppressive action by repeated administration, and was considered to be a compound having excellent quality as a pharmaceutical product.

Also, the similar effect as that of the compound (1-1) was observed by oral administration of the following compounds (1-2), (1-3), (1-4), (1-5), which were considered to have high quality as pharmaceutical products:

a compound represented by the following formula (I-2), wherein for the general formula (1), $Ar_1$ is a 2,5-difluorophenyl group, $Ar_2$ is a 4-fluorophenyl group, X is —SO$_2$—, Y is a (hydroxymethyl)amino group, Z is an oxygen atom, and $R^3$ is a methyl group:

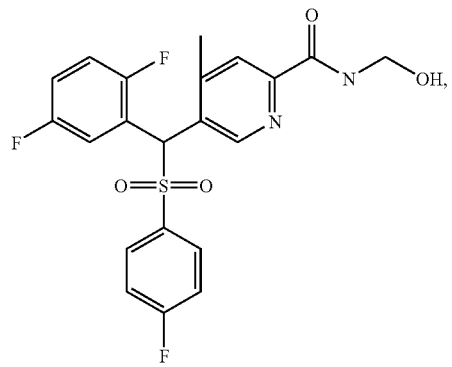

(1-2)

namely, 5-[(2,5-difluorophenyl) [(4-fluorophenyl)sulfonyl]methyl]-N-(1-hydroxymethyl)-4-methylpyridine-2-carboxamide;

a compound represented by the following formula (I-3), wherein for the general formula (1), $Ar_1$ is a 2,3,6-trifluorophenyl group, $Ar_2$ is a 4-fluorophenyl group, X is —SO$_2$—, Y is a (hydroxymethyl)amino group, Z is an oxygen atom, and $R^3$ is a methyl group:

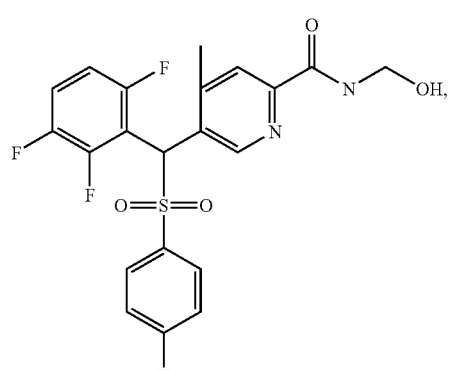

(1-3)

namely, 5-[[(fluorophenyl)sulfonyl](2,3,6-trifluorophenyl)methyl]-N-(1-hydroxymethyl)-4-methylpyridine-2-carboxamide;

a compound represented by the following formula (I-4), wherein for the general formula (1), $Ar_1$ is a 2,3,6-trifluorophenyl group, $Ar_2$ is a phenyl group, X is —SO$_2$—, Y is a (hydroxymethyl)amino group, Z is an oxygen atom, and $R^3$ is a methyl group:

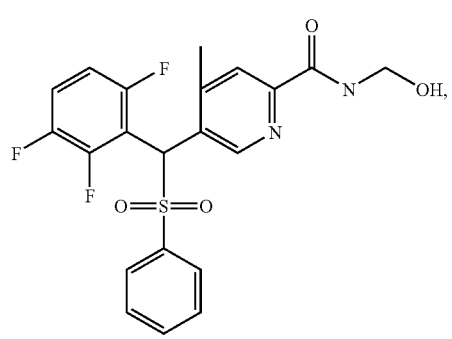

(1-4)

namely, N-(1-hydroxymethyl)-4-methyl-5-[(phenylsulfonyl)(2,3,6-trifluorophenyl) methyl]pyridine-2-carboxamide; and a compound represented by the following formula (1-5), wherein for the general formula (1), $Ar_1$ is a 2,3,6-trifluorophenyl group, $Ar_2$ is a 6-(trifluoromethyl)pyridin-3-yl group, X is —$SO_2$—, Y is a (hydroxymethyl)amino group, Z is an oxygen atom, and $R^3$ is a methyl group:

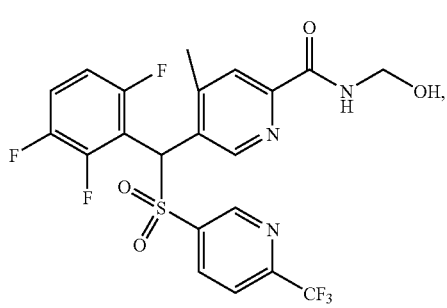

(1-5)

namely, N-(hydroxymethyl)-4-methyl-5-[[[6-(trifluoromethyl)pyridin-3-yl]sulfonyl](2,3,6-trifluorophenyl)methyl]pyridine-2-carboxamide.

In the case of using the compound of the present invention as a medicament for human, the dosage for an adult is in the range of 1 mg to 1 g, preferably 10 mg to 300 mg, per day. Furthermore, the dosage for animal use may vary with the purpose of administration (treatment or prevention), the type or size of the animal to be treated, the type of the infected pathogen, or the severity of condition, but the daily dosage is generally in the range of 0.1 mg to 200 mg, preferably 0.5 mg to 100 mg, per kg of the body weight of the animal. This daily dosage is administered once a day, or in 2 to 4 divided times. Also, the daily dosage may exceed the aforementioned amounts, if necessary.

A pharmaceutical composition containing the compound of the present invention can be prepared by selecting an appropriate formulation in accordance with the method of administration, and using preparative methods for various formulations that are commonly used. As the dosage form for the pharmaceutical composition containing the compound of the present invention as the main agent, for example, tablets, powders, granules, capsules, liquids, syrups, elixirs, oily or aqueous suspensions and the like may be mentioned as oral formulations.

For an injectable preparation, stabilizers, preservatives or dissolution aids may be optionally used in the formulation, and a solution which may contain these adjuvants may be inserted into a container, and then subjected to freeze-drying or the like so as to be formed into a solid formulation, which will be used as a "prepared-on-use" formulation. A single dose may be contained in one container, or multiple doses may be contained in one container.

As external formulations, liquids, suspensions, emulsions, ointments, gels, creams, lotions, sprays, patches and the like may be mentioned.

Solid formulations can be formulated by combining the compound of the present invention and optionally selected pharmaceutically acceptable additives, such as fillers, bulking agents, binders, disintegrants, dissolution aids, wetting agents, lubricants and the like.

As liquid formulations, solutions, suspensions, emulsions and the like may be mentioned, and they may contain suspending agents, emulsifying agents and the like as additives.

EXAMPLES

Hereinafter, the present invention will be specifically described by way of Examples, but the scope of the invention is not intended to be limited to the Examples as follows. Moreover, in the following Examples, if no information is given about E-isomer or Z-isomer, the obtained compound is either an E-isomer or a Z-isomer.

Reference Example 1

(6-Bromo-4-methylpyridin-3-yl)(2,5-difluorophenyl)methanol

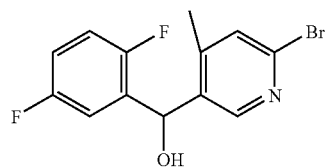

In an argon atmosphere, a hexane solution of n-butyllithium M, 8.22 ml, 13.2 mmol) was added to a solution of 2,5-dibromo-4-methylpyridine (3.00 g, 12.0 mmol) in diethyl ether (120 ml) at −78° C. After stirring the reaction mixture for 30 minutes, 2,5-difluorobenzaldehyde (1.34 ml, 12.0 mmol) was added. After stirring for 1 hour at the same temperature, saturated aqueous ammonium chloride was added at room temperature. After the organic layer was separated, the organic layer was dried over anhydrous sodium sulfate and filtered, and then the filtrate was concentrated under reduced pressure. The resulting residue was subjected to flash silica gel chromatography. The fraction obtained from an elution with hexane:ethyl acetate=4:1 was concentrated under reduced pressure, to obtain the title compound (1.26 g, 4.01 mmol, 34%) as a white solid.

$^1$H-NMR (400 MHz, $CDCl_3$) δ: 2.27 (3H, s), 2.53 (1H, d, J=4.2 Hz), 6.22 (1H, d, J=4.2 Hz), 6.95-7.06 (2H, m), 7.08-7.14 (1H, m), 7.29 (1H, s), 8.36 (1H, s).

MS m/z: 314, 316 ($M^+$+H).

Example 1

2-Bromo-5-[[(4-chlorophenyl)thio](2,5-difluorophenyl)methyl]-4-methylpyridine

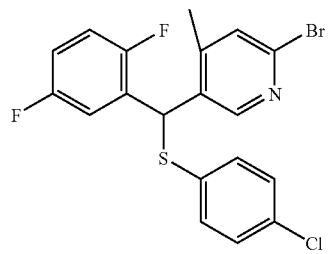

In a nitrogen atmosphere, thionyl chloride (2.90 ml, 39.8 mmol) and N,N-dimethylformamide (0.20 ml) were added to a solution of (6-bromo-4-methylpyridin-3-yl)(2,5-difluorophenyl)methanol (1.25 g, 3.98 mmol) in methylene chloride (20 ml) at 0° C., and the resulting mixture was stirred for 30 minutes at room temperature. The reaction mixture was concentrated under reduced pressure, and methylene chloride was added to the residue. The mixture was washed with saturated aqueous sodium hydrogencarbonate and then with saturated brine, and the organic layer was dried over anhydrous sodium sulfate and filtered. The filtrate was concentrated under reduced pressure.

To a solution of the resulting residue in N,N-dimethylformamide (45 ml), a solution of 4-chlorobenzenethiol (575 mg, 3.98 mmol) in N,N-dimethylformamide (5 ml), and then potassium carbonate (550 mg, 3.98 mmol) were added in a nitrogen atmosphere at 0° C., and the resulting mixture was stirred for 30 minutes at room temperature. Ethyl acetate and water were added to the reaction mixture at 0° C., the organic layer was separated, and then the organic layer was washed with saturated brine. The organic layer was dried over anhydrous sodium sulfate and filtered, the filtrate was concentrated under reduced pressure, and the resulting residue was subjected to flash silica gel chromatography. The fraction obtained from an elution with hexane:ethyl acetate=20:1 was concentrated under reduced pressure to obtain the title compound (1.48 g, 3.36 mmol, 84%) as a white solid.

$^1$H-NMR (400 MHz, CDCl$_3$) δ: 2.31 (3H, s), 5.77 (1H, s), 6.92-7.03 (2H, m), 7.19-7.25 (4H, m), 7.28-7.34 (1H, m), 7.29 (1H, s), 8.39 (1H, s).

MS m/z: 440, 442 (M$^+$+H).

Example 2

5-[[(4-Chlorophenyl)thio](2,5-difluorophenyl)methyl]-4-methylpyridine-2-carbaldehyde

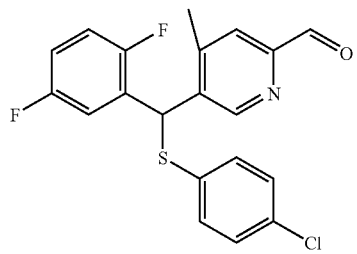

In an argon atmosphere, a hexane solution of n-butyllithium (1.60 M, 2.52 ml, 4.03 mmol) was added to a solution of 2-bromo-5-[[(4-chlorophenyl)thio](2,5-difluorophenyl)methyl]-4-methylpyridine (1.48 g, 3.36 mmol) in toluene (40 ml) at −78° C. The reaction mixture was stirred for 1 hour, and then N,N-dimethylformamide (0.312 ml, 4.03 mmol) was added at the same temperature. After stirring the reaction mixture for 30 minutes, water was added thereto at the same temperature, and the mixture was allowed to warm to room temperature. Ethyl acetate was added to the reaction mixture, and the resulting mixture was washed with saturated aqueous ammonium chloride, and then with saturated brine. The organic layer was dried over anhydrous sodium sulfate and filtered, the filtrate was concentrated under reduced pressure, and the resulting residue was subjected to flash silica gel chromatography. The fraction obtained from an elution with hexane:ethyl acetate=10:1 was concentrated under reduced pressure, to obtain the title compound mg, 1.07 mmol, 32%) as a white solid.

$^1$H-NMR (400 MHz, CDCl$_3$) δ: 2.43 (3H, s), 5.88 (1H, s), 6.94-7.05 (2H, m), 7.20-7.27 (4H, m), 7.36-7.42 (1H, m), 7.75 (1H, s), 8.79 (1H, s) 10.02 (1H, s).

MS m/z: 390 (M$^+$+H).

Example 3

5-[[(4-Chlorophenyl)sulfonyl](2,5-difluorophenyl)methyl]-4-methylpyridine-2-carboxylic acid

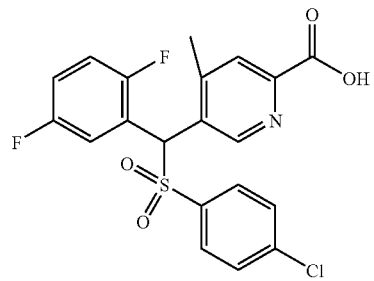

31% aqueous hydrogen peroxide (2 ml) was added to a solution of 5-[[(4-chlorophenyl)thio](2,5-difluorophenyl)methyl]-4-meth ylpyridine-2-carbaldehyde (415 mg, 1.06 mmol) in formic acid (20 ml), and the resulting mixture was stirred for 2 hours at room temperature. Water was added to the reaction mixture, and the solid thus precipitated was collected by filtration and washed with water. The obtained solid was dissolved in methylene chloride, and washed with 1 N hydrochloric acid. The organic layer was dried over anhydrous sodium sulfate and filtered, and the filtrate was concentrated under reduced pressure. The resulting residue was washed with diethyl ether, and collected by filtration to obtain the title compound (347 mg, 0.79 mmol, 74%) as a white solid.

$^1$H-NMR (400 MHz, CDCl$_3$) δ: 2.31 (3H, s), 5.98 (1H, s), 6.93-7.01 (1H, m), 7.03-7.10 (1H, m), 7.44-7.48 (2H, m), 7.61-7.65 (2H, m), 7.72-7.78 (1H, m), 8.03 (1H, s), 9.22 (1H, s).

IR(ATR)cm$^{-1}$: 1739, 1712, 1495, 1417, 1311, 1155, 1092, 727.

mp: 208-209° C.

Anal. Calcd for C$_{20}$H$_{14}$ClF$_2$NO$_4$S: C, 54.86; H, 3.22; Cl, 8.10; F, 8.68; N, 3.20; S, 7.32. Found: C, 54.55; H, 3.15; Cl, 8.02; F, 8.60; N, 3.25; S, 7.44.

MS m/z: 438 (M$^+$+H).

Example 4

5-[[(4-Chlorophenyl)sulfonyl](2,5-difluorophenyl)methyl]-N,4-dimethylpyridine-2-carboxamide

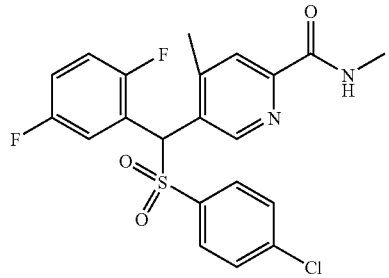

To a solution of 5-[[(4-chlorophenyl)sulfonyl](2,5-difluorophenyl)methyl]-4-methylpyridine-2-carboxylic acid (88 mg, 0.20 mmol) in methylene chloride (2 ml), methylamine hydrochloride (15 mg, 0.22 mmol), 1-hydroxybenzotriazole (30 mg, 0.22 mmol), 4-methylmorpholine (0.048 ml, 0.44 mmol), and 1-ethyl-3-(3-dimethylaminopropyl)carbodiimide hydrochloride (42 mg, 0.22 mmol) were added at room temperature. After stirring for 5 hours at room temperature, the reaction mixture was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=3:1 was concentrated under reduced pressure, and the resulting residue was washed with a mixed solvent of diethyl ether and hexane and then collected by filtration to obtain the title compound (73 mg, 0.16 mmol, 81%) as a white solid.

$^1$H-NMR (400 MHz, CDCl$_3$) δ: 2.21 (3H, s), 3.04 (3H, d, J=5.1 Hz), 5.96 (1H, s) 6.92-7.08 (2H, m), 7.43 (2H, d, J=8.6 Hz), 7.61 (2H, d, J=8.6 Hz) 7.74-7.81 (1H, m), 7.97 (1H, s), 8.00 (1H, br d, J=5.1 Hz), 9.13 (1H, s).

IR(ATR)cm$^{-1}$: 1674, 1533, 1495, 1329, 1151.
mp: 200-201° C.
Anal. Calcd for C$_{21}$H$_{17}$ClF$_2$N$_2$O$_3$S: C, 55.94; H, 3.80; Cl, 7.86; F, 8.43; N, 6.21; S, 7.11. Found: C, 55.70; H, 3.72; Cl, 7.91; F, 8.51; N, 6.17; S, 7.26.
MS m/z: 451 (M$^+$+H).

Example 5

5-[[(4-Chlorophenyl)sulfonyl](2,5-difluorophenyl)methyl]-N,N,4-trimethylpyridine-2-carboxamide

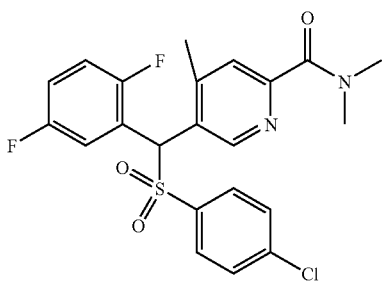

To a solution of 5-[[(4-chlorophenyl)sulfonyl](2,5-difluorophenyl)methyl]-4-methylpyridine-2-carboxylic acid (88 mg, 0.20 mmol) obtained in Example 3 in methylene chloride (2 ml), dimethylamine hydrochloride (18 mg, 0.22 mmol), 1-hydroxybenzotriazole (30 mg, 0.22 mmol), 4-methylmorpholine (0.048 ml, 0.44 mmol), and 1-ethyl-3-(3-dimethylaminopropyl)carbodiimide hydrochloride (42 mg, 0.22 mmol) were added at room temperature. After stirring for 6 hours at room temperature, the reaction mixture was washed with saturated aqueous sodium hydrogencarbonate. The organic layer was dried over anhydrous sodium sulfate and filtered then the filtrate was concentrated under reduced pressure, and the resulting residue was subjected to flash silica gel chromatography. The fraction obtained from an elution with hexane:ethyl acetate=1:1 was concentrated under reduced pressure, and the resulting residue was washed with a mixed solvent of diethyl ether and hexane, and collected by filtration to obtain the title compound (83 mg, 0.18 mmol, 89%) as a white solid.

$^1$H-NMR (400 MHz, CDCl$_3$) δ: 2.24 (3H, s), 3.14 (6H, s), 5.96 (1H, s), 6.91-6.98 (1H, m), 7.00-7.07 (1H, m), 7.44 (2H, d, J=8.6 Hz), 7.47 (1H, s), 7.65 (2H, d, J=8.6 Hz), 7.72-7.78 (1H, m), 9.16 (1H, s).
IR(ATR)cm$^{-1}$: 1633, 1493, 1327, 1151, 1084.
mp: 207-208° C.

Anal. Calcd for C$_{22}$H$_{19}$ClF$_2$N$_2$O$_3$S: C, 56.84; H, 4.12; Cl, 7.63; F, 8.17; N, 6.03; S, 6.90. Found: C, 56.53; H, 4.08; Cl, 7.53; F, 8.25; N, 5.93; S, 7.00.
MS m/z: 465 (M$^+$+H).

Example 6

5-[[(4-Chlorophenyl)thio](2,5-difluorophenyl)methyl]-4-meth ylpyridine-2-carboxylic acid

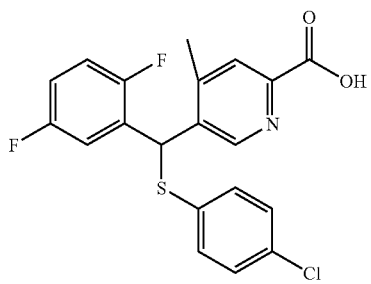

To a solution of 2-bromo-5-[[(4-chlorophenyl)thio](2,5-difluorophenyl)methyl]-4-methylpyridine (5.04 g, 11.4 mmol) obtained in Example 1 in toluene (100 ml), a hexane solution of n-butyllithium (1.54 M, 8.91 ml, 13.7 mmol) was added in an argon atmosphere at −78° C. The reaction mixture was stirred for 30 minutes at −40° C., and then cooled again to −78° C., and carbon dioxide was bubbled therein The reaction mixture was stirred for 30 minutes and then allowed to warm to room temperature, and saturated aqueous ammonium chloride was added thereto. The reaction mixture was concentrated under reduced pressure, then chloroform was added to the residue, and the mixture was washed with 1 N hydrochloric acid. The organic layer was dried over anhydrous sodium sulfate and filtered, the filtrate was concentrated under reduced pressure, and the resulting residue was subjected to flash silica gel chromatography. The fraction obtained from an elution with methylene chloride:methanol=10:1 was concentrated under reduced pressure, and the resulting residue was washed with a mixed solvent of ethanol and diethyl ether and collected by filtration to obtain the title compound (2.06 g, 5.08 mmol, 44%) as a white solid.

$^1$H-NMR (400 MHz, CDCl$_3$) δ: 2.46 (3H, s), 5.88 (1H, s), 6.95-7.05 (2H, m), 7.24 (4H, s), 7.36-7.42 (1H, m), 8.02 (1H, s), 8.61 (1H, s).
MS m/z: 406 (M$^+$+H).

Example 7

5-[[(4-Chlorophenyl)thio](2,5-difluorophenyl)methyl]-4-methylpyridine-2-carboxamide

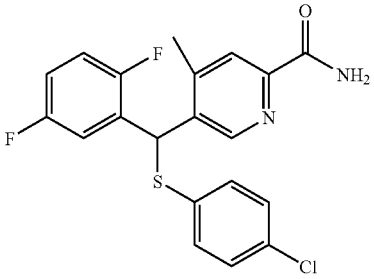

To a solution of 5-[[(4-chlorophenyl)thio](2,5-difluorophenyl)methyl]-4-meth ylpyridine-2-carboxylic acid (406 mg, 1.00 mmol) in N,N-dimethylformamide (10 ml), (benzotriazol-1-yloxy)tripyrrolidinophosphonium hexafluorophosphate (781 mg, 1.50 mmol), 1-hydroxybenzotriazole (203 mg, 1.50 mmol), ammonium chloride (107 mg, 2.00 mmol), and N-ethyldiisopropylamine (0.697 ml, 4.00 mmol) were added in an argon atmosphere at room temperature. After stirring for 12 hours at room temperature, ethyl acetate was added to the reaction mixture, and the mixture was washed with 0.5 N hydrochloric acid. The organic layer was dried over anhydrous sodium sulfate and filtered, the filtrate was concentrated under reduced pressure, and the resulting residue was subjected to flash silica gel chromatography. The fraction obtained from an elution with hexane:ethyl acetate=2:1 was concentrated under reduced pressure, to obtain the title compound (398 mg, 0.98 mmol, 98%) as a white solid.

$^1$H-NMR (400 MHz, CDCl$_3$) δ: 2.42 (3H, s), 5.55 (1H, br s), 5.88 (1H, s), 6.93-7.04 (2H, m) 7.22 (4H, s), 7.35-7.41 (1H, m), 7.77 (1H, br s), 8.00 (1H, s), 8.58 (1H, s).

MS m/z: 405 (M$^+$+H).

Example 8

5-[[(4-Chlorophenyl)sulfinyl](2,5-difluorophenyl)methyl]-4-methylpyridine-2-carboxamide

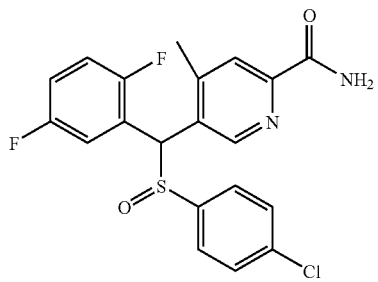

3-Chloroperbenzoic acid (259 mg, 0.98 mmol) was added to a solution of 5-[[(4-chlorophenyl)thio](2,5-difluorophenyl)methyl]-4-methylpyridine-2-carboxamide (395 mg, 0.98 mmol) in methylene chloride (10 ml) at 0° C. After stirring for 14 days at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure, and the resulting residue was washed with a mixed solvent of ethanol and diethyl ether, and collected by filtration, thus to obtain the title compound (243 mg, 0.58 mmol, 59%) as a white solid.

$^1$H-NMR (400 MHz, CDCl$_3$) δ: 1.95 (2.1H, s), 2.15 (0.9H, s), 5.35 (0.3H, s), 5.37 (0.7H, s), 5.51-5.62 (1H, m), 6.88-7.08 (2H, m), 7.23-7.55 (5H, m), 7.80-7.90 (1H, m), 7.94 (0.7H, s), 7.99 (0.3H, s), 8.87 (0.7H, m), 9.05 (0.3H, s).

IR(ATR)cm$^{-1}$: 3126, 1695, 1595, 1493, 1421, 1053, 823.

Anal. Calcd for C$_{20}$H$_{15}$ClF$_2$N$_2$O$_2$S: C, 57.08; H, 3.59; Cl, 8.42; F, 9.03; N, 6.66; S, 7.62. Found: C, 56.75; H, 3.59; Cl, 8.35; F, 9.06; N, 6.65; S, 7.71.

MS m/z: 421 (M$^+$+H).

Example 9

5-[[(4-Chlorophenyl)sulfonyl](2,5-difluorophenyl)methyl]-4-methylpyridine-2-carboxamide

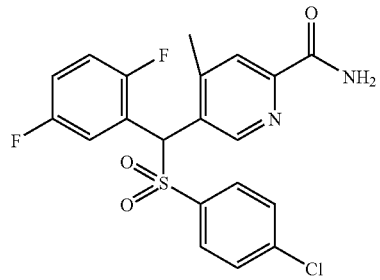

3-Chloroperbenzoic acid (66 mg, 0.25 mmol) was added to a solution of 5-[[(4-chlorophenyl)sulfinyl](2,5-difluorophenyl)methyl]-4-methylpyridine-2-carboxamide (105 mg, 0.25 mmol) in methylene chloride (5 ml) at 0° C. After stirring for 5 days at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to preparative thin-layer chromatography (developed with methylene chloride:methanol=40:1, and eluted with methylene chloride:methanol=4:1). The obtained fraction was concentrated under reduced pressure, and the resulting residue was washed with a mixed solvent of ethanol and diethyl ether and collected by filtration, thus to obtain the title compound (56 mg, 0.13 mmol, 51%) as a white solid.

$^1$H-NMR (400 MHz, CDCl$_3$) δ: 2.23 (3H, s), 5.57 (1H, br s), 5.97 (1H, s), 6.92-7.00 (1H, m) 7.01-7.09 (1H, m), 7.44 (2H, d, J=8.5 Hz), 7.62 (2H, d, J=8.5 Hz) 7.75-7.81 (1H, m), 7.82 (1H, brs), 7.99 (1H, s), 9.16 (1H, s).

IR(ATR)cm$^{-1}$: 3442, 3288, 1701, 1493, 1315, 1153, 1088.

mp: 241-242° C.

MS m/z: 437 (M$^+$+H).

Reference Example 2

2-Bromo-5-[chloro(2,5-difluorophenyl)methyl]-4-methylpyridine

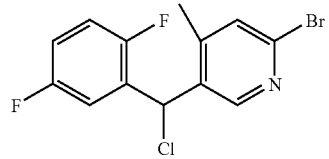

To a solution of (6-bromo-4-methylpyridin-3-yl)(2,5-difluorophenyl)methanol (9.42 g, 30.0 mmol) obtained in Reference Example 1 in methylene chloride (150 ml), thionyl chloride (21.9 ml, 300 mmol) and N,N-dimethylformamide (0.232 ml) were added at 0° C., and the mixture was stirred for 2 hours at room temperature. The reaction mixture was concentrated under reduced pressure, ethyl acetate was added to the residue, and the mixture was washed with saturated aqueous sodium hydrogencarbonate. The organic layer was dried over anhydrous sodium sulfate, and filtered, and the filtrate was concentrated under reduced pressure to obtain the title compound (9.82 g, 29.5 mmol, 98%) as a brown solid.

¹H-NMR (400 MHz, CDCl₃) δ: 2.36 (3H, s), 6.42 (1H, s), 7.01-7.07 (2H, m), 7.26-7.32 (1H, m), 7.33 (1H, s), 8.31 (1H, s).

MS m/z: 332, 334 (M⁺+H).

Example 10

2-Bromo-5-[(2,5-difluorophenyl)[(4-fluorophenyl)thio]methyl]-4-methylpyridine

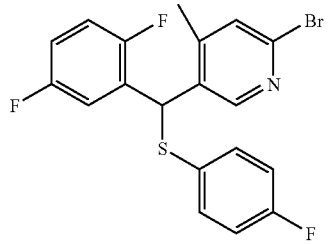

To a solution of 2-bromo-5-[chloro(2,5-difluorophenyl)methyl]-4-methylpyridine (6.44 g, 19.4 mmol) in N,N-dimethylformamide (100 ml), 4-fluorobenzenethiol (2.06 ml, 19.4 mmol), and then potassium carbonate (2.94 g, 21.3 mmol) were added in an argon atmosphere, at 0° C., and the mixture was stirred for 1 hour at room temperature. Ethyl acetate and water were added to the reaction mixture, the organic layer was separated, and then the organic layer was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elution of hexane:ethyl acetate=30:1 was concentrated under reduced pressure, to obtain the title compound (8.20 g, 19.3 mmol, 100%) as a pale brown solid.

¹H-NMR (400 MHz, CDCl₃) δ: 2.28 (3H, s), 0.72 (1H, s), 6.91-6.98 (4H, m), 7.27-7.34 (3H, m), 7.28 (1H, s), 8.43 (1H, s).

MS m/z: 424, 426 (M⁺+H).

Example 11

5-[(2,5-difluorophenyl)[(4-fluorophenyl)thio]methyl]-4-methylpyridine-2-carbaldehyde

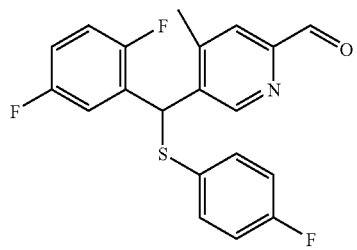

In an argon atmosphere, a hexane solution of n-butyllithium M, 22.3 ml, 34.4 mmol) was added to a solution of 2-bromo-5-[(2,5-difluorophenyl)[(4-fluorophenyl)thio]methyl]-4-methylpyridine (8.10 g, 19.1 mmol) in toluene (200 ml) at −78° C. The reaction mixture was stirred for 30 minutes, and then N,N-dimethylformamide (1.63 ml, 21.0 mmol) was added at the same temperature. The reaction mixture was stirred for 30 minutes, then water was added at the same temperature, and the mixture was allowed to warm to room temperature. Ethyl acetate was added to the reaction mixture, and the resulting mixture was washed with saturated aqueous ammonium chloride, and then with saturated brine. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=10:1 was concentrated under reduced pressure, and the resulting residue was washed with a mixed solvent of diethyl ether and hexane and then collected by filtration, thus to obtain the title compound (4.27 g, 11.4 mmol, 60%) as a white solid.

¹H-NMR (400 MHz, CDCl₃) δ: 2.39 (3H, s), 5.83 (1H, s), 6.92-7.00 (4H, m), 7.30-7.36 (2H, m), 7.37-7.43 (1H, m), 7.73 (1H, s), 8.83 (1H, s), 10.03 (1H, s).

MS m/z: 374 (M⁺+H).

Example 12

5-[(2,5-difluorophenyl)[(4-fluorophenyl)sulfonyl]methyl]-4-methylpyridine-2-carboxylic acid

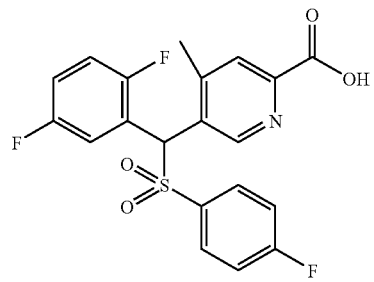

31% aqueous hydrogen peroxide (10 ml) was added to a solution of 5-[(2,5-difluorophenyl) [(4-fluorophenyl)thio]methyl]-4-meth ylpyridine-2-carbaldehyde (4.22 g, 11.3 mmol) in formic acid (100 ml), and the resulting mixture was stirred for 3 hours at room temperature. Water was added to the reaction mixture, the solid thus precipitated was collected by filtration and washed with 0.1N hydrochloric acid. The resulting solid was dissolved in methylene chloride, and the solution was washed with 0.1 N hydrochloric acid. Then, the organic layer was dried over anhydrous sodium sulfate and filtered, and then the filtrated was concentrated under reduced pressure. The resulting residue was washed with a mixed solvent of ethanol and hexane, and was collected by filtration to obtain the title compound (4.34 g, 10.3 mmol, 91%) as a white solid.

¹H-NMR (400 MHz, CDCl₃) δ: 2.30 (3H, s), 5.97 (1H, s), 6.91-6.99 (1H, m), 7.03-7.10 (1H, m), 7.16 (2H, t, J=8.4 Hz), 7.68-7.78 (3H, m) 8.02 (1H, s), 9.23 (1H, s).

IR(ATR)cm⁻¹: 3361, 1763, 1593, 1493, 1402, 1288, 1236, 1149.

Anal. Calcd for $C_{20}H_{14}F_3NO_4S$: C, 57.01; H, 3.35; F, 13.53; N, 3.32; S, 7.61. Found: C, 56.87; H, 3.23; F, 13.54; N, 3.39; S, 7.86.

MS m/z: 422 (M⁺+H).

Example 13

5-[(2,5-difluorophenyl)[(4-fluorophenyl)sulfonyl]methyl]-N,4-dimethylpyridine-2-carboxamide

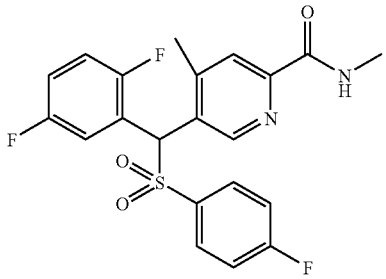

To a solution of 5-[(2,5-difluorophenyl)[(4-fluorophenyl)sulfonyl]methyl]-4-methylpyridine-2-carboxylic acid (105 mg, 0.25 mmol) in methylene chloride (3 ml), methylamine hydrochloride (19 mg, 0.28 mmol), 1-hydroxybenzotriazole (37 mg, 0.28 mmol), 4-methylmorpholine (0.061 ml, 0.55 mmol), and 1-ethyl-3-(3-dimethylaminopropyl)carbodiimide hydrochloride (53 mg, 0.28 mmol) were added at room temperature. After stirring for 2 hours at room temperature, water was added to the reaction mixture, and the mixture was washed with saturated aqueous sodium hydrogencarbonate. The organic layer dried over anhydrous sodium sulfate and filtered, then the filtrate was concentrated under reduced pressure, and the resulting residue was subjected to flash silica gel chromatography. The fraction obtained from an elution with hexane:ethyl acetate=7:3 was concentrated under reduced pressure, and the resulting residue was washed with a mixed solvent of ethanol and hexane and then collected by filtration, to obtain the title compound (73 mg, 0.17 mmol, 67%) as a white solid.

$^1$H-NMR (400 MHz, CDCl$_3$) δ: 2.20 (3H, s), 3.04 (3H, d, J=5.1 Hz), 5.95 (1H, s), 6.92-6.99 (1H, m), 7.01-7.08 (1H, m), 7.10-7.17 (2H, m), 7.66-7.72 (2H, m), 7.75-7.80 (1H, m), 7.96 (1H, s), 8.01 (1H, br d, J=5.1 Hz), 9.14 (1H, s).

IR(ATR)cm$^{-1}$: 1672, 1591, 1533, 1493, 1327, 1294, 1236, 1146, 1082.

mp: 201-202° C.

Anal. Calcd for C$_{21}$H$_{17}$F$_3$N$_2$O$_3$S: C, 58.06; H, 3.94; F, 13.12; N, 6.45; S, 7.38. Found: C, 58.05; H, 3.83; F, 13.05; N, 6.47; S, 7.51.

MS m/z: 435 (M$^+$+H).

Example 14

5-[(2,5-Difluorophenyl)[(4-fluorophenyl)sulfonyl]methyl]-N,N,4-trimethylpyridine-2-carboxamide

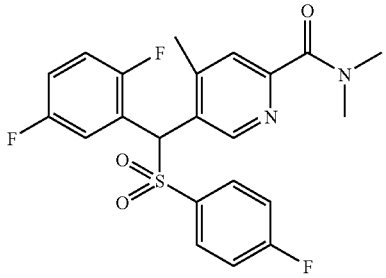

To a solution of 5-[(2,5-difluorophenyl)[(4-fluorophenyl)sulfonyl]methyl]-4-methylpyridine-2-carboxylic acid (105 mg, 0.25 mmol) obtained in Example 12 in methylene chloride (3 ml), dimethylamine hydrochloride (23 mg, 0.28 mmol), 1-hydroxybenzotriazole (37 mg, 0.28 mmol), 4-methylmorpholine (0.061 ml, 0.55 mmol), and 1-ethyl-3-(3-dimethylaminopropyl)carbodiimide hydrochloride (53 mg, 0.28 mmol) were added at room temperature. After stirring for 3 hours at room temperature, water was added to the reaction mixture, and the mixture was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elusion with hexane:ethyl acetate=3:2 was concentrated under reduced pressure, and the resulting residue was washed with a mixed solvent of ethanol and hexane, and was collected by filtration, to obtain the title compound (77 mg, 0.17 mmol, 69%) as a white solid.

$^1$H-NMR (400 MHz, CDCl$_3$) δ: 2.23 (3H, s), 3.14 (6H, s), 5.95 (1H, s), 6.90-6.97 (1H, m), 7.00-7.07 (1H, m), 7.11-7.18 (2H, m), 7.47 (1H, s), 7.70-7.78 (3H, m), 9.18 (1H, s).

IR(ATR)cm$^{-1}$: 1633, 1589, 1493, 1404, 1327, 1294, 1236, 1147, 1084.

mp: 176-177° C.

Anal. Calcd for C$_{22}$H$_{19}$F$_3$N$_2$O$_3$S: C, 58.92; H, 4.27; F, 12.71; N, 6.25; S, 7.15. Found: C, 58.74; H, 4.18; F, 12.68; N, 6.32; S, 7.26.

MS m/z: 449 (M$^+$+H).

Example 15

5-[(2,5-Difluorophenyl)[(4-fluorophenyl)sulfonyl]methyl]-4-methylpyridine-2-carboxamide

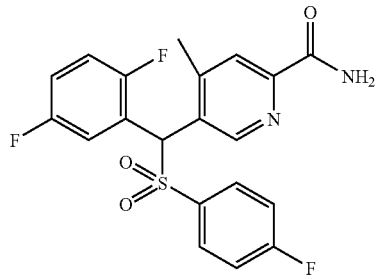

To a solution of 5-[(2,5-difluorophenyl)[(4-fluorophenyl)sulfonyl]methyl]-4-methylpyridine-2-carboxylic acid (211 mg, 0.50 mmol) obtained in Example 12 in N,N-dimethylformamide (5 ml), (benzotriazol-1-yloxy)tripyrrolidinophosphonium hexafluorophosphate (390 mg, 0.75 mmol), 1-hydroxybenzotriazole (101 mg, 0.75 mmol), ammonium chloride (54 mg, 1.00 mmol), and N-ethyldiisopropylamine (0.348 ml, 2.00 mmol) were added in an argon atmosphere at room temperature. After stirring for 5 hours at room temperature, ethyl acetate and water were added to the reaction mixture, and the resulting mixture was washed with saturated aqueous ammonium chloride. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=7:3 was concentrated under reduced pressure, and the resulting residue was washed with a mixed solvent of ethanol and hexane, and was collected by filtration, to obtain the title compound (154 mg, 0.37 mmol, 73%) as a white solid.

$^1$H-NMR (400 MHz, CDCl$_3$) δ: 2.22 (3H, s), 5.58 (1H, br s), 5.96 (1H, s), 6.91-6.99 (1H, m), 7.01-7.08 (1H, m), 7.11-7.18 (2H, m), 7.67-7.73 (2H, m), 7.76-7.82 (1H, m), 7.83 (1H, br s), 7.98 (1H, s), 9.17 (1H, s).

IR(ATR)cm$^{-1}$: 3429, 3168, 1691, 1589, 1491, 1421, 1313, 1234, 1146, 1080.

Anal. Calcd for C$_{20}$H$_{15}$F$_3$N$_2$O$_3$S: C, 57.14; H, 3.60; F, 13.56; N, 6.66; S, 7.63. Found: C, 56.96; H, 3.55; F, 13.76; N, 6.67; S, 7.82.

MS m/z: 421 (M$^+$+H).

Example 16

5-[(2,5-Difluorophenyl)[(4-fluorophenyl)sulfonyl]methyl]-N-ethyl-4-methylpyridine-2-carboxamide

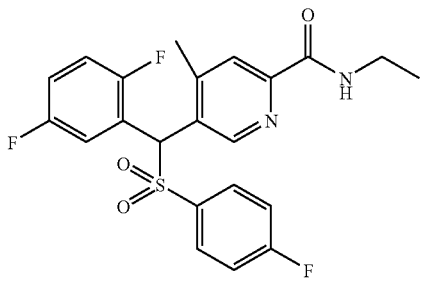

To a solution of 5-[(2,5-difluorophenyl)[(4-fluorophenyl)sulfonyl]methyl]-4-methylpyridine-2-carboxylic acid (126 mg, 0.30 mmol) obtained in Example 12 in methylene chloride (3 ml), ethylamine hydrochloride (27 mg, 0.33 mmol), 1-hydroxybenzotriazole (45 mg, 0.33 mmol), 4-methylmorpholine (0.073 ml, 0.66 mmol), and 1-ethyl-3-(3-dimethylaminopropyl)carbodiimide hydrochloride (63 mg, 0.33 mmol) were added at room temperature. After stirring for 7 days at room temperature, the reaction mixture was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=7:3 was concentrated under reduced pressure, and the resulting residue was washed with a mixed solvent of ethanol and hexane, and was collected by filtration, to obtain the title compound (120 mg, 0.27 mmol, 89%) as a white solid.

$^1$H-NMR (400 MHz, CDCl$_3$) δ: 1.27 (3H, t, J=7.4 Hz), 2.19 (3H, s), 3.51 (2H, dq, J=7.4, 6.1 Hz), 5.95 (1H, s), 6.92-6.99 (1H, m), 7.01-7.08 (1H, m), 7.11-7.17 (2H, m), 7.66-7.73 (2H, m), 7.75-7.81 (1H, m) 7.96 (1H, s), 8.00 (1H, brt, J=6.1 Hz), 9.14 (1H, s).

IR(ATR)cm$^{-1}$: 1672, 1591, 1520, 1493, 1292, 1240, 1149.

mp: 191-193° C.

Anal. Calcd for C$_{22}$H$_9$F$_3$N$_2$O$_3$S: C, 58.92; H, 4.27; F, 12.71; N, 6.25; S, 7.15. Found: C, 58.64; H, 4.31; F, 12.84; N, 6.22; S, 7.20.

MS m/z: 449 (M$^+$+H).

Example 17

5-[(2,5-Difluorophenyl)[(4-fluorophenyl)sulfonyl]methyl]-N-(2-hydroxyethyl)-4-methylpyridine-2-carboxamide

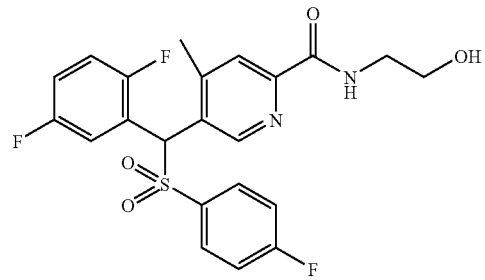

To a solution of 5-[(2,5-difluorophenyl)[(4-fluorophenyl)sulfonyl]methyl]-4-methylpyridine-2-carboxylic acid (421 mg, 1.00 mmol) obtained in Example 12 in methylene chloride (10 ml), 2-aminoethanol (0.067 ml, 1.10 mmol), 1-hydroxybenzotriazole (149 mg, 1.10 mmol) 4-methylmorpholine (0.12 ml, 1.10 mmol), and 1-ethyl-3-(3-dimethylaminopropyl)carbodiimide hydrochloride (211 mg, 1.10 mmol) were added at room temperature. After stirring for 7 days at room temperature, the reaction mixture was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=2:3 was concentrated under reduced pressure, and the resulting residue was washed with a mixed solvent of ethanol and hexane, and was collected by filtration, to obtain the title compound (427 mg, 0.92 mmol, 92%) as a white solid.

$^1$H-NMR (400 MHz, CDCl$_3$) δ: 2.21 (3H, s), 2.58 (1H, br s), 3.63-3.68 (2H, m), 3.85 (2H, t, J=4.9 Hz), 5.95 (1H, s), 6.92-6.99 (1H, m), 7.01-7.08 (1H, m), 7.11-7.18 (2H, m), 7.67-7.73 (2H, m), 7.75-7.80 (1H, m), 7.96 (1H, s), 8.40 (1H, br t, J=6.1 Hz), 9.16 (1H, s).

IR(ATR)cm$^{-1}$: 3554, 3410, 1676, 1589, 1520, 1493, 1279, 1236, 1144.

mp: 153-154° C.

Anal. Calcd for C$_{22}$H$_{19}$F$_3$N$_2$O$_4$S: C, 56.89; H, 4.12; F, 12.27; N, 6.03; S, 6.90. Found: C, 56.85; H, 4.05; F, 12.56; N, 6.03; S, 6.97.

MS m/z: 465 (M$^+$+H).

Example 18

5-[(2,5-Difluorophenyl)[(4-fluorophenyl)sulfonyl]methyl]-N-ethyl-N,4-dimethylpyridine-2-carboxamide

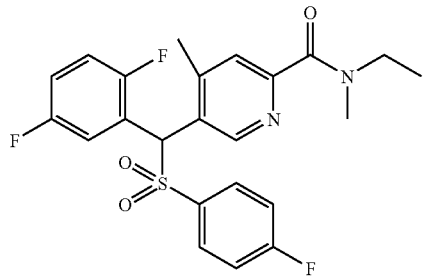

To a solution of 5-[(2,5-difluorophenyl)[(4-fluorophenyl)sulfonyl]methyl]-4-methylpyridine-2-carboxylic acid (126 mg, 0.30 mmol) obtained in Example 12 in methylene chloride (3 ml), N-methylethylamine (0.060 ml, 0.66 mmol), 1-hydroxybenzotriazole (45 mg, 0.33 mmol) and 1-ethyl-3-(3-dimethylaminopropyl)carbodiimide hydrochloride (63 mg, 0.33 mmol) were added at room temperature. After stirring for 4 hours at room temperature, the reaction mixture was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure, and the resulting residue was washed with a mixed solvent of diethyl ether and hexane, and was collected by filtration, to obtain the title compound (38 mg, 0.08 mmol, 27%) as a white solid.

$^1$H-NMR (400 MHz, CDCl$_3$) δ: 1.19-1.30 (3H, m), 2.23 (3H, s), 3.10 (3H, s), 3.47 (1.2H, q, J=7.4 Hz), 3.60 (0.8H, q, J=7.4 Hz), 5.95 (1H, s), 6.89-6.97 (1H, m), 6.99-7.07 (1H, m), 7.14 (2H, t, J=8.3 Hz), 7.44 (0.6H, s), 7.46 (0.4H, s), 7.69-7.79 (3H, m), 9.17 (0.6H, s), 9.18 (0.4H, s).

IR (ATR)cm$^{-1}$: 1626, 1591, 1493, 1286, 1240, 1147, 1084.
mp: 165-167° C.
Anal. Calcd for C$_{23}$H$_{21}$F$_3$N$_2$O$_3$S: C, 59.73; H, 4.58; F, 12.32; N, 6.06; S, 6.93. Found: C, 59.31; H, 4.31; F, 12.59; N, 6.00; S, 7.05.
MS m/z: 463 (M$^+$+H).

Example 19

5-[(2,5-Difluorophenyl)[(4-fluorophenyl)sulfonyl]methyl]-N-(2-hydroxyethyl)-N,4-dimethylpyridine-2-carboxamide

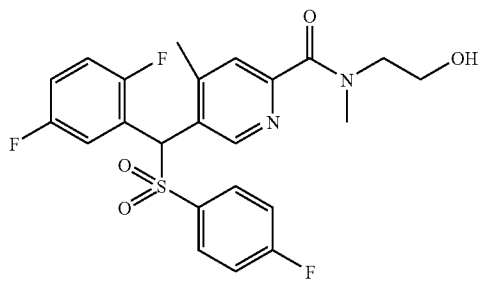

To a solution of 5-[(2,5-difluorophenyl)[(4-fluorophenyl)sulfonyl]methyl]-4-methylpyridine-2-carboxylic acid (337 mg, 0.80 mmol) obtained in Example 12 in methylene chloride (8 ml), 2-(methylamino)ethanol (0.077 ml, 0.96 mmol), 1-hydroxybenzotriazole (130 mg, 0.96 mmol), 4-methylmorpholine (0.194 ml, 1.76 mmol), and 1-ethyl-3-(3-dimethylaminopropyl)carbodiimide hydrochloride (184 mg, 0.96 mmol) were added at room temperature. After stirring for 24 hours at room temperature, the reaction mixture was washed with 1 N hydrochloric acid. The organic layer was dried over anhydrous sodium sulfate and filtered, then the filtrate was concentrated under reduced pressure, and the resulting residue was subjected to flash silica gel chromatography. The fraction obtained from an elution with ethyl acetate was concentrated under reduced pressure, and the resulting residue was washed with a mixed solvent of ethanol and diethyl ether, and was collected by filtration, to obtain the title compound (328 mg, 0.69 mmol, 85%) as a white solid.

$^1$H-NMR (400 MHz, CDCl$_3$) δ: 2.24 (0.3H, s), 2.29 (2.7H, s), 3.17 (2.7H, s), 3.21 (0.3H, s), 3.47-4.01 (4H, m), 5.95 (1H, s), 6.89-6.96 (1H, m), 7.01-7.08 (1H, m), 7.15 (2H, t, J=8.5 Hz), 7.52 (0.1H, s), 7.68 (0.9H, s), 7.70-7.78 (3H, m), 9.08 (0.9H, s), 9.19 (0.1H, s).

IR(ATR)cm$^{-1}$: 3228, 1626, 1591, 1495, 1236, 1149, 833.
mp: 123-125° C.
Anal. Calcd for C$_{23}$H$_{21}$F$_3$N$_2$O$_4$S.0.25H$_2$O: C, 57.20; H, 4.49; F, 11.80; N, 5.80; S, 6.64. Found: C, 57.13; H, 4.34; F, 11.92; N, 5.86; S, 6.84.
MS m/z: 479 (M$^+$+H).

Example 20

5-[(2,5-Difluorophenyl)[(4-fluorophenyl)thio]methyl]-4-methylpyridine-2-carboxylic acid

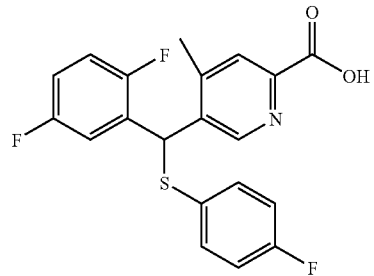

To a solution of 2-bromo-5-[(2,5-difluorophenyl)[(4-fluorophenyl)thio]methyl]-4-methylpyridine (1.39 g, 3.28 mmol) obtained in Example 10 in toluene (60 ml), a hexane solution of n-butyllithium (1.54 M, 2.55 ml, 3.93 mmol) was added in an argon atmosphere at −78° C. After stirring for 1 hour at the same temperature, carbon dioxide was bubbled thereinto the mixture. The reaction mixture was allowed to warm to room temperature over 2 hours, subsequently 0.1 N hydrochloric acid was added thereto, and the mixture was extracted with ethyl acetate. The organic layer was dried over anhydrous sodium sulfate and filtered, then the filtrate was concentrated under reduced pressure, and the resulting residue was subjected to flash silica gel chromatography. The fraction obtained from an elution with methylene chloride:methanol=10:1 was concentrated under reduced pressure, and the resulting residue was washed with a mixed solvent of ethanol, diethyl ether and hexane, and was collected by filtration, to obtain the title compound (815 mg, 2.09 mmol, 64%) as a white solid.

$^1$H-NMR (400 MHz, CDCl$_3$) δ: 2.41 (3H, s), 5.83 (1H, s), 6.89-7.03 (4H, m), 7.27-7.44 (3H, m), 8.00 (1H, s), 8.67 (1H, s).
MS m/z: 390 (M$^+$+H).

Example 21

5-[(2,5-Difluorophenyl)[(4-fluorophenyl)sulfinyl]methyl]-N,4-dimethylpyridine-2-carboxamide

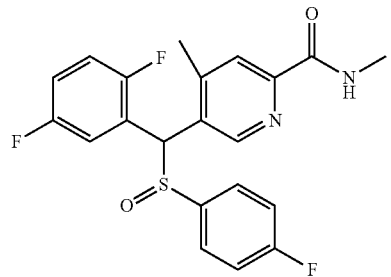

To a solution of 5-[(2,5-difluorophenyl) [(4-fluorophenyl)thio]methyl]-4-methylpyridine-2-carboxylic acid (307 mg, 0.79 mmol) in methylene chloride (8 ml), methylamine hydrochloride (108 mg, 1.58 mmol), 1-hydroxybenzotriazole (213 mg, 1.58 mmol), 4-methylmorpholine (0.347 ml, 3.15 mmol), and 1-ethyl-3-(3-dimethylaminopropyl)carbodiimide hydrochloride (302 mg, 1.58 mmol) were added at room temperature. After stirring for 16 hours at room temperature, the reaction mixture was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=3:1 was concentrated under reduced pressure. To a solution of the resulting residue in methylene chloride (5 ml), 3-chloroperbenzoic acid (110 mg, 0.41 mmol) was added at 0° C. After stirring for 1 hour at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to preparative thin-layer chromatography (developed with hexane:ethyl acetate=2:1, eluted with methylene chloride:methanol=4:1). The obtained fraction was concentrated under reduced pressure, and the resulting residue was washed with a mixed solvent of ethanol and hexane, and was collected by filtration, to obtain the title compound (129 mg, 0.31 mmol, 39%) as a white solid.

$^1$H-NMR (400 MHz, CDCl$_3$) δ: 1.94 (1.95H, s), 2.13 (1.05H, s), 3.04 (1.95H, d, J=5.1 Hz), 3.05 (1.05H, d, J=5.1 Hz), 5.32 (0.35H, s), 5.35 (0.65H, s), 6.87-7.13 (4H, m), 7.27-7.35 (2.35H, m), 7.48-7.54 (0.65H, m), 7.92 (0.65H, s), 7.97 (0.35H, s), 8.00 (0.35H, br d, J=5.1 Hz), 8.03 (0.65H, br d, J=5.1 Hz), 8.84 (0.65H, s), 9.01 (0.35H, s).

IR(ATR)cm$^{-1}$: 3359, 1664, 1591, 1529, 1491, 1228, 1086, 1051.

Anal. Calcd for C$_{21}$H$_{17}$F$_3$N$_2$O$_2$S: C, 60.28; H, 4.10; F, 13.62; N, 6.69; S, 7.66. Found: C, 59.86; H, 4.04; F, 13.65; N, 6.65; S, 7.67.

MS m/z: 419 (M$^+$+H).

Example 22

5-[(2,5-Difluorophenyl)[(4-fluorophenyl)sulfinyl]methyl]-N,N,4-trimethylpyridine-2-carboxamide

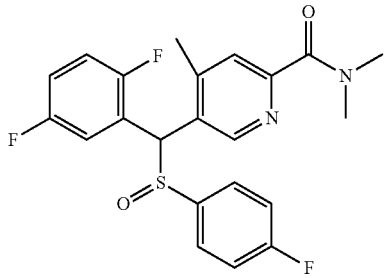

To a solution of 5-[(2,5-difluorophenyl)[(4-fluorophenyl)thio]methyl]-4-meth ylpyridine-2-carboxylic acid (307 mg, 0.79 mmol) obtained in Example 20 in methylene chloride (8 ml), dimethylamine hydrochloride (130 mg, 1.58 mmol), 1-hydroxybenzotriazole (213 mg, 1.58 mmol), 4-methylmorpholine (0.347 ml, 3.15 mmol), and 1-ethyl-3-(3-dimethylaminopropyl)carbodiimide hydrochloride (302 mg, 1.58 mmol) were added at room temperature. After stirring for 17 hours at room temperature, the reaction mixture was washed with saturated aqueous sodium hydrogencarbonate. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure. To a solution the resulting residue in methylene chloride (5 ml), 3-chloroperbenzoic acid (112 mg, 0.42 mmol) was added at 0° C. After stirring for 1 hour at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to preparative thin-layer chromatography (developed with hexane:ethyl acetate=1:2, eluted with methylene chloride:methanol=4:1). The obtained fraction was concentrated under reduced pressure, and the resulting residue was washed with a mixed solvent of ethanol and hexane, and was collected by filtration, to obtain the title compound (78 mg, 0.18 mmol, 23%) as a white solid.

$^1$H-NMR (400 MHz, CDCl$_3$) δ: 2.03 (2H, s), 2.11 (1H, s), 3.14 (4H, s), 3.15 (2H, s), 5.31 (0.33H, s), 5.37 (0.67H, s), 6.87-7.13 (4H, m), 7.30-7.40 (3H, m), 7.43 (0.67H, s), 7.46 (0.33H, s), 8.96 (0.67H, s), 9.03 (0.33H, s).

IR(ATR)cm$^{-1}$: 1631, 1587, 1493, 1408, 1217, 1049.

Anal. Calcd for C$_{22}$H$_{11}$F$_3$N$_2$O$_2$S: C, 61.10; H, 4.43; F, 13.18; N, 6.48; S, 7.41. Found: C, 60.83; H, 4.36; F, 13.43; N, 6.44; S, 7.42

MS m/z: 433 (M$^+$+H).

Example 23

5-[(2,5-Difluorophenyl)[(4-fluorophenyl)thio]methyl]-4-methylpyridine-2-carboxamide

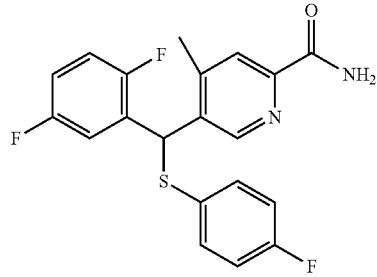

To a solution of 5-[(2,5-difluorophenyl)[(4-fluorophenyl)thio]methyl]-4-meth ylpyridine-2-carboxylic acid (178 mg, 0.46 mmol) obtained in Example 20 in N,N-dimethylformamide (5 ml), (benzotriazol-1-yloxy)tripyrrolidinophosphonium hexafluorophosphate (357 mg, 0.69 mmol), 1-hydroxybenzotriazole (93 mg, 0.69 mmol), ammonium chloride (49 mg, 0.91 mmol), and N-ethyldiisopropylamine (0.319 ml, 1.83 mmol) were added in an argon atmosphere at room temperature.

After stirring for 5 hours at room temperature, ethyl acetate and water were added to the reaction mixture, and the resulting mixture was washed with saturated aqueous sodium hydrogencarbonate, and then with saturated brine. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=4:1 was concentrated under reduced pressure to obtain the title compound (156 mg, 0.40 mmol, 88%) as a white solid.

$^1$H-NMR (400 MHz, CDCl$_3$) δ: 2.38 (3H, s), 5.56 (1H, br s), 5.83 (1H, s), 6.91-7.01 (4H, m), 7.28-7.34 (2H, m), 7.36-7.41 (1H, m), 7.77 (1H, br s), 7.99 (1H, s), 8.61 (1H, s).

MS m/z: 389 (M$^+$+H).

Example 24

5-[(2,5-Difluorophenyl) [(4-fluorophenyl)sulfinyl]methyl]-4-methylpyridine-2-carboxamide

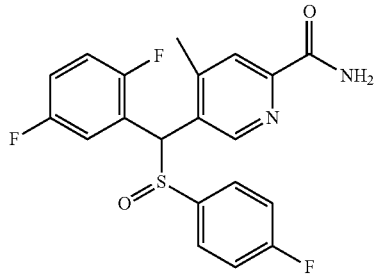

To a solution of 5-[(2,5-difluorophenyl) [(4-fluorophenyl)thio]methyl]-4-methylpyridine-2-carboxamide (152 mg, 0.39 mmol) in methylene chloride (5 ml), 3-chloroperbenzoic acid (104 mg, 0.39 mmol) was added at 0° C. After stirring for 2 hours at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=7:3 was concentrated under reduced pressure, and the resulting residue was washed with a mixed solvent of ethanol and hexane, and was collected by filtration to obtain the title compound (91 mg, 0.23 mmol, 58%) as a white solid.

$^1$H-NMR (400 MHz, CDCl$_3$) δ: 1.95 (1.9H, s), 2.14 (1.1H, s), 5.33 (0.37H, s), 5.36 (0.63H, s), 5.51-5.64 (1H, m), 6.87-7.14 (4H, m), 7.27-7.37 (2.37H, m), 7.49-7.56 (0.63H, m), 7.80-7.90 (1H, m), 7.94 (0.63H, s), 7.98 (0.37H, s), 8.87 (0.63H, s), 9.05 (0.37H, s).

IR(ATR)cm$^{-1}$: 3458, 3377, 3155, 1697, 1491, 1421, 1348, 1227, 1082, 1043.

Anal. Calcd for C$_{20}$H$_{15}$F$_3$N$_2$O$_2$S: C, 59.40; H, 3.74; F, 14.09; N, 6.93; S, 7.93. Found: C, 59.29; H, 3.76; F, 13.88; N, 6.88; S, 7.93.

MS m/z: 405 (M$^+$+H).

Example 25

2-Bromo-5-[(2,5-difluorophenyl)[[6-(trifluoromethyl)pyridin-3-yl]thio]methyl]-4-methylpyridine

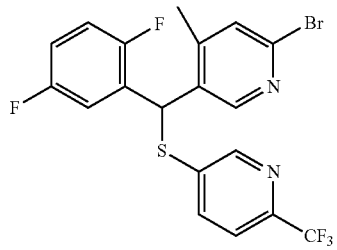

To a solution of O-ethyl S-[6-(trifluoromethyl)pyridin-3-yl]dithiocarbonate (2.67 g, 10.0 mmol) in ethanol (30 ml), 1 N aqueous sodium hydroxide (30 ml) was added, and the resulting mixture was stirred for 2 hours at 50° C. The reaction mixture was cooled to room temperature, and washed with methylene chloride. Subsequently, the aqueous layer was acidified with 1 N hydrochloric acid, and was extracted with methylene chloride. The organic layer was dried over anhydrous sodium sulfate and filtered, and then the filtrate was concentrated under reduced pressure, to obtain 6-(trifluoromethyl)pyridin-3-thiol as a crude product.

To a solution of (6-bromo-4-methylpyridin-3-yl)(2,5-difluorophenyl)methanol (3.14 g, 10.0 mmol) obtained in Reference Example 1 in methylene chloride (50 ml), thionyl chloride (7.29 ml, 100 mmol) and N,N-dimethylformamide (0.50 ml) were added at 0° C., and the resulting mixture was stirred for 2 hours at room temperature. The reaction mixture was concentrated under reduced pressure, subsequently ethyl acetate was added to the residue, and water and then saturated aqueous sodium hydrogencarbonate were added dropwise at 0° C. After the organic layer was separated, the organic layer was dried over anhydrous sodium sulfate and filtered, and then the filtrate was concentrated under reduced pressure. To a solution of the resulting residue in N,N-dimethylformamide (45 ml), a solution of 6-(trifluoromethyl)pyridine-3-thiol in N,N-dimethylformamide (5 ml), and then potassium carbonate (1.52 g, 11.0 mmol) were added in a nitrogen atmosphere at 0° C., and the resulting mixture was stirred for 16 hours at room temperature. Ethyl acetate and water were added to the reaction mixture at 0° C., the organic layer was separated, and then the organic layer was washed with saturated brine. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=19:1 was concentrated under reduced pressure, and the resulting residue was washed with a mixed solvent of diethyl ether and hexane, and was collected by filtration, to obtain the title compound (3.43 g, 7.22 mmol, 72%) as a pale yellow solid.

$^1$H-NMR (400 MHz, CDCl$_3$) δ: 2.36 (3H, s), 5.93 (1H, s), 6.97-7.09 (2H, m), 7.25-7.32 (1H, m), 7.35 (1H, s), 7.55 (1H, d, J=8.3 Hz), 7.67 (1H, dd, J=8.3, 2.2 Hz), 8.39 (1H, s), 8.53 (1H, d, J=2.2 Hz).

MS m/z: 475, 477 (M$^+$+H).

Example 26

5-[(2,5-Difluorophenyl)[[6-(trifluoromethyl)pyridin-3-yl]thio]methyl]-4-methylpyridine-2-carboxylic acid

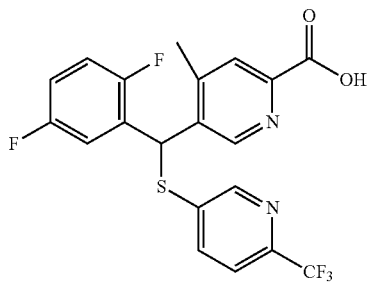

To a solution of 2-bromo-5-[(2,5-difluorophenyl)[[6-(trifluoromethyl)pyridin-3-yl]thio]methyl]-4-methylpyridine (3.43 g, 7.22 mmol) in toluene (70 ml), a hexane solution of n-butyllithium (1.54 M, 5.62 ml, 8.66 mmol) was added in an argon atmosphere at −78° C. The reaction mixture was stirred for 30 minutes at −40° C., and then cooled again to −78° C., and carbon dioxide was bubbled therein. After stirring for 1 hour at the same temperature, the reaction mixture was allowed to warm to room temperature, and saturated aqueous ammonium chloride was added. The reaction mixture was concentrated under reduced pressure, and then methylene chloride and water were added to the residue. After the organic layer was separated, 1 N hydrochloric acid was added to the aqueous layer, which was then extracted with methylene chloride. The organic layers were combined and dried over anhydrous sodium sulfate and filtered, the filtrate was concentrated under reduced pressure, and the resulting residue was subjected to flash silica gel chromatography. The fraction obtained from an elution with methylene chloride:methanol=100:1 was concentrated under reduced pressure, and the resulting residue was washed with a mixed solvent of ethanol and diethyl ether, and was collected by filtration, to obtain the title compound (862 mg, 1.96 mmol, 27%) as a white solid.

$^1$H-NMR (400 MHz, CDCl$_3$) δ: 2.52 (3H, s), 6.04 (1H, s), 7.01-7.11 (2H, m), 7.33-7.39 (1H, m), 7.57 (1H, d, J=8.3 Hz), 7.70 (1H, dd, J=8.3, 2.2 Hz), 8.08 (1H, s), 8.55 (1H, d, J=2.2 Hz), 8.62 (1H, s).

MS m/z: 441 (M$^+$+H).

Example 27

5-[(2,5-Difluorophenyl)[[6-(trifluoromethyl)pyridin-3-yl]thio]methyl]-N,N,4-trimethylpyridine-2-carboxamide

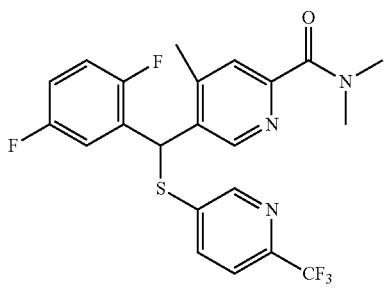

To a solution of 5-[(2,5-difluorophenyl)[[6-(trifluoromethyl)pyridin-3-yl]thio]methyl]-4-methylpyridine-2-carboxylic acid (352 mg, 0.80 mmol) in methylene chloride (10 ml), dimethylamine hydrochloride (73 mg, 0.88 mmol), 1-hydroxybenzotriazole (119 mg, 0.88 mmol) 4-methylmorpholine (0.194 ml, 1.76 mmol), and 1-ethyl-3-(3-dimethylaminopropyl)carbodiimide hydrochloride (169 mg, 0.88 mmol) were added at room temperature. After stirring for 13 hours at room temperature, the reaction mixture was washed with 0.5 N hydrochloric acid. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure to obtain the title compound (370 mg, 0.79 mmol, 99%) as a colorless oily substance.

$^1$H-NMR (400 MHz, CDCl$_3$) δ: 2.43 (3H, s), 3.08 (3H, s), 3.12 (3H, s), 6.02 (1H, s), 6.97-7.08 (2H, m), 7.31-7.37 (1H, m), 7.49 (1H, s), 7.55 (1H, d, J=8.1 Hz), 7.68 (1H, dd, J=8.1, 2.0 Hz), 8.54 (1H, d, J=2.0 Hz), 8.57 (1H, s).

MS m/z: 468 (M$^+$+H).

Example 28

5-[(2,5-Difluorophenyl) [[6-(trifluoromethyl)pyridin-3-yl]sulfonyl]methyl]-N,N,4-trimethylpyridine-2-carboxamide (Compound A), and 5-[(2,5-difluorophenyl)[[6-(trifluoromethyl)pyridin-3-yl]sulfinyl]methyl]-N,N,4-trimethylpyridine-2-carboxamide (Compound B)

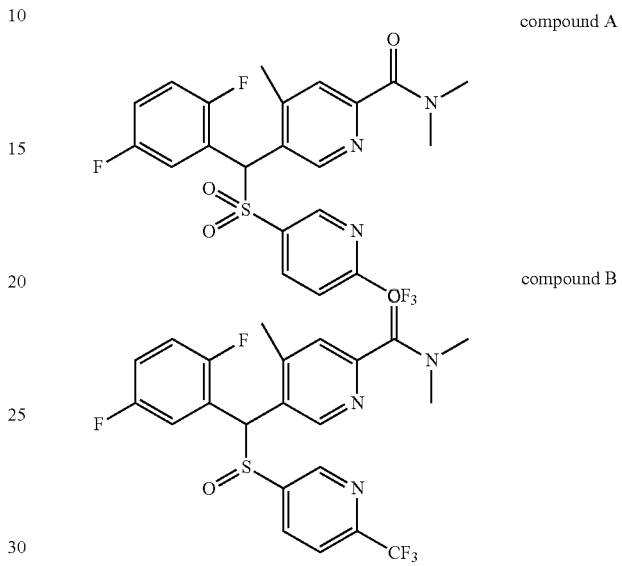

To a solution of 5-[(2,5-difluorophenyl)[[6-(trifluoromethyl)pyridin-3-yl]thio]methyl]-N,N,4-trimethylpyridine-2-carboxamide (365 mg, 0.78 mmol) in methylene chloride (10 ml), 3-chloroperbenzoic acid (259 mg, 0.98 mmol) was added at 0° C. After stirring for 6 hours at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure, and the resulting residue was washed with a mixed solvent of ethanol and diethyl ether, and was collected by filtration, to obtain the title compound A (94 mg, 0.19 mmol, 24%) as a white solid. Next, the fraction obtained from an elution with hexane:ethyl acetate=1:2 was concentrated under reduced pressure, and the resulting residue was washed with a mixed solvent of ethanol and diethyl ether, and was collected by filtration, to obtain the title compound B (114 mg, 0.24 mmol, 30%) as a white solid.

Compound A $^1$H-NMR (400 MHz, CDCl$_3$) δ: 2.30 (3H, s), 3.15 (6H, s), 6.01 (1H, s), 6.91-6.99 (1H, m), 7.05-7.12 (1H, m), 7.52 (1H, s), 7.65-7.71 (1H, m), 7.80 (1H, d, J=8.1 Hz), 8.20 (1H, dd, J=8.1, 2.2 Hz), 8.99 (1H, d, J=2.2 Hz), 9.22 (1H, s).

IR(ATR)cm$^{-1}$: 1630, 1493, 1333, 1155, 1105, 1076, 723, 625.

Anal. Calcd for C$_{22}$H$_{18}$F$_5$N$_3$O$_3$S: C, 52.90; H, 3.63; F, 19.02; N, 8.41; S, 6.42. Found: C, 52.69; H, 3.58; F, 19.14; N, 8.42; S, 6.51.

MS m/z: 500 (M$^+$+H).

Compound B $^1$H-NMR (400 MHz, CDCl$_3$) δ: 2.10 (2.1H, s), 2.17 (0.9H, s), 3.14 (2.1H, s), 3.15 (2.1H, s), 3.16 (0.9H, s), 3.16 (0.9H, s), 5.38 (0.3H, s), 5.51 (0.7H, s), 6.84-7.11 (2H, m), 7.19-7.32 (1H, m), 7.47 (0.7H, s), 7.52 (0.3H, s), 7.72 (0.3H, dd, J=8.1, 0.7 Hz), 7.77 (0.7H, dd, J=8.1.0.7 Hz), 7.84 (0.3H, dd, J=8.1, 2.0 Hz), 8.04 (0.7H, dd, J=8.1, 2.0 Hz), 8.50 (0.7H, d, J=2.0 Hz), 8.65 (0.3H, d, J=2.0 Hz), 9.02 (0.7H, s), 9.15 (0.3H, s).

IR(ATR)cm$^{-1}$: 1631, 1493, 1331, 1169, 1132, 1068.

Anal. Calcd for $C_{22}H_{18}F_5N_3O_2S$: C, 54.66; H, 3.75; F, 19.65; N, 8.69; S, 6.63. Found: C, 54.38; H, 3.66; F, 19.94; N, 8.70; S, 6.68.

MS m/z: 484 (M$^+$+H).

Example 29

5-[(2,5-Difluorophenyl)[[6-(trifluoromethyl)pyridin-3-yl]thio]methyl]-N-(2-hydroxyethyl)-4-methylpyridine-2-carboxamide

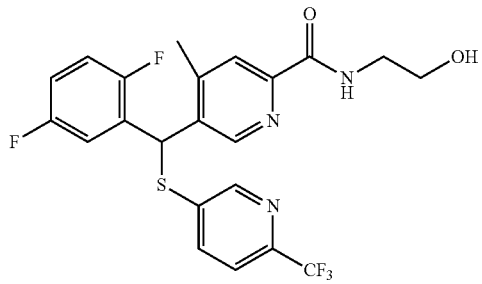

To a solution of 5-[(2,5-difluorophenyl)[[6-(trifluoromethyl)pyridin-3-yl]thio]methyl]-4-methylpyridine-2-carboxylic acid (132 mg, 0.30 mmol) obtained in Example 26 in methylene chloride (5 ml), 2-aminoethanol (0.020 ml, 0.33 mmol), 1-hydroxybenzotriazole (45 mg, 0.33 mmol), 4-methylmorpholine (0.036 ml, 0.33 mmol) and 1-ethyl-3-(3-dimethylaminopropyl)carbodiimide hydrochloride (63 mg, 0.33 mmol) were added at room temperature. After stirring for 6 hours at room temperature, the reaction mixture was washed with 0.5 N hydrochloric acid. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure to obtain the title compound (143 mg, 0.30 mmol, 99%) as a colorless oily substance.

$^1$H-NMR (400 MHz, CDCl$_3$) δ: 2.46 (3H, s), 2.52 (1H, br s), 3.61-3.67 (2H, m), 3.84 (2H, t, J=4.9 Hz), 6.03 (1H, s), 6.98-7.09 (2H, m), 7.29-7.35 (1H, m) 7.55 (1H, d, J=8.3 Hz), 7.67 (1H, dd, J=8.3, 2.2 Hz), 8.04 (1H, s), 8.33 (1H, brt, J=6.1 Hz), 8.54 (1H, d, J=2.2 Hz), 8.59 (1H, s).

MS m/z: 484 (M$^+$+H).

Example 30

5-[(2,5-Difluorophenyl) [[6-(trifluoromethyl)pyridin-3-yl]sulfonyl]methyl]-N-(2-hydroxyethyl)-4-methylpyridine-2-carboxamide

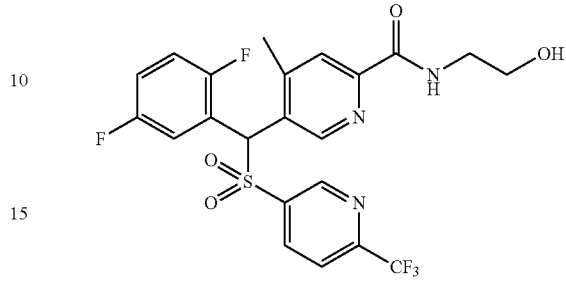

To a solution of 5-[(2,5-difluorophenyl)[[6-(trifluoromethyl)pyridin-3-yl]thio]methyl]-N-(2-hydroxyethyl)-4-methylpyridine-2-carboxamide (195 mg, 0.40 mmol) in methylene chloride (8 ml), 3-chloroperbenzoic acid (214 mg, 0.81 mmol) was added at 0° C. After stirring for 10 hours at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=2:3 was concentrated under reduced pressure, and the resulting residue was washed with a mixed solvent of ethanol and diethyl ether, and was collected by filtration, to obtain the title compound (118 mg, 0.23 mmol, 57%) as a white solid.

$^1$H-NMR (400 MHz, CDCl$_3$) δ: 2.30 (3H, s), 2.49 (1H, br s), 3.64-3.70 (2H, m), 3.86 (2H, t, J=4.7 Hz), 6.02 (1H, s), 6.92-7.00 (1H, m), 7.05-7.13 (1H, m), 7.64-7.71 (1H, m), 7.80 (1H, d, J=8.3 Hz), 8.04 (1H, s), 8.18 (1H, dd, J=8.3, 2.0 Hz), 8.41 (1H, br t, J=5.6 Hz), 8.97 (1H, d, J=2.0 Hz), 9.22 (1H, s).

IR(ATR)cm$^{-1}$: 3373, 1662, 1533, 1493, 1327, 1238, 1184, 1155, 1138, 1074, 723.

Anal. Calcd for $C_{22}H_{18}F_5N_3O_4S$: C, 51.26; H, 3.52; F, 18.43; N, 8.15; S, 6.22. Found: C, 51.02; H, 3.46; F, 18.86; N, 8.14; S, 6.29.

MS m/z: 516 (M$^+$+H).

Example 31

5-[(2,5-Difluorophenyl)[[6-(trifluoromethyl)pyridin-3-yl]thio]methyl]-4-methylpyridine-2-carboxamide

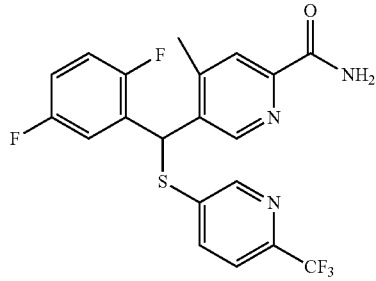

To a solution of 5-[(2,5-difluorophenyl)[[6-(trifluoromethyl)pyridin-3-yl]thio]methyl]-4-methylpyridine-2-carboxylic acid (176 mg, 0.40 mmol) obtained in Example 26 in N,N-dimethylformamide (4 ml), (benzotriazol-1-yloxy)tripyrrolidinophosphonium hexafluorophosphate (312 mg, 0.60 mmol), 1-hydroxybenzotriazole (81 mg, 0.60 mmol), ammonium chloride (43 mg, 0.80 mmol), and N-ethyldiisopropylamine (0.279 ml, 1.60 mmol) were added in an argon atmosphere at room temperature. After stirring for 5 hours at room temperature, ethyl acetate and water were added to the reaction mixture, and the resulting mixture was washed with saturated brine. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=2:1 was concentrated under reduced pressure to obtain the title compound (168 mg, 0.38 mmol, 96%) as a white solid.

$^1$H-NMR (400 MHz, CDCl$_3$) δ: 2.47 (3H, s), 5.56 (1H, br s), 6.04 (1H, s), 6.98-7.09 (2H, m), 7.31-7.37 (1H, m), 7.56 (1H, d, J=8.3 Hz), 7.67 (1H, dd, J=8.3, 2.2 Hz), 7.75 (1H, brs), 8.06 (1H, s), 8.54 (1H, d, J=2.2 Hz), 8.59 (1H, s).

MS m/z: 440 (M$^+$+H).

Example 32

5-[(2,5-Difluorophenyl)[[6-(trifluoromethyl)pyridin-3-yl]sulfonyl]methyl]-4-methylpyridine-2-carboxamide

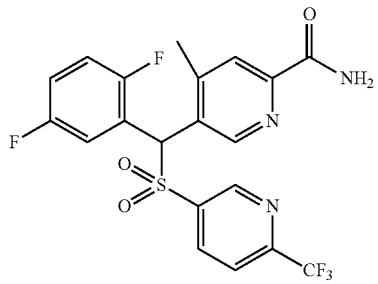

To a solution of 5-[(2,5-difluorophenyl)[[6-(trifluoromethyl)pyridin-3-yl]thio]methyl]-4-methylpyridine-2-carboxamide (164 mg, 0.37 mmol) in methylene chloride (4 ml), 3-chloroperbenzoic acid (215 mg, 0.81 mmol) was added at 0° C. After stirring for 4 days at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to flash silica gel chromatography. The fraction obtained from an elution with methylene chloride:methanol=100:1 was concentrated under reduced pressure, and the resulting residue was washed with ethanol, and was collected by filtration, to obtain the title compound (109 mg, 0.23 mmol, 62%) as a white solid.

$^1$H-NMR (400 MHz, CDCl$_3$) δ: 2.31 (3H, s), 5.59 (1H, br s), 6.03 (1H, s), 6.92-7.00 (1H, m), 7.06-7.13 (1H, m), 7.66-7.72 (1H, m), 7.80 (1H, d, J=8.3 Hz), 7.82 (1H, br s), 8.05 (1H, s), 8.19 (1H, dd, J=8.3, 2.0 Hz), 8.98 (1H, d, J=2.0 Hz), 9.24 (1H, s).

IR(ATR)cm$^{-1}$: 3410, 1685, 1495, 1331, 1157, 1136, 1103, 1076.

Anal. Calcd for C$_{20}$H$_{14}$F$_5$N$_3$O$_3$S: C, 50.96; H, 2.99; F, 20.15; N, 8.91; S, 6.80. Found: C, 51.06; H, 2.94; F, 20.25; N, 8.94; S, 6.96.

MS m/z: 472 (M$^+$+H).

Reference Example 3

(6-Bromo-4-methylpyridin-3-yl)(2,3,6-trifluorophenyl)methanol

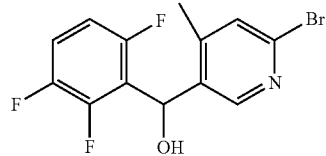

A hexane solution of n-butyllithium (1.54 M, 12.2 ml, 18.7 mmol) was added to a solution of 2,5-dibromo-4-methylpyridine (4.27 g, 17.0 mmol) in diethyl ether (200 ml) in an argon atmosphere at −78° C. After stirring the reaction mixture for 30 minutes, 2,3,6-trifluorobenzaldehyde (1.99 ml, 17.0 mmol) was added thereto. After stirring for 30 minutes at the same temperature, saturated aqueous ammonium chloride was added to the mixture at room temperature. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=4:1 was concentrated under reduced pressure to obtain the title compound (4.60 g, 13.9 mmol, 81%) as a pale yellow solid.

$^1$H-NMR (400 MHz, CDCl$_3$) δ: 2.25 (3H, s), 2.83 (1H, br s), 6.29 (1H, s), 6.84-6.92 (1H, m), 7.11-7.21 (1H, m), 7.28 (1H, s), 8.53 (1H, s).

MS m/z: 332, 334 (M$^+$+H).

Reference Example 4

2-Bromo-5-[chloro(2,3,6-trifluorophenyl)methyl]-4-methylpyridine

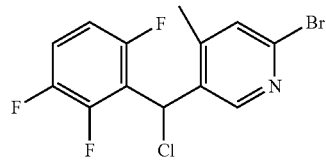

To a solution of (6-bromo-4-methylpyridin-3-yl)(2,3,6-trifluorophenyl)methanol (4.60 g, 13.9 mmol) in methylene chloride (70 ml), thionyl chloride (10.1 ml, 139 mmol) and N,N-dimethylformamide (0.60 ml) were added at 0° C., and the resulting mixture was stirred for 2 hours at room temperature. The reaction mixture was concentrated under reduced pressure, ethyl acetate was added to the resulting residue, and subsequently water and then saturated aqueous sodium hydrogencarbonate were added thereto at 0° C. After the organic layer was separated, the organic layer was washed with saturated brine, dried over anhydrous sodium sulfate, and filtered, and the filtrate was concentrated under reduced pressure, to obtain the title compound (4.65 g, 13.3 mmol, 96%) as a pale brown solid.

$^1$H-NMR (400 MHz, CDCl$_3$) δ: 2.25 (3H, s), 6.45 (1H, s), 6.86-6.93 (1H, m), 7.14-7.23 (1H, m), 7.29 (1H, s), 8.80 (1H, s).

MS m/z: 350, 352 (M$^+$+H).

Example 33

2-Bromo-5-[[(4-fluorophenyl)thio](2,3,6-trifluorophenyl)methyl]-4-methylpyridine

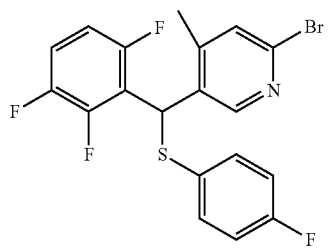

To a solution of 2-bromo-5-[chloro(2,3,6-trifluorophenyl)methyl]-4-methylpyridine (4.65 g, 13.3 mmol) in N,N-dimethylformamide (70 ml), 4-fluorobenzenethiol (1.41 ml, 13.3 mmol) and then potassium carbonate (2.02 g, 14.6 mmol) were added in an argon atmosphere at 0° C., and the resulting mixture was stirred for 4 hours at room temperature. Ethyl acetate and water were added to the reaction mixture at 0° C., the organic layer was separated, and then the organic layer was washed with saturated brine. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=19:1 was concentrated under reduced pressure, and the resulting residue was washed with hexane, and then was collected by filtration, to obtain the title compound (5.17 g, 11.7 mmol, 88%) as a white solid.

$^1$H-NMR (400 MHz, CDCl$_3$) δ: 2.16 (3H, s), 5.67 (1H, s), 6.75-6.82 (1H, m), 6.91-6.99 (2H, m), 7.01-7.11 (1H, m), 7.24 (1H, s), 7.33-7.39 (2H, m), 8.88 (1H, s).

MS m/z: 442, 444 (M$^+$+H).

Example 34

5-[[(4-Fluorophenyl)thio](2,3,6-trifluorophenyl)methyl]-4-methylpyridine-2-carboxylic acid

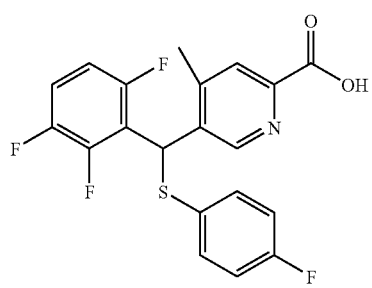

To a solution of 2-bromo-5-[[(4-fluorophenyl)thio](2,3,6-trifluorophenyl)methyl]-4-methylpyridine (2.65 g, 6.00 mmol) in toluene (60 ml), a hexane solution of n-butyllithium (1.54 M, 4.68 ml, 7.20 mmol) was added in an argon atmosphere at −78° C. The reaction mixture was stirred for 30 minutes at −40° C., and cooled again to −78° C., and then carbon dioxide was bubbled therein. After stirring for 30 minutes at the same temperature, the reaction mixture was allowed to warm to 0° C., and saturated aqueous ammonium chloride was added. The reaction mixture was concentrated under reduced pressure, and then chloroform and 1 N hydrochloric acid were added to the residue. After the organic layer was separated, the organic layer was dried over anhydrous sodium sulfate and filtered, then the filtrate was concentrated under reduced pressure, and the resulting residue was subjected to flash silica gel chromatography. The fraction obtained from an elution with methylene chloride:methanol=10:1 was concentrated under reduced pressure, and the resulting residue was washed with a mixed solvent of diethyl ether and hexane, and was collected by filtration, to obtain the title compound (981 mg, 2.41 mmol, 40%) as a white solid.

$^1$H-NMR (400 MHz, CDCl$_3$) δ: 2.21 (3H, s), 3.47 (1H, br s), 5.74 (1H, s), 6.73-6.81 (1H, m), 6.90-6.98 (2H, m), 7.00-7.10 (1H, m), 7.29-7.35 (2H, m), 7.93 (1H, s), 9.12 (1H, s).

MS m/z: 408 (M$^+$+H).

Example 35

5-[[(4-Fluorophenyl)thio](2,3,6-trifluorophenyl)methyl]-N,N,4-trimethylpyridine-2-carboxamide

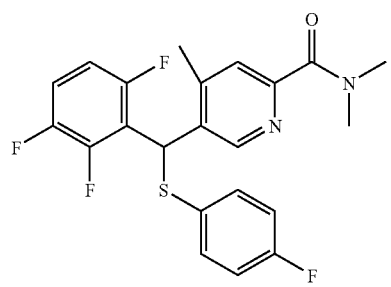

To a solution of 5-[[(4-fluorophenyl)thio](2,3,6-trifluorophenyl)methyl]-4-m ethylpyridine-2-carboxylic acid (383 mg, 0.94 mmol) in methylene chloride (10 ml), dimethylamine hydrochloride (85 mg, 1.03 mmol), 1-hydroxybenzotriazole (140 mg, 1.03 mmol), 4-methylmorpholine (0.227 ml, 2.07 mmol), and 1-ethyl-3-(3-dimethylaminopropyl)carbodiimide hydrochloride (198 mg, 1.03 mmol) were added at room temperature. After stirring for 17 hours at room temperature, the reaction mixture was washed with 0.5 N hydrochloric acid. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure to obtain the title compound (373 mg, 0.86 mmol, 91%) as a white solid.

$^1$H-NMR (400 MHz, CDCl$_3$) δ: 2.23 (3H, s), 3.12 (3H, s), 3.13 (3H, s), 5.77 (1H, s), 6.75-6.83 (1H, m), 6.91-6.99 (2H, m), 7.02-7.11 (1H, m), 7.33-7.39 (2H, m), 7.42 (1H, s), 9.07 (1H, s).

MS m/z: 435 (M$^+$+H).

Example 36

5-[[(4-Fluorophenyl)sulfonyl](2,3,6-trifluorophenyl)methyl]-N,N,4-trimethylpyridine-2-carboxamide (Compound A), and 5-[[(4-fluorophenyl)sulfinyl](2,3,6-trifluorophenyl)methyl]-N,N,4-trimethylpyridine-2-carboxamide (Compound B)

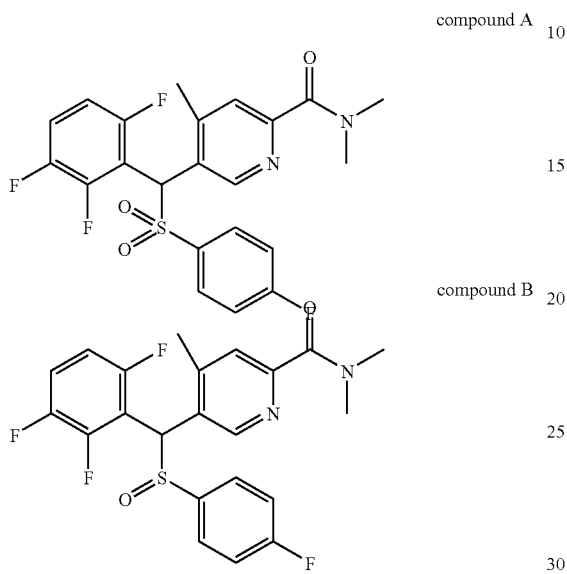

compound A compound B

To a solution of 5-[[(4-fluorophenyl)thio](2,3,6-trifluorophenyl)methyl]-N,N,4-trimethylpyridine-2-carboxamide (370 mg, 0.85 mmol) in methylene chloride (10 ml), 3-chloroperbenzoic acid (283 mg, 1.07 mmol) was added at 0° C. After stirring for 18 hours at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=1:1 was concentrated under reduced pressure, and the resulting residue was washed with a mixed solvent of ethanol and diethyl ether, and was collected by filtration, to obtain the title compound A (110 mg, 0.24 mmol, 28%) as a white solid. Next, the fraction obtained from an elution with hexane:ethyl acetate=1:4 was concentrated under reduced pressure, and the resulting residue was washed with a mixed solvent of ethanol and diethyl ether, and was collected by filtration, to obtain the title compound B (157 mg, 0.35 mmol, 41%) as a white solid.

Compound A
$^1$H-NMR (400 MHz, CDCl$_3$) δ: 2.13 (3H, s), 3.13 (3H, s), 3.15 (3H, s), 5.90 (1H, s), 6.82-6.90 (1H, m), 7.13-7.24 (3H, m), 7.47 (1H, s), 7.75-7.82 (2H, m), 9.40 (1H, s).
IR(ATR)cm$^{-1}$: 1631, 1587, 1491, 1406, 1329, 1234, 1146.
Anal. Calcd for C$_{22}$H$_{18}$F$_4$N$_2$O$_3$S: C, 56.65; H, 3.89; F, 16.29; N, 6.01; S, 6.87. Found: C, 56.63; H, 3.91; F, 16.54; N, 6.01; S, 7.04.
MS m/z: 467 (M$^+$+H).

Compound B
$^1$H-NMR (400 MHz, CDCl$_3$) δ: 1.88 (0.9H, s), 2.36 (2.1H, s), 3.10 (0.9H, s), 3.13 (0.9H, s), 3.14 (2.1H, s), 3.15 (2.1H, s), 5.41 (0.3H, s), 5.44 (0.7H, s), 6.72-6.80 (0.7H, m), 6.91-6.98 (0.3H, m), 7.02-7.23 (3H, m), 7.36 (0.3H, s), 7.42-7.47 (0.6H, m), 7.51 (0.7H, s), 7.55-7.61 (1.4H, m), 9.00 (0.3H, s), 9.12 (0.7H, s).
IR(ATR)cm$^{-1}$: 1637, 1589, 1491, 1223, 1086, 1066.
Anal. Calcd for C$_{22}$H$_{18}$F$_4$N$_2$O$_2$S: C, 58.66; H, 4.03; F, 16.87; N, 6.22; S, 7.12. Found: C, 58.51; H, 3.98; F, 16.84; N, 6.15; S, 7.22.
MS m/z: 451 (M$^+$+H).

Example 37

5-[[(4-Fluorophenyl)thio](2,3,6-trifluorophenyl)methyl]-4-methylpyridine-2-carboxamide

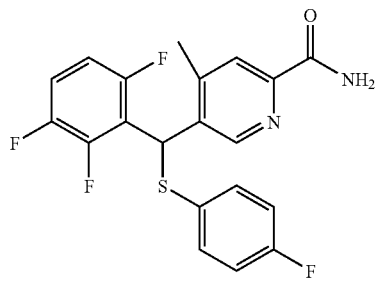

To a solution of 5-[[(4-fluorophenyl)thio](2,3,6-trifluorophenyl)methyl]-4-m ethylpyridine-2-carboxylic acid (407 mg, 1.00 mmol) obtained in Example 34 in N,N-dimethylformamide (10 ml), (benzotriazol-1-yloxy)tripyrrolidinophosphonium hexafluorophosphate (781 mg, 1.50 mmol), 1-hydroxybenzotriazole (203 mg, 1.50 mmol), ammonium chloride (107 mg, 2.00 mmol), and N-ethyldiisopropylamine (0.697 ml, 4.00 mmol) were added in an argon atmosphere at room temperature. After stirring for 16 hours at room temperature, ethyl acetate was added to the reaction mixture, and the resulting mixture was washed with 0.5 N hydrochloric acid. The organic layer was dried over anhydrous sodium sulfate and filtered, then the filtrate was concentrated under reduced pressure, and the resulting residue was subjected to flash silica gel chromatography. The fraction obtained from an elution with hexane:ethyl acetate=2:1 was concentrated under reduced pressure to obtain the title compound (392 mg, 0.96 mmol, 96%) as a white solid.
$^1$H-NMR (400 MHz, CDCl$_3$) δ: 2.25 (3H, s), 5.55 (1H, br s), 5.78 (1H, s), 6.75-6.83 (1H, m) 6.92-6.99 (2H, m), 7.02-7.12 (1H, m), 7.32-7.38 (2H, m), 7.84 (1H, br s), 7.96 (1H, s), 9.08 (1H, s).
MS m/z: 407 (M$^+$+H).

Example 38

5-[[(4-Fluorophenyl)sulfinyl](2,3,6-trifluorophenyl)methyl]-4-methylpyridine-2-carboxamide

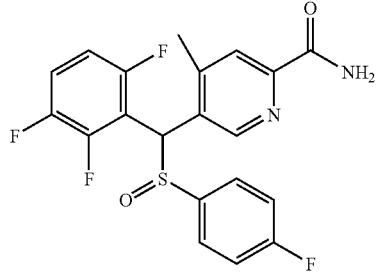

To a solution of 5-[[(4-fluorophenyl)thio](2,3,6-trifluorophenyl)methyl]-4-m ethylpyridine-2-carboxamide (389 mg, 0.96 mmol) in methylene chloride (10 ml), 3-chloroperbenzoic acid (254 mg, 0.96 mmol) was added at 0° C. After stirring for 13 days at room temperature, the reaction mixture was washed with 1 N aqueous sodium hydroxide. The organic layer was dried over anhydrous sodium sulfate and filtered, then the filtrate was concentrated under reduced pressure, and the resulting residue was subjected to preparative thin-layer chromatography (developed with hexane:ethyl acetate=1:2, eluted with methylene chloride:methanol=4:1). The obtained fraction was concentrated under reduced pressure, and the resulting residue was washed with a mixed solvent of ethanol and diethyl ether, and was collected by filtration, to obtain the title compound (78 mg, 0.18 mmol, 19%) as a white solid.

$^1$H-NMR (400 MHz, CDCl$_3$) δ: 2.36 (3H, s), 5.46 (1H, s), 5.60 (1H, br s), 6.74-6.82 (1H, m), 7.04-7.16 (3H, m), 7.52-7.59 (2H, m), 7.85 (1H, br s), 8.05 (1H, s), 9.12 (1H, s).

IR(ATR)cm$^{-1}$: 3446, 3209, 1689, 1587, 1495, 1412, 1342, 1230, 1043.

Anal. Calcd for C$_{20}$H$_{14}$F$_4$N$_2$O$_2$S: C, 56.87; H, 3.34; F, 17.99; N, 6.63; S, 7.59. Found: C, 56.66; H, 3.38; F, 18.12; N, 6.63; S, 7.65.

MS m/z: 423 (M$^+$+H).

Example 39

5-[[(4-Fluorophenyl)sulfonyl](2,3,6-trifluorophenyl) methyl]-4-methylpyridine-2-carboxamide

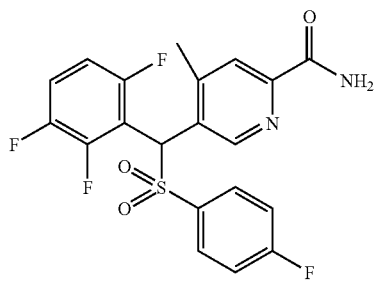

To a solution of 5-[[(4-fluorophenyl)sulfinyl](2,3,6-trifluorophenyl)methyl]-4-methylpyridine-2-carboxamide (106 mg, 0.25 mmol) in methylene chloride (5 ml), 3-chloroperbenzoic acid (66 mg, 0.25 mmol) was added at 0° C. After stirring for 5 days at room temperature, the reaction mixture was washed with 1 N aqueous sodium hydroxide. The organic layer was dried over anhydrous sodium sulfate and filtered, then the filtrate was concentrated under reduced pressure, and the obtained residue was subjected to preparative thin-layer chromatography (developed with hexane:ethyl acetate=2:3, eluted with methylene chloride:methanol=4:1). The obtained fraction was concentrated under reduced pressure, and the resulting residue was washed with a mixed solvent of ethanol and diethyl ether, and was collected by filtration, to obtain the title compound (67 mg, 0.15 mmol, 61%) as a white solid.

$^1$H-NMR (400 MHz, CDCl$_3$) δ: 2.14 (3H, s), 5.59 (1H, br s), 5.90 (1H, s), 6.82-6.90 (1H, m), 7.14-7.25 (3H, m), 7.73-7.79 (2H, m), 7.87 (1H, br s), 7.98 (1H, s), 9.43 (1H, s).

IR(ATR)cm$^{-1}$: 3396, 3167, 1687, 1587, 1496, 1419, 1296, 1234, 1144, 1078, 845, 816.

Anal. Calcd for C$_{20}$H$_{14}$F$_4$N$_2$O$_3$S: C, 54.79; H, 3.22; F, 17.33; N, 6.39; S, 7.31. Found: C, 54.54; H, 3.26; F, 17.17; N, 6.37; S, 7.39.

MS m/z: 439 (M$^+$+H).

Example 40

2-Bromo-5-[(2,5-difluorophenyl)[(4-methoxyphenyl) thio]methyl]-4-methylpyridine

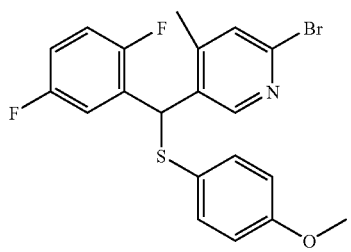

To a solution of 2-bromo-5-[chloro(2,5-difluorophenyl) methyl]-4-methylpyridine (1.00 g, 3.01 mmol) obtained in Reference Example 2 in N,N-dimethylformamide (15 ml), 4-methoxybenzenethiol (0.381 ml, 3.01 mmol) and then potassium carbonate (457 mg, 3.31 mmol) were added in an argon atmosphere at 0° C., and the resulting mixture was stirred for 13 hours at room temperature. Ethyl acetate and water were added to the reaction mixture at 0° C., and after the organic layer was separated, the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=20:1 was concentrated under reduced pressure to obtain the title compound (1.08 g, 2.48 mmol, 82%) as a white solid.

$^1$H-NMR (400 MHz, CDCl$_3$) δ: 2.26 (3H, s), 3.77 (3H, s), 5.66 (1H, s), 6.77 (2H, d, J=8.5 Hz), 6.89-6.98 (2H, m), 7.25 (1H, s), 7.29 (2H, d, J=8.5 Hz), 7.31-7.38 (1H, m), 8.43 (1H, s).

MS m/z: 436, 438 (M$^+$+H).

Example 41

5-[(2,5-Difluorophenyl)[(4-methoxyphenyl)thio] methyl]-4-methylpyridine-2-carbaldehyde

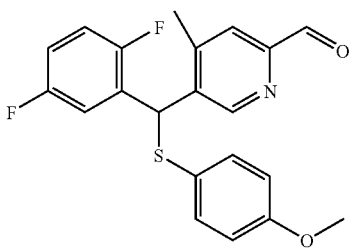

To a solution of 2-bromo-5-[(2,5-difluorophenyl)[(4-methoxyphenyl)thio]methyl]-4-methylpyridine (1.08 g, 2.48 mmol) in toluene (30 ml), a hexane solution of n-butyllithium (1.54 M, 1.77 ml, 2.72 mmol) was added in an argon atmosphere at −78° C. The reaction mixture was stirred for 30 minutes at −40° C., and then cooled again to −78° C., and N,N-dimethylformamide (0.221 ml, 2.72 mmol) was added thereto. After stirring the reaction mixture for 2 hours, water was added thereto at the same temperature, and the mixture was allowed to warm to room temperature. Ethyl acetate was added to the reaction mixture, and the resulting mixture was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=10:1 was concentrated under reduced pressure to obtain the title compound (597 mg, 1.55 mmol, 63%) as a yellow oily substance.

$^1$H-NMR (400 MHz, CDCl$_3$) δ: 2.36 (3H, s), 3.76 (3H, s), 5.77 (1H, s), 6.77 (2H, d, J=8.8 Hz), 6.93-6.98 (2H, m), 7.29 (2H, d, J=8.8 Hz), 7.42-7.47 (1H, m), 7.71 (1H, s), 8.82 (1H, s), 10.02 (1H, s).

MS m/z: 386 (M$^+$+H).

Example 42

5-[(2,5-Difluorophenyl)[(4-methoxyphenyl)sulfonyl] methyl]-4-methylpyridine-2-carboxylic acid

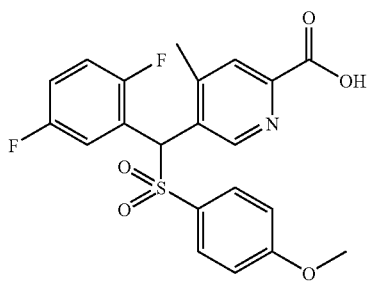

31% aqueous hydrogen peroxide (1.50 ml) was added to a solution of 5-[(2,5-difluorophenyl)[(4-methoxyphenyl)thio] methyl]-4-methylpyridine-2-carbaldehyde (595 mg, 1.54 mmol) in formic acid (15 ml), and the resulting mixture was stirred for 3 hours at room temperature. Water was added to the reaction mixture, and the solid thus precipitated was collected by filtration, and was washed with 0.01 N hydrochloric acid. The obtained solid was dissolved in methylene chloride, and the solution was washed with 0.1 N hydrochloric acid. Subsequently, the organic layer was dried over anhydrous sodium sulfate and filtered, and then the filtrate was concentrated under reduced pressure. The resulting residue was washed with a mixed solvent of ethanol and hexane, and was collected by filtration to obtain the title compound (404 mg, 0.93 mmol, 60%) as a white solid.

$^1$H-NMR (400 MHz, CDCl$_3$) δ: 2.25 (3H, s), 3.87 (3H, s), 5.95 (1H, s), 6.91 (2H, d, J=8.8 Hz), 6.93-6.99 (1H, m), 7.01-7.08 (1H, m), 7.59 (2H, d, J=8.8 Hz), 7.80-7.86 (1H, m), 7.98 (1H, s), 9.18 (1H, s).

mp: 194-195° C.

MS m/z: 434 (M$^+$+H).

Example 43

5-[(2,5-Difluorophenyl)[(4-methoxyphenyl)sulfonyl] methyl]-N-(2-hydroxyethyl)-4-methylpyridine-2-carboxamide

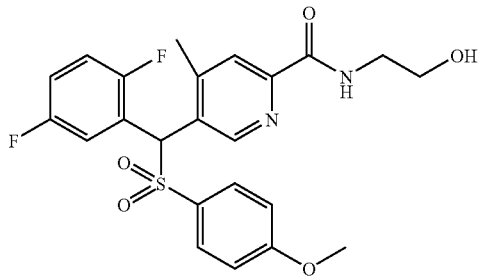

To a solution of 5-[(2,5-difluorophenyl)[(4-methoxyphenyl)sulfonyl]methyl]-4-methylpyridine-2-carboxylic acid (108 mg, 0.25 mmol) in methylene chloride (3 ml), 2-aminoethanol (0.017 ml, 0.28 mmol), 1-hydroxybenzotriazole (37 mg, 0.28 mmol), 4-methylmorpholine (0.0.0 ml, 0.28 mmol), and 1-ethyl-3-(3-dimethylaminopropyl)carbodiimide hydrochloride (53 mg, 0.28 mmol) were added at room temperature. After stirring for 17 hours at room temperature, the reaction mixture was washed with water and then with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=1:4 was concentrated under reduced pressure, and the resulting residue was washed with a mixed solvent of ethanol and diethyl ether, and then was collected by filtration, to obtain the title compound (96 mg, 0.20 mmol, 81%) as a white solid.

$^1$H-NMR (400 MHz, CDCl$_3$) δ: 2.15 (3H, s), 2.56 (1H, br s), 3.62-3.68 (2H, m), 3.82-3.88 (2H, m), 3.86 (3H, s), 5.93 (1H, s), 6.90 (2H, d, J=8.8 Hz), 6.92-7.07 (2H, m), 7.57 (2H, d, J=8.8 Hz), 7.82-7.88 (1H, m), 7.93 (1H, s), 8.40 (1H, br t, J=5.6 Hz), 9.11 (1H, s).

IR(ATR)cm$^{-1}$: 3456, 3367, 1653, 1591, 1535, 1493, 1294, 1265, 1147.

mp: 134-135° C.

Anal. Calcd for C$_{23}$H$_{22}$F$_2$N$_2$O$_5$S: C, 57.97; H, 4.65; F, 7.97; N, 5.88; S, 6.73. Found: C, 57.93; H, 4.39; F, 8.18; N, 5.91; S, 6.79.

MS m/z: 477 (M$^+$+H).

Reference Example 5

O-ethyl S-(3-fluoro-4-methoxyphenyl)dithiocarbonate

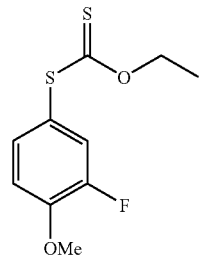

3-Fluoro-4-methoxyaniline (5.0 g, 35.4 mmol) was dissolved in methanol (35 ml), and 1 N hydrochloric acid (106 ml) was added thereto at −5° C. Subsequently, a solution of sodium nitrite (2.9 g, 42.5 mmol) in water (20 ml) was added dropwise to the mixture, which was then stirred for 30 minutes at the same temperature. The resulting reaction solution was added dropwise to a solution of O-ethyl potassium dithiocarbonate (8.5 g, 53.1 mmol) in water (100 ml) at 65° C. The reaction mixture was heated to 90° C., stirred for 30 minutes, and then cooled to room temperature. Water was added thereto and the mixture was extracted two times with ethyl acetate. The combined organic layer was washed sequentially with water (2 times), saturated aqueous sodium hydrogencarbonate, and saturated brine. The organic layer was dried over anhydrous sodium sulfate and filtered, and then the filtrate was concentrated under reduced pressure. The resulting residue was subjected to flash silica gel column chromatography. The fraction obtained from an elution with hexane:ethyl acetate=99:1 was concentrated under reduced pressure to obtain the title compound (3.0 g, 12.2 mmol, 34%) as a yellow oily substance.

$^1$H-NMR (400 MHz, CDCl$_3$) δ: 1.33-1.37 (3H, m), 3.93 (3H, s), 4.60-4.63 (2H, m), 6.98-7.00 (1H, m), 7.23-7.25 (2H, m).

Example 44

2-Bromo-5-[(2,5-difluorophenyl)[(3-fluoro-4-methoxyphenyl)thio]methyl]-4-methylpyridine

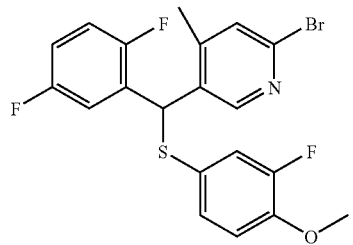

To a solution of O-ethyl S-(3-fluoro-4-methoxyphenyl) dithiocarbonate (1.23 g, 5.00 mmol) methanol (15 ml), 1 N aqueous sodium hydroxide (15 ml) was added, and the resulting mixture was stirred for 2 hours at 50° C. The reaction mixture was cooled to room temperature, and was washed with methylene chloride. Subsequently, the aqueous layer was acidified with 1 N hydrochloric acid, and extracted with methylene chloride. The organic layer was dried over anhydrous sodium sulfate and filtered, and then the filtrate was concentrated under reduced pressure. To a solution of the resulting residue and 2-bromo-5-[chloro(2,5-difluorophenyl)methyl]-4-methylpyridine (1.66 g, 5.00 mmol) obtained in Reference Example 2 in N,N-dimethylformamide (25 ml), potassium carbonate (760 mg, 5.50 mmol) was added in a nitrogen atmosphere, and the resulting mixture was stirred for 19 hours at room temperature. Ethyl acetate and water were added to the reaction mixture at 0° C., the organic layer was separated, and then the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=10:1 was concentrated under reduced pressure to obtain the title compound (1.85 g, 4.07 mmol, 81%) as a green oily substance.

$^1$H-NMR (400 MHz, CDCl$_3$) δ: 2.29 (3H, s), 3.85 (3H, s), 5.69 (1H, s), 6.79-7.12 (5H, m), 7.28 (1H, s), 7.28-7.33 (1H, m), 8.42 (1H, m).

Example 45

5-[(2,5-Difluorophenyl)[(3-fluoro-4-methoxyphenyl)thio]methyl]-4-methylpyridine-2-carbaldehyde

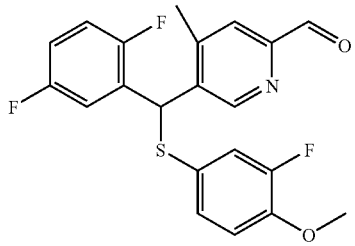

To a solution of 2-bromo-5-[(2,5-difluorophenyl)[(3-fluoro-4-methoxyphenyl)thio]methyl]-4-methylpyridine (1.85 g, 4.07 mmol) in toluene (40 ml), a hexane solution of n-butyllithium (1.54 M, 3.17 ml, 4.89 mmol) was added in an argon atmosphere at −78° C. The reaction mixture was stirred for 30 minutes at −40° C., and then was cooled again to −78° C., and N,N-dimethylformamide (0.378 ml, 4.89 mmol) was added. After completion of dropwise addition, the reaction mixture was allowed to warm to 0° C., and water was added at the same temperature. Ethyl acetate was added to the reaction mixture, the organic layer was separated, and the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=12:1 was concentrated under reduced pressure to obtain the title compound g, 2.97 mmol, 73%) as a yellow oily substance.

$^1$H-NMR (400 MHz, CDCl$_3$) δ: 2.40 (3H, s), 3.85 (3H, s), 5.80 (1H, s), 6.79-6.85 (1H, m), 6.94-7.01 (2H, m), 7.06-7.13 (2H, m), 7.36-7.42 (1H, m), 7.73 (1H, s), 8.82 (1H, m), 10.03 (1H, s).

Example 46

5-[(2,5-Difluorophenyl)[(3-fluoro-4-methoxyphenyl)sulfonyl]methyl]-4-methylpyridine-2-carboxylic acid

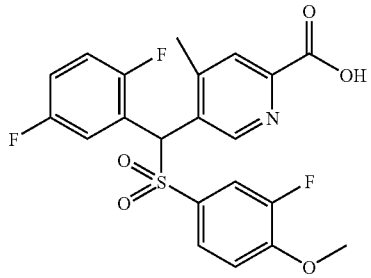

31% aqueous hydrogen peroxide (3 ml) was added to a solution of 5-[(2,5-difluorophenyl) [(3-fluoro-4-methoxyphenyl)thio]meth yl]-4-methylpyridine-2-carbaldehyde (1.20 g, 2.97 mmol) in formic acid (30 ml), and the resulting mixture was stirred for 2 hours at room temperature. Water was added to the reaction mixture, and the solid thus precipitated was collected by filtration and washed with 0.01 N hydrochloric acid. The resulting solid was dissolved in methylene chloride, and the solution was washed with 0.1 N hydrochloric acid. Subsequently, the organic layer was dried over anhydrous sodium sulfate and filtered, and then the filtrate was concentrated under reduced pressure. The resulting residue was washed with a mixed solvent of ethanol and hexane, and was collected by filtration to obtain the title compound (825 mg, 1.83 mmol, 61%) as a white solid.

$^1$H-NMR (400 MHz, CDCl$_3$) δ: 2.31 (3H, s), 3.96 (3H, s), 5.97 (1H, s), 6.91-7.10 (3H, m), 7.37-7.45 (2H, m), 7.72-7.78 (1H, m), 8.02 (1H, s), 9.21 (1H, s).

mp: 196-197° C.

MS m/z: 452 (M$^+$+H).

Example 47

5-[(2,5-Difluorophenyl)[(3-fluoro-4-methoxyphenyl)sulfonyl]methyl]-N-(2-hydroxyethyl)-4-methylpyridine-2-carboxamide

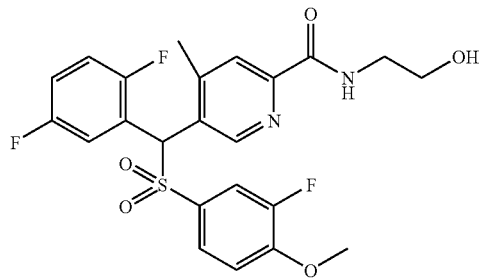

To a solution of 5-[(2,5-difluorophenyl)[(3-fluoro-4-methoxyphenyl)sulfonyl]methyl]-4-methylpyridine-2-carboxylic acid (113 mg, 0.25 mmol) in methylene chloride (3 ml), 2-aminoethanol (0.017 ml, 0.28 mmol), 1-hydroxybenzotriazole (37 mg, 0.28 mmol), 4-methylmorpholine (0.030 ml, 0.28 mmol), and 1-ethyl-3-(3-dimethylaminopropyl)carbodiimide hydrochloride (53 mg, 0.28 mmol) were added at room temperature. After stirring for 19 hours at room temperature, the reaction mixture was washed with water and then with saturated brine. The organic layer was dried over anhydrous sodium sulfate and filtered, then the filtrate was concentrated under reduced pressure, and the obtained residue was subjected to flash silica gel chromatography. The fraction obtained from an elution with ethyl acetate was concentrated under reduced pressure, and the resulting residue was washed with a mixed solvent of ethanol and diethyl ether, and was collected by filtration, to obtain the title compound (99 mg, 0.20 mmol, 80%) as a white solid.

$^1$H-NMR (400 MHz, CDCl$_3$) δ: 2.22 (3H, s), 2.55 (1H, br s), 3.62-3.68 (2H, m), 3.85 (2H, t, J=4.9 Hz), 3.95 (3H, s), 5.95 (1H, s), 6.92-7.08 (3H, m), 7.37-7.45 (2H, m), 7.74-7.80 (1H, m), 7.96 (1H, s), 8.40 (1H, br t, J=5.4 Hz), 9.14 (1H, s).

IR(ATR)cm$^{-1}$: 3460, 3371, 1651, 1599, 1535, 1493, 1281, 1219, 1134.

mp: 137-138° C.

Anal. Calcd for C$_{23}$H$_{21}$F$_3$N$_2$O$_5$S: C, 55.87; H, 4.28; F, 11.53; N, 5.67; S, 6.48. Found: C, 55.73; H, 4.00; F, 11.77; N, 5.66; S, 6.58.

MS m/z: 495 (M$^+$+H).

Reference Example 6

S-(4-ethoxyphenyl)O-ethyl dithiocarbonate

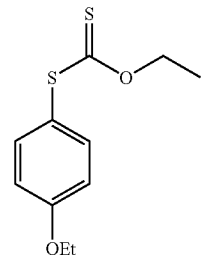

4-Ethoxyaniline (5.0 g, 36.4 mmol) was dissolved in methanol (20 ml), and 1 N hydrochloric acid (110 ml) was added thereto at −10° C. Subsequently, a solution of sodium nitrite (3.0 g, 43.7 mmol) in water (20 ml) was added dropwise, and the resulting mixture was stirred for 30 minutes at the same temperature. The obtained reaction solution was added dropwise to a solution of O-ethyl potassium dithiocarbonate (8.8 g, 54.6 mmol) in water (100 ml) at 65° C. The reaction mixture was heated to 90° C., stirred for 30 minutes, and then cooled to room temperature. Water was added to the mixture, which was then extracted twice with ethyl acetate. The combined organic layer was washed sequentially with water (2 times), saturated aqueous sodium hydrogencarbonate and saturated brine. The organic layer was dried over anhydrous sodium sulfate and filtered, and then the filtrate was concentrated under reduced pressure. The resulting residue was subjected to flash silica gel column chromatography. The fraction obtained from an elution with hexane:ethyl acetate=99:1 was concentrated under reduced pressure to obtain the title compound (2.08 g, 8.58 mmol, 24%) as a yellow oily substance.

$^1$H-NMR (400 MHz, CDCl$_3$) δ: 1.24-1.43 (6H, m), 4.03-4.07 (2H, m), 4.60 (2H, q, J=7.1 Hz), 6.92-6.93 (2H, m), 7.38-7.40 (2H, m).

Example 48

2-Bromo-5-[(2,5-difluorophenyl) [(4-ethoxyphenyl)thio]methyl]-4-methylpyridine

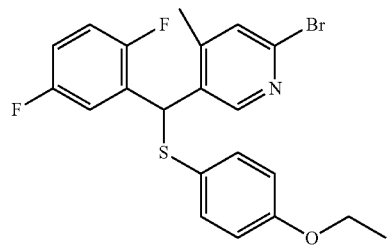

To a solution of S-(4-ethoxyphenyl)O-ethyl dithiocarbonate (1.45 g, 6.00 mmol) in ethanol (15 ml), 1 N aqueous sodium hydroxide (15 ml) was added, and the resulting mixture was stirred for 2 hours at 50° C. The reaction mixture was cooled to room temperature, and was washed with methylene chloride. Subsequently, the aqueous layer was acidified with 1 N hydrochloric acid, and extracted with methylene chloride. The organic layer was dried over anhydrous sodium sulfate and filtered, and then the filtrate was concentrated under reduced pressure. To a solution of the resulting residue and 2-bromo-5-[chloro(2,5-difluorophenyl)methyl]-4-methylpyridine (1.66 g, 5.00 mmol) obtained in Reference Example 2 in N,N-dimethylformamide (25 ml), potassium carbonate (760 mg, 5.50 mmol) was added in a nitrogen atmosphere, and the resulting mixture was stirred for 3 hours at room temperature. Ethyl acetate and water were added to the reaction mixture at 0° C., the organic layer was separated, and then the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=20:1 was concentrated under reduced pressure to obtain the title compound (1.18 g, 2.62 mmol, 52%) as a pale green solid.

$^1$H-NMR (400 MHz, CDCl$_3$) δ: 1.39 (3H, t, J=7.1 Hz), 2.25 (3H, s), 3.98 (2H, q, J=7.1 Hz), 5.65 (1H, s), 6.75 (2H, d, J=8.8 Hz), 6.89-6.98 (2H, m), 7.25 (1H, m), 7.27 (2H, d, J=8.8 Hz), 7.31-7.37 (1H, m), 8.43 (1H, m).

Example 49

5-[(2,5-Difluorophenyl)[(4-ethoxyphenyl)thio]methyl]-4-methylpyridine-2-carbaldehyde

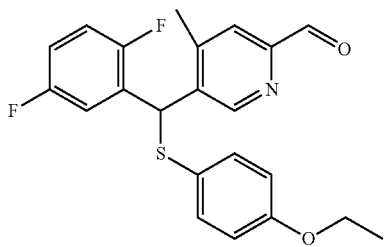

To a solution of 2-bromo-5-[(2,5-difluorophenyl)[(4-ethoxyphenyl)thio]methyl]-4-methylpyridine (1.18 g, 2.62 mmol) in toluene (30 ml), a hexane solution of n-butyllithium (1.54 M, 2.04 ml, 3.14 mmol) was added in an argon atmosphere at −78° C. The reaction mixture was stirred for 30 minutes at −40° C., and then cooled again to −78° C., and N,N-dimethylformamide (0.243 ml, 3.14 mmol) was added thereto. After completion of dropwise addition, the reaction mixture was allowed to warm to −40° C., and water was added at the same temperature. Ethyl acetate was added to the reaction mixture, the organic layer was separated, and then the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=10:1 was concentrated under reduced pressure to obtain the title compound (786 mg, 1.97 mmol, 75%) as a white solid.

$^1$H-NMR (400 MHz, CDCl3) δ: 1.38 (3H, t, J=7.1 Hz), 2.36 (3H, s), 3.98 (2H, q, J=7.1 Hz), 5.76 (1H, s), 6.75 (2H, d, J=8.6 Hz), 6.92-6.99 (2H, m), 7.27 (2H, d, J=8.6 Hz), 7.41-7.48 (1H, m), 7.71 (1H, s), 8.82 (1H, s), 10.02 (1H, s).

Example 50

5-[(2,5-Difluorophenyl)[(4-ethoxyphenyl)sulfonyl]methyl]-4-methylpyridine-2-carboxylic acid

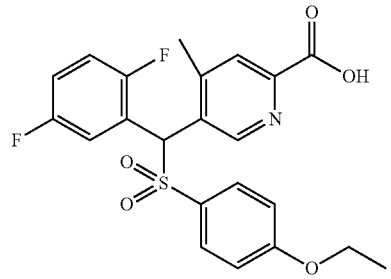

31% aqueous hydrogen peroxide (2 ml) was added to a solution of 5-[(2,5-difluorophenyl)[(4-ethoxyphenyl)thio]methyl]-4-meth ylpyridine-2-carbaldehyde (783 mg, 1.96 mmol) in formic acid (20 ml), and the resulting mixture was stirred for 2 hours at room temperature. Water was added to the reaction mixture, and the solid thus precipitated was collected by filtration, and washed with water. The resulting solid was dissolved in methylene chloride, and the solution was washed with 0.1 N hydrochloric acid. Subsequently, the organic layer was dried over anhydrous sodium sulfate and filtered, and then the filtrate was concentrated under reduced pressure. The resulting residue was washed with a mixed solvent of ethanol and hexane, and was collected by filtration, to obtain the title compound (797 mg, 1.78 mmol, 91%) as a white solid.

$^1$H-NMR (400 MHz, CDCl$_3$) δ: 1.44 (3H, t, J=7.1 Hz), 2.24 (3H, s), 4.08 (2H, q, J=7.1 Hz), 5.95 (1H, s), 6.89 (2H, d, J=8.8 Hz), 6.92-6.99 (1H, m), 7.01-7.08 (1H, m), 7.57 (2H, d, J=8.8 Hz), 7.80-7.86 (1H, m), 7.98 (1H, s), 9.17 (1H, s).

MS m/z: 448 (M$^+$+H).

Example 51

5-[(2,5-Difluorophenyl)[(4-ethoxyphenyl)sulfonyl]methyl]-N-(2-hydroxyethyl)-4-methylpyridine-2-carboxamide

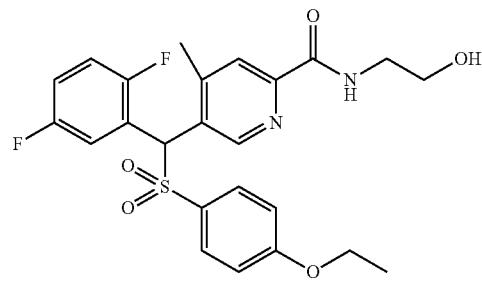

To a solution of 5-[(2,5-difluorophenyl)[(4-ethoxyphenyl)sulfonyl]methyl]-4-methylpyridine-2-carboxylic acid (112 mg, 0.25 mmol) in methylene chloride (3 ml), 2-aminoethanol (0.017 ml, 0.28 mmol), 1-hydroxybenzotriazole (37 mg, 0.28 mmol), 4-methylmorpholine (0.030 ml, 0.28 mmol), and 1-ethyl-3-(3-dimethylaminopropyl)carbodiimide hydrochloride (53 mg, 0.28 mmol) were added at room temperature. After stirring for 3 hours at room temperature, the reaction mixture was washed with water and then saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=1:2 was concentrated under reduced pressure, and the resulting residue was washed with a mixed solvent of ethanol and diethyl ether, and was collected by filtration to obtain the title compound mg, 0.20 mmol, 79%) as a white solid.

$^1$H-NMR (400 MHz, CDCl$_3$) δ: 1.44 (3H, t, J=7.1 Hz), 2.15 (3H, s), 2.57 (1H, br t, J=5.1 Hz), 3.62-3.68 (2H, m), 3.82-3.88 (2H, m), 4.07 (2H, q, J=7.1 Hz), 5.93 (1H, s), 6.87 (2H, d, J=8.8 Hz), 6.92-7.06 (2H, m), 7.56 (2H, d, J=8.8 Hz), 7.82-7.89 (1H, m), 7.92 (1H, s), 8.40 (1H, br t, J=5.6 Hz), 9.11 (1H, s).

IR(ATR)cm$^{-1}$: 3381, 1668, 1593, 1527, 1493, 1321, 1269, 1140.

Anal. Calcd for C$_{24}$H$_{24}$F$_2$N$_2$O$_5$S: C, 58.77; H, 4.93; F, 7.75; N, 5.71; S, 6.54. Found: C, 58.41; H, 4.90; F, 7.91; N, 5.73; S, 6.66.

MS m/z: 491 (M$^+$+H).

Reference Example 7

5-(Trifluoromethyl)pyridine-2-thiol

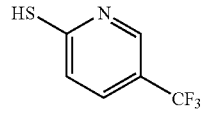

Thiourea (684 mg, 8.80 mmol) was added to a solution of 2-chloro-5-(trifluoromethyl)pyridine (1.45 g, 8.00 mmol) in ethanol (4 ml), and the resulting mixture was heated to reflux for 2 hours. The reaction mixture was cooled to room temperature, subsequently a solution of potassium hydroxide (792 mg, 12.0 mmol) in water (4 ml) was added thereto, and the resulting mixture was heated to reflux for 2 hours. The reaction mixture was cooled again to room temperature, and 1 N sodium hydroxide and methylene chloride were added thereto. After the aqueous layer was separated, acetic acid added to the aqueous layer, which was then extracted with methylene chloride. The organic layer was dried over anhydrous sodium sulfate and filtered, and then the filtrate was concentrated under reduced pressure. The obtained residue was washed with a mixed solvent of to hexane and diethyl ether, and was collected by filtration to obtain the title compound (860 mg, 4.80 mmol, 60%) as a pale yellow solid.

$^1$H-NMR (400 MHz, CDCl$_3$) δ: 7.45 (1H, dd, J=9.0, 2.2 Hz), 7.59 (1H, d, J=9.0 Hz), 7.81 (1H, m).

MS m/z: 180 (M$^+$+H).

Example 52

2-Bromo-5-[(2,5-difluorophenyl)[[5-(trifluoromethyl)pyridin-2-yl]thio]methyl]-4-methylpyridine

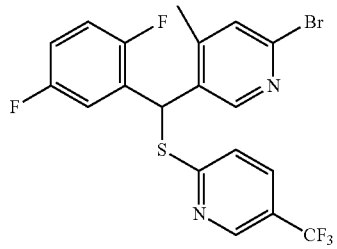

To a solution of 2-bromo-5-[chloro(2,5-difluorophenyl) methyl]-4-methylpyridine (1.59 g, 4.78 mmol) obtained in Reference Example 2 in N,N-dimethylformamide (25 ml), 5-(trifluoromethyl)pyridine-2-thiol (857 mg, 4.78 mmol) and then potassium carbonate (992 mg, 7.18 mmol) were added in an argon atmosphere at 0° C., and the resulting mixture was stirred for 2 hours at room temperature. Ethyl acetate and water were added to the reaction mixture at 0° C., the organic layer was separated, and then the organic layer was washed with saturated brine. The organic layer was dried over anhydrous sodium sulfate and filtered, then the filtrate was concentrated under reduced pressures and the obtained residue was subjected to flash silica gel chromatography. The fraction obtained from an elution with hexane:ethyl acetate=20:1 was concentrated under reduced pressure to obtain the title compound (1.97 g, 4.15 mmol, 87%) as a pale green oily substance.

$^1$H-NMR (400 MHz, CDCl$_3$) δ: 2.43 (3H, s), 6.72 (1H, s), 6.93-7.07 (2H, m), 7.19-7.25 (1H, m), 7.28 (1H, d, J=8.3 Hz), 7.32 (1H, s), 7.70 (1H, dd, J=8.3, 2.2 Hz), 8.35 (1H, m), 8.58-8.60 (1H, m).

MS m/z: 475, 477 (M$^+$+H).

Example 53

5-[(2,5-Difluorophenyl)[[5-(trifluoromethyl)pyridin-2-yl]thio]methyl]-4-methylpyridine-2-carbaldehyde

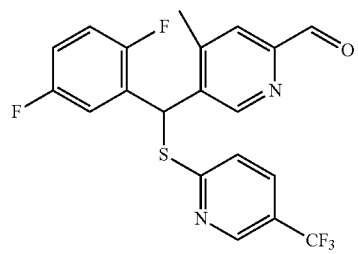

To a solution of 2-bromo-5-[(2,5-difluorophenyl)[[5-(trifluoromethyl)pyridin-2-yl]thio]methyl]-4-methylpyridine (1.97 g, 4.15 mmol) in toluene (45 ml), a hexane solution of n-butyllithium (1.54 M, 3.23 ml, 4.97 mmol) was added in an argon atmosphere at −78° C. The reaction mixture was stirred for 30 minutes at −40° C., and then cooled again to −78° C., and N,N-dimethylformamide (0.385 ml, 4.97 mmol) was added thereto. After completion of dropwise addition, the reaction mixture was allowed to warm to 0° C., and water was added thereto at the same temperature. Ethyl acetate was added to the reaction mixture, the organic layer was separated, and then the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=15:1 was concentrated under reduced pressure to obtain the title compound (1.07, 2.52 mmol, 61%) as a yellow oily substance.

$^1$H-NMR (400 MHz, CDCl$_3$) δ: 2.56 (3H, s), 6.85 (1H, s), 6.95-7.09 (2H, m), 7.23-7.29 (1H, m) 7.31 (1H, d, J=8.5 Hz), 7.71 (1H, dd, J=8.5, 2.0 Hz), 7.79 (1H, m) 8.58-8.60 (1H, m), 8.79 (1H, s), 10.02 (1H, s).

Example 54

5-[(2,5-Difluorophenyl)[[5-(trifluoromethyl)pyridin-2-yl]sulfonyl]methyl]-4-methylpyridine-2-carboxylic acid

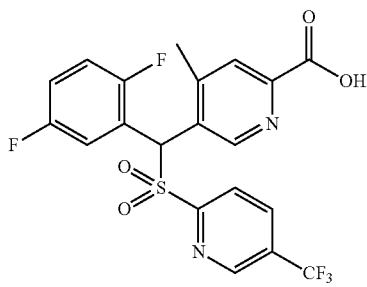

31% aqueous hydrogen peroxide (2 ml) was added to a solution of 5-[(2,5-difluorophenyl)[[5-(trifluoromethyl)pyridin-2-yl]thio]methyl]-4-methylpyridine-2-carbaldehyde (1.07 g, 2.52 mmol) in formic acid (20 ml), and the resulting mixture was stirred for 2 hours at room temperature. Water was added to the reaction mixture, and the solid thus precipitated was collected by filtration and washed with water. The resulting solid was dissolved in methylene chloride, and the solution was washed with 0.1 N hydrochloric acid. Subsequently, the organic layer was dried over anhydrous sodium sulfate and filtered, and then the filtrate was concentrated under reduced pressure. The resulting residue was washed with a mixed solvent of ethanol and hexane, and was collected by filtration to obtain the title compound (604 mg, 1.28 mmol, 51%) as a white solid.

$^1$H-NMR (400 MHz, CDCl$_3$) δ: 2.63 (3H, s), 6.95 (1H, s), 6.97-7.07 (2H, m) 7.67-7.73 (1H, m) 8.09 (1H, s), 8.15-8.17 (2H, m), 8.96 (1H, s) 9.07 (1H, s).

MS m/z: 473 (M$^+$+H).

Example 55

5-[(2,5-Difluorophenyl)[[5-(trifluoromethyl)pyridin-2-yl]sulfonyl]methyl]-N-(2-hydroxyethyl)-4-methylpyridine-2-carboxamide

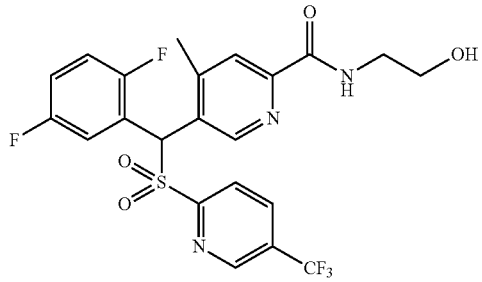

To a solution of 5-[(2,5-difluoromethyl)pyridin-2-yl]sulfonyl]methyl]-4-methylpyridine-2-carboxylic acid (118 mg, 0.25 mmol) in methylene chloride (3 ml), 2-aminoethanol (0.017 ml, 0.28 mmol), 1-hydroxybenzotriazole (37 mg, 0.28 mmol), 4-methylmorpholine (0.030 ml, 0.28 mmol), and 1-ethyl-3-(3-dimethylaminopropyl)carbodiimide hydrochloride (53 mg, 0.28 mmol) were added at room temperature. After stirring for 5 hours at room temperature, the reaction mixture was washed with water and then with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=1:1 was concentrated under reduced pressure, and the resulting residue was washed with hexane, and was dried under reduced pressure to obtain the title compound (91 mg, 0.18 mmol, 71%) as a colorless foamy substance.

$^1$H-NMR (400 MHz, CDCl$_3$) δ: 2.46 (1H, br s), 2.55 (3H, s), 3.61-3.66 (2H, m), 3.83 (2H, br t, J=5.1 Hz), 6.90 (1H, s), 6.97-7.07 (2H, m), 7.66-7.72 (1H, m), 8.02 (1H, s), 8.12-8.15 (2H, m), 8.34 (1H, br t, J=5.6 Hz), 8.96 (1H, s), 9.03 (1H, s).

IR(ATR)cm$^{-1}$: 3377, 1664, 1529, 1495, 1325, 1165, 1138, 1099, 1072.

Anal. Calcd for C$_{22}$H$_{18}$F$_5$N$_3$O$_4$S: C, 51.26; H, 3.52; F, 18.43; N, 8.15; S, 6.22. Found: C, 51.39; H, 3.61; F, 18.36; N, 8.04; S, 6.31.

MS m/z: 516 (M$^+$+H).

Example 56

2-Bromo-5-[(2,5-difluorophenyl)(phenylthio)methyl]-4-methylpyridine

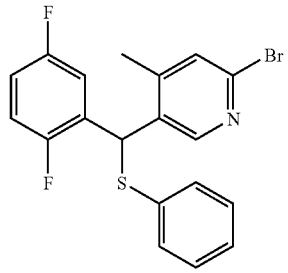

2-Bromo-5-[chloro(2,5-difluorophenyl)methyl]-4-methylpyridine (2.0 g, 6.0 mmol) obtained in Reference Example 2 and benzenethiol (618 μl, 6.0 mmol) were dissolved in N,N-dimethylformamide (30 ml), potassium carbonate (996 mg, 7.2 mmol) was added thereto at 0° C., and then the resulting mixture was stirred overnight at room temperature. Water was added to the reaction mixture, and the mixture was extracted twice with ethyl acetate. The combined organic layers was washed with saturated brine, subsequently dried over anhydrous sodium sulfate, and filtered, and then the filtrate was concentrated under reduced pressure. The resulting solid was washed with a mixed solution of hexane and ethyl acetate, and was filtered to obtain the title compound (1.6 g, 3.9 mmol, 66%) as a white solid.

$^1$H-NMR (400 MHz, CDCl$_3$) δ: 2.31 (3H, s), 5.81 (1H, s), 6.93-7.00 (2H, m), 7.22-7.39 (7H, m), 8.37 (1H, s).

Example 57

5-[(2,5-Difluorophenyl)(phenylthio)methyl]-4-methylpyridine-2-carbaldehyde

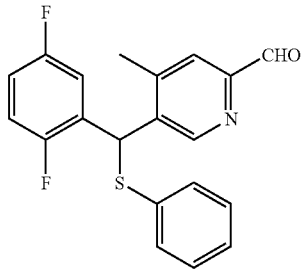

A solution of 2-bromo-5-[(2,5-difluorophenyl)(phenylthio)methyl]-4-methyl pyridine (1.2 g, 3.0 mmol) in toluene (30 ml) was cooled to −78° C., and n-butyllithium (1.54 M hexane solution, 2.5 ml, 3.9 mmol) was added in an argon atmosphere. After stirring for 10 minutes at the same temperature, the mixture was allowed to warm to −40° C., stirred for 30 minutes, and cooled again to −78° C., and N,N-dimethylformamide (302 µl, 3.9 mmol) was added thereto. After stirring for 30 minutes at the same temperature, water was added to the mixture, and the mixture was extracted twice with ethyl acetate. The combined organic layer was washed with saturated brine, subsequently dried over anhydrous sodium sulfate, and filtered, and then the filtrate was concentrated under reduced pressure. The resulting residue was subjected to flash silica gel column chromatography. The fraction obtained from an elution with hexane:ethyl acetate=93:7 was concentrated under reduced pressure to obtain the title compound mg, 0.70 mmol, 25%) as a colorless oily substance.

$^1$H-NMR (400 MHz, CDCl$_3$) δ: 2.42 (3H, s), 5.91 (1H, s), 6.95-7.01 (2H, m), 7.23-7.32 (5H, m), 7.44-7.47 (1H, m), 7.74 (1H, s), 8.78 (1H, s), 10.02 (1H, s).

Example 58

5-[(2,5-Difluorophenyl)(phenylsulfonyl)methyl]-4-methylpyridine-2-carboxylic acid

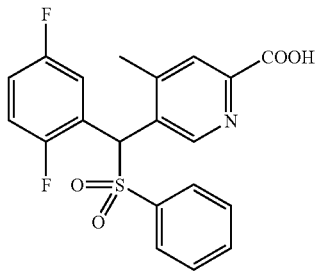

5-[(2,5-Difluorophenyl)(phenylthio)methyl]-4-methylpyridine-2-carbaldehyde (250 mg, 0.70 mmol) was dissolved in formic acid (7 ml), and 31% aqueous hydrogen peroxide (0.7 ml) was added thereto at 0° C. After stirring for 3 hours at room temperature, water was added to the reaction solution, and the solid thus precipitated was collected by filtration. The solid was washed sufficiently with water, and then was dried under reduced pressure to obtain the title compound (90 mg, 0.22 mmol, 32%) as a white solid.

$^1$H-NMR (400 MHz, CDCl$_3$) δ: 2.23 (3H, s), 5.99 (1H, s), 6.91-7.08 (2H, m), 7.46-7.52 (2H, m), 7.64-7.70 (3H, m), 7.80-7.84 (1H, m), 7.98 (1H, s), 9.20 (1H, s).

MS m/z: 404 (M$^+$+H).

Example 59

5-[(2,5-Difluorophenyl)(phenylsulfonyl)methyl]-N-(2-hydroxyethyl)-4-methylpyridine-2-carboxamide

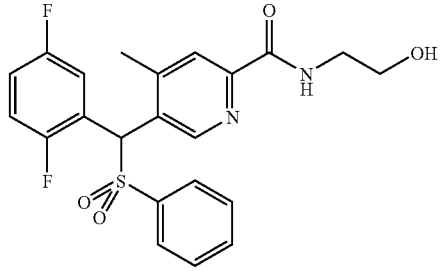

5-[(2,5-Difluorophenyl) (phenylsulfonyl)methyl]-4-methylpyridine-2-carboxylic acid (90 mg, 0.22 mmol), 2-aminoethanol (27 µl, 0.45 mmol), 1-ethyl-3-(3-dimethylaminopropyl)carbodiimide hydrochloride (64 mg, 0.34 mmol), 1-hydroxybenzotriazole (30 mg, 0.22 mmol), and triethylamine (92 µl, 0.66 mmol) were dissolved in methylene chloride (15 ml), and the resulting solution was stirred overnight at room temperature. Water was added to the reaction mixture, and the resulting mixture was extracted twice with methylene chloride. The combined organic layer was dried over anhydrous sodium sulfate and filtered, and then the filtrate was concentrated under reduced pressure. The resulting residue was purified by preparative thin-layer chromatography (developed with 5% methanol/methylene chloride, eluted with 30% methanol/methylene chloride), to obtain the title compound (30 mg, 0.067 mmol, 30%) as a white amorphous substance.

$^1$H-NMR (400 MHz, CDCl$_3$) δ: 2.14 (3H, s), 2.52-2.56 (1H, m), 3.62-3.68 (2H, m), 3.82-3.87 (2H, m), 5.97 (1H, s), 6.90-7.07 (2H, m), 7.43-7.49 (2H, m), 7.62-7.69 (3H, m), 7.81-7.87 (1H, m), 7.93 (1H, s), 8.39 (1H, br s), 9.13 (1H, s).

IR (ATR)cm$^{-1}$: 3413, 2940, 1662, 1650, 1529, 1496, 1307, 1143.

MS m/z: 447 (M$^+$+H).

FAB-MS: 447.1194 (Calcd for C$_{22}$H$_{21}$F$_2$N$_2$O$_4$S: 447.1190).

Example 60

2-Bromo-5-[(2,5-difluorophenyl)[(4-methylphenyl)thio]methyl]-4-methylpyridine

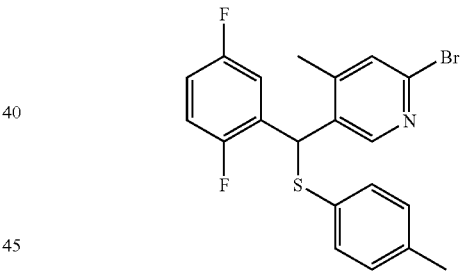

2-Bromo-5-[chloro(2,5-difluorophenyl)methyl]-4-methylpyridine (2.0 g, 6.0 mmol) obtained in Reference Example 2 and 4-methylbenzenethiol (746 mg, 6.0 mmol) were dissolved in N,N-dimethylformamide (30 ml), and potassium carbonate (996 mg, 7.2 mmol) was added thereto at 0° C. Subsequently, the mixture was stirred overnight at room temperature. Water was added to the reaction mixture, which was then extracted twice with ethyl acetate. The combined organic layer was washed with saturated brine, subsequently dried over anhydrous sodium sulfate, and filtered, and then the filtrate was concentrated under reduced pressure. The resulting residue was subjected to flash silica gel column chromatography. The fraction obtained from an elution with hexane:ethyl acetate=95:5 was concentrated under reduced pressure to obtain the title compound (2.5 g, 6.0 mmol, quantitative) as a pale green oily substance.

$^1$H-NMR (400 MHz, CDCl$_3$) δ: 2.29 (3H, s), 2.30 (3H, s), 5.75 (1H, s), 6.90-6.99 (2H, m), 7.05 (2H, d, J=8.1 Hz), 7.21 (2H, d, J=7.8 Hz), 7.26 (1H, s), 7.33-7.39 (1H, m), 8.38 (1H, s).

Example 61

5-[(2,5-Difluorophenyl)[(4-methylphenyl)thio]methyl]-4-methylpyridine-2-carbaldehyde

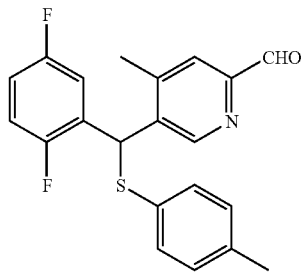

A solution of 2-bromo-5-[(2,5-difluorophenyl)[(4-methylphenyl)thio]methyl]-4-methylpyridine (2.5 g, 6.0 mmol) in toluene (60 ml) was cooled to −78° C., and in an argon atmosphere, n-butyllithium (1.54 M hexane solution, 4.6 ml, 7.1 mmol) was added thereto. After stirring for 10 minutes at the same temperature, the mixture was allowed to warm to −40° C. and stirred for 30 minutes. The mixture was cooled again to −78° C., and then N,N-dimethylformamide (720 µl, 7.1 mmol) was added. After stirring for 30 minutes at the same temperature, water was added, and the mixture was extracted twice with ethyl acetate. The combined organic layer was washed with saturated brine, subsequently dried over anhydrous sodium sulfate, and filtered, and then the filtrate was concentrated under reduced pressure. The resulting residue was subjected to flash silica gel column chromatography. The fraction obtained from an elution with hexane: ethyl acetate=95:5 was concentrated under reduced pressure to obtain the title compound (900 mg, 2.4 mmol, 41%) as a pale yellow oily substance.

$^1$H-NMR (400 MHz, CDCl$_3$) δ: 2.29 (3H, s) 2.41 (3H, s) 5.85 (1H, s), 6.96-6.98 (2H, m), 7.05 (2H, d, J=8.1 Hz), 7.22 (2H, d, J=8.1 Hz), 7.45-7.47 (1H, m), 7.72 (1H, s), 8.78 (1H, s), 10.02 (1H, s).

Example 62

5-[(2,5-Difluorophenyl)[(4-methylphenyl)sulfonyl]methyl]-4-methylpyridine-2-carboxylic acid

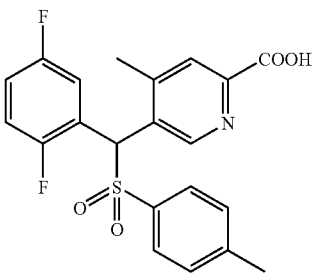

5-[(2,5-Difluorophenyl) [(4-methylphenyl)thio]methyl]-4-methylpyridine-2-carbaldehyde (900 mg, 2.4 mmol) was dissolved in formic acid (20 ml), and 31% aqueous hydrogen peroxide (2.5 ml) was added at 0° C. After stirring for 5 hours at room temperature, water was added to the reaction solution, and the solid thus precipitated was collected by filtration. The solid was washed sufficiently with water, and then was dried under reduced pressure to obtain the title compound (520 mg, 1.2 mmol, 51%) as a white solid.

$^1$H-NMR (400 MHz, CDCl$_3$) δ: 2.23 (3H, s), 2.43 (3H, s), 5.97 (1H, s), 6.92-7.08 (2H, m), 7.26 (2H, d, J=8.3 Hz), 7.56 (2H, d, J=8.3 Hz), 7.81-7.86 (1H, m), 7.98 (1H, s), 9.17 (1H, s).
MS m/z: 418 (M$^+$+H).

Example 63

5-[(2,5-Difluorophenyl)[(4-methylphenyl)sulfonyl]methyl]-N-(2-hydroxyethyl)-4-methylpyridine-2-carboxamide

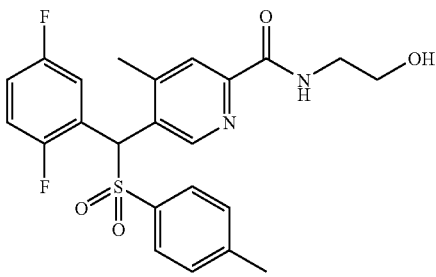

5-[(2,5-Difluorophenyl)[(4-methylphenyl)sulfonyl]methyl]-4-methylpyridine-2-carboxylic acid (208 mg, 0.5 mmol), 2-aminoethanol (46 µl, 0.75 mmol), 1-ethyl-3-(3-dimethylaminopropyl)carbodiimide hydrochloride (0.75 mmol), 1-hydroxybenzotriazole (68 mg, 0.5 mmol), and triethylamine (209 µl, 1.5 mmol) were dissolved in methylene chloride (35 ml), and the resulting solution was stirred overnight at room temperature. Water was added to the reaction mixture, and the resulting mixture was extracted twice with methylene chloride. The combined organic layer was dried over anhydrous sodium sulfate and filtered, and then the filtrate was concentrated under reduced pressure. The resulting residue was purified by preparative thin-layer chromatography (developed with 6% methanol/methylene chloride, eluted with 30% methanol/methylene chloride), to obtain the title compound (125 mg, 0.27 mmol, 54%) as a white amorphous substance.

$^1$H-NMR (400 MHz, CDCl$_3$) δ: 2.14 (3H, s), 2.42 (3H, s), 2.58 (1H, t, J=5.2 Hz), 3.62-3.67 (2H, m), 3.85 (2H, q, J=5.2 Hz), 5.95 (1H, s), 6.92-7.07 (2H, m), 7.24 (2H, d, J=8.3 Hz), 7.54 (2H, d, J=8.3 Hz), 7.83-7.88 (1H, m), 7.92 (1H, s), 8.40 (1H, br s), 9.11 (1H, s).
IR(ATR)cm$^{-1}$: 3388, 1664, 1594, 1527, 1492, 1145.
MS m/z: 461 (M$^+$+H).
Anal. Calcd for C$_{23}$H$_{22}$F$_2$N$_2$O$_4$S: C, 59.99; H, 4.82; F, 8.25; N, 6.08, S, 6.96. Found: C, 59.94; H, 4.81; F, 8.03; N, 5.94; S, 6.81.

Reference Example 8

S-(4-chloro-3-methylphenyl)O-ethyl dithiocarbonate

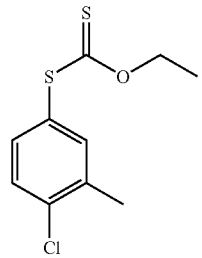

4-Chloro-3-methylaniline (4.5 g, 31.8 mmol) was dissolved in methanol (20 ml), and 1 N hydrochloric acid (95 ml)

was added at −5° C. Subsequently, a solution of sodium nitrite (2.6 g, 38.2 mmol) in water (20 ml) was added dropwise thereto, and the mixture was stirred for 30 minutes at the same temperature. The resulting reaction solution was added dropwise to a solution of O-ethyl potassium dithiocarbonate (7.6 g, 47.7 mmol) in water (100 ml) at 65° C. The reaction mixture was heated to 90° C., stirred for 30 minutes, and then cooled to room temperature. Water was added thereto, and the mixture was extracted twice with ethyl acetate. The combined organic layer was washed sequentially with water (2 times), saturated aqueous sodium hydrogen carbonate and saturated brine, dried over anhydrous sodium sulfate, and filtered, and then the filtrate was concentrated under reduced pressure. The resulting residue was subjected to flash silica gel column chromatography. The fraction obtained from an elution with hexane:ethyl acetate=99:1 was concentrated under reduced pressure to obtain the title compound (3.9 g, 15.8 mmol, 50%) as a pale brown oily substance.

$^1$H-NMR (400 MHz, CDCl$_3$) δ: 1.34 (3H, t, J=7.1 Hz), 2.39 (3H, s), 4.61 (2H, q, J=7.1 Hz), 7.25-7.40 (3H, m).

Example 64

2-Bromo-5-[[(4-chloro-3-methylphenyl)thio](2,5-difluorophenyl)methyl]-4-methylpyridine

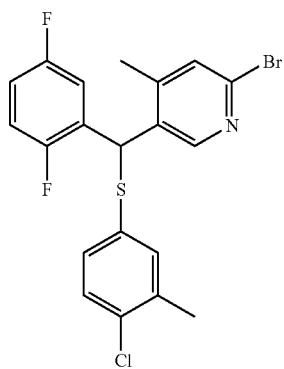

To a solution of S-(4-chloro-3-methylphenyl)O-ethyl dithiocarbonate (3.9 g, 15.8 mmol) in ethanol (50 ml) and tetrahydrofuran (20 ml), 1 N aqueous sodium hydroxide (48 ml) was added, and the resulting mixture was stirred for 3 hours at 60° C. The reaction mixture was cooled to room temperature, water was added thereto, and the mixture was washed with methylene chloride. The aqueous layer was acidified with 5N hydrochloric acid, and then was extracted with methylene chloride. The organic layer was dried over anhydrous sodium sulfate and filtered, and then the filtrate was concentrated under reduced pressure. The resulting residue and 2-bromo-5-[chloro(2,5-difluorophenyl)methyl]-4-methylpyridine (4.5 g, 13.8 mmol) obtained in Reference Example 2 were dissolved in N,N-dimethylformamide (80 ml), and potassium carbonate (2.4 g, 18 mmol) was added thereto, followed by stirring overnight at room temperature Water was added to the reaction mixture, and the mixture was extracted twice with ethyl acetate. The combined organic layer was washed with saturated brine, subsequently dried over anhydrous sodium sulfate and filtered, and the filtrate was concentrated under reduced pressure. The resulting solid was washed with a mixed solution of hexane and ethyl acetate, and was filtered to obtain the title compound g, 9.5 mmol, 60%) as a pale brown solid.

$^1$H-NMR (400 MHz, CDCl$_3$) δ: 2.29 (3H, s), 2.31 (3H, s), 5.78 (1H, s), 6.93-7.33 (7H, m), 8.39 (1H, s).

MS m/z: 454, 456 (M$^+$+H).

Example 65

5-[[(4-Chloro-3-methylphenyl)thio](2,5-difluorophenyl)methyl]-4-methylpyridine-2-carbaldehyde

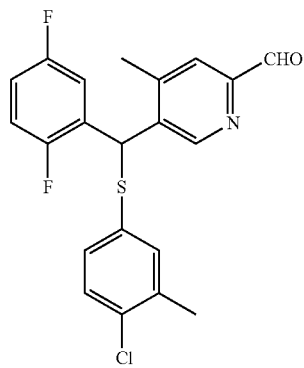

A solution of 2-bromo-5-[[(4-chloro-3-methylphenyl)thio](2,5-difluorophenyl) methyl]-4-methylpyridine (2.0 g, 4.4 mmol) in toluene (50 ml) was cooled to −78° C., and in an argon atmosphere, n-butyllithium (1.54 M hexane solution, 3.4 ml, 5.3 mmol) was added thereto. After stirring for 10 minutes at the same temperature, the mixture was allowed to warm to −40° C., stirred for 30 minutes, and cooled again to −78° C., and then N,N-dimethylformamide (409 μl, 5.3 mmol) was added. After stirring for 30 minutes at the same temperature, water was added, and the mixture was extracted twice with ethyl acetate. The combined organic layer was washed with saturated brine, subsequently dried over anhydrous sodium sulfate, and filtered, and then the filtrate was concentrated under reduced pressure. The resulting residue was subjected to flash silica gel column chromatography. The fraction obtained from an elution with hexane:ethyl acetate=95:5 was concentrated under reduced pressure to obtain the title compound (700 mg, 1.7 mmol, 40%) as a colorless oily substance.

$^1$H-NMR (400 MHz, CDCl$_3$) δ: 2.29 (3H, s), 2.43 (3H, s), 5.88 (1H, s), 6.99-7.05 (3H, m), 7.19-7.21 (2H, m), 7.38-7.41 (1H, m), 7.75 (1H, s), 8.79 (1H, s), 10.02 (1H, s).

MS m/z: 404 (M$^+$+H).

Example 66

5-[[(4-Chloro-3-methylphenyl)sulfonyl](2,5-difluorophenyl)methyl]-4-methylpyridine-2-carboxylic acid

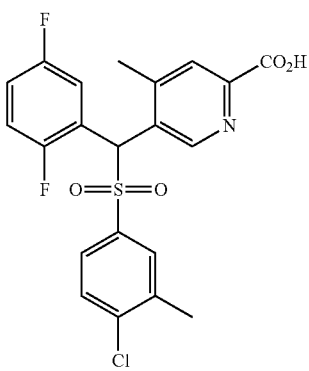

5-[[(4-Chloro-3-methylphenyl)thio](2,5-difluorophenyl) methyl]-4-methylpyridine-2-carbaldehyde (700 mg, 1.7 mmol) was dissolved in formic acid (15 ml), and 31% aqueous hydrogen peroxide (1.7 ml) was added at 0° C. After stirring for 2 hours at room temperature, water was added to the reaction mixture, and the solid thus precipitated was collected by filtration. The solid was washed sufficiently with water, and was dried under reduced pressure to obtain the title compound (600 mg, 1.3 mmol, 78%) as a white solid.

$^1$H-NMR (400 MHz, CDCl$_3$) δ: 2.31 (3H, s), 2.38 (3H, s), 5.97 (1H, s), 6.93-7.09 (2H, m), 7.41-7.44 (2H, m), 7.56-7.57 (1H, m), 7.73-7.77 (1H, m), 8.03 (1H, s), 9.22 (1H, s).

MS m/z: 452 (M$^+$+H).

Example 67

5-[[(4-Chloro-3-methylphenyl)sulfonyl](2,5-difluorophenyl)methyl]-N-(2-hydroxyethyl)-4-methylpyridine-2-carboxamide

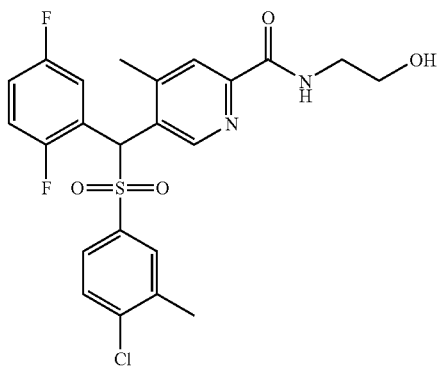

5-[[(4-Chloro-3-methylphenyl)sulfonyl](2,5-difluorophenyl) methyl]-4-methylpyridine-2-carboxylic acid (300 mg, 0.66 mmol), 2-aminoethanol (60 μl, 0.99 mmol), 1-ethyl-3-(3-dimethylaminopropyl)carbodiimide hydrochloride (191 mg, 0.99 mmol), 1-hydroxybenzotriazole (89 mg, 0.66 mmol), and triethylamine (275 μl, 1.98 mmol) were dissolved in methylene chloride (60 ml), and the resulting mixture was stirred overnight at room temperature. Water was added to the reaction mixture, and the mixture was extracted twice with methylene chloride. The combined organic layer was dried over anhydrous sodium sulfate and filtered, and then the filtrate was concentrated under reduced pressure. The resulting residue was purified by preparative thin-layer chromatography (developed with 5% methanol/methylene chloride, eluted with 30% methanol/methylene chloride), to obtain the title compound (190 mg, 0.38 mmol, 58%) as a white amorphous substance.

$^1$H-NMR (400 MHz, CDCl$_3$) δ: 2.22 (3H, s), 2.38 (3H, s), 2.58-2.59 (1H, m), 3.65-3.66 (2H, m), 3.84-3.86 (2H, m), 5.95 (1H, s), 6.92-7.07 (2H, m), 7.37-7.43 (2H, m), 7.55 (1H, s), 7.74-7.80 (1H, m), 7.97 (1H, s), 8.40 (1H, br s), 9.14 (1H, s).

IR(ATR)cm$^{-1}$: 3390, 1664, 1527, 1492, 1147, 1049.

MS m/z: 495 (M$^+$+H).

Anal. Calcd for C$_{23}$H$_{21}$ClF$_2$N$_2$O$_4$S.0.25H$_2$O: C, 55.31; H, 4.34; Cl, 7.10; F, 7.61; N, 5.61, S, 6.42. Found: C, 55.29; H, 4.24; Cl, 7.50; F, 7.56; N, 5.64; S, 6.51.

Reference Example 9

O-ethyl S-(4-fluoro-3-methylphenyl)dithiocarbonate

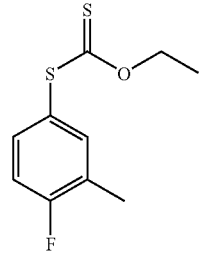

4-Fluoro-3-methylaniline (5.0 g, 40 mmol) was dissolved in methanol (20 ml), and 1 N hydrochloric acid (120 ml) was added thereto at −5° C. Subsequently, a solution of sodium nitrite (3.3 g, 48 mmol) in water (20 ml) was added dropwise, and then the resulting mixture was stirred for 30 minutes at the same temperature. The obtained reaction solution was added dropwise to a solution of O-ethyl potassium dithiocarbonate (9.6 g, 60 mmol) in water (100 ml) at 65° C. The reaction mixture was heated to 90° C., stirred for 30 minutes, and then cooled to room temperature. Water was added, and the mixture was extracted twice with ethyl acetate. The combined layer was washed sequentially with water (2 times), saturated aqueous sodium hydrogencarbonate and saturated brine, subsequently dried over anhydrous sodium sulfate, and filtered, and then the filtrate was concentrated under reduced pressure. The resulting residue was subjected to flash silica gel column chromatography. The fraction obtained from an elution with hexane:ethyl acetate=99:1 was concentrated under reduced pressure to obtain the title compound (4.0 g, 17.4 mmol, 43%) as a yellow oily substance.

$^1$H-NMR (400 MHz, CDCl$_3$) δ: 1.30-1.35 (3H, m), 2.29 (3H, s), 4.59-4.63 (2H, m), 7.05 (1H, t, J=8.9 Hz), 7.26-7.37 (2H, m).

Example 68

2-Bromo-5-[(2,5-difluorophenyl)[(4-fluoro-3-methylphenyl)thio]methyl]-4-methylpyridine

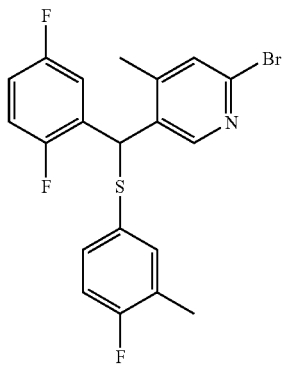

To a solution of O-ethyl S-(4-fluoro-3-methylphenyl) dithiocarbonate (4.0 g, 17.4 mmol) in ethanol (55 ml) and tetrahydrofuran (10 ml), 1 N aqueous sodium hydroxide (48 ml) was added, and the mixture was stirred for 3 hours at 60° C. The reaction mixture was cooled to room temperature, water was added, and then the mixture was washed with methylene chloride. The aqueous layer was acidified with 5 N hydrochloric acid, and then was extracted with methylene chloride. The organic layer was dried over anhydrous sodium sulfate and filtered, and then the filtrate was concentrated under reduced pressure. The resulting residue and 2-bromo-5-[chloro(2,5-difluorophenyl)methyl]-4-methylpyridine (4.8 g, 14.7 mmol) obtained in Reference Example 2 were dissolved in N,N-dimethylformamide (80 ml), and potassium carbonate (2.6 g, 19.2 mmol) was added thereto, followed by stirring overnight at room temperature. Water was added to the reaction mixture, and the resulting mixture was extracted twice with ethyl acetate. The combined organic layer was washed with saturated brine, subsequently dried over anhydrous sodium sulfate and filtered, and then the filtrate was concentrated under reduced pressure. The resulting solid was washed with a mixed solution of hexane and ethylacetate, and then was filtered to obtain the title compound (3.1 g, 7.1 mmol, 41%) as a white solid.

$^1$H-NMR (400 MHz, CDCl$_3$) δ: 2.19 (3H, s), 2.28 (3H, s) 5.71 (1H, s), 6.85-7.33 (7H, m), 8.43 (1H, s).

MS m/z: 438, 440 (M$^+$+H).

Example 69

5-[(2,5-Difluorophenyl) [(4-fluoro-3-methylphenyl)thio]methyl]-4-methylpyridine-2-carbaldehyde

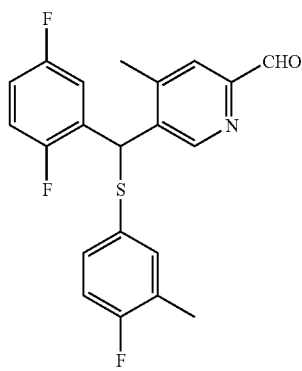

A solution of 2-bromo-5-[(2,5-difluorophenyl)[(4-fluoro-3-methylphenyl)thio]methyl]-4-methylpyridine (2.0 g, 4.6 mmol) in toluene (50 ml) was cooled to −78° C., and in an argon atmosphere, n-butyllithium (1.54 M hexane solution, 3.6 ml, 5.5 mmol) was added thereto. After stirring for 10 minutes at the same temperature, the mixture was allowed to warm to −40° C., stirred for 30 minutes, and cooled again to −78° C., and then N,N-dimethylformamide (424 µl, 5.5 mmol) was added. After stirring for 30 minutes at the same temperature, water was added thereto, and the mixture was extracted twice with ethyl acetate. The combined organic layer was washed with saturated brine, subsequently dried over anhydrous sodium sulfate, and filtered, and then the filtrate was concentrated under reduced pressure. The resulting residue was subjected to flash silica gel column chromatography. The fraction obtained from an elution with hexane:ethyl acetate=95:5 was concentrated under reduced pressure to obtain the title compound (1.1 g, 2.8 mmol, 63%) as a colorless oily substance.

$^1$H-NMR (400 MHz, CDCl$_3$) δ: 2.18 (3H, s), 2.39 (3H, s), 5.82 (1H, s), 6.85-6.99 (3H, m), 7.09-7.19 (2H, m), 7.37-7.41 (1H, m), 7.73 (1H, s), 8.82 (1H, s), 10.02 (1H, s).

MS m/z: 388 (M$^+$+H).

Example 70

5-[(2,5-Difluorophenyl)[(4-fluoro-3-methylphenyl)sulfonyl]methyl]-4-methylpyridine-2-carboxylic acid

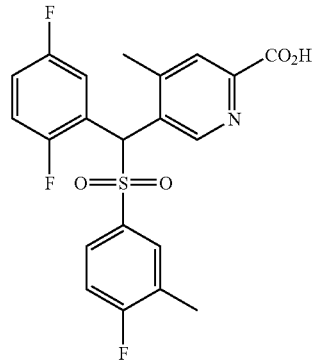

5-[(2,5-Difluorophenyl)[(4-fluoro-3-methylphenyl)thio]methyl]-4-methylpyridine-2-carbaldehyde (1.1 g, 2.8 mmol) was dissolved in formic acid (20 ml), and 31% aqueous hydrogen peroxide (2.8 ml) was added thereto at 0° C. After stirring for 2 hours at room temperature, water was added to the reaction solution, and the solid thus precipitated was collected by filtration. The solid was washed sufficiently with water, and was dried under reduced pressure to obtain the title compound (1.0 g, 2.3 mmol, 81%) as a white solid.

$^1$H-NMR (400 MHz, CDCl$_3$) δ: 2.28 (3H, s), 2.30 (3H, s), 5.96 (1H, s), 6.93-7.10 (3H, m), 7.48-7.58 (2H, m), 7.73-7.77 (1H, m), 8.02 (1H, s), 9.23 (1H, s).

MS m/z: 436 (M$^+$+H).

Example 71

5-[(2,5-Difluorophenyl)[(4-fluoro-3-methylphenyl)sulfonyl]methyl]-N-(2-hydroxyethyl)-4-methylpyridine-2-carboxamide

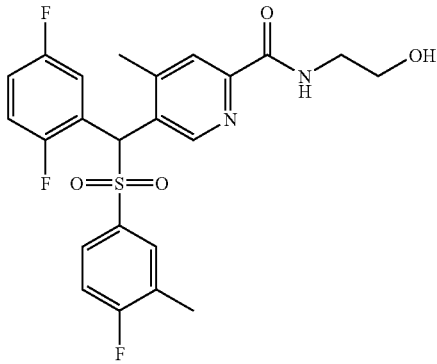

5-[(2,5-Difluorophenyl)[(4-fluoro-3-methylphenyl)sulfonyl]methyl]-4-methylpyridine-2-carboxylic acid (300 mg, 0.69 mmol), 2-aminoethanol (60 µl, 1.0 mmol), 1-ethyl-3-(3-dimethylaminopropyl)carbodiimide hydrochloride (193 mg, 1.0 mmol), 1-hydroxybenzotriazole (93 mg, 0.69 mmol), and triethylamine (292 µl, 2.1 mmol) were dissolved in methylene chloride (60 ml), and the solution was stirred overnight at room temperature. Water was added to the reaction mixture, and the mixture was extracted twice with methylene chloride. The combined organic layer was dried over anhydrous

Example 72

5-[(2,5-Difluorophenyl)[(4-fluorophenyl)sulfonyl]methyl]-4-methyl-N-[3-(methylthio)propyl]pyridine-2-carboxamide

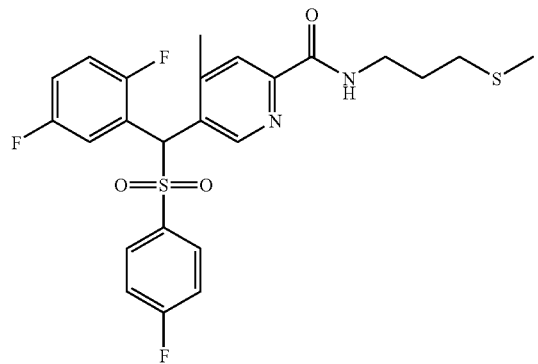

To a solution of 5-[(2,5-difluorophenyl)[(4-fluorophenyl)sulfonyl]methyl]-4-methylpyridine-2-carboxylic acid (222 mg, 0.527 mmol) obtained in Example 12 in methylene chloride (5 ml), 3-methylthiopropylamine (66 mg, 0.632 mmol), 1-hydroxybenzotriazole (71 mg, 0.527 mmol), 1-ethyl-3-(3-dimethylaminopropyl)carbodiimide hydrochloride (121 mg, 0.632 mmol) and 4-methylmorpholine (69 μl, 0.632 mmol) were added. The reaction solution was stirred for 3 days at room temperature, and was concentrated under reduced pressure. The concentration residue was subjected to silica gel column chromatography, and the fraction obtained from an elution with ethyl acetate:methylene chloride (=1:20) was concentrated under reduced pressure, to obtain the title compound (253 mg, 0.497 mmol, 94%) as a white solid.

$^1$H-NMR (400 MHz, CDCl$_3$) δ: 1.90-2.00 (2H, m), 2.13 (3H, s), 2.20 (3H, s), 2.60 (2H, t, J=7.2 Hz), 3.55-3.65 (2H, m), 5.95 (1H, s), 6.90-7.20 (4H, m), 7.66-7.75 (2H, m), 7.75-7.84 (1H, m), 7.96 (1H, s), 8.13-8.20 (1H, m), 9.14 (1H, s).

IR(ATR)cm$^{-1}$: 3421, 1679, 1589, 1525, 1494, 1295, 1278, 1234, 1143, 850, 825.

MS m/z: 509 (M$^+$+H).

Example 73

5-[(2,5-Difluorophenyl)[(4-fluorophenyl)sulfonyl]methyl]-4-methyl-N-[3-(methylsulfinyl)propyl]pyridine-2-carboxamide

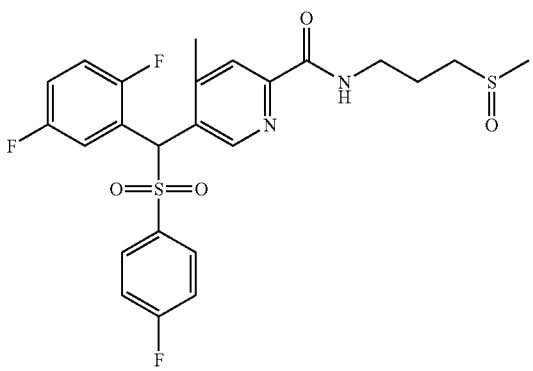

To a solution of 5-[(2,5-difluorophenyl)[(4-fluorophenyl)sulfonyl]methyl]-4-methyl-N-[3-(methylthio)propyl]pyridine-2-carboxamide (149 mg, 0.293 mmol) in methylene chloride (5 ml), 3-chloroperbenzoic acid (51 mg, 0.293 mmol) was added under ice cooling, and the mixture was stirred for 30 minutes. 3-Chloroperbenzoic acid (20 mg, 0.116 mmol) was added to the reaction solution under ice cooling, and the resulting mixture was stirred for 15 minutes. 1 N aqueous sodium hydroxide was added to the reaction solution, and the mixture was extracted with methylene chloride. The organic layer was dried over anhydrous sodium sulfate and filtered, and then the filtrate was concentrated under reduced pressure. The resulting concentration residue was subjected to silica gel column chromatography, and the fraction obtained from an elution with methanol:methylene chloride (=1:30) was concentrated under reduced pressure. Ethylacetate-hexane was added to the resulting concentration residue, and the solid thus precipitated was collected by filtration, to obtain the title compound (122 mg, 0.232 mmol, 79%) as a white powder.

$^1$H-NMR (400 MHz, CDCl$_3$) δ: 2.10-2.20 (2H, m), 2.23 (3H, s), 2.58-2.61 (3H, m), 2.76-2.83 (2H, m), 3.60-3.71 (2H, m), 5.96 (1H, s), 6.90-7.09 (2H, m), 7.11-7.19 (2H, m), 7.68-7.74 (2H, m), 7.75-7.82 (1H, m), 7.96 (1H, s), 8.21-8.29 (1H, m), 9.15 (1H, s).

IR(ATR)cm$^{-1}$: 3394, 1670, 1590, 1525, 1492, 1319, 1288, 1236, 1149, 1049.

mp: 170-173° C.

MS m/z: 525 (M$^+$+H).

Anal. calcd for C$_{24}$H$_{23}$F$_3$N$_2$O$_4$S$_2$: C, 54.95; H, 4.42; F, 10.87; N, 5.34; S, 12.23.

Found: C, 54.96; H, 4.34; F, 11.14; N, 5.42; S, 12.20.

--- sodium sulfate and filtered, and then the filtrate was concentrated under reduced pressure. The resulting residue was purified by preparative thin-layer chromatography (developed with 5% methanol/methylene chloride, eluted with 30% methanol/methylene chloride), to obtain the title compound (190 mg, 0.39 mmol, 58%) as a white amorphous substance.

$^1$H-NMR (400 MHz, CDCl$_3$) δ: 2.21 (3H, s), 2.27 (3H, s), 2.57 (1H, t, J=5.2 Hz), 3.63-3.67 (2H, m), 3.85 (2H, q, J=5.2 Hz), 5.94 (1H, s), 6.92-7.08 (3H, m), 7.44-7.49 (1H, m), 7.54-7.57 (1H, m), 7.74-7.78 (1H, m), 7.96 (1H, s), 8.40 (1H, br s), 9.15 (1H, s).

IR(ATR)cm$^{-1}$: 3388, 1664, 1527, 1490, 1240, 1141.

MS m/z: 479 (M$^+$+H).

Anal. Calcd for C$_{23}$H$_{21}$F$_3$N$_2$O$_4$S: C, 57.73; H, 4.42; F, 11.91; N, 5.85, S, 6.70. Found: C, 57.57; H, 4.63; F, 11.66; N, 5.60; S, 6.59.

Example 74

5-[(2,5-Difluorophenyl)[(4-fluorophenyl)sulfonyl]methyl]-4-methyl-N-[3-(methylsulfonyl)propyl]pyridine-2-carboxamide

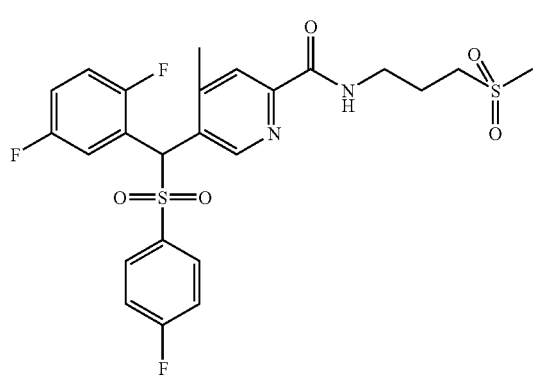

To a solution of 5-[(2,5-difluorophenyl)[(4-fluorophenyl)sulfonyl]methyl]-4-methyl-N-[3-(methylthio)propyl]pyridine-2-carboxamide (100 mg, 0.197 mmol) obtained in Example 72 in methylene chloride (5 ml), 3-chloroperbenzoic acid (68 mg, 0.393 mmol) was added. The reaction solution was stirred for 15 minutes at room temperature, and then 3-chloroperbenzoic acid (30 mg, 0.174 mmol) was added. The reaction solution was stirred for 15 minutes at room temperature. 1 N aqueous sodium hydroxide was added to the reaction solution, and the mixture was extracted with methylene chloride. The organic layer was dried over anhydrous sodium sulfate and filtered, and then the filtrate was concentrated under reduced pressure. The resulting concentration residue was subjected to silica gel column chromatography, and the fraction obtained from an elution with methylene chloride:ethyl acetate (=3:2) was concentrated under reduced pressure. Ethyl acetate-hexane was added to the resulting concentration residue, and the solid thus precipitated was collected by filtration, to obtain the title compound (79 mg, 0.146 mmol, 74%) as a white powder.

$^1$H-NMR (400 MHz, CDCl$_3$) δ: 2.17-2.28 (2H, m) 2.23 (3H, s), 2.93 (3H, s), 3.09-3.17 (2H, m), 3.62-3.70 (2H, m), 5.96 (1H, s), 6.90-7.09 (2H, m), 7.10-7.20 (2H, m), 7.67-7.82 (3H, m), 7.95 (1H, s), 8.18-8.28 (1H, m), 9.15 (1H, s).

IR(ATR)cm$^{-1}$: 3392, 1668, 1590, 1525, 1494, 1317, 1288, 1236, 1151, 1141, 1081.

mp: 182-185° C.

MS m/z: 541 (M$^+$+H).

Anal. calcd for C$_{24}$H$_{23}$F$_3$N$_2$O$_5$S$_2$: C, 53.32; H, 4.29; F, 10.54; N, 5.18; S, 11.86.

Found: C, 53.38; H, 4.24; F, 10.54; N, 5.19; S, 12.01.

Example 75

5-[(2,5-Difluorophenyl)[(4-fluorophenyl)sulfonyl]methyl]-N-[2-hydroxy-1-(hydroxymethyl)ethyl]-4-methylpyridine-2-carboxamide

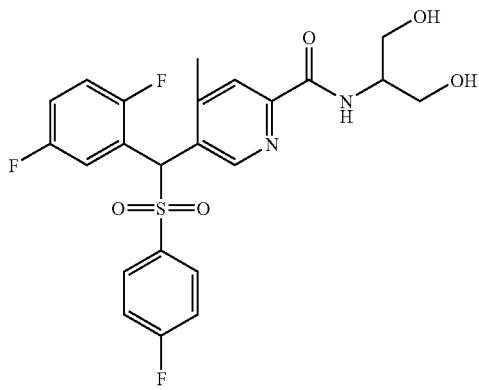

To a solution of 5-[(2,5-difluorophenyl)[(4-fluorophenyl)sulfonyl]methyl]-4-methylpyridine-2-carboxylic acid (93 mg, 0.221 mmol) obtained in Example 12 in methylene chloride (3 ml), 2-amino-1,3-propanediol (24 mg, 0.265 mmol), 1-hydroxybenzotriazole (30 mg, 0.221 mmol), 1-ethyl-3-(3-dimethylaminopropyl)carbodiimide hydrochloride (51 mg, 0.265 mmol) and 4-methylmorpholine (29 μl, 0.265 mmol) were added, and the resulting mixture was stirred for 17 hours at room temperature. Ethyl acetate was added to the reaction solution, and the mixture was washed sequentially with a saturated solution of sodium hydrogencarbonate and saturated brine. The organic layer was dried over anhydrous sodium sulfate and filtered, and the filtrate was concentrated under reduced pressure. The resulting concentration residue was subjected to silica gel column chromatography, and the fraction obtained from an elution with methanol:methylene chloride (=1:20) was concentrated under reduced pressure. Ethylacetate-hexane was added to the resulting concentration residue, and the solid thus precipitated was collected by filtration, to obtain the title compound (81 mg, 0.164 mmol, 74%) as a white powder.

$^1$H-NMR (400 MHz, CDCl$_3$) δ: 2.21 (3H, s), 2.46-2.57 (2H, m), 3.87-4.03 (4H, m), 4.10-4.19 (1H, m), 5.96 (1H, s), 6.90-7.09 (2H, m), 7.11-7.19 (2H, m), 7.67-7.74 (2H, m), 7.75-7.82 (1H, m), 7.96 (1H, s), 8.63 (1H, br d, J=7.6 Hz), 9.17 (1H, s).

IR(ATR)cm$^{-1}$: 3421, 3278, 1639, 1590, 1536, 1494, 1319, 1292, 1234, 1143, 1076, 1041.

mp: 150-152° C.

MS m/z: 495 (M$^+$+H).

Anal. calcd for C$_{23}$H$_{21}$F$_3$N$_2$O$_5$S: C, 55.87; H, 4.28; F, 11.53; N, 5.67; S, 6.48.

Found: C, 55.74; H, 4.13; F, 11.74; N, 5.68; S, 6.63.

Example 76

1-[[5-[(2,5-Difluorophenyl)[(4-fluorophenyl)sulfonyl]methyl]-4-methylpyridin-2-yl]carbonyl]piperidin-4-ol

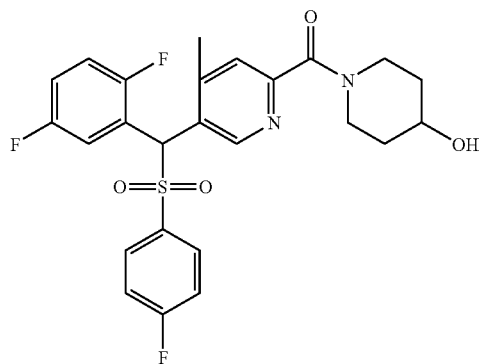

To a solution of 5-[(2,5-difluorophenyl)[(4-fluorophenyl)sulfonyl]methyl]-4-methylpyridine-2-carboxylic acid (94 mg, 0.223 mmol) obtained in Example 12 in methylene chloride (3 ml), 4-hydroxypiperidine (27 mg, 0.268 mmol), 1-hydroxybenzotriazole (30 mg, 0.223 mmol), 1-ethyl-3-(3-dimethylaminopropyl)carbodiimide hydrochloride mg, 0.268 mmol) and 4-methylmorpholine (29 µl, 0.268 mmol) were added, and the resulting mixture was stirred for 18 hours at room temperature. Ethyl acetate was added to the reaction solution, and the mixture was washed sequentially with an aqueous sodium hydrogencarbonate and saturated brine. The organic layer was dried over anhydrous sodium sulfate and filtered, and then the filtrate was concentrated under reduced pressure. The resulting concentration residue was subjected to silica gel column chromatography, and the fraction obtained from an elution with methanol:methylene chloride (=1:30) was concentrated under reduced pressure. Ethyl acetate-hexane was added to the resulting concentration residue, and the solid thus precipitated was collected by filtration, to obtain the title compound (76 mg, 0.151 mmol, 68%) as a white powder.

$^1$H-NMR (400 MHz, CDCl$_3$) δ: 1.60-1.72 (2H, m), 1.90-2.09 (2H, m), 2.25 (3H, s), 3.30-3.50 (2H, m), 3.82-4.08 (2H, m), 4.12-4.28 (1H, m), 5.95 (1H, s), 6.89-6.98 (1H, m), 7.00-7.08 (1H, m), 7.10-7.20 (2H, m), 7.46 (1H, s), 7.70-7.80 (3H, m), 9.17 (1H, s).

IR(ATR)cm$^{-1}$: 3463, 1606, 1589, 1492, 1444, 1326, 1282, 1238, 1147, 1081, 1027.

mp: 171-173° C.

MS m/z: 505 (M$^+$+H).

Anal. calcd for C$_{25}$H$_{23}$F$_3$N$_2$O$_4$S: C, 59.52; H, 4.59; F, 11.30; N, 5.55; S, 6.36.

Found: C, 59.43; H, 4.68; F, 11.41; N, 5.55; S, 6.53.

Example 77

4-[[5-[(2,5-Difluorophenyl)[(4-fluorophenyl)sulfonyl]methyl]-4-methylpyridin-2-yl]carbonyl]morpholine

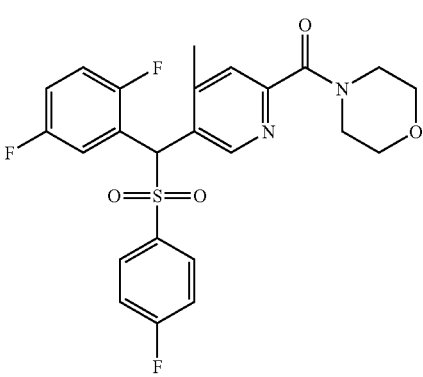

To a solution of 5-[(2,5-difluorophenyl)[(4-fluorophenyl)sulfonyl]methyl]-4-methylpyridine-2-carboxylic acid (119 mg, 0.282 mmol) obtained in Example 12 in methylene chloride (3 ml), morpholine (30 µl, 0.339 mmol), 1-hydroxybenzotriazole (38 mg, 0.282 mmol), 1-ethyl-3-(3-dimethylaminopropyl)carbodiimide hydrochloride mg, 0.339 mmol) and 4-methylmorpholine (37 µl, 0.339 mmol) were added. The reaction solution was stirred for 5 days at room temperature, and was concentrated under reduced pressure. The resulting concentration residue was subjected to silica gel column chromatography, and the fraction obtained from an elution with 65% ethyl acetate/hexane was concentrated under reduced pressure. Ethyl acetate-hexane was added to the resulting concentration residue, and the solid thus precipitated was collected by filtration, to obtain the title compound (94 mg, 0.192 mmol, 68%) as a white powder.

$^1$H-NMR (400 MHz, CDCl$_3$) δ: 2.26 (3H, s), 3.68-3.86 (8H, m), 5.95 (1H, s), 6.89-7.08 (2H, m), 7.10-7.20 (2H, m), 7.53 (1H, s), 7.70-7.80 (3H, m), 9.17 (1H, s).

IR(ATR)cm$^{-1}$: 1629, 1590, 1492, 1461, 1324, 1280, 1226, 1147, 1114, 1083.

mp: 165-167° C.

MS m/z: 491 (M$^+$+H).

Anal. calcd for C$_{24}$H$_{21}$F$_3$N$_2$O$_4$S: C, 58.77; H, 4.32; F, 11.62; N, 5.71; S, 6.54.

Found: C, 58.81; H, 4.25; F, 11.94; N, 5.78; S, 6.71.

Example 78

5-[(2,5-Difluorophenyl)[(4-fluorophenyl)sulfonyl]methyl]-N-methoxy-4-methylpyridine-2-carboxamide

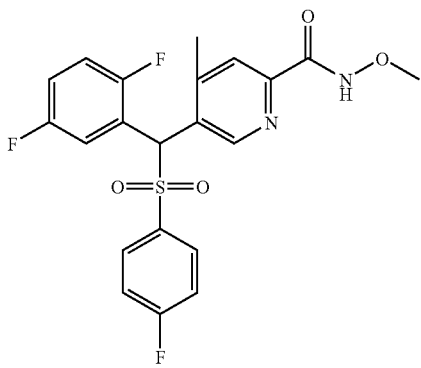

To a solution of 5-[(2,5-difluorophenyl)[(4-fluorophenyl)sulfonyl]methyl]-4-methylpyridine-2-carboxylic acid (96 mg, 0.228 mmol) obtained in Example 12 in methylene chloride (3 ml), O-methylhydroxyamine hydrochloride (23 mg, 0.273 mmol), 1-hydroxybenzotriazole (31 mg, 0.228 mmol), 1-ethyl-3-(3-dimethylaminopropyl)carbodiimide hydrochloride (52 mg, 0.273 mmol) and 4-methylmorpholine (59 µl, 0.546 mmol) were added. The reaction solution was stirred for 5 days at room temperature, and was concentrated under reduced pressure. The resulting concentration residue was subjected to silica gel column chromatography, and the fraction obtained from an elution with 65% ethyl acetate/hexane was concentrated under reduced pressure to obtain a white solid. The resulting solid was washed with ethylacetate-hexane, and then was collected by filtration, to obtain the title compound (66 mg, 0.147 mmol, 64%) as a white powder.

$^1$H-NMR (400 MHz, CDCl$_3$) δ: 2.22 (3H, s), 3.91 (3H, s), 5.94 (1H, s), 6.90-7.10 (2H, m), 7.11-7.20 (2H, m), 7.65-7.80 (3H, m), 7.95 (1H, s), 9.11 (1H, s), 10.21 (1H, br s).

IR(ATR)cm$^{-1}$: 3343, 1689, 1587, 1475, 1295, 1238, 1207, 1172, 1141, 1112, 1079.

mp: 231-234° C.

MS m/z: 451 (M$^+$+H).

Anal. calcd for C$_{21}$H$_{17}$F$_3$N$_2$O$_4$S: C, 56.00; H, 3.80; F, 12.65; N, 6.22; S, 7.12.

Found: C, 56.00; H, 3.80; F, 12.85; N, 6.32; S, 7.23.

Example 79

5-[(2,5-Difluorophenyl)[(4-fluorophenyl)sulfonyl]methyl]-N-methoxy-N,4-dimethylpyridine-2-carboxamide

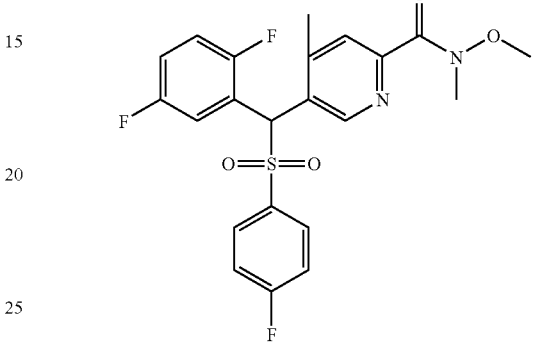

To a solution of 5-[(2,5-difluorophenyl)[(4-fluorophenyl)sulfonyl]methyl]-4-methylpyridine-2-carboxylic acid (99 mg, 0.235 mmol) obtained in Example 12 in methylene chloride (3 ml), N, O-dimethylhydroxyamine hydrochloride (28 mg, 0.282 mmol), 1-hydroxybenzotriazole (32 mg, 0.235 mmol), 1-ethyl-3-(3-dimethylaminopropyl)carbodiimide hydrochloride mg, 0.382 mmol) and 4-methylmorpholine (61 µl, 0.564 mmol) were added. The reaction solution was stirred for 5 days at room temperature, and was concentrated under reduced pressure. The resulting concentration residue was subjected to silica gel column chromatography, and the fraction obtained from an elution with hexane:ethylacetate (=1:1) was concentrated under reduced pressure. Ethyl acetate-hexane was added to the resulting concentration residue, and the solid thus precipitated was collected by filtration, to obtain the title compound (73 mg, 0.157 mmol, 67%) as a white powder.

$^1$H-NMR (400 MHz, CDCl$_3$) δ: 2.21 (3H, s), 3.42 (3H, br s), 3.81 (3H, s), 5.95 (1H, s), 6.90-7.09 (2H, m), 7.10-7.19 (2H, m), 7.48-7.59 (1H, m), 7.68-7.81 (3H, m), 9.20 (1H, s).

IR(ATR)cm$^{-1}$: 1631, 1590, 1490, 1425, 1324, 1286, 1232, 1147, 1083, 987, 904.

mp: 156-158° C.

MS m/z: 465 (M$^+$+H).

Anal. calcd for C$_{22}$H$_{19}$F$_3$N$_2$O$_4$S: C, 56.89; H, 4.12; F, 12.27; N, 6.03; S, 6.90.

Found: C, 56.96; H, 4.11; F, 12.53; N, 6.08; S, 7.02.

Example 80

N-[[5-[(2,5-difluorophenyl)[(4-fluorophenyl)sulfonyl]methyl]-4-methylpyridin-2-yl]carbonyl]-β-alanine ethyl ester

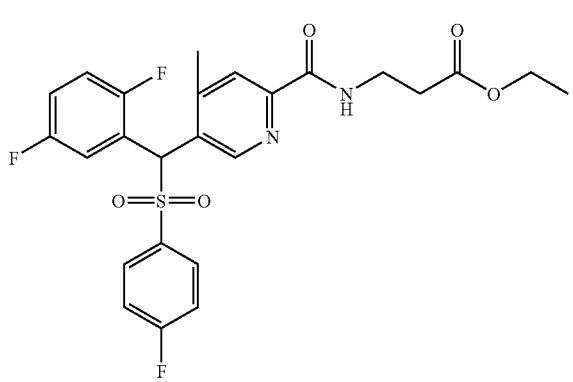

To a solution of 5-[(2,5-difluorophenyl)[(4-fluorophenyl)sulfonyl]methyl]-4-methylpyridine-2-carboxylic acid (106 mg, 0.252 mmol) obtained in Example 12 in methylene chloride (3 ml), β-alanine ethyl ester hydrochloride (46 mg, 0.302 mmol), 1-hydroxybenzotriazole (34 mg, 0.252 mmol), 1-ethyl-3-(3-dimethylaminopropyl)carbodiimide hydrochloride mg, 0.302 mmol) and 4-methylmorpholine (66 μl, 0.604 mmol) were added. The reaction solution was stirred for 15 hours at room temperature, and was concentrated under reduced pressure. The resulting concentration residue was subjected to silica gel column chromatography, and the fraction obtained from an elution with hexane:ethyl acetate (=1:1) was concentrated under reduced pressure, to obtain the title compound (126 mg, 0.242 mmol, 96%) as an amorphous substance.

$^1$H-NMR (400 MHz, CDCl$_3$) δ: 1.29 (3H, t, J=7.1 Hz), 2.20 (3H, s), 2.64 (2H, t, J=6.1 Hz), 3.70-3.79 (2H, m), 4.20 (2H, q, J=7.1 Hz), 5.95 (1H, s), 6.90-7.09 (2H, m), 7.14 (2H, t, J=8.6 Hz), 7.65-7.73 (2H, m), 7.76-7.83 (1H, m), 7.95 (1H, s), 8.40-8.50 (1H, m), 9.14 (1H, s).

IR(ATR)cm$^{-1}$: 3396, 1727, 1671, 1589, 1521, 1492, 1326, 1292, 1236, 1186, 1147, 1081.

MS m/z: 520 (M$^+$).

Example 81

N-[[5-[(2,5-difluorophenyl)[(4-fluorophenyl)sulfonyl]methyl]-4-methylpyridin-2-yl]carbonyl]-β-alanine

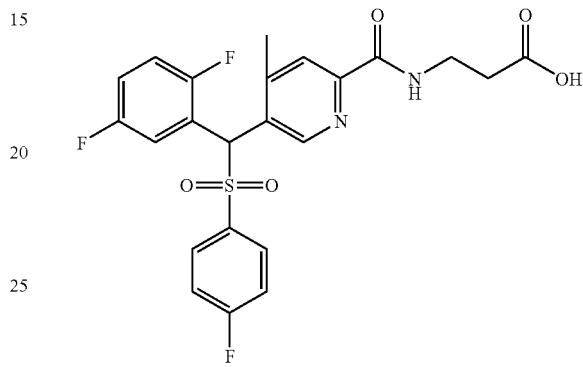

To a solution of N-[[5-[(2,5-difluorophenyl)[(4-fluorophenyl)sulfonyl]methyl]-4-methylpyridin-2-yl]carbonyl]-1-alanine ethyl ester (120 mg, 0.231 mmol) in tetrahydrofuran (5 ml) and water (3 ml), lithium hydroxide monohydrate (12 mg, 0.277 mmol) was added thereto, and the mixture was stirred for 2.5 hours at room temperature. 1 N hydrochloric acid (0.3 ml) and water were added to the reaction solution, and the mixture was extracted with methylene chloride. The organic layer was dried over anhydrous sodium sulfate and filtered, and then the filtrate was concentrated under reduced pressure. Ethyl acetate-hexane was added to the resulting concentration residue, and the solid thus precipitated was collected by filtration, to obtain the title compound (102 mg, 0.207 mmol, 90%) as a white powder.

$^1$H-NMR (400 MHz, CDCl$_3$) δ: 2.20 (3H, s), 2.74 (2H, t, J=6.3 Hz), 3.78 (2H, q, J=6.3 Hz), 5.95 (1H, s), 6.90-7.09 (2H, m), 7.14 (2H, t, J=8.5 Hz), 7.65-7.75 (2H, m), 7.76-7.82 (1H, m), 7.96 (1H, s), 8.47 (1H, br t, J=6.3 Hz), 9.17 (1H, s).

IR(ATR)cm$^{-1}$: 3062, 2969, 1716, 1654, 1589, 1531, 1490, 1326, 1230, 1182, 1145, 1085.

mp: 223-226° C.

MS m/z: 493 (M$^+$+H).

Anal. calcd for C$_{23}$H$_{19}$F$_3$N$_2$O$_5$S: C, 56.09; H, 3.89; F, 11.57; N, 5.69; S, 6.51.

Found: C, 56.00; H, 3.91; F, 11.57; N, 5.67; S, 6.60.

Example 82

Tert-butyl[2-[[[5-[(2,5-difluorophenyl)[(4-fluorophenyl)sulfonyl]methyl]-4-methylpyridin-2-yl]carbonyl]amino]ethyl]carbamate

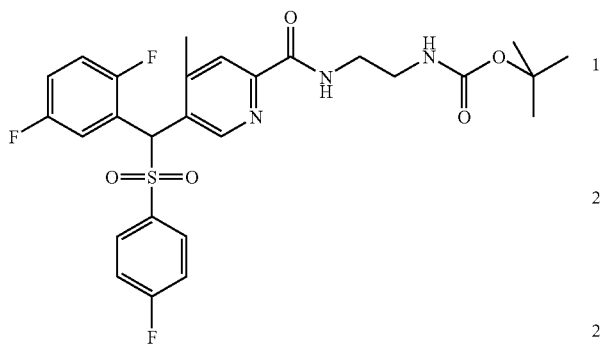

To a solution of 5-[(2,5-difluorophenyl)[(4-fluorophenyl)sulfonyl]methyl]-4-methylpyridine-2-carboxylic acid (374 mg, 0.888 mmol) obtained in Example 12 in methylene chloride (10 ml), tert-butyl (2-aminoethyl)carbamate (170 μl, 1.07 mmol), 1-hydroxybenzotriazole (120 mg, 0.888 mmol), 1-ethyl-3-(3-dimethylaminopropyl)carbodiimide hydrochloride (206 mg, 1.07 mmol) and 4-methylmorpholine (116 μl, 1.07 mmol) were added, and the mixture was stirred for 19 hours at room temperature. Ethyl acetate was added to the reaction solution, and the mixture was washed sequentially with saturated aqueous sodium hydrogencarbonate and saturated brine. The organic layer was dried over anhydrous sodium sulfate and filtered, and the filtrate was concentrated under reduced pressure. The resulting concentration residue was subjected to silica gel column chromatography, and the fraction obtained from an elution with hexane:ethylacetate (=1:1) was concentrated under reduced pressure, to obtain the title compound (491 mg, 0.871 mmol, 98%) as an amorphous substance.

$^1$H-NMR (400 MHz, CDCl$_3$) δ: 1.43 (9H, s), 2.20 (3H, s), 3.32-3.45 (2H, m), 3.53-3.65 (2H, m), 4.87-4.97 (1H, m), 5.95 (1H, s), 6.90-7.09 (2H, m), 7.14 (2H, t, J=8.4 Hz), 7.67-7.82 (3H, m), 7.95 (1H, s), 8.25-8.35 (1H, m), 9.15 (1H, s).

IR(ATR)cm$^{-1}$: 3334, 1700, 1670, 1589, 1521, 1492, 1365, 1328, 1236, 1145, 1081.

MS m/z: 564 (M$^+$+H).

Example 83

N-[2-(acetylamino)ethyl]-5-[(2,5-difluorophenyl)[(4-fluorophenyl)sulfonyl]methyl]-4-methylpyridine-2-carboxamide

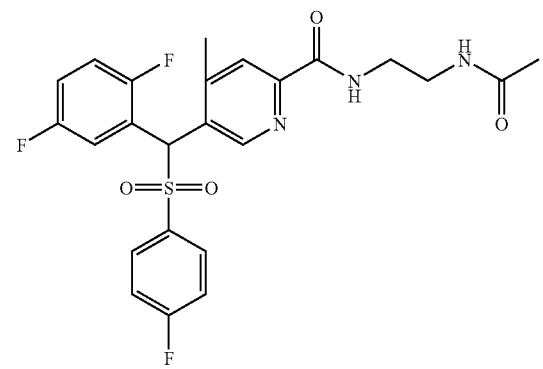

To a solution of tert-butyl[2-[[[5-[(2,5-difluorophenyl)[(4-fluorophenyl)sulfonyl]methyl]-4-methylpyridin-2-yl]carbonyl]amino]ethyl]carbamate (90 mg, 0.160 mmol) in methylene chloride (5 ml), trifluoroacetic acid (2 ml) was added, and the resulting mixture was stirred for 2.5 hours at room temperature. The reaction solution was concentrated under reduced pressure, and methylene chloride and a 0.5 N aqueous sodium hydroxide were added thereto. The organic layer was separated, dried over anhydrous sodium sulfate, and filtered, and then the filtrate was concentrated under reduced pressure. The resulting concentration residue was dissolved in methylene chloride (5 ml), and acetic anhydride (23 μl, 0.240 mmol), triethylamine (26 μl, 0.240 mmol) and a catalytic amount of 4-dimethylaminopyridine were added thereto. The reaction solution was stirred for 20 hours at room temperature, and was concentrated under reduced pressure. The resulting concentration residue was subjected to silica gel column chromatography, and the fraction obtained from an elution with methanol:methylene chloride (=1:20) was concentrated under reduced pressure, to obtain the title compound (79 mg, 0.156 mmol, 98%) as an amorphous substance.

$^1$H-NMR (400 MHz, CDCl$_3$) δ: 1.99 (3H, s), 2.23 (3H, s), 3.46-3.54 (2H, m), 3.58-3.59 (2H, m), 5.96 (1H, s), 6.18-6.28 (1H, m), 6.90-7.09 (2H, m), 7.15 (2H, t, J=8.5 Hz), 7.77-7.92 (3H, m), 7.96 (1H, s), 8.33-8.43 (1H, m), 9.16 (1H, s).

IR(ATR)cm$^{-1}$: 3392, 3361, 1587, 1536, 1490, 1454, 1317, 1276, 1232, 1147.

MS m/z: 505 (M$^+$).

Anal. calcd for $C_{24}H_{22}F_3N_3O_4S$: C, 57.02; H, 4.39; F, 11.27; N, 8.31; S, 6.34.

Found: C, 56.88; H, 4.47; F, 11.45; N, 8.25; S, 6.44.

Example 84

Methyl[2-[[[5-[(2,5-difluorophenyl)[(4-fluorophenyl)sulfonyl]methyl]-4-methylpyridin-2-yl]carbonyl]amino]ethyl]carbamate

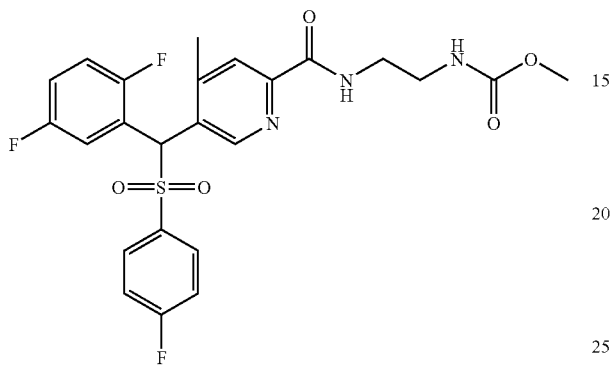

To a solution of tert-butyl[2-[[[5-[(2,5-difluorophenyl)[(4-fluorophenyl)sulfonyl]meth yl]-4-methylpyridin-2-yl]carbonyl]amino]ethyl]carbamate (90 mg, 0.160 mmol) obtained in Example 82 in methylene chloride (5 ml), trifluoroacetic acid (2 ml) was added, and the mixture was stirred for 3 hours at room temperature. The reaction solution was concentrated under reduced pressure, and methylene chloride and a 0.5 N aqueous sodium hydroxide were added thereto. The organic layer was separated, subsequently dried over anhydrous sodium sulfate, and filtered, and then the filtrate was concentrated under reduced pressure. The resulting concentration residue was dissolved in methylene chloride (5 ml), and methyl chloroformate (19 μl, 0.240 mmol) and triethylamine (26 μl, 0.240 mmol) were added thereto. The reaction solution was stirred for 20 hours at room temperature, and was concentrated under reduced pressure. The resulting concentration residue was subjected to silica gel column chromatography, and the fraction obtained from an elution with 60% ethylacetate/hexane was concentrated under reduced pressure. Ethyl acetate-hexane was added to the resulting concentration residue, and the solid thus precipitated was collected by filtration, to obtain the title compound (71 mg, 0.136 mmol, 85%) as a white powder.

$^1$H-NMR (400 MHz, CDCl$_3$) δ: 2.21 (3H, s), 3.40-3.48 (2H, m), 3.58-3.65 (2H, m), 3.68 (3H, s), 5.11-5.22 (1H, m), 5.96 (1H, s), 6.90-7.09 (2H, m), 7.15 (2H, t, J=8.5 Hz), 7.68-7.73 (2H, m), 7.75-7.82 (1H, m), 7.95 (1H, s), 8.28-8.35 (1H, m), 9.15 (1H, s).

IR(ATR)cm$^{-1}$: 3396, 3340, 1718, 1670, 1589, 1533, 1490, 1452, 1315, 1270, 1234, 1145.

mp: 167-169° C.

MS m/z: 521 (M$^+$).

Anal. calcd for C$_{24}$H$_{22}$F$_3$N$_3$O$_5$S: C, 55.27; H, 4.25; F, 10.93; N, 8.06; S, 6.15.

Found: C, 55.23; H, 4.21; F, 11.13; N, 7.96; S, 6.20.

Example 85

5-[(2,5-difluorophenyl)[(4-fluorophenyl)sulfonyl]methyl]-N-(1-hydroxymethyl)-4-methylpyridine-2-carboxamide

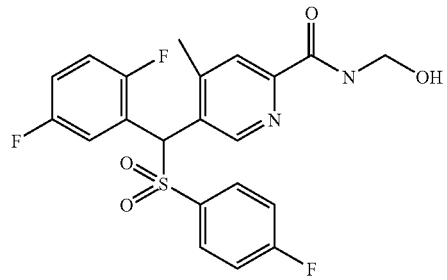

To a solution of 5-[(2,5-difluorophenyl)[(4-fluorophenyl)sulfonyl]methyl]-4-methylpyridine-2-carboxamide (744 mg, 1.84 mmol) obtained in Example 15 in ethylene glycol dimethyl ether (8 ml), an aqueous solution of formaldehyde (37%, 0.4 ml) and 5% aqueous sodium hydroxide (1.6 ml) were added at 0° C., and the resulting mixture was stirred for 3 hours at room temperature. Sodium carbonate (80 mg) was added to the reaction mixture, and the mixture was stirred for 10 minutes at room temperature. The mixture was concentrated under reduced pressure, and then the residue was dissolved in chloroform, dried over magnesium sulfate, and filtered. Subsequently, the filtrate was concentrated under reduced pressure, and the resulting residue was washed with diethyl ether, and then was collected by filtration, to obtain the title compound (524 mg, 1.16 mmol, 63%) as a white solid.

$^1$H-NMR (400 MHz, CDCl$_3$) δ: 2.22 (3H, s), 3.06 (1H, br), 5.01 (2H, t, J=6.8 Hz), 5.96 (1H, s), 6.92-6.98 (1H, m), 7.01-7.08 (1H, m), 7.14 (2H, t, J=8.8 Hz), 7.67-7.73 (2H, m), 7.75-7.80 (1H, m), 7.96 (1H, s), 8.78-8.85 (1H, br), 9.17 (1H, s).

IR(ATR)cm$^{-1}$: 3405, 1683, 1589, 1511, 1492, 1236, 1147, 1035, 723, 593, 555, 522

Mp: 164-166° C.

MS m/z: 451 (M$^+$+H).

Anal. Calcd for C$_{21}$H$_{17}$F$_3$N$_2$O$_4$S: C, 56.00; H, 3.80; F, 12.65; N, 6.22; S, 7.12.

Found: C, 55.97; H, 3.80; F, 12.83; N, 6.12; S, 7.18.

Example 86

[[[5-[(2,5-Difluorophenyl)(4-fluorophenylsulfonyl)methyl]-4-methylpyridin-2-yl]carbonyl]amino]methyl acetate

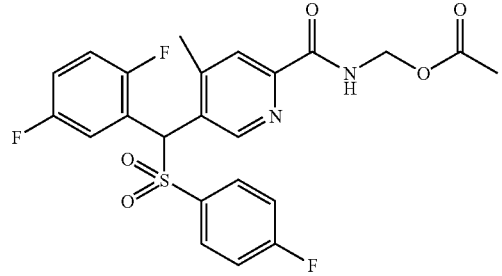

To a solution of 5-[(2,5-difluorophenyl)[(4-fluorophenyl)sulfonyl]methyl]-N-(1-hydroxymethyl)-4-methylpyridine-2-carboxamide (200 mg, 0.44 mmol) obtained in Example 85 in pyridine (2 ml), acetic anhydride (2 ml) was added, and the mixture was stirred for 3 hours at room temperature. The reaction mixture was concentrated under reduced pressure, and then the residue was dissolved in ethyl acetate, and was washed with water. The solution was dried over anhydrous sodium sulfate and filtered, then the filtrate was concentrated under reduced pressure, and the obtained residue was subjected to silica gel column chromatography. The fraction obtained from an elution with hexane:ethyl acetate=10:3 was concentrated under reduced pressure, washed with diethyl ether, and was collected by filtration, to obtain the title compound (86 mg, 0.17 mmol, 39%) as a white solid.

$^1$H-NMR (400 MHz, CDCl$_3$) δ: 2.08 (3H, s), 2.23 (3H, s), 5.47 (2H, d, J=7.3 Hz) 5.96 (1H, s), 6.91-6.97 (1H, m), 7.01-7.08 (1H, m), 7.14 (2H, t, J=8.8 Hz), 7.70 (2H, dd, J=8.8, 5.1 Hz), 7.74-7.80 (1H, m), 7.99 (1H, s), 8.96 (1H, t, J=7.3 Hz), 9.17 (1H, s).

IR(ATR)cm$^{-1}$: 3280, 1735, 1677, 1519, 1492, 1234, 1147, 1018, 715, 568, 530.

Mp 111-113° C.

MS m/z: 493 (M$^+$+H).

Anal. Calcd for C$_{23}$H$_{19}$F$_3$N$_2$O$_5$S: C, 56.09; H, 3.89; F, 11.57; N, 569; S, 6.51

Found: C, 55.91; H, 3.77; F, 11.68; N, 5.66; S, 6.67.

Example 87

5-[(2,5-Difluorophenyl)[(4-fluorophenyl)sulfonyl]methyl]-N-(trans-4-hydroxycyclohexyl)-4-methylpyridine-2-carboxamide

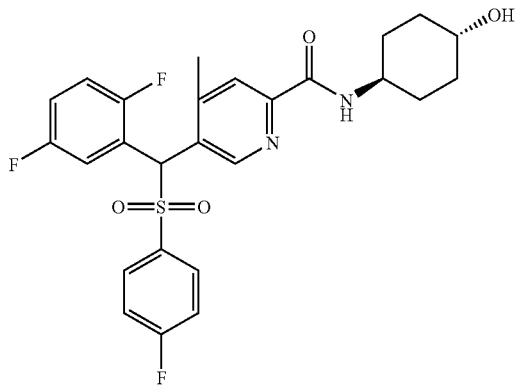

To a solution of 5-[(2,5-difluorophenyl)[(4-fluorophenyl)sulfonyl]methyl]-4-methylpyridine-2-carboxylic acid (114 mg, 0.271 mmol) obtained in Example 12 in methylene chloride (3 ml), trans-4-aminocyclohexanol hydrochloride (49 mg, 0.325 mmol), 1-hydroxybenzotriazole (37 mg, 0.271 mmol), 1-ethyl-3-(3-dimethylaminopropyl)carbodiimide hydrochloride (62 mg, 0.325 mmol) and 4-methylmorpholine (71 μl, 0.650 mmol) were added, and the mixture was stirred for 17 hours at room temperature. Ethyl acetate was added to the reaction solution, and the mixture was washed sequentially with saturated aqueous sodium hydrogencarbonate and saturated brine. The organic layer was dried over anhydrous sodium sulfate and filtered, and then the filtrate was concentrated under reduced pressure. The resulting concentration residue was subjected to silica gel column chromatography, and the fraction obtained from an elution with methanol:methylene chloride (=1:40) was concentrated under reduced pressure, to obtain the title compound (129 mg, 0.249 mmol, 92%) as an amorphous substance.

$^1$H-NMR (400 MHz, CDCl$_3$) δ: 1.32-1.60 (4H, m), 1.98-2.18 (4H, m), 2.20 (3H, s), 3.64-3.75 (1H, m), 3.89-4.00 (1H, m), 5.95 (1H, s), 6.90-7.09 (2H, m), 7.11-719 (2H, m), 7.68-7.74 (2H, m), 7.75-7.82 (1H, m), 7.88 (1H, br d, J=8.8 Hz), 7.96 (1H, s), 9.13 (1H, s).

IR(ATR)cm$^{-1}$: 3380, 2933, 1664, 1589, 1521, 1492, 1326, 1292, 1236, 1145, 1081.

MS m/z: 518 (M$^+$).

Anal. calcd for C$_{26}$H$_{25}$F$_3$N$_2$O$_4$S: C, 60.22; H, 4.86; F, 10.99; N, 5.40; S, 6.18.

Found: C, 60.15; H, 4.86; F, 10.82; N, 5.41; S, 6.21.

Example 88

1-[[5-[(2,5-Difluorophenyl)[(4-fluorophenyl)sulfonyl]methyl]-4-methylpyridin-2-yl]carbonyl]azetidin-3-ol

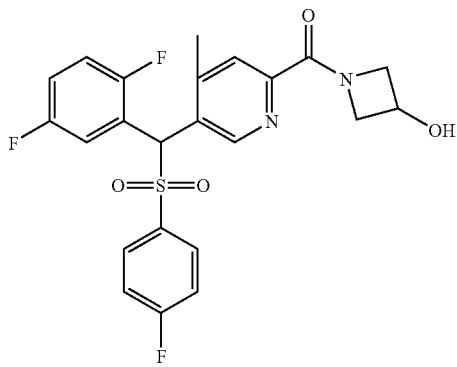

To a solution of 1-(diphenylmethyl)azetidin-3-ol (230 mg, 0.961 mmol) in ethanol (10 ml), palladium-carbon (50 mg) was added, and the mixture was stirred for 1.5 hours in a hydrogen atmosphere. The reaction suspension was filtered, and then the filtrate was concentrated under reduced pressure. The resulting concentration residue was dissolved in methylene chloride (10 ml), and 5-[(2,5-difluorophenyl)[(4-fluorophenyl)sulfonyl]methyl]-4-methylpyridine-2-carboxylic acid (113 mg, 0.268 mmol) obtained in Example 12, 1-hydroxybenzotriazole (36 mg, 0.268 mmol), 1-ethyl-3-(3-dimethylaminopropyl)carbodiimide hydrochloride (62 mg, 0.322 mmol) and 4-methylmorpholine (35 μl, 0.322 mmol) were added. The mixture was stirred for 4 days at room temperature. The reaction solution was concentrated under reduced pressure, ethyl acetate was added, and the mixture was washed sequentially with saturated aqueous sodium hydrogencarbonate and saturated brine. The organic layer was dried over anhydrous sodium sulfate and filtered, and then the filtrate was concentrated under reduced pressure. The resulting concentration residue was subjected to silica gel column chromatography, and the fraction obtained from an elution with methanol:methylene chloride (=1:40) was concentrated under reduced pressure, to obtain a solid. The obtained solid was washed with ethanol, and then was collected by filtration to obtain the title compound (72 mg, 0.151 mmol, 56%) as a white powder.

$^1$H-NMR (400 MHz, CDCl$_3$) δ: 2.08-2.14 (1H, m), 2.17 (1.5H, s), 2.19 (1.5H, s), 4.02-4.12 (1H, m), 4.42-4.62 (2H, m), 4.70-4.80 (1H, m), 4.95-5.07 (1H, m), 5.94 (1H, s), 6.90-7.09 (2H, m), 7.11-7.19 (2H, m), 7.65-7.72 (2H, m), 7.75-7.82 (1H, m), 7.89 (0.5H, s), 7.91 (0.5H, s), 9.17 (1H, s).

IR(ATR)cm$^{-1}$: 3409, 1612, 1587, 1546, 1494, 1461, 1419, 1359, 1324, 1294, 1234, 1216, 1143.

mp: 219-221° C.

MS m/z: 477 (M$^+$+H).

Anal. calcd for C$_{23}$H$_{19}$F$_3$N$_2$O$_4$S: C, 57.98; H, 4.02; F, 11.96; N, 5.88; S, 6.73.

Found: C, 57.70; H, 4.04; F, 12.21; N, 5.90; S, 6.79.

Example 89

4-[[5-[(2,5-Difluorophenyl)[(4-fluorophenyl)sulfonyl]methyl]-4-methylpyridin-2-yl]carbonyl]piperazin-2-one

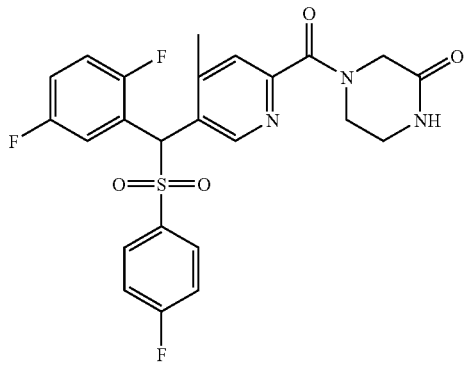

To a solution of 5-[(2,5-difluorophenyl)[(4-fluorophenyl)sulfonyl]methyl]-4-methylpyridine-2-carboxylic acid (114 mg, 0.271 mmol) obtained in Example 12 in methylene chloride (3 ml), piperazin-2-one (33 mg, 0.325 mmol), 1-hydroxybenzotriazole (37 mg, 0.271 mmol), 1-ethyl-3-(3-dimethylaminopropyl)carbodiimide hydrochloride (62 mg, 0.325 mmol) and 4-methylmorpholine (35 µl, 0.325 mmol) were added. The reaction mixture was stirred for 4 days at room temperature, and was concentrated under reduced pressure. Ethyl acetate was added to the resulting concentration residue, and the mixture was washed sequentially with saturated aqueous sodium hydrogencarbonate and saturated brine. The organic layer was dried over anhydrous sodium sulfate and filtered, and then the filtrate was concentrated under reduced pressure. The resulting concentration residue was subjected to silica gel column chromatography, and the fraction obtained from an elution with methanol:methylene chloride (=1:30) was concentrated under reduced pressure. The resulting solid was washed with ether, and then was collected by filtration, to obtain the title compound (116 mg, 0.230 mmol, 85%) as a white powder.

$^1$H-NMR (400 MHz, CDCl$_3$) δ: 2.22 (1.5H, s), 2.27 (1.5H, s), 3.49-3.65 (2H, m), 3.92-4.15 (2H, m), 4.40-4.53 (2H, m) 5.96 (1H, s), 5.99-6.10 (1H, m), 6.89-7.10 (2H, m), 7.11-7.20 (2H, m), 7.58 (0.5H, s), 7.65 (0.5H, s), 7.70-7.83 (3H, m), 9.16 (0.5H, s), 9.18 (0.5H, s).

IR(ATR)cm$^{-1}$: 1681, 1660, 1619, 1589, 1492, 1471, 1413, 1322, 1297, 1236, 1218.

MS m/z: 504 (M$^+$+H)

FAB-MS: 504.1189 (Calcd for C$_{24}$H$_{21}$O$_4$N$_3$F$_3$S: 504.1205)..

Example 90

N-(2-chloroethyl)-5-[(2,5-difluorophenyl)[(4-fluorophenyl)sulfonyl]methyl]-4-methylpyridine-2-carboxamide

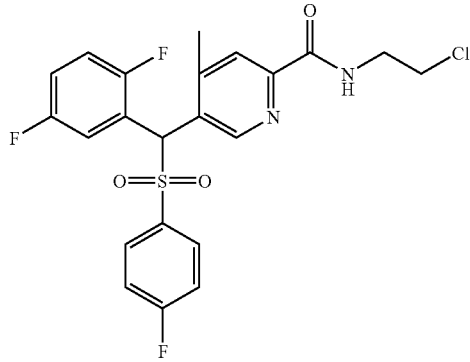

To a solution of 5-[(2,5-difluorophenyl)[(4-fluorophenyl)sulfonyl]methyl]-N-(2-hydroxyethyl)-4-methylpyridine-2-carboxamide (120 mg, 0.258 mmol) obtained in Example 17 in methylene chloride (5 ml), thionyl chloride (100 µl) was added, and the mixture was stirred for 4 hours at room temperature. Thionyl chloride (100 µl) was added to the reaction solution, and the mixture was stirred for 1.5 hours at room temperature. The reaction solution was concentrated under reduced pressure, subsequently saturated aqueous sodium hydrogencarbonate was added thereto, and the mixture was extracted with methylene chloride. The organic layer was dried over anhydrous sodium sulfate and filtered, and then the filtrate was concentrated under reduced pressure. The resulting concentration residue was subjected to silica gel column chromatography, and the fraction obtained from an elution with 35% ethyl acetate/hexane was concentrated under reduced pressure, to obtain the title compound (102 mg, 0.211 mmol, 82%) as a white solid.

$^1$H-NMR (400 MHz, CDCl$_3$) δ: 2.22 (3H, s), 3.69-3.90 (4H, m), 5.96 (1H, s), 6.90-7.09 (2H, m) 7.11-7.20 (2H, m), 7.67-7.74 (2H, m), 7.77-7.83 (1H, m), 7.96 (1H, s), 8.37-8.45 (1H, m), 9.17 (1H, s).

IR(ATR)cm$^{-1}$: 3369, 1685, 1590, 1525, 1488, 1438, 1328, 1295, 1232, 1147, 1078.

MS m/z: 483 (M$^+$+H).

Example 91

Diethyl 5-[(2,5-difluorophenyl)[(4-fluorophenyl)sulfonyl]methyl]-4-methylpyridine-2-carboxylic acid

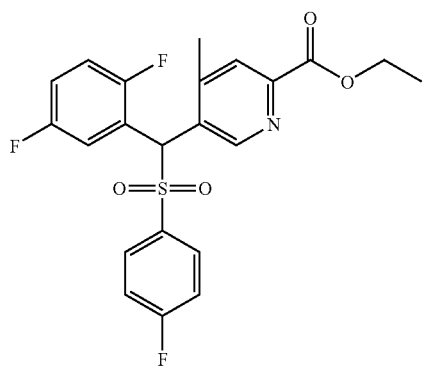

An ethanol solution of 5-[(2,5-difluorophenyl)[(4-fluorophenyl)sulfonyl]methyl]-4-methylpyridine-2-carboxylic acid (104 mg, 0.247 mmol) obtained in Example 12 and concentrated hydrochloric acid (50 μl) was heated to reflux for 21 hours. The reaction solution was returned to room temperature, and then was concentrated under reduced pressure. Saturated aqueous sodium hydrogencarbonate was added to the resulting concentration residue, and the mixture was extracted with ethylacetate. The organic layer was washed with saturated brine, dried over anhydrous sodium sulfate, and filtered, and the filtrate was concentrated under reduced pressure. The resulting concentration residue was subjected to silica gel column chromatography, and the fraction obtained from an elution with 30% ethyl acetate/hexane was concentrated under reduced pressure, to obtain a solid. The obtained solid was washed with ethanol, and then was collected by filtration, to obtain the title compound (90 mg, 0.200 mmol, 81%) as a white powder.

$^1$H-NMR (400 MHz, CDCl$_3$) δ: 1.45 (3H, t, J=7.1 Hz), 2.23 (3H, s), 4.47 (2H, q, J=7.1 Hz), 5.97 (1H, s), 6.90-7.09 (2H, m), 7.10-7.18 (2H, m), 7.69-7.80 (3H, m), 7.90 (1H, s), 9.36 (1H, s).

IR(ATR)cm$^{-1}$: 1739, 1589, 1556, 1332, 1317, 1278, 1232, 1216, 1145, 1101, 1081.

mp: 151-153° C.

MS m/z: 450 (M$^+$+H).

FAB-MS: 450.1008 (Calcd for C$_{22}$H$_{19}$O$_4$NF$_3$S: 450.0987).

Example 92

5-[(2,5-Difluorophenyl)[(4-fluorophenyl)sulfonyl]methyl]-N,N,4-trimethylpyridine-2-carbothioamide

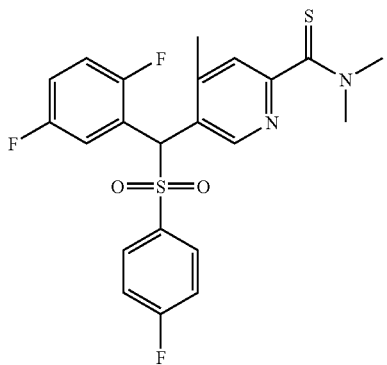

A solution of 5-[(2,5-difluorophenyl)[(4-fluorophenyl)sulfonyl]methyl]-N,N,4-trimethylpyridine-2-carboxamide (168 mg, 0.375 mmol) obtained in Example 14 and Lowesson's Reagent (167 mg, 0.413 mmol) in toluene (10 ml) was heated to reflux for 3 hours. The reaction solution was returned to room temperature, and then was concentrated under reduced pressure. The resulting concentration residue was subjected to silica gel column chromatography, and the fraction obtained from an elution with 40% ethyl acetate/hexane was concentrated under reduced pressure Ether was added to the resulting concentration residue, and the solid thus precipitated was collected by filtration, to obtain the title compound (119 mg, 0.256 mmol, 68%) as a pale yellow powder.

$^1$H-NMR (400 MHz, CDCl$_3$) δ: 2.26 (3H, s), 3.24 (3H, s), 3.60 (3H, s), 5.94 (1H, s), 6.88-7.08 (2H, m), 7.10-7.19 (2H, m), 7.43 (1H, s), 7.70-7.80 (3H, m), 9.09 (1H, s).

IR(ATR)cm$^{-1}$: 1585, 1527, 1492, 1407, 1315, 1292, 1230, 1139, 1081.

mp: 161-164° C.

MS m/z: 465 (M$^+$+H).

Anal. calcd for C$_{22}$H$_{19}$F$_3$N$_2$O$_2$S$_2$: C, 56.88; H, 4.12; F, 12.27; N, 6.03; S, 13.81.

Found: C, 56.60; H, 4.10; F, 12.27; N, 6.06; S, 13.64.

Example 93

5-[[(4-Fluorophenyl)thio](2,3,6-trifluorophenyl)methyl]-N-(2-hydroxyethyl)-4-methylpyridine-2-carboxamide

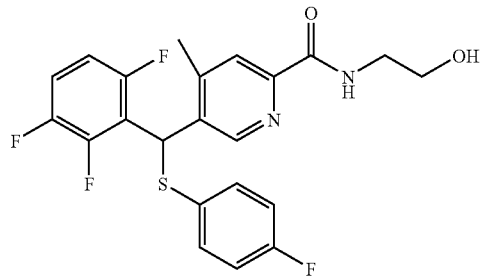

To a solution of 5-[[(4-fluorophenyl)thio](2,3,6-trifluorophenyl)methyl]-4-m ethylpyridine-2-carboxylic acid (163 mg, 0.40 mmol) obtained in Example 34 in methylene chloride (5 ml), 2-aminoethanol (0.027 ml, 0.44 mmol), 1-hydroxybenzotriazole (60 mg, 0.44 mmol), 4-methylmorpholine (0.048 ml, 0.44 mmol), and 1-ethyl-3-(3-dimethylaminopropyl)carbodiimide hydrochloride (84 mg, 0.44 mmol) were added at room temperature. After stirring for 3 hours at room temperature, the reaction mixture was washed with water and then with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=2:3 was concentrated under reduced pressure to obtain the title compound (175 mg, 0.39 mmol, 97%) as a colorless oily substance.

$^1$H-NMR (400 MHz, CDCl$_3$) δ: 2.25 (3H, s), 2.68-2.75 (1H, m), 3.62-3.68 (2H, m), 3.82-3.89 (2H, m), 5.78 (1H, s), 6.75-6.84 (1H, m), 6.92-7.00 (2H, m), 7.02-7.12 (1H, m), 7.32-7.39 (2H, m), 7.94 (1H, s), 8.37-8.45 (1H, m), 9.07 (1H, s).

MS m/z: 451 (M$^+$+H).

Example 94

5-[[(4-Fluorophenyl)sulfonyl](2,3,6-trifluorophenyl)methyl]-N-(2-hydroxyethyl)-4-methylpyridine-2-carboxamide

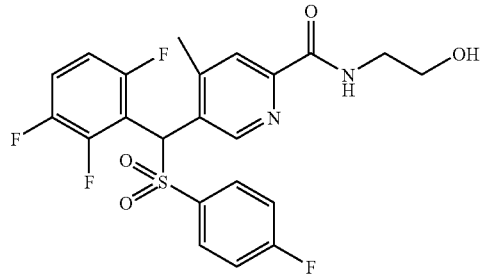

To a solution of 5-[[(4-fluorophenyl)thio](2,3,6-trifluorophenyl)methyl]-N-(2-hydroxyethyl)-4-methylpyridine-2-carboxamide (173 mg, 0.38 mmol) in methylene chloride (5 ml), 3-chloroperbenzoic acid (204 mg, 0.77 mmol) was added at room temperature. After stirring for 3 hours at room temperature, 3-chloroperbenzoic acid (102 mg, 0.38 mmol) was further added, and the mixture was stirred for 1 hour at the same temperature. The reaction mixture was washed with 1 N aqueous sodium hydroxide, the organic layer was dried over anhydrous sodium sulfate and filtered, and then the filtrate was concentrated under reduced pressure. The resulting residue was subjected to flash silica gel chromatography, and the fraction obtained from an elution with hexane:ethyl acetate=1:2 was concentrated under reduced pressure. The resulting residue was washed with diethyl ether, and then was collected by filtration, to obtain the title compound (126 mg, 0.26 mmol, 68%) as a white solid.

$^1$H-NMR (400 MHz, CDCl$_3$) δ: 2.14 (3H, s), 2.60 (1H, t, J=5.4 Hz), 3.63-3.69 (2H, m), 3.83-3.89 (2H, m), 5.89 (1H, s), 6.82-6.90 (1H, m), 7.14-7.25 (3H, m), 7.73-7.79 (2H, m), 7.97 (1H, s), 8.41-8.48 (1H, m), 9.42 (1H, s).

IR(ATR)cm$^{-1}$: 3379, 1662, 1533, 1493, 1329, 1230, 1146, 1082, 820.

mp: 164-165° C.

Anal. Calcd for C$_{22}$H$_{18}$F$_4$N$_2$O$_4$S: C, 54.77; H, 3.76; F, 15.75; N, 5.81; S, 6.65. Found: C, 54.76; H, 3.69; F, 15.76; N, 5.84; S, 6.75.

MS m/z: 483 (M$^+$+H).

Example 95

5-[(2,5-Difluorophenyl) [(4-fluorophenyl)thio]methyl]-N-(2-hydroxyethyl)-4-methylpyridine-2-carboxamide

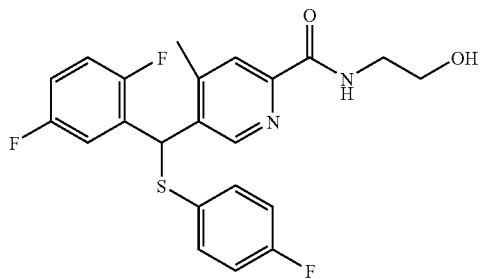

To a solution of 5-[(2,5-difluorophenyl) [(4-fluorophenyl)thio]methyl]-4-methylpyridine-2-carboxylic acid (483 mg, 1.24 mmol) obtained in Example 20 in methylene chloride (10 ml), 2-aminoethanol (0.083 ml, 1.36 mmol), 1-hydroxybenzotriazole (184 mg, 1.36 mmol), 4-methylmorpholine (0.150 ml, 1.36 mmol), and 1-ethyl-3-(3-dimethylaminopropyl)carbodiimide hydrochloride (262 mg, 1.36 mmol) were added at room temperature. After stirring for 4 hours at room temperature, water was added to the reaction mixture, and the mixture was washed with saturated aqueous ammonium chloride. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=1:3 was concentrated under reduced pressure, to obtain the title compound (481 mg, 1.11 mmol, 90%) as a colorless foamy substance.

$^1$H-NMR (400 MHz, CDCl$_3$) δ: 2.37 (3H, s), 2.57-2.65 (1H, m), 3.61-3.66 (2H, m), 3.80-3.87 (2H, m), 5.82 (1H, s), 6.91-7.00 (4H, m), 7.28-7.38 (3H, m), 8.00 (1H, s), 8.31-8.37 (1H, m), 8.61 (1H, s).

LC-MS m/z: 433 (M$^+$+H).

Example 96

5-[(2,5-Difluorophenyl)[(4-fluorophenyl)sulfinyl] methyl]-N-(2-hydroxyethyl)-4-methylpyridine-2-carboxamide

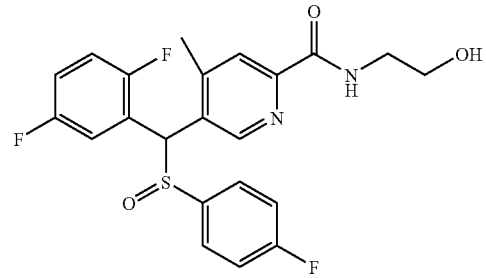

To a solution of 5-[(2,5-difluorophenyl)[(4-fluorophenyl) thio]methyl]-N-(2-hydroxyethyl)-4-methylpyridine-2-carboxamide (478 mg, 1.11 mmol) in methylene chloride (15 ml), 3-chloroperbenzoic acid (293 mg, 1.11 mmol) was added at 0° C. After stirring for 3 hours at the same temperature, the reaction mixture was washed with 1 N aqueous sodium hydroxide, the organic layer was dried over anhydrous sodium sulfate and filtered, and then the filtrate was concentrated under reduced pressure. The resulting residue was subjected to flash silica gel chromatography, and the fraction obtained from an elution with hexane:ethyl acetate=1:2 was concentrated under reduced pressure. The resulting residue was washed with hexane, and then the residue was dried under reduced pressure, to obtain the title compound (238 mg, 0.53 mmol, 48%) as a colorless foamy substance.

$^1$H-NMR (400 MHz, CDCl$_3$) δ: 1.94 (1.5H, s), 2.13 (1.5H, s), 2.51-2.65 (1H, m), 3.63-3.70 (2H, m), 3.83-3.90 (2H, m), 5.33 (0.5H, s), 5.35 (0.5H, s), 6.87-7.14 (4H, m), 7.28-7.37 (2.5H, m), 7.48-7.54 (0.5H, m) 7.92 (0.5H, s), 7.97 (0.5H, s), 8.36-8.46 (1H, m), 8.85 (0.5H, s), 9.03 (0.5H, s).

IR(ATR)cm$^{-1}$: 3383, 1660, 1589, 1527, 1489, 1225, 1082, 1049.

Anal. Calcd for C$_{22}$H$_{19}$F$_3$N$_2$O$_3$S: C, 58.92; H, 4.27; F, 12.71; N, 6.25; S, 7.15. Found: C, 58.53; H, 4.30; F, 12.91; N, 6.16; S, 7.08.

MS m/z: 449 (M$^+$+H).

Reference Example 10

O-ethyl S-(3,5-difluorophenyl)dithiocarbonate

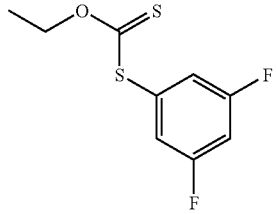

3,5-Difluoroaniline (7.11 g, 54.0 mmol) was dissolved in methanol (30 ml), and 1 N hydrochloric acid (150 ml) was added at −10° C. Subsequently, a solution of sodium nitrite (4.54 g, 64.8 mmol) in water (30 ml) was added dropwise thereto at the same temperature, and then the mixture was stirred for 30 minutes at the same temperature. The obtained reaction solution was added dropwise to a solution of O-ethyl potassium dithiocarbonate (commercial product) (13.0 g, 81.0 mmol) in water (150 ml) at 65° C. The reaction mixture

103 was heated to 100° C., stirred for 30 minutes, and then cooled to room temperature, and the mixture was extracted with ethyl acetate. The organic layer was washed with saturated aqueous sodium hydrogencarbonate, subsequently dried over anhydrous sodium sulfate, and filtered, and then the filtrate was concentrated under reduced pressure. The resulting residue was subjected to flash silica gel column chromatography, and the fraction obtained from an elution with hexane was concentrated under reduced pressure, to obtain the title compound (1.86 g, 7.94 mmol, 15%) as a yellow oily substance.

$^1$H-NMR (400 MHz, CDCl$_3$) δ: 1.36 (3H, t, J=7.1 Hz), 4.63 (2H, q, J=7.1 Hz), 6.87-6.94 (1H, m), 7.03-7.10 (2H, m).

Example 97

2-Bromo-5-[(2,5-difluorophenyl)[(3,5-difluorophenyl)thio]methyl]-4-methylpyridine

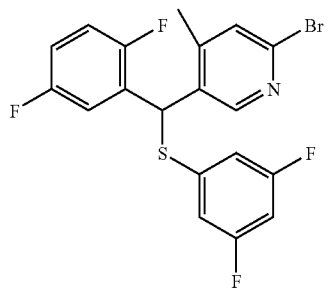

To a solution of O-ethyl S-(3,5-difluorophenyl) dithiocarbonate (1.86 g, 7.94 mmol) methanol (20 ml), 1 N aqueous sodium hydroxide (20 ml) was added, and the mixture was stirred for 2 hours at 65° C. The reaction mixture was cooled to room temperature, and was washed with methylene chloride. Subsequently, the aqueous layer was acidified with 1 N hydrochloric acid, and was extracted with methylene chloride. The organic layer was dried over anhydrous sodium sulfate and Filtered, and then the filtrate was concentrated under reduced pressure. To a solution of the resulting residue and 2-bromo-5-[chloro(2,5-difluorophenyl)methyl]-4-methylpyridine (2.64 g, 7.94 mmol) obtained in Reference Example 2 in N,N-dimethylformamide (40 ml), potassium carbonate (1.21 g, 8.73 mmol) was added in a nitrogen atmosphere at 0° C., and the mixture was stirred for 2 hours at room temperature. Ethyl acetate and water were added to the reaction mixture at 0° C., the organic layer was separated, and the organic layer was washed with saturated aqueous sodium hydrogencarbonate, and then with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=30:1 was concentrated under reduced pressure, and the resulting residue was washed with hexane, and then was collected by filtration, to obtain the title compound (2.35 g, 5.31 mmol, 67%) as a white solid.

$^1$H-NMR (40 MHz, CDCl$_3$) δ: 2.37 (3H, s) 5.86 (1H, s), 6.62-6.69 (1H, m), 6.71-6.78 (2H, m), 6.96-7.07 (2H, m), 7.27-7.32 (1H, m), 7.33 (1H, s), 8.32 (1H, m).

MS m/z: 442, 444 (M$^+$+H).

Example 98

5-[(2,5-Difluorophenyl)[(3,5-difluorophenyl)thio]methyl]-4-methylpyridine-2-carbaldehyde

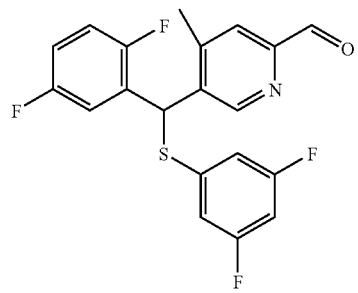

To a solution of 2-bromo-5-[(2,5-difluorophenyl)[(3,5-difluorophenyl)thio]methyl]-4-methylpyridine (2.35 g, 5.31 mmol) in toluene (60 ml), a hexane solution of n-butyllithium (1.54 M, 4.14 ml, 6.38 mmol) was added in an argon atmosphere at −78° C. The reaction mixture was stirred for 30 minutes at −40° C., and then cooled again to −78° C., and N,N-dimethylformamide (0.494 ml, 6.38 mmol) was added. After completion of dropwise addition, the reaction mixture was Allowed to warm to 0° C., and water was added at the same temperature. Ethyl acetate was added to the reaction mixture, the organic layer was separated, and then the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=10:1 was concentrated under reduced pressure to obtain the title compound (1.36 g, 3.47 mmol, 65%) as a white solid.

$^1$H-NMR (400 MHz, CDCl$_3$) δ: 2.49 (3H, s), 5.97 (1H, s), 6.63-6.70 (1H, m), 6.73-6.80 (2H, m), 6.98-7.09 (2H, m), 7.33-7.39 (1H, m), 7.79 (1H, s), 8.74 (1H, m), 10.03 (1H, s).

MS m/z: 392 (M$^+$+H).

Example 99

5-[(2,5-Difluorophenyl)[(3,5-difluorophenyl)sulfonyl]methyl]-4-methylpyridine-2-carboxylic acid

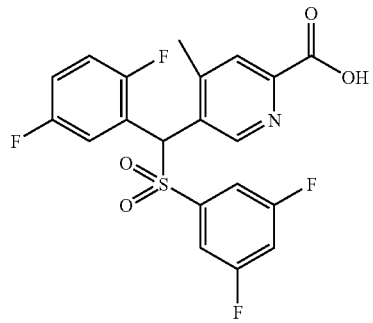

To a solution of 5-[(2,5-difluorophenyl)[(3,5-difluorophenyl)thio]methyl]-4-methylpyridine-2-carbaldehyde (1.36 g, 3.47 mmol) in formic acid (40 ml), 31% aqueous hydrogen peroxide (4 ml) was added and the mixture was stirred for 2 hours at 0° C. After stirring for another 2 hours at room temperature, water was added to the reaction mixture, and the solid thus precipitated was collected by filtration, and was washed with water. The resulting solid was dissolved in methylene chloride, and the solution was washed with 0.1 N hydrochloric acid. Subsequently, the organic layer was dried over anhydrous sodium sulfate and filtered, and then the filtrate was concentrated under reduced pressure. The resulting residue was washed with diethyl ether, and then was collected by filtration, to obtain the title compound (1.39 g, 3.16 mmol, 91%) as a white solid.

$^1$H-NMR (400 MHz, CDCl$_3$) δ: 2.38 (3H, s), 6.02 (1H, s), 6.95-7.02 (1H, m), 7.06-7.15 (2H, m), 7.23-7.30 (2H, m), 7.64-7.70 (1H, m), 8.07 (1H, s), 9.24 (1H, s).

MS m/z: 440 (M$^+$+H).

Example 100

5-[(2,5-Difluorophenyl)[(3,5-difluorophenyl)sulfonyl]methyl]-N-(2-hydroxyethyl)-4-methylpyridine-2-carboxamide

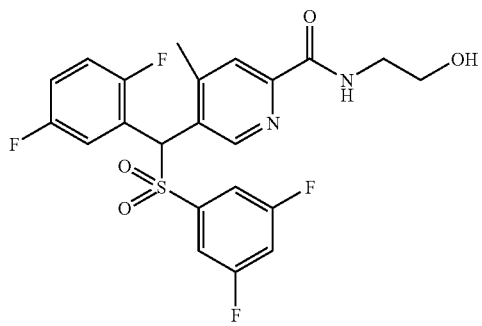

To a solution of 5-[(2,5-difluorophenyl)[(3,5-difluorophenyl)sulfonyl]methyl]-4-methylpyridine-2-carboxylic acid (105 mg, 0.24 mmol) in methylene chloride (5 ml), 2-aminoethanol (0.016 ml, 0.26 mmol), 1-hydroxybenzotriazole (36 mg, 0.26 mmol), 4-methylmorpholine (0.029 ml, 0.26 mmol), and 1-ethyl-3-(3-dimethylaminopropyl)carbodiimide hydrochloride (51 mg, 0.26 mmol) were added at room temperature. After stirring for 4 hours at room temperature, the reaction mixture was washed with 1 N hydrochloric acid. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=2:3 was concentrated under reduced pressure, and the resulting residue was washed with a mixed solvent of ethanol and diethyl ether, and was collected by filtration, to obtain the title compound (36 mg, 0.07 mmol, 31%) as a white solid.

$^1$H-NMR (400 MHz, CDCl$_3$) δ: 2.30 (3H, s), 2.47-2.53 (1H, m), 3.63-3.69 (2H, m), 3.82-3.89 (2H, m), 6.00 (1H, s), 6.93-7.13 (3H, m), 7.22-7.30 (2H, m), 7.65-7.72 (1H, m), 8.01 (1H, s), 8.36-8.44 (1H, m), 9.17 (1H, s).

IR(ATR)cm$^{-1}$: 3388, 1660, 1604, 1529, 1493, 1444, 1333, 1298, 1146, 1078, 989.

mp: 82-84° C.

Anal. Calcd for C$_{22}$H$_{18}$F$_4$N$_2$O$_4$S: C, 54.77; H, 3.76; F, 15.75; N, 5.81; S, 6.65. Found: C, 54.89; H, 3.95; F, 15.46; N, 5.76; S, 6.78.

MS m/z: 483 (M$^+$+H).

Example 101

5-[[(4-Fluorophenyl)sulfonyl](2,3,6-trifluorophenyl)methyl]-N-(1-hydroxymethyl)-4-methylpyridine-2-carboxamide

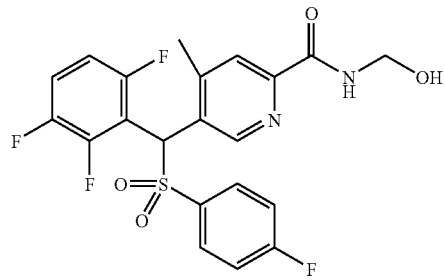

To a solution of 5-[[(4-fluorophenyl)sulfonyl](2,3,6-trifluorophenyl)methyl]-4-methylpyridine-2-carboxamide (150 mg, 0.34 mmol) obtained in Example 39 in ethylene glycol dimethyl ether (3 ml), an aqueous solution of formaldehyde (37%, 0.1 ml) and 5% aqueous sodium hydroxide (0.4 ml) were added at 0° C., and the mixture was stirred overnight at room temperature. Sodium carbonate (20 mg) was added to the reaction mixture, and the mixture was stirred for 20 minutes at room temperature. The mixture was concentrated under reduced pressure, and then the residue was dissolved in chloroform, dried over magnesium sulfate, and filtered. Subsequently, the filtrate was concentrated under reduced pressure, and the resulting residue was subjected to silica gel chromatography. The fraction obtained from an elution with hexane:ethyl acetate=1:1 was concentrated under reduced pressure, and the resulting residue was washed with diethyl ether, and then was collected by filtration, to obtain the title compound (93 mg, 0.20 mmol, 58%) as a white solid.

$^1$H-NMR (400 MHz, CDCl$_3$) δ: 2.15 (3H, s), 3.04-3.09 (1H, m), 5.01 (2H, t, J=7.2 Hz), 5.89 (1H, s), 6.85-6.88 (1H, m), 7.15-7.23 (3H, m), 7.74-7.78 (2H, m), 7.97 (1H, s), 8.84-8.88 (1H, br), 9.43 (1H, s).

IR(ATR)cm$^{-1}$: 3332, 1650, 1592, 1521, 1496, 1145, 1054, 817, 582.

MS m/z: 469 (M$^+$+H).

Anal. Calcd for C$_{21}$H$_{16}$F$_4$N$_2$O$_4$S 0.5H$_2$O: C, 52.83; H, 3.59; F, 15.92; N, 5.87; S, 6.72. Found: C, 52.65; H, 3.56; F, 15.87; N, 5.81; S, 6.65.

Example 102

2-Bromo-4-methyl-5-[(phenylthio)(2,3,6-trifluorophenyl)methyl]pyridine

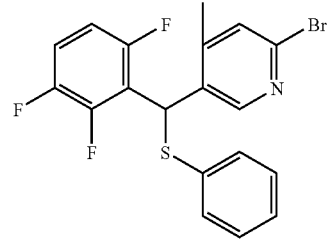

To a solution of 2-bromo-5-[chloro(2,3,6-trifluorophenyl)methyl]-4-methylpyridine (1.80 g, 5.13 mmol) obtained in Reference Example 4 in N,N-dimethylformamide (25 ml), potassium carbonate (1.21 g, 8.73 mmol) and benzenethiol (0.58 ml, 5.65 mmol) were added in a nitrogen atmosphere at 0° C., and the mixture was stirred for 24 hours at room temperature. Ethyl acetate and water were added to the reaction mixture at 0° C., the organic layer was separated, and the organic layer was washed with water and then with saturated brine. The organic layer was dried over anhydrous magnesium sulfate and filtered, subsequently the filtrate was concentrated under reduced pressure, and the resulting residue was subjected to flash silica gel chromatography. The fraction obtained from an elution with hexane:ethyl acetate was concentrated under reduced pressure to obtain the title compound (2.05 g, 4.83 mmol, 94%) as a colorless oily substance.

$^1$H-NMR (400 MHz, CDCl$_3$) δ: 2.17 (3H, s), 5.76 (1H, s), 6.76-6.82 (1H, m), 7.02-7.10 (1H, m), 7.24-7.36 (6H, m), 8.90 (1H, s).

MS m/z: 424 (M$^+$+H).

Example 103

4-Methyl-5-[(phenylthio)(2,3,6-trifluorophenyl)methyl]pyridine-2-carbaldehyde

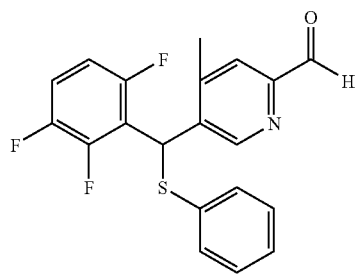

To a solution of 2-bromo-4-methyl-5-[(phenylthio)(2,3,6-trifluorophenyl)methyl]pyridine (2.00 g, 4.40 mmol) in toluene (40 ml), a hexane solution of n-butyllithium (1.58 M, 3.3 ml, 5.28 mmol) was added in an argon atmosphere at −75° C. The reaction mixture was stirred for 1 hour at −40° C., and then cooled again to −75° C., and N,N-dimethylformamide (0.68 ml, 8.80 mmol) was added. After Completion of dropwise addition, the reaction mixture was allowed to warm to 0° C., and water was added to the same temperature. Ethyl acetate was added to the reaction mixture, the organic layer was separated, and then the organic layer was washed with saturated brine. The organic layer was dried over anhydrous magnesium sulfate and filtered, and then the filtrate was concentrated under reduced pressure. The resulting residue was subjected to flash silica gel chromatography. The fraction obtained from an elution with hexane:ethyl acetate was concentrated under reduced pressure to obtain the title compound (1.03 g, 2.76 mmol, 63%) as a pale yellow oily substance.

$^1$H-NMR (400 MHz, CDCl$_3$) δ: 2.28 (3H, s), 5.88 (1H, s), 6.78-6.84 (1H, m), 7.04-7.12 (1H, m), 7.24-7.38 (5H, m), 7.70 (1H, s), 9.34 (1H, s), 10.06 (1H, s).

MS m/z: 374 (M$^+$+H).

Example 104

4-Methyl-5-[(phenylsulfonyl)(2,3,6-trifluorophenyl)methyl]pyridine-2-carboxylic acid

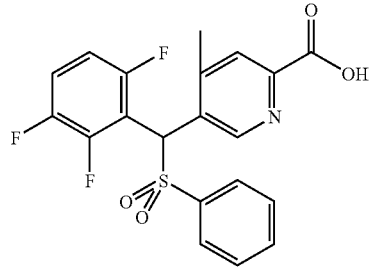

To a solution of 4-methyl-5-[(phenylthio)(2,3,6-trifluorophenyl)methyl]pyridine-2-carbaldehyde (1.00 g, 2.68 mmol) in formic acid (10 ml), 31% aqueous hydrogen peroxide (3 ml) was added, and the mixture was stirred for 4 hours at 0° C. Water was added to the reaction mixture, and the solid thus precipitated was collected by filtration, and was washed with water. The resulting solid was dissolved in ethyl acetate, and was washed with water and then with saturated brine. The organic layer was dried over anhydrous magnesium sulfate and filtered, and then the filtrate was concentrated under reduced pressure. The resulting residue was washed with ethanol, and then was collected by filtration, to obtain the title compound (0.99 g, 2.36 mmol, 88%) as a white solid.

$^1$H-NMR (400 MHz, CDCl$_3$) δ: 2.16 (3H, s), 5.91 (1H, s), 6.82-6.88 (1H, m), 7.17-7.25 (1H, m), 7.50-7.54 (2H, m), 7.68 (1H, t, J=7.5 Hz), 7.72 (2H, d, J=7.3 Hz), 7.99 (1H, s) 9.53 (1H, s).

MS m/z: 422 (M$^+$+H).

Example 105

4-Methyl-5-[(phenylsulfonyl)(2,3,6-trifluorophenyl)methyl]pyridine-2-carboxamide

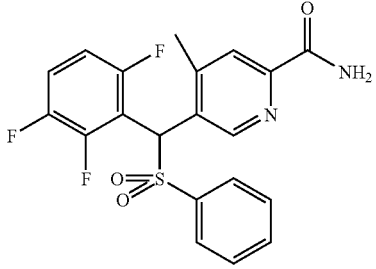

To a solution of 4-methyl-5-[(phenylsulfonyl)(2,3,6-trifluorophenyl)methyl]pyridine-2-carboxylic acid (300 mg, 0.71 mmol) in N,N-dimethylformamide (6 ml), (benzotriazol-1-yloxy)tripyrrolidinophosphonium hexafluorophosphate (556 mg, 1.07 mmol), benzotriazol-1-ol (144 mg, 1.07 mmol), ammonium chloride (76 mg, 1.42 mmol), and N-ethyldiisopropylamine (0.5 ml, 2.85 mmol) were added in an Argon atmosphere at room temperature. After stirring for 3 hours at room temperature, ethyl acetate and water were added to the reaction mixture, and the mixture was extracted with ethyl acetate, and then was washed with saturated brine. The organic layer was dried over anhydrous sodium sulfate and filtered, subsequently the filtrate was concentrated under reduced pressure, and the resulting residue was washed with diethyl ether, and then was collected by filtration, to obtain the title compound (227 mg, 0.54 mmol, 76%) as a white solid.

¹H-NMR (400 MHz, CDCl₃) δ: 2.09 (3H, s), 5.67 (1H, br s), 5.92 (1H, s), 6.82-6.88 (1H, m) 7.14-7.24 (1H, m), 7.50 (2H, t, J=7.5 Hz), 7.67 (1H, t, J=7.5 Hz), 7.74 (2H, d, J=7.5 Hz), 7.88 (1H, bs), 7.96 (1H, s), 9.45 (1H, s).

MS m/z: 421 (M⁺+H).

Example 106

N-(1-hydroxymethyl)-4-methyl-5-[(phenylsulfonyl) (2,3,6-trifluorophenyl) methyl]pyridine-2-carboxamide

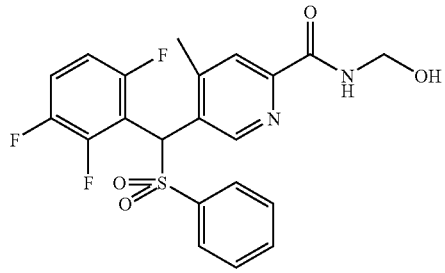

To a solution of 4-methyl-5-[(phenylsulfonyl)(2,3,6-trifluorophenyl)methyl]pyridine-2-carboxamide (215 mg, 0.51 mmol) in ethylene glycol dimethyl ether (6 ml), an aqueous solution of formaldehyde (37%, 0.2 ml) and 5% aqueous sodium hydroxide (0.8 ml) were added at 0° C., and the mixture was stirred for 1 hour at room temperature. Sodium carbonate (40 mg) was added to the reaction mixture, and the mixture was stirred for 20 minutes at room temperature. The mixture was concentrated under reduced pressure, and then the residue was dissolved in chloroform, dried over magnesium sulfate, and filtered. Subsequently, the filtrate was concentrated under reduced pressure, and the resulting residue was subjected to silica gel chromatography. The fraction obtained from an elution with hexane:ethyl acetate=1:2 was concentrated under reduced pressure, and the resulting residue was washed with diethyl ether, and then was collected by filtration, to obtain the title compound (90 mg, 0.20 mmol, 39%) as a white solid.

¹H-NMR (400 MHz, CDCl₃) δ: 2.11 (3H, s), 3.14-3.18 (1H, m), 5.01 (2H, t, J=7.1 Hz), 5.91 (1H, s), 6.80-6.90 (1H, m), 7.12-7.24 (1H, m), 7.45-7.53 (2H, m), 7.61-7.78 (3H, m), 7.94 (1H, s), 8.88 (1H, br), 9.45 (1H, s).

IR(ATR)cm⁻¹: 3382, 3334, 1654, 1494, 1149, 1054, 987, 723, 595, 555.

MS m/z: 451 (M⁺+H).

Example 107

N-acetyl-5-[(2,5-difluorophenyl)[(4-fluorophenyl) sulfonyl]methyl]-4-methylpyridine-2-carboxamide

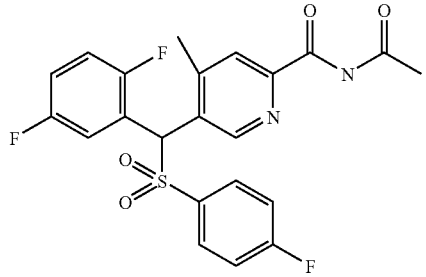

To a solution of 5-[(2,5-difluorophenyl)[(4-fluorophenyl) sulfonyl]methyl]-4-methylpyridine-2-carboxamide (150 mg, 0.36 mmol) obtained in Example 15 in N,N-dimethylformamide (7 ml), sodium hydride (60%, 34 mg, 0.79 mmol) was added at 0° C., and the mixture was stirred for 1 hour at room temperature. Subsequently, acetic anhydride (40 μl) was added to the reaction solution at 0° C., and the mixture was stirred for 1 hour at room temperature. Water was added to the reaction mixture, and the mixture was extracted with ethyl acetate, and was dried over anhydrous magnesium sulfate. The solvent was concentrated under reduced pressure, and the resulting residue was subjected to silica gel chromatography. The fraction obtained from an elution with hexane:ethyl acetate=10:3 was concentrated under reduced pressure, and the resulting residue was washed with diethyl ether and n-hexane, and then was collected by filtration, to obtain the title compound (80 mg, 0.17 mmol, 48%) as a white solid.

¹H-NMR (400 MHz, CDCl₃) δ: 2.29 (3H, s), 2.60 (2H, s), 5.96 (1H, s), 5.97 (1H, s), 6.92-6.98 (1H, m), 7.02-7.08 (1H, m), 7.15 (2H, t, J=8.8 Hz), 7.72 (2H, d, J=8.8 Hz), 7.74-7.79 (1H, m), 8.03 (1H, s), 9.20 (1H, s), 10.38 (1H, bs).

IR(ATR)cm⁻¹: 1725, 1706, 1589, 1463, 1259, 1234, 1187, 1143, 1079, 970, 844, 717, 671, 593, 520, 487.

mp: 182-183° C.

MS m/z: 463 (M⁺+H).

Anal. Calcd for C₂₂H₁₇F₃N₂O₄S: C, 57.14; H, 3.71; F, 12.32; N, 6.06; S, 6.93.

Found: C, 57.33; H, 3.62; F, 12.64; N, 6.09; S, 7.00.

Reference Example 11

(4-Methoxybenzyloxy)acetate

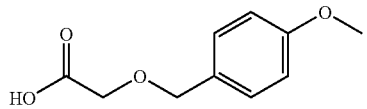

To a solution of 4-methoxybenzyl alcohol (1.00 g, 7.24 mmol) in tetrahydrofuran (20 ml), sodium hydride (695 mg, 17.4 mmol) and bromoacetic acid (1.00 g, 7.24 mmol) were added at 0° C., and the mixture was stirred overnight at room temperature. Water was added to the reaction solution, and the mixture was extracted with ethyl acetate, and was dried over anhydrous magnesium sulfate. The solvent was concentrated under reduced pressure, and the resulting residue was subjected to silica gel chromatography. The fraction obtained from an elution with dichloromethane:methanol=10:1 was concentrated under reduced pressure, and the resulting residue was washed with diethyl ether and n-hexane, and then was collected by filtration, to obtain the title compound (448 mg, 2.28 mmol, 32%) as a white solid.

¹H-NMR (400 MHz, CDCl₃) δ: 3.82 (3H, s), 4.11 (2H, s), 4.58 (2H, m), 6.89 (2H, d, J=8.5 Hz), 7.29 (2H, d, J=8.5 Hz), 9.50 (1H, bs).

Example 108

[[[5-[(2,5-Difluorophenyl)][(4-fluorophenyl)sulfonyl]methyl]-4-methylpyridin-2-yl]carbonyl]amino]methyl (4-methoxybenzyloxy)acetate

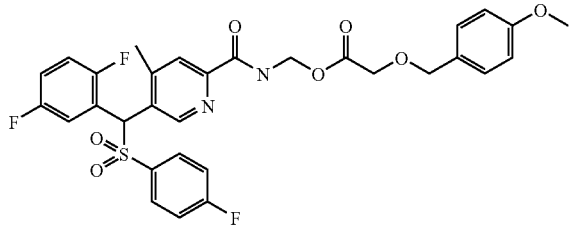

To a solution (78 mg, 0.40 mmol) of 5-[(2,5-difluorophenyl)][(4-fluorophenyl)sulfonyl]methyl]-N-(1-hydroxymethyl)-4-methylpyridine-2-carboxamide (150 mg, 0.33 mmol) obtained in Example 85 in N,N-dimethylformamide (3 ml), 1-ethyl-3-(3-dimethylaminopropyl)carbodiimide hydrochloride (96 mg, 0.50 mmol) and a catalytic amount of dimethylaminopyridine were added, and the mixture was stirred overnight at room temperature. Water was added to the reaction mixture, and the mixture was extracted with ethyl acetate, and was dried over anhydrous sodium sulfate. The solvent was concentrated under reduced pressure, and the resulting residue was subjected to silica gel chromatography. The fraction obtained from an elution with hexane:ethyl acetate=2:1 was concentrated under reduced pressure, to obtain the title compound mg, 0.33 mmol, 99%) as a white solid.

$^1$H-NMR (400 MHz, CDCl$_3$) δ: 2.23 (3H, s), 3.79 (3H, s), 4.56 (2H, s), 5.56 (2H, d, J=7.5 Hz), 5.96 (1H, s), 6.86 (2H, d, J=8.8 Hz), 6.91-6.98 (1H, m), 7.01-7.07 (1H, m), 7.14 (2H, t, J=8.8 Hz), 7.28 (2H, d, J=8.8 Hz), 7.70 (2H, d, J=8.8 Hz), 7.74-7.79 (1H, m), 7.98 (1H, s), 9.00 (1H, t, J=7.5 Hz), 9.17 (1H, s).

IR(ATR)cm$^{-1}$: 3386, 1751, 1691, 1589, 1511, 1492, 1236, 1145, 1105, 1081, 817, 723, 590, 524.

Example 109

[[[5-[(2,5-Difluorophenyl)][(4-fluorophenyl)sulfonyl]methyl]-4-methylpyridin-2-yl]carbonyl]amino]methyl hydroxyacetate

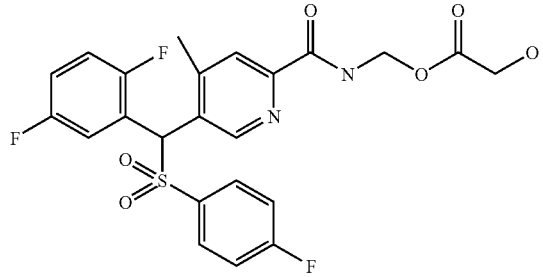

To a mixed solution of [[[5-[(2,5-difluorophenyl)][(4-fluorophenyl)sulfonyl]methyl]-4-methylpyridin-2-yl]carbonyl]amino]methyl (4-methoxybenzyloxy)acetate (150 mg, 0.24 mmol) in dichloromethane-water (1:1, 10 ml), 2,3-dichloro-5,6-dicyano-1,4-benzoquinone (65 mg, 0.29 mmol) was added, and the mixture was stirred overnight at room temperature. Water was added to the reaction solution, and the mixture was extracted with dichloromethane. The extract was washed with saturated brine, dried over anhydrous sodium sulfate, subsequently the solvent was concentrated under reduced pressure, and the resulting residue was subjected to silica gel column chromatography. The fraction obtained from an elution with dichloromethane:methanol=50:3 was concentrated under reduced pressure, washed with diethyl ether, and collected by filtration, to obtain the title compound (26 mg, 0.05 mmol, 21%) as a white solid.

$^1$H-NMR (400 MHz, CDCl$_3$) δ: 2.24 (3H, s), 4.19 (2H, s), 5.60 (2H, d, J=7.5 Hz), 5.96 (1H, s), 6.91-6.98 (1H, m), 7.01-7.08 (1H, m), 7.15 (2H, t, J=8.8 Hz), 7.70 (2H, d, J=8.8 Hz), 7.74-7.78 (1H, m), 7.99 (1H, s), 9.02 (1H, t, J=7.5 Hz), 9.18 (1H, s).

IR(ATR)cm$^{-1}$: 3386, 1747, 1687, 1589, 1515, 1492, 1236, 1145, 1081, 590, 526.

mp: 84° C.

MS m/z: 509 (M$^+$+H).

Anal. Calcd for C$_{23}$H$_{11}$F$_3$N$_2$O$_6$S: C, 54.33; H, 3.77; F, 11.21; N, 5.51; S, 6.31.

Found: C, 54.61; H, 3.93; F, 11.32; N, 5.59; S, 6.33.

Example 110

5-[(2,5-difluorophenyl)][(4-fluorophenyl)sulfonyl]methyl]-N-(dimethylaminomethyl)-4-methylpyridine-2-carboxamide

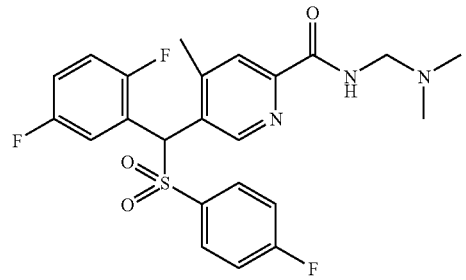

To a solution of 5-[(2,5-difluorophenyl)][(4-fluorophenyl)sulfonyl]methyl]-4-methylpyridine-2-carboxamide (150 mg, 0.33 mmol) obtained in Example 15 in N,N-dimethylformamide (3 ml), a formaldehyde solution (37%, 54 μl) and dimethylamine hydrochloride (136 mg, 1.67 mmol) were added at 0° C., and the mixture was stirred for 2 hours at room temperature. Water was added to the reaction mixture, and the mixture was extracted with ethyl acetate, and was dried over anhydrous sodium sulfate. The solvent was concentrated under reduced pressure, and the resulting residue was subjected to silica gel chromatography. The fraction obtained from an elution with dichloromethane:methanol=10:1 was concentrated under reduced pressure, and the resulting residue was washed with diethyl ether and dichloromethane and dried, to obtain the title compound (99 mg, 0.21 mmol, 63%) as a white solid.

$^1$H-NMR (400 MHz, CDCl$_3$) δ: 2.22 (3H, s), 2.38 (6H, s), 4.33 (2H, d, J=5.6 Hz), 5.97 (1H, s), 6.91-6.98 (1H, m), 7.01-7.08 (1H, m), 7.15 (2H, t, J=8.8 Hz), 7.70 (2H, d, J=8.8 Hz), 7.75-7.81 (1H, m), 7.98 (1H, s), 8.43 (1H, t, J=5.6 Hz), 9.16 (1H, s).

IR(ATR)cm$^{-1}$: 3340, 1670, 1592, 1521, 1494, 1238, 1145, 1039, 838, 817, 711, 657, 590, 530.

Anal. Calcd for C$_{23}$H$_{22}$F$_3$N$_3$O$_3$S.0.75H$_2$O: C, 56.26; H, 4.82; F, 11.61; N, 8.56; S, 6.53.

Found: C, 55.97; H, 4.56; F, 12.44; N, 8.46; S, 6.51.

Example 111

N-[[2-(tert-butyldiphenylsilyloxy)ethoxy]methyl]-5-[(2,5-difluorophenyl)[(4-fluorophenyl)sulfonyl]methyl]-4-methylpyridine-2-carboxamide

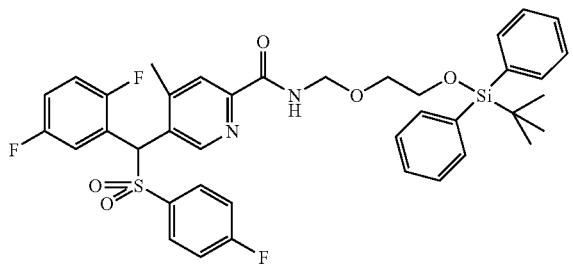

5-[(2,5-Difluorophenyl)[(4-fluorophenyl)sulfonyl]methyl]-N-(1-hydroxymethyl)-4-methylpyridine-2-carboxamide (113 mg, 0.251 mmol) obtained in Example 85, and a solution of 2-(tert-butyldiphenylsilyloxy)ethanol (136 mg, 0.453 mmol) and p-toluenesulfonic acid (10 mg) in benzene (5 ml) were stirred for 3 hours with heating to 60° C. The reaction solution was returned to room temperature, and then was concentrated under reduced pressure. Ethyl acetate was added to the resulting concentration residue, and the mixture was washed sequentially with saturated aqueous sodium hydrogencarbonate and saturated brine. The organic layer was dried over anhydrous sodium sulfate and filtered, and then the filtrate was concentrated under reduced pressure. The resulting concentration residue was subjected to flash silica gel column chromatography, and the fraction obtained from an elution with 25% ethyl acetate/hexane was concentrated under reduced pressure, to obtain the title compound (93 mg, 0.127 mmol, 51%) as an amorphous substance.

$^1$H-NMR (400 MHz, CDCl$_3$) δ: 1.04 (9H, s), 2.21 (3H, s), 3.65-3.85 (4H, m), 4.95-5.05 (2H, m), 5.96 (1H, s), 6.90-7.08 (4H, m), 7.30-7.43 (6H, m), 7.60-7.80 (7H, m), 7.98 (1H, s), 8.65-7.02 (1H, m), 9.14 (1H, s).

MS m/z: 733 (M$^+$+H).

Example 112

5-[(2,5-Difluorophenyl)[(4-fluorophenyl)sulfonyl]methyl]-N-[(2-hydroxyethoxy)methyl]-4-methylpyridine-2-carboxamide

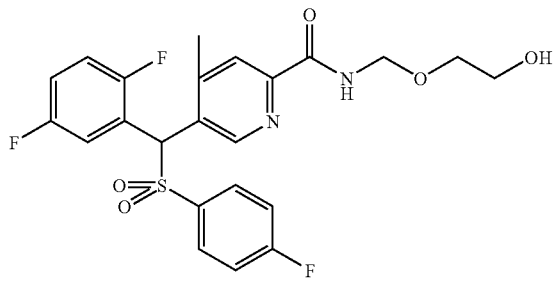

To a solution of N-[[2-(tert-butyldiphenylsilyloxy)ethoxy]methyl]-5-[(2,5-difluorophenyl)[(4-fluorophenyl)sulfonyl]methyl]-4-methylpyridine-2-carboxamide (56 mg, 0.076 mmol) and acetic acid (5 μl, 0.091 mmol) in tetrahydrofuran (5 ml), tetrabutylammonium fluoride (1 M tetrahydrofuran solution) (91 μl, 0.091 mmol) was added, and the mixture was stirred for 6 hours at room temperature. Acetic acid (5 μl, 0.091 mmol) and tetrabutylammonium fluoride (1 M tetrahydrofuran solution) (91 μl, 0.091 mmol) were further added to the reaction solution, and the mixture was stirred for 16 hours at room temperature. Acetic acid (5 μl, 0.091 mmol) and tetrabutylammonium fluoride (1 M tetrahydrofuran solution) (91 μl, 0.091 mmol) were further added to the reaction solution, and the mixture was stirred for 5 hours at room temperature. Saturated aqueous ammonium chloride was added to the reaction solution, and the mixture was extracted with ethyl acetate. The organic layer was washed with saturated brine, subsequently dried over anhydrous sodium sulfate, and filtered, and then the filtrate was concentrated under reduced pressure. The resulting concentration residue was subjected to flash silica gel column chromatography, and the fraction obtained from an elution with 70% ethyl acetate/hexane was concentrated under reduced pressure. Ether was added to the resulting concentration residue to precipitate a solid, and ether was distilled off to obtain the title compound (35 mg, 0.071 mmol, 93%) as a white solid.

$^1$H-NMR (400 MHz, CDCl$_3$) δ: 2.22 (3H, s), 3.68-3.80 (4H, m), 4.95-5.05 (2H, m), 5.96 (1H, s), 6.90-7.08 (2H, m), 7.10-7.18 (2H, m), 7.60-7.80 (3H, m), 7.99 (1H, s), 8.75 (1H, br t, J=7.0 Hz), 9.18 (1H, s).

IR(ATR)cm$^{-1}$: 3347, 1668, 1589, 1513, 1494, 1309, 1282, 1230, 1147.

mp: 175-177° C.

MS m/z: 495 (M$^+$+H).

Anal. calcd for C$_{23}$H$_{21}$F$_3$N$_2$O$_5$S: C, 55.87; H, 4.28; F, 11.53; N, 5.67; S, 6.48. Found: C, 55.63; H, 4.27; F, 11.40; N, 5.54; S, 6.43.

Example 113

5-[(2,5-Difluorophenyl) [(4-fluorophenyl)sulfonyl]methyl]-4-methyl-N-[(pyridin-3-ylmethoxy)methyl]pyridine-2-carboxamide

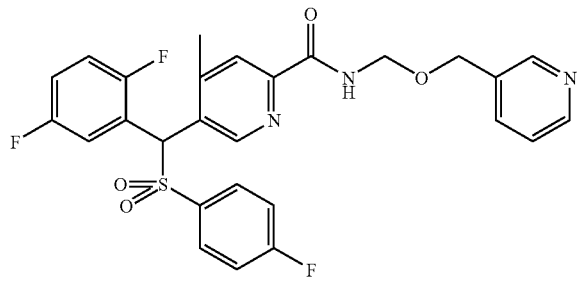

A benzene solution of 5-[(2,5-difluorophenyl)[(4-fluorophenyl)sulfonyl]methyl]-N-(1-hydroxymethyl)-4-methylpyridine-2-carboxamide (155 mg, 0.344 mmol) obtained in Example 85, 3-pyridinemethanol (40 μl, 0.413 mmol) and p-toluenesulfonic acid dihydrate (98 mg, 0.516 mmol) was heated to reflux for 2 hours while distilling off water. The reaction solution was returned to room temperature, subsequently saturated aqueous sodium hydrogencarbonate was added, and the mixture was extracted with ethyl acetate. The organic layer was washed with saturated brine, subsequently dried over anhydrous sodium sulfate, and filtered, and then the filtrate was concentrated under reduced pressure. The resulting concentration residue was subjected to flash silica gel column chromatography, and the fraction obtained from an elution with 70% ethyl acetate/hexane was concentrated under reduced pressure. Ether was added to the resulting concentration residue, and the solid thus precipitated was collected by filtration, to obtain the title compound (46 mg, 0.085 mmol, 25%) as a white powder.

$^1$H-NMR (400 MHz, CDCl$_3$) δ: 2.25 (3H, s), 4.66 (2H, s), 5.00-5.10 (2H, m), 5.97 (1H, s), 6.90-7.08 (2H, m), 7.10-7.18 (2H, m), 7.25-7.33 (1H, m), 7.67-7.80 (4H, m), 8.01 (1H, s), 8.50-8.55 (1H, m), 8.60 (1H, br s), 8.74 (1H, br t, J=7.1 Hz), 9.18 (1H, s).

IR(ATR)cm$^{-1}$: 1675, 1590, 1523, 1492, 1309, 1295, 1236, 1147.

mp: 121-123° C.

MS m/z: 541 (M$^+$).

Anal. calcd for $C_{27}H_{22}F_3N_3O_4S$: C, 59.88; H, 4.09; F, 10.52; N, 7.79; S, 5.92. Found: C, 59.80; H, 4.07; F, 10.73; N, 7.70; S, 6.13.

Example 114

2-Bromo-4-methyl-5-[[[6-(trifluoromethyl)pyridin-3-yl]thio](2,3,6-trifluorophenyl)methyl]pyridine

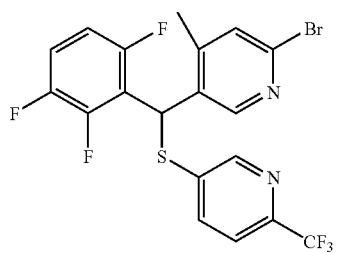

To a solution of O-ethyl S-[6-(trifluoromethyl)pyridin-3-yl]dithiocarbonate (3.09 g, 11.6 mmol) in ethanol (30 ml), 1 N aqueous sodium hydroxide (30 ml) was added, and the mixture was stirred in a nitrogen atmosphere for 1 hour at 60° C. The reaction mixture was cooled to room temperature, water was added, and the mixture was washed with dichloromethane. Subsequently, the aqueous layer was acidified with 1 N hydrochloric acid, and was extracted with dichloromethane. The organic layer was dried over anhydrous sodium sulfate and filtered, and then the filtrate was concentrated under reduced pressure. The resulting residue was dissolved in N,N-dimethylformamide (50 ml), and in a nitrogen atmosphere, 2-bromo-5-[chloro(2,3,6-trifluorophenyl)methyl]-4-methylpyridine (3.94 g, 11.2 mmol) obtained in Reference Example 4, and then potassium carbonate (1.71 g, 12.4 mmol) were added at 0° C. The mixture was stirred for 16 hours at room temperature. Ethyl acetate and water were added to the reaction mixture at 0° C., the organic layer was separated, and then the organic layer was washed with saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=9:1 was concentrated under reduced pressure to obtain the title compound (4.76 g, 9.65 mmol, 86%) as a pale yellow oily substance.

$^1$H-NMR (400 MHz, CDCl$_3$) δ: 2.24 (3H, s), 5.87 (1H, s), 6.81-6.90 (1H, m), 7.08-7.18 (1H, m), 7.30 (1H, s), 7.57 (1H, d, J=8.3 Hz), 7.76 (1H, dd, J=8.3, 2.0 Hz), 8.60 (1H, d, J=2.0 Hz), 8.85 (1H, s).

MS m/z: 493, 495 (M$^+$+H).

Example 115

4-Methyl-5-[[[6-(trifluoromethyl)pyridin-3-yl]thio](2,3,6-trifluorophenyl) methyl]pyridine-2-carbaldehyde

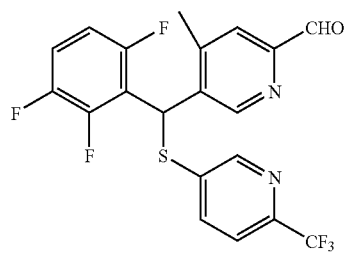

To a solution of 2-bromo-4-methyl-5-[[[6-(trifluoromethyl)pyridin-3-yl]thio](2,3,6-trifluorophenyl)methyl]pyridine (4.76 g, 9.65 mmol) in toluene (100 ml), a hexane solution of n-butyllithium (1.58 M, 6.72 ml, 10.6 mmol) was added in an argon atmosphere at −78° C. The reaction mixture was stirred for 30 minutes at −40° C., and then cooled again to −78° C., and N,N-dimethylformamide (0.897 ml, 11.6 mmol) was added. After completion of dropwise addition, the reaction mixture was allowed to warm to 0° C., and saturated aqueous ammonium chloride was added thereto at the same temperature. Dichloromethane and water were added to the reaction mixture, and the organic layer was separated. Subsequently, the organic layer was dried over anhydrous sodium sulfate and filtered, and then the filtrate was concentrated under reduced pressure. The resulting residue was subjected to flash silica gel chromatography, and the fraction obtained from an elution with hexane:ethyl acetate=5:1 was concentrated under reduced pressure, to obtain the title compound (2.52 g, 5.70 mmol, 59%) as a yellow oily substance.

$^1$H-NMR (400 MHz, CDCl$_3$) δ: 2.35 (3H, s), 5.99 (1H, s), 6.83-6.91 (1H, m), 7.10-7.20 (1H, m), 7.58 (1H, d, J=8.3 Hz), 7.76 (1H, s), 7.79 (1H, dd, J=8.3, 2.0 Hz), 8.60 (1H, d, J=2.0 Hz), 9.29 (1H, s), 10.06 (1H, s).

MS m/z: 443 (M$^+$+H).

Example 116

4-Methyl-5-[[[6-(trifluoromethyl)pyridin-3-yl]sulfonyl](2,3,6-trifluorophenyl)methyl]pyridine-2-carboxylic acid

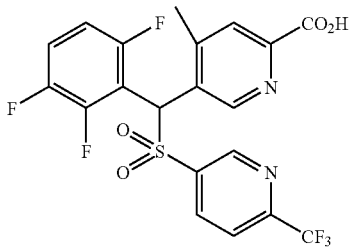

To a solution of 4-methyl-5-[[[6-(trifluoromethyl)pyridin-3-yl]thio](2,3,6-trifluorophenyl) methyl]pyridine-2-carbaldehyde (2.52 g, 5.70 mmol) in formic acid (60 ml), 31% aqueous hydrogen peroxide (6 ml) was added at 0° C. After stirring the reaction mixture for 5 hours at room temperature, water and then dichloromethane were added thereto. After the organic layer was separated, the organic layer was washed with saturated aqueous ammonium chloride, and then with 10% aqueous sodium thiosulfate. The organic layer was dried over anhydrous sodium sulfate and filtered, and then the filtrate was concentrated under reduced pressure. The resulting residue was washed with ethanol, and then was collected by filtration to obtain the title compound (2.19 g, 4.47 mmol, 78%) as a white solid.

¹H-NMR (400 MHz, CDCl₃) δ: 2.26 (3H, s), 5.93 (1H, s), 6.85-6.93 (1H, m), 7.23-7.33 (1H, m), 7.86 (1H, d, J=8.3 Hz), 8.07 (1H, s), 8.26 (1H, dd, J=8.3, 2.2 Hz), 8.99 (1H, d, J=2.2 Hz), 9.50 (1H, s).

MS m/z: 491 (M⁺+H).

Example 117

4-Methyl-5-[[[6-(trifluoromethyl)pyridin-3-yl]sulfonyl](2,3,6-trifluorophenyl)methyl]pyridine-2-carboxamide

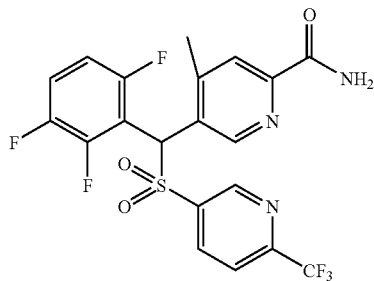

To a solution 4-methyl-5-[[[6-(trifluoromethyl)pyridin-3-yl]sulfonyl](2,3,6-trifluorophenyl)methyl]pyridine-2-carboxylic acid (392 mg, 0.800 mmol) in N,N-dimethylformamide (10 ml), (benzotriazol-1-yloxy)tripyrrolidinophosphonium hexafluorophosphate (624 mg, 1.20 mmol), benzotriazol-1-ol (162 mg, 1.20 mmol), ammonium chloride (85.6 mg, 1.60 mmol), and N-ethyldiisopropylamine (0.557 ml, 3.20 mmol) were added in a nitrogen atmosphere at room temperature. After stirring for 2 hours at the same temperature, the reaction mixture was dissolved in ethyl acetate, and the solution was washed with 1 N hydrochloric acid, 1 N aqueous sodium hydroxide, saturated aqueous ammonium chloride, and then saturated brine. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=1:1 was concentrated under reduced pressure, and the resulting residue was washed with a mixed solvent of ethanol and diethyl ether, and then was collected by filtration, to obtain the title compound (229 mg, 0.468 mmol, 58%) as a white solid. The filtrate was concentrated under reduced pressure, and the resulting residue was washed with a mixed solvent of ethanol and diethyl ether, and then was collected by filtration, to obtain the title compound (66 mg, 0.135 mmol, 17%) as a white solid.

¹H-NMR (400 MHz, CDCl₃) δ: 2.21 (3H, s), 5.61 (1H, br s), 5.96 (1H, s), 6.85-6.93 (1H, m), 7.21-7.31 (1H, m), 7.84 (1H, d, J=8.3 Hz), 7.85 (1H, brs), 8.04 (1H, s), 8.24 (1H, dd, J=8.3, 2.2 Hz), 8.99 (1H, d, J=2.2 Hz), 9.39 (1H, s).

IR(ATR)cm⁻¹: 3462, 3159, 1701, 1595, 1495, 1329, 1192, 1163, 1140, 1107, 1078, 1018, 989.

mp: 237-238° C.

MS m/z: 490 (M⁺+H).

Anal. Calcd for C₂₀H₁₃F₆N₃O₃S: C, 49.08; H, 2.68; F, 23.29; N, 8.59; S, 6.55. Found: C, 48.99; H, 2.70; F, 23.14; N, 8.60; S, 6.70.

Example 118

N-(1-hydroxymethyl)-4-methyl-5-[[[6-(trifluoromethyl)pyridin-3-yl]sulfonyl](2,3,6-trifluorophenyl)methyl]pyridine-2-carboxamide

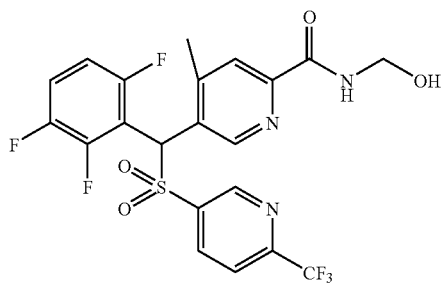

To a solution of 4-methyl-5-[[[6-(trifluoromethyl)pyridin-3-yl]sulfonyl](2,3,6-trifluorophenyl)methyl]pyridine-2-carboxamide (147 mg, 0.300 mmol) in ethylene glycol dimethyl ether (0.8 ml), an aqueous solution of formaldehyde (37%, 0.200 ml) and 1 N aqueous sodium hydroxide (0.200 ml) were added at room temperature, and the mixture was stirred for 16 hours. Ethyl acetate was added to the reaction mixture, and the mixture was washed with saturated aqueous sodium hydrogencarbonate. The organic layer was dried over anhydrous sodium sulfate and filtered, then the filtrate was concentrated under reduced pressure, and the obtained residue was subjected to flash silica gel chromatography. The fraction obtained from an elution with hexane:ethyl acetate=1:1 was concentrated under reduced pressure, and the resulting residue was washed with a mixed solvent of ethyl acetate and diethyl ether, and then was collected by filtration to obtain the title compound (113 mg, 0.218 mmol, 73%) as a white solid.

¹H-NMR (400 MHz, CDCl₃) δ: 2.22 (3H, s), 3.10 (1H, t, J=7. Hz), 5.02 (2H, dd, J=7.8, 6.4 Hz), 5.95 (1H, s), 6.84-6.93 (1H, m), 7.21-7.31 (1H, m) 7.84 (1H, d, J=8.3 Hz) 8.02 (1H, s), 8.24 (1H, dd, J=8.3, 2.2 Hz) 8.86 (1H, t, J=6.4 Hz) 8.99 (1H, d, J=2.2 Hz), 939 (1H, s).

IR(ATR)cm⁻¹: 3249, 1655, 1541, 1496, 1333, 1186, 1161, 1105, 1078, 1043.

mp: 181-182° C.

MS m/z: 520 (M⁺+H).

Anal. Calcd for C₂₁H₁₅F₆N₃O₄S: C, 48.56; H, 2.91; F, 21.95; N, 8.09; S, 6.17. Found: C, 48.48; H, 2.84; F, 21.67; N, 8.18; S, 6.39.

Reference Example 12

2-Bromo-5-[[[tert-butyl(diphenyl)silyl]oxy](2,3,6-trifluorophenyl)methyl]-4-methylpyridine

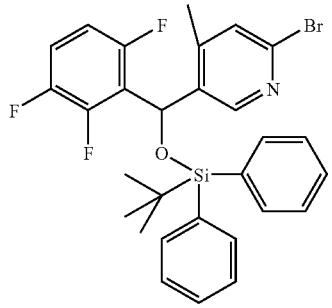

To a solution of (6-bromo-4-methylpyridin-3-yl)(2,3,6-trifluorophenyl)methanol (51.3 g, 154 mmol) obtained in Reference Example 3, and tert-butyl chloro(diphenyl)silane (43.0 ml, 162 mmol) in N,N-dimethylformamide (350 ml), imidazole (22.1 g, 324 mmol) was added at room temperature, and the mixture was stirred for days at room temperature. Water and ethyl acetate were added to the reaction mixture, the organic layer was separated, and the organic layer was washed with saturated aqueous ammonium chloride, and then with saturated brine. The organic layer was dried over anhydrous sodium sulfate and filtered, and then the filtrate was concentrated under reduced pressure. The resulting residue was subjected to flash silica gel chromatography, and the fraction obtained from an elution with hexane:ethyl acetate=20:1 was concentrated under reduced pressure, to obtain the title compound (75.6 g, 133 mmol, 86%) as a colorless foamy substance.

$^1$H-NMR (400 MHz, CDCl$_3$) δ: 1.07 (9H, s), 1.85 (3H, s), 6.11 (1H, s), 6.58-6.65 (1H, m), 6.91-7.01 (1H, m), 7.12 (1H, s), 7.20-7.54 (10H, m), 9.12 (1H, s).

MS m/z: 570, 572 (M$^+$+H).

Reference Example 13

5-[[[Tert-butyl(diphenyl)silyl]oxy](2,3,6-trifluorophenyl)methyl]-4-methylpyridine-2-carboxamide

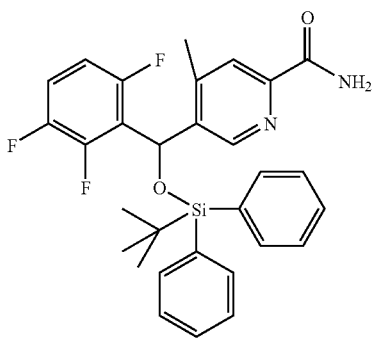

To a solution of 2-bromo-5-[[[tert-butyl(diphenyl)silyl]oxy](2,3,6-trifluoro phenyl)methyl]-4-methylpyridine (75.6 g, 133 mmol) in toluene (1200 ml), a hexane solution of n-butyllithium (1.60 M, 99.4 ml, 159 mmol) was added in an argon atmosphere at –78° C. The reaction mixture was stirred for 30 minutes at –50° C., and then cooled again to –78° C., and carbon dioxide was bubbled therein. After stirring for 30 minutes at the same temperature, the reaction mixture was allowed to warm to 0° C., water and then 1 N hydrochloric acid were added thereto, and the mixture was concentrated under reduced pressure. Ethyl acetate was added to the resulting residue, and the organic layer was washed with saturated brine. The organic layer was dried over anhydrous sodium sulfate and filtered, and then the filtrate was concentrated under reduced pressure. The resulting residue was dissolved in tetrahydrofuran (1000 ml), and isobutyl chlorocarbonate (25.3 ml, 195 mmol) and then triethylamine (36.2 ml, 260 mmol) were added thereto at –5° C. After stirring the mixture for 30 minutes at the same temperature, a 7 N methanol solution of ammonia (100 ml, 700 mmol) was added, and the mixture was stirred for 1 hour at room temperature. The reaction mixture was concentrated under reduced pressure, and ethyl acetate and water were added to the resulting residue. After the organic layer was separated, the organic layer was washed with 1 N hydrochloric acid, saturated aqueous sodium hydrogencarbonate and then saturated brine, and the organic layer was dried over anhydrous sodium sulfate and filtered. Subsequently, the filtrate was concentrated under reduced pressure. The resulting residue was subjected to flash silica gel chromatography, and the fraction obtained from an elution with hexane:ethyl acetate=1:1 was concentrated under reduced pressure to obtain the title compound (50.0 g, 93.5 mmol, 70%) as a pale brown oily substance.

$^1$H-NMR (400 MHz, CDCl$_3$) δ: 1.09 (9H, s), 1.96 (3H, s), 5.56 (1H, br s), 6.23 (1H, s), 6.58-6.65 (1H, m), 6.92-7.01 (1H, m), 7.20-7.54 (10H, m), 7.85 (1H, s), 7.88 (1H, br s), 9.33 (1H, s).

MS m/z: 535 (M$^+$+H).

Reference Example 14

5-[Hydroxy(2,3,6-trifluorophenyl)methyl]-4-methylpyridine-2-carboxamide

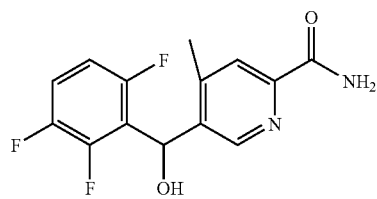

To a solution of 5-[[[tert-butyl(diphenyl)silyl]oxy](2,3,6-trifluorophenyl)methyl]-4-methylpyridine-2-carboxamide (50.0 g, 93.5 mmol) in tetrahydrofuran (500 ml), a 1 N solution of tetrabutylammonium fluoride in tetrahydrofuran (100 ml, 100 mmol) was added at 0° C. After stirring the mixture for 2 hours at room temperature, saturated aqueous ammonium chloride was added, and the mixture was concentrated under reduced pressure. Ethyl acetate and water were added to the resulting residue. After the organic layer was separated, the organic layer was washed with saturated brine, dried over anhydrous sodium sulfate and filtered, and then the filtrate was concentrated under reduced pressure. The residue was washed with a mixed solvent of ethyl acetate and diethyl ether and then with diethyl ether, and then the residue was dried under reduced pressure, to obtain the title compound g, 70.2 mmol, 75%) as a white solid.

$^1$H-NMR (400 MHz, CD$_3$OD) δ: 2.22 (3H, s), 6.35 (1H, s), 6.93-7.02 (1H, m), 7.24-7.34 (1H, m), 7.85 (1H, s), 8.99 (1H, s).

MS m/z: 297 (M$^+$+H).

Reference Example 15

[6-Carbamoyl-4-methylpyridin-3-yl](2,3,6-trifluorophenyl)methyl methanesulfonate

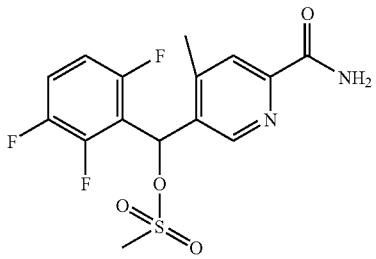

To a solution of 5-[hydroxy(2,3,6-trifluorophenyl)methyl]-4-methylpyridine-2-carboxamide (7.11 g, 24.0 mmol) in N,N-dimethylformamide (150 ml), methanesulfonyl chloride (3.72 ml, 48.0 mmol) and then triethylamine (13.4 ml, 96.0 mmol) were added in a nitrogen atmosphere at 0° C., and the mixture was stirred for 2 hours at room temperature. Water and ethyl acetate were added to the reaction mixture at 0° C., the organic layer was separated, and the organic layer was washed sequentially with 1 N hydrochloric acid, saturated aqueous sodium hydrogencarbonate and saturated brine. The organic layer was dried over anhydrous sodium sulfate and filtered, and then the filtrate was concentrated under reduced pressure. The resulting residue was subjected to flash silica gel chromatography, and the fraction obtained from an elution with dichloromethane:methanol=49:1 was concentrated under reduced pressure, to obtain the title compound (4.71 g, 12.6 mmol, 52%) as a pale brown foamy substance.

$^1$H-NMR (400 MHz, CDCl$_3$) δ: 2.38 (3H, s), 3.04 (3H, s), 5.65 (1H, br s), 6.91-6.98 (1H, m), 7.16 (1H, s), 7.21-7.30 (1H, m), 7.84 (1H, br s), 8.02 (1H, s), 8.88 (1H, s).

MS m/z: 375 (M$^+$+H).

Example 119

5-[[(4-Chlorophenyl)sulfonyl](2,3,6-trifluorophenyl)methyl]-4-methylpyridine-2-carboxamide

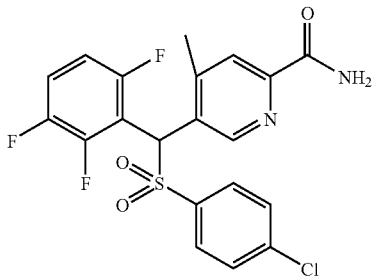

To a solution of [6-carbamoyl-4-methylpyridin-3-yl](2,3,6-trifluorophenyl)methyl methanesulfonate (187 mg, 0.500 mmol) obtained in Reference Example 15 in N,N-dimethylformamide (5 ml), 4-chlorobenzenethiol (72.2 mg, 0.500 mmol) and then potassium carbonate (82.9 mg, 0.600 mmol) were added in a nitrogen atmosphere at 0° C., and the mixture was stirred for 3 days at room temperature. Ethyl acetate and water were added to the reaction mixture, the organic layer was separated, and the organic layer was washed with saturated aqueous sodium hydrogencarbonate and then with saturated brine. The organic layer was dried over anhydrous sodium sulfate and filtered, and then the filtrate was concentrated under reduced pressure. The resulting residue was dissolved in dichloromethane (5 ml), and 3-chloroperbenzoic acid (318 mg, 1.20 mmol) was added thereto at 0° C. After stirring for 4 hours at room temperature, the reaction mixture was washed with 1 N aqueous sodium hydroxide. The organic layer was dried over anhydrous sodium sulfate and filtered, then the filtrate was concentrated under reduced pressure, and the obtained residue was subjected to flash silica gel chromatography. The fraction obtained from an elution with dichloromethane:methanol=99:1 was concentrated under reduced pressure to obtain the title compound (190 mg, 0.418 mmol, 84%) as a white solid.

$^1$H-NMR (400 MHz, CDCl$_3$) δ: 2.15 (3H, s), 5.62 (1H, br s), 5.90 (1H, s), 6.83-6.91 (1H, m), 7.16-7.26 (1H, m), 7.45-7.50 (2H, m), 7.65-7.70 (2H, m), 7.87 (1H, br s), 7.99 (1H, s), 9.42 (1H, s).

IR(ATR)cm$^{-1}$: 3396, 3168, 1687, 1496, 1419, 1311, 1238, 1146, 1082.

MS m/z: 455 (M$^+$+H).

Example 120

5-[[(4-Chlorophenyl)sulfonyl](2,3,6-trifluorophenyl)methyl]-N-(hydroxymethyl)-4-methylpyridine-2-carboxamide

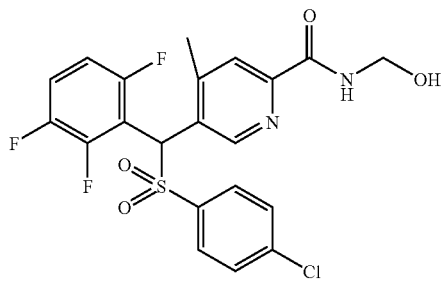

To a solution of 5-[[(4-chlorophenyl)sulfonyl](2,3,6-trifluorophenyl)methyl]-4-methylpyridine-2-carboxamide (190 mg, 0.418 mmol) in ethylene glycol dimethyl ether (4 ml), an aqueous solution of formaldehyde (37%, 94.2 μl) and 1 N aqueous sodium hydroxide (21.0 μl) were added at room temperature, and the mixture was stirred for 17 hours. Ethyl acetate was added to the reaction mixture, and the mixture was washed with saturated aqueous ammonium chloride. Subsequently, 1 N hydrochloric acid was added to the organic layer, and the mixture was stirred for 1 hour. After the organic layer was separated, the organic layer was washed with saturated brine, dried over anhydrous sodium sulfate, and filtered, and then the filtrate was concentrated under reduced pressure. The resulting residue was subjected to flash silica gel chromatography, and the fraction obtained from an elution with hexane:ethyl acetate=1:1 was concentrated under reduced pressure. The resulting residue was washed with a mixed solvent of ethyl acetate and diethyl ether, and then was collected by filtration, to obtain the title compound (113 mg, 0.233 mmol, 56%) as a white solid.

$^1$H-NMR (400 MHz, CDCl$_3$) δ: 2.16 (3H, s), 3.06 (1H, t, J=7.8 Hz), 5.01 (2H, dd, J=7.8, 6.6 Hz), 5.90 (1H, s), 6.83-6.91 (1H, m), 7.16-7.26 (1H, m), 7.45-7.50 (2H, m), 7.65-7.70 (2H, m), 7.97 (1H, s), 8.88 (1H, t, J=6.6 Hz), 9.42 (1H, s).

IR(ATR)cm$^{-1}$: 3251, 1657, 1537, 1493, 1335, 1232, 1149, 1088, 1047.

mp: 177-178° C.

MS m/z: 485 (M$^+$+H)

Anal. Calcd for $C_{21}H_{16}ClF_3N_2O_4S$: C, 52.02; H, 3.33; Cl, 7.31; F, 11.75; N, 5.78; S, 6.61. Found: C, 52.06; H, 3.31; Cl, 7.23; F, 11.46; N, 5.78; S, 6.69.

Example 121

5-[[(3,4-Difluorophenyl)sulfonyl](2,3,6-trifluorophenyl)methyl]-4-methylpyridine-2-carboxamide

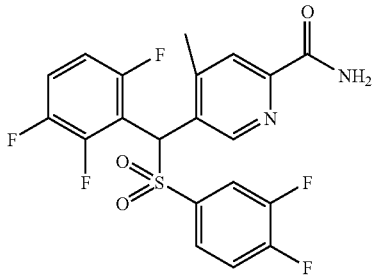

To a solution of [6-carbamoyl-4-methylpyridin-3-yl](2,3,6-trifluorophenyl)methyl methanesulfonate (262 mg, 0.700 mmol) obtained in Reference Example 15 in N,N-dimethylformamide (7 ml), 3,4-difluorobenzenethiol (80.6 μl, 0.700 mmol) and then potassium carbonate (116 mg, 0.840 mmol) were added in a nitrogen atmosphere at 0° C., and the resulting mixture was stirred for 3 days at room temperature. Ethyl acetate and water were added to the reaction mixture, the organic layer was separated, and the organic layer was washed with saturated aqueous sodium hydrogencarbonate and then with saturated brine. The organic layer was dried over anhydrous sodium sulfate and filtered, and then the filtrate was concentrated under reduced pressure. The resulting residue was dissolved in dichloromethane (7 ml), and 3-chloroperbenzoic acid (446 mg, 1.68 mmol) was added thereto at 0° C. After stirring for 5 hours at room temperature, the reaction mixture was washed with 1 N aqueous sodium hydroxide. The organic layer was dried over anhydrous sodium sulfate and filtered, then the filtrate was concentrated under reduced pressure, and the obtained residue was subjected to flash silica gel chromatography. The fraction obtained from a dichloromethane:methanol=99:1 was concentrated under reduced pressure, and the resulting residue was washed with 2-propanol and collected by filtration, to thus obtain the title compound (213 mg, 0.467 mmol, 67%) as a white solid.

$^1$H-NMR (400 MHz, CDCl$_3$) δ: 2.18 (3H, s), 5.59 (1H, br s), 5.90 (1H, s), 6.84-6.92 (1H, m), 7.18-7.35 (2H, m), 7.49-7.56 (1H, m), 7.58-7.65 (1H, m), 7.87 (1H, br s), 8.01 (1H, s), 9.42 (1H, s).
IR(ATR)cm$^{-1}$: 3396, 3165, 1691, 1597, 1498, 1417, 1333, 1279, 1238, 1142.
mp: 200-201° C.
MS m/z: 457 (M$^+$+H).
Anal. Calcd for C$_{20}$H$_{13}$F$_5$N$_2$O$_3$S: C, 52.63; H, 2.87; F, 20.81; N, 6.14; S, 7.03. Found: C, 52.58; H, 2.77; F, 20.94; N, 6.18; S, 7.14.

Example 122

5-[[(3,4-Difluorophenyl)sulfonyl](2,3,6-trifluorophenyl)methyl]-N-(hydroxymethyl)-4-methylpyridine-2-carboxamide

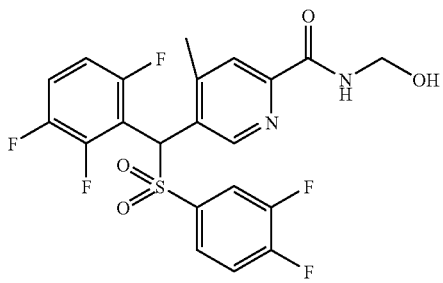

To a solution of 5-[[(3,4-difluorophenyl)sulfonyl](2,3,6-trifluorophenyl)methyl]-4-methylpyridine-2-carboxamide (160 mg, 0.350 mmol) in ethylene glycol dimethyl ether (3 ml), an aqueous solution of formaldehyde (37%, 78.9 μl) and 1 N aqueous sodium hydroxide (17.5 μl) were added at room temperature, and the mixture was stirred for 18 hours. Ethyl acetate was added to the reaction mixture, and the resulting mixture was washed with saturated aqueous ammonium chloride. Subsequently, 1 N hydrochloric acid was added to the organic layer, and the mixture was stirred for 1 hour. After the organic layer was separated, the organic layer was washed with saturated brine, dried over anhydrous sodium sulfate, and filtered, and then the filtrate was concentrated under reduced pressure. The resulting residue was subjected to flash silica gel chromatography, and the fraction obtained from an elution with hexane:ethyl acetate=1:1 was concentrated under reduced pressure. The resulting residue was washed with a mixed solvent of ethyl acetate and diethyl ether, and then was collected by filtration, to obtain the title compound (100 mg, 0.206 mmol, 59%) as a white solid.

$^1$H-NMR (400 MHz, CDCl$_3$) δ: 2.19 (3H, s), 3.15 (1H, t, J=7.6 Hz) 5.01 (2H, dd, J=7.6, 6.8 Hz) 5.90 (1H, s) 6.84-6.92 (1H, m), 7.19-7.35 (2H, m), 7.50-7.56 (1H, m), 7.58-7.64 (1H, m), 7.99 (1H, s), 8.87 (1H, t, J=6.8 Hz), 9.42 (1H, s).
IR(ATR)cm$^{-1}$: 3394, 3332, 1647, 1522, 1496, 1417, 1335, 1284, 1213, 1141, 1055.
mp: 119-120° C.
MS m/z: 487 (M$^+$+H).
Anal. Calcd for C$_{21}$H$_{15}$F$_5$N$_2$O$_4$S: C, 51.85; H, 3.11; F, 19.53; N, 5.76; S, 6.59. Found: C, 51.64; H, 3.01; F, 19.45; N, 5.81; S, 6.74.

Example 123

4-Methyl-5-[[[4-(trifluoromethoxy)phenyl]sulfonyl](2,3,6-trifluorophenyl)methyl]pyridine-2-carboxamide

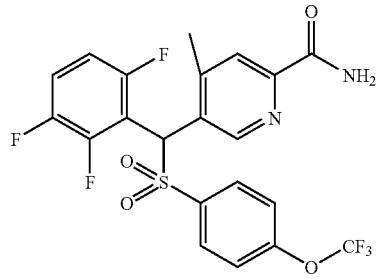

To a solution of [6-carbamoyl-4-methylpyridin-3-yl](2,3,6-trifluorophenyl)methyl methanesulfonate (262 mg, 0.700 mmol) obtained in Reference Example 15 in N,N-dimethylformamide (7 ml), 4-(trifluoromethoxy)benzenethiol (136 mg, 0.700 mmol) and then potassium carbonate (116 mg, 0.840 mmol) were added in a nitrogen atmosphere at 0° C., and the mixture was stirred for 3 days at room temperature. Ethyl acetate and water were added to the reaction mixture, the organic layer was separated, and the organic layer was washed with saturated aqueous sodium hydrogencarbonate, and then with saturated brine. The organic layer was dried over anhydrous sodium sulfate and filtered, and then the filtrate was concentrated under reduced pressure. The resulting residue was dissolved in dichloromethane (7 ml), and 3-chloroperbenzoic acid (446 mg, 1.68 mmol) was added thereto at 0° C. After stirring for 3 hours at room temperature, the reaction mixture was washed with 1 N aqueous sodium hydroxide. The organic layer was dried over anhydrous sodium sulfate and filtered, then the filtrate was concentrated under reduced pressure, and the obtained residue was subjected to flash silica gel chromatography. The fraction obtained from an elution with dichloromethane:methanol=99:1 was concentrated under reduced pressure, and the resulting residue was washed with a mixed solvent of ethy lacetate and diethyl ether, and then was collected by filtration, to obtain the title compound (244 mg, 0.484 mmol, 69%) as a white solid.

$^1$H-NMR (400 MHz, CDCl$_3$) δ: 2.15 (3H, s), 5.62 (1H, br s), 5.90 (1H, s), 6.83-6.91 (1H, m), 7.16-7.26 (1H, m), 7.45-7.50 (2H, m), 7.66-7.71 (2H, m), 7.88 (1H, br s), 7.99 (1H, s), 9.42 (1H, s).

IR(ATR)cm$^{-1}$: 3438, 3161, 1703, 1597, 1493, 1419, 1323, 1255, 1217, 1151.

mp: 219-220° C.

MS m/z: 505 (M$^+$+H).

Anal. Calcd for C$_{21}$H$_{14}$F$_6$N$_2$O$_4$S: C, 50.00; H, 2.80; F, 22.60; N, 5.55; S, 6.36. Found: C, 49.65; H, 2.74; F, 22.49; N, 5.52; S, 6.43.

Example 124

N-(hydroxymethyl)-4-methyl-5-[[[4-(trifluoromethoxy)phenyl]sulfonyl](2,3,6-trifluorophenyl)methyl]pyridine-2-carboxamide

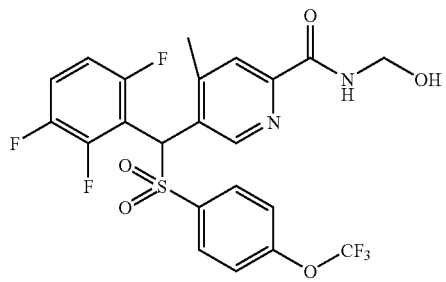

To a solution of 4-methyl-5-[[[4-(trifluoromethoxy)phenyl]sulfonyl](2,3,6-trifluorophenyl) methyl]pyridine-2-carboxamide (177 mg, 0.350 mmol) in ethylene glycol dimethyl ether (3 ml), an aqueous solution of formaldehyde (37%, 78.9 μl) and 1 N aqueous sodium hydroxide (17.5 μl) were added at room temperature, and the mixture was stirred for 2 days. Ethyl acetate was added to the reaction mixture, and the mixture was washed with saturated aqueous ammonium chloride. Subsequently, 1 N hydrochloric acid was added to the organic layer, and the mixture was stirred for 1 hour. After the organic layer was separated, the organic layer was washed with saturated brine, dried over anhydrous sodium sulfate and filtered, and then the filtrate was concentrated under reduced pressure. The resulting residue was subjected to flash silica gel chromatography, and the fraction obtained from an elution with hexane:ethyl acetate=1:1 was concentrated under reduced pressure. The resulting residue was washed with a mixed solvent of ethyl acetate and diethyl ether, and then was collected by filtration, to obtain the title compound (59.4 mg, 0.111 mmol, 32%) as a white solid.

$^1$H-NMR (400 MHz, CDCl$_3$) δ: 2.15 (3H, s), 3.09 (1H, t, J=7.6 Hz), 5.01 (2H, dd, J=7.6, 6.6 Hz), 5.89 (1H, s), 6.82-6.90 (1H, m), 7.16-7.36 (3H, m), 7.77-7.83 (2H, m), 7.98 (1H, s), 8.88 (1H, t, J=6.6 Hz), 9.43 (1H, s).

IR(ATR)cm$^{-1}$: 3236, 1657, 1541, 1495, 1252, 1227, 1151, 1043.

mp: 140-141° C.

MS m/z: 535 (M$^+$+H).

Anal. Calcd for C$_{22}$H$_{16}$F$_6$N$_2$O$_5$S: C, 49.44; H, 3.02; F, 21.33; N, 5.24; S, 6.00. Found: C, 49.44; H, 2.94; F, 21.42; N, 5.29; S, 6.15.

Reference Example 16

S-(benzofuran-6-yl)O-ethyl dithiocarbonate

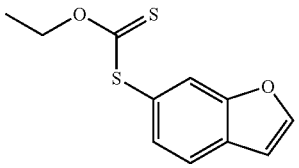

To a solution of benzofuran-6-ylamine (574 mg, 4.31 mmol) in methanol (2 ml), 1 N hydrochloric acid (10 ml) and then a solution of sodium nitrite (362 mg, 5.17 mmol) in water (2 ml) were added dropwise at 0° C., and the mixture was stirred for 1 hour at the same temperature. The reaction mixture was added to a solution of potassium O-ethyldithiocarbonate (1.38 g, 8.62 mmol) in water (2 ml) which had been warmed to 65° C. After stirring for 2 hours at the same temperature, the reaction mixture was cooled to room temperature, water was added, and the product was extracted with ethyl acetate. The organic layer was dried over anhydrous sodium sulfate and filtered, then the filtrate was concentrated under reduced pressure, and the obtained residue was subjected to flash silica gel column chromatography. The fraction obtained from an elution with hexane:ethyl acetate=50:1 was concentrated under reduced pressure to obtain the title compound (351 mg, 1.47 mmol, 34%) as a yellow oily substance.

$^1$H-NMR (400 MHz, CDCl$_3$) δ: 1.33 (3H, t, J=7.1 Hz), 4.62 (2H, q, J=7.1 Hz), 6.80-6.84 (1H, m), 7.35-7.40 (1H, m), 7.64 (1H, d, J=8.1 Hz), 7.68-7.69 (1H, m), 7.71 (1H, d, J=2.2 Hz).

MS m/z: 239 (M$^+$+H).

Example 125

5-[(1-Benzofuran-6-ylthio)(2,3,6-trifluorophenyl)methyl]-4-methylpyridine-2-carboxamide

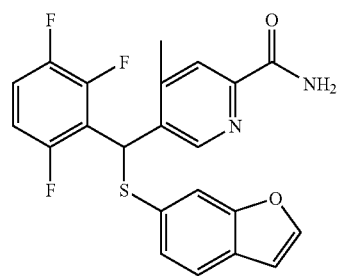

S-(benzofuran-6-yl)O-ethyl dithiocarbonate (145 mg, 0.604 mmol) obtained in Reference Example 16 was dissolved in ethanol (3 ml), 1 N aqueous sodium hydroxide (3 ml) was added thereto, and the mixture was stirred for 2 hours at 60° C. The reaction mixture was cooled to room temperature, water and 1 N aqueous sodium hydroxide (4 ml) were added, and then the mixture was washed with dichloromethane. The aqueous layer was acidified with 1 N hydrochloric acid; and then was extracted with ethyl acetate. The extract was washed with water and saturated brine, subsequently dried over magnesium sulfate, and concentrated. In an argon atmosphere, N,N-dimethylformamide (4 ml) was added to the residue. [6-Carbamoyl-4-methylpyridin-3-yl](2,3,6-trifluorophenyl)methyl methanesulfonate (271 mg, 0.725 mmol) obtained in Reference Example 15, and then potassium carbonate (100 mg, 0.725 mmol) were added at 0° C., and then the mixture was stirred for 4 hours at room temperature. The reaction mixture was cooled to 0° C., and then ethyl acetate and water were sequentially added. The organic layer was separated, and then was washed with water and saturated brine. After drying over magnesium sulfate, the organic layer was concentrated, and the resulting residue was subjected to flash silica gel column chromatography. The fraction obtained from an elution with hexane:ethyl acetate=1:1 was concentrated to obtain the title compound (226 mg, 0.528 mmol, 87%) as a white solid.

$^1$H-NMR (400 MHz, CDCl$_3$) δ: 2.26 (3H, s), 5.48-5.54 (1H, m), 5.88 (1H, s), 6.74 (1H, m), 6.76-6.83 (1H, m), 7.06 (1H, ddd, J=18.1, 9.0, 4.9 Hz), 7.26-7.28 (1H, m), 7.49 (1H, d, J=8.0 Hz), 7.54 (1H, s), 7.63 (1H, d, J=2.2 Hz), 7.84 (1H, s), 7.94 (1H, s), 9.14 (1H, s).

MS m/z: 429 (M$^+$+H).

Example 126

5-[(1-Benzofuran-6-ylsulfonyl)(2,3,6-trifluorophenyl)methyl]-4-methylpyridine-2-carboxamide

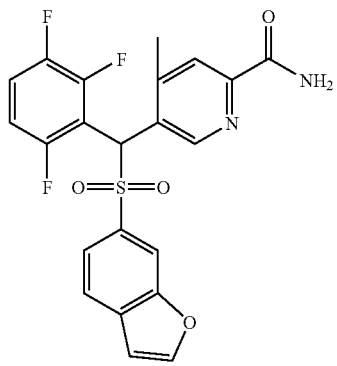

To a solution of 5-[(1-benzofuran-6-ylthio)(2,3,6-trifluorophenyl)methyl]-4-methylpyridine-2-carboxamide (93.0 mg, 0.217 mmol) in ethyl acetate (5 ml) and methanol (5 ml), 30% aqueous hydrogen peroxide (2.5 ml) and hexaammonium heptamolybdate tetrahydrate (10 mg, 0.00809 mmol) were added, and the mixture was stirred for 9 hours at room temperature. Hexaammonium heptamolybdate tetrahydrate (10 mg, 0.00809 mmol) was added to the reaction mixture, and the mixture was stirred for 16 hours at room temperature. Furthermore, 30 aqueous hydrogen peroxide (1.0 ml) was added to the reaction mixture, and the resulting mixture was stirred for 3 hours. Water was added to the reaction mixture, and the organic solvent was distilled off under reduced pressure. The resulting residue was extracted with ethyl acetate, and was washed sequentially with water, sodium thiosulfate, water and saturated brine. The residue was dried over magnesium sulfate, and then was concentrated. The resulting residue was subjected to flash silica gel column chromatography, and the fraction obtained from an elution with hexane:ethyl acetate=2:3 was concentrated. The resulting solid was recrystallized from ethyl acetate to obtain the title compound (35.8 mg, 0.0778 mmol, 36%) as a white solid.

$^1$H-NMR (400 MHz, CDCl$_3$) δ: 2.08 (3H, s), 5.55 (1H, s), 5.98 (1H, s), 6.80-6.87 (1H, m), 6.89 (1H, dd, J=2.2, 1.0 Hz), 7.19 (1H, ddd, J=18.0, 9.3, 4.9 Hz), 7.60 (1H, dd, J=8.1, 1.7 Hz), 7.69 (1H, d, J=8.1 Hz), 7.85 (1H, d, J=2.2 Hz), 7.86-7.90 (1H, br s), 7.94 (2H, m), 9.48 (1H, s).

IR(ATR)cm$^{-1}$: 3456, 3153, 1699, 1597, 1493, 1427, 1313, 1242, 1182, 1149, 1124, 1051, 989, 887, 829, 771, 727, 708, 633, 586, 563, 501, 420.

mp: 237-240° C.

MS m/z: 461 (M$^+$+H).

Anal. calcd for C$_{22}$H$_{15}$F$_3$N$_2$O$_4$S: C, 57.39; H, 3.28; F, 12.38; N, 6.08; S, 6.96. Found: C, 57.25; H, 3.25; F, 12.37; N, 5.91; S, 6.97.

Example 127

5-[(1-Benzofuran-6-ylsulfonyl)(2,3,6-trifluorophenyl)methyl]-N-(hydroxymethyl)-4-methylpyridine-2-carboxamide

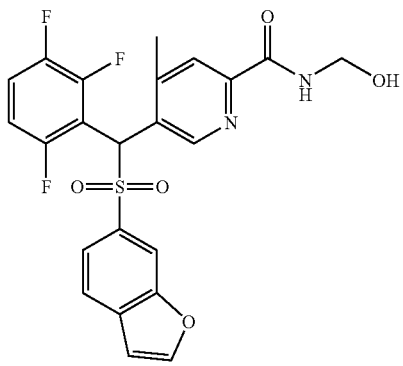

To a 1,2-dimethoxyethane solution (5 ml) of 5-[(1-benzofuran-6-ylsulfonyl)(2,3,6-trifluorophenyl)methyl]-4-methylpyridine-2-carboxamide (210 mg, 0.457 mmol), an aqueous solution of formaldehyde (37%, 0.111 ml) and 1 N aqueous sodium hydroxide (0.023 ml) were added, and the mixture was stirred for 4 hours at room temperature. An aqueous solution of formaldehyde (37%, 0.111 ml) and 1 N aqueous sodium hydroxide (0.023 ml) were added to the reaction mixture, and the mixture was stirred for 5 hours at room temperature. An aqueous solution of formaldehyde (37%, 0.111 ml) was further added, and then the mixture was stirred for 18 hours at room temperature. Water was added to the reaction solution, and the mixture was extracted with ethyl acetate, and then was washed with water and saturated brine. The mixture was dried over magnesium sulfate and concentrated, and the resulting residue was subjected to flash silica gel column chromatography. The fraction obtained from an elution with hexane:ethyl acetate=2:3 was concentrated. The resulting solid was recrystallized from 2-propanol to obtain the title compound (138 mg, 0.273 mmol, 60%) as a white solid.

$^1$H-NMR (400 MHz, CDCl$_3$) δ: 2.09 (3H, s), 3.04 (1H, t, J=7.3 Hz), 5.01 (2H, t, J=7.3 Hz), 5.98 (1H, s), 6.80-6.87 (1H, m), 6.89 (1H, dd, J=2.2, 0.7 Hz), 7.19 (1H, ddd, J=17.8, 9.0, 4.9 Hz), 7.60 (1H, dd, J=8.0, 1.7 Hz), 7.69 (1H, d, J=8.0 Hz), 7.85 (1H, d, J=2.2 Hz), 7.93 (2H, m), 8.85-8.91 (1H, m), 9.48 (1H, s).

IR(ATR)cm$^{-1}$: 3394, 1670, 1601, 1516, 1496, 1423, 1321, 1302, 1230, 1186, 1144, 1126, 1054, 1036, 822, 729, 714, 633, 586, 552, 532, 496.

mp: 185-186° C. (dec.).

MS m/z: 491 (M$^+$+H).

Anal. calcd for C$_{23}$H$_{17}$F$_3$N$_2$O$_5$S.0.25C$_3$H$_8$O: C, 56, 43; H, 3.79; F, 11.28; N, 5.54; S, 6.34. Found: C, 56.38; H, 3.76; F, 11.51; N, 5.49; S, 6.43.

Example 128

4-Methyl-5-[[[4-(trifluoromethyl)phenyl]sulfonyl](2,3,6-trifluorophenyl)methyl]pyridine-2-carboxamide

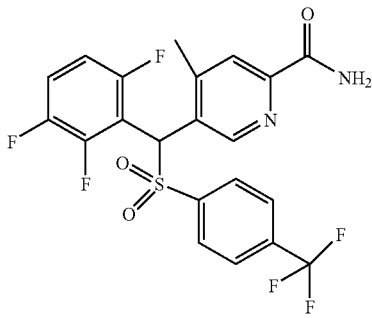

To a solution of [6-(aminocarbonyl)-4-methylpyridin-3-yl](2,3,6-trifluorophenyl) methyl methanesulfonate (262 mg, 0.700 mmol) obtained in Reference Example 15, and 4-(trifluoromethyl)benzenethiol (129 mg, 0.700 mmol) in N,N-dimethylformamide (10 ml), potassium carbonate (116 mg, 0.840 mmol) was added in a nitrogen atmosphere at 0° C., and the mixture was stirred for 2 hours at room temperature. Ethyl acetate and water were added to the reaction mixture, the organic layer was separated, and then the organic layer was washed with saturated brine. The organic layer was dried over anhydrous sodium sulfate and filtered, and then the filtrate was concentrated under reduced pressure. The resulting residue was dissolved in dichloromethane (10 ml), and 3-chloroperbenzoic acid (465 mg, 1.75 mmol) was added at 0° C. After stirring for 14 hours at room temperature, the reaction mixture was washed with 1 N aqueous sodium hydroxide. The organic layer was dried over anhydrous sodium sulfate and filtered, then the filtrate was concentrated under reduced pressure, and the obtained residue was subjected to flash silica gel chromatography. The fraction obtained from an elution with dichloromethane:methanol=99:1 was concentrated under reduced pressure, to obtain the title compound (260 mg, 0.532 mmol, 76%) as a white solid.

$^1$H-NMR (400 MHz, CDCl$_3$) δ: 2.14 (3H, s), 5.58 (1H, br s), 5.93 (1H, s), 6.83-6.91 (1H, m), 7.17-7.26 (1H, m), 7.75-7.81 (2H, m), 7.84-7.94 (3H, m), 8.00 (1H, s), 9.43 (1H, s).
MS m/z: 489 (M$^+$+H).

Example 129

N-(hydroxymethyl)-4-methyl-5-[[[4-(trifluoromethyl)phenyl]sulfonyl](2,3,6-trifluorophenyl)methyl]pyridine-2-carboxamide

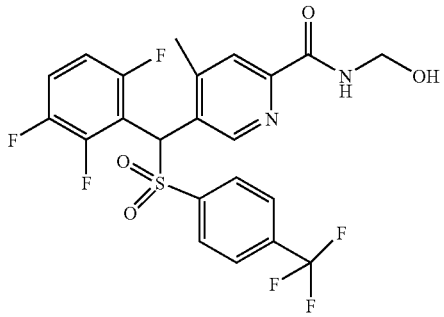

To a solution of 4-methyl-5-[[[4-(trifluoromethyl)phenyl]sulfonyl](2,3,6-trifluorophenyl) methyl]pyridine-2-carboxamide (171 mg, 0.350 mmol) in ethylene glycol dimethyl ether (5 ml), an aqueous solution of formaldehyde (37%, 78.9 µl) and an aqueous sodium hydroxide (17.5 µl) were added at room temperature, and the mixture was stirred for 15 hours. Ethyl acetate was added to the reaction mixture, and the mixture was washed with saturated aqueous ammonium chloride. Subsequently, 1 N hydrochloric acid was added to the organic layer, and the mixture was stirred for 1 hour. After the organic layer was separated, the organic layer was washed with saturated brine, dried over anhydrous sodium sulfate, and filtered, and then the filtrate was concentrated under reduced pressure. The resulting residue was subjected to flash silica gel chromatography, and the fraction obtained from an elution with hexane:ethyl acetate=1:1 was concentrated under reduced pressure. The resulting residue was washed with a mixed solvent of 2-propanol and hexane, and then was collected by filtration, to obtain the title compound (139 mg, 0.268 mmol, 77%) as a white solid.

$^1$H-NMR (400 MHz, CDCl$_3$) δ: 2.15 (3H, s), 3.03-3.08 (1H, m), 4.98-5.05 (2H, m), 5.93 (1H, s), 6.83-6.91 (1H, m), 7.18-7.26 (1H, m), 7.77 (2H, d, J=8.5 Hz), 7.89 (2H, d, J=8.5 Hz), 7.98 (1H, s), 8.83-8.91 (1H, m), 9.43 (1H, s).
IR(ATR)cm$^{-1}$: 3479, 3381, 1682, 1520, 1491, 1402, 1321, 1255, 1186, 1171, 1147, 1128, 1055, 1016.
mp: 190-192° C.
Anal. Calcd for C$_{22}$H$_{16}$F$_6$N$_2$O$_4$S: C, 50.97; H, 3.11; F, 21.99; N, 5.40; S, 6.19. Found: C, 50.95; H, 3.06; F, 22.24; N, 5.47; S, 6.31.
MS m/z: 519 (M$^+$+H).

Example 130

Ethyl [[[[5-[(2,5-difluorophenyl)[(4-fluorophenyl)sulfonyl]methyl]-4-methylpyridin-2-yl]carbonyl]amino]methoxy]acetate

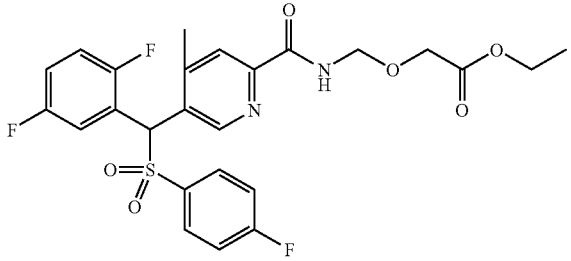

A solution of 5-[(2,5-difluorophenyl)[(4-fluorophenyl)sulfonyl]methyl]-N-(hydroxymethyl)-4-methylpyridine-2-carboxamide (421 mg, 0.935 mmol) obtained from Example 85, ethyl hydroxyacetate (106 µl, 1.12 mmol), p-toluenesulfonic acid monohydrate (18 mg, 0.094 mmol) in benzene (10 ml) was heated to reflux for 30 minutes. The reaction solution was returned to room temperature, and then was concentrated under reduced pressure. Saturated aqueous sodium hydrogencarbonate was added to the resulting concentration residue, and the mixture was extracted from ethyl acetate. The organic layer was washed with saturated brine, dried over anhydrous sodium sulfate, and filtered, and then the filtrate was concentrated under reduced pressure. The resulting concentration residue was subjected to flash silica gel column chromatography, and the fraction obtained from an elution with 35% ethyl acetate/hexane was concentrated under reduced pressure, to obtain the title compound (175 mg, 0.326 mmol, 35%) as a white solid.

$^1$H-NMR (400 MHz, CDCl$_3$) δ: 1.27 (3H, t, J=7.2 Hz), 2.22 (3H, s), 4.15-4.25 (4H, m), 5.08 (2H, d, J=7.2 Hz), 5.96 (1H, s), 6.90-7.20 (4H, m), 7.67-7.82 (3H, m), 7.98 (1H, s), 8.76 (1H, br t, J=7.2 Hz), 9.18 (1H, s).
IR(ATR)cm$^{-1}$: 1752, 1683, 1590, 1513, 1494, 1286, 1236, 1203, 1149, 1093.

MS (m/z): 537 (M⁺+H).
Anal. calcd for $C_{25}H_{23}F_3N_2O_6S$: C, 55.97; H, 4.32; F, 10.62; N, 5.22; S, 5.98. Found: C, 55.93; H, 4.24; F, 10.33; N, 5.28; S, 6.06.

Example 131

[[[[5-[(2,5-Difluorophenyl)[(4-fluorophenyl)sulfonyl]methyl]-4-methylpyridin-2-yl]carbonyl]amino]methoxy]acetic acid

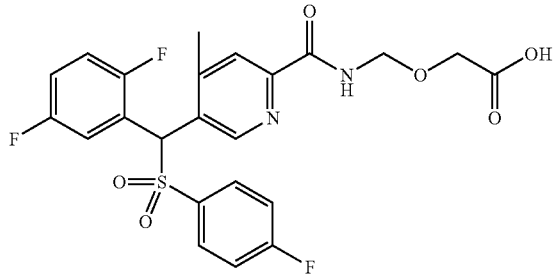

To a mixed solution of ethyl [[[[5-[(2,5-difluorophenyl)[(4-fluorophenyl)sulfonyl]methyl]-4-methylpyridin-2-yl]carbonyl]amino]methoxy]acetate (167 mg, 0.311 mmol) in tetrahydrofuran (6 ml) and water (3 ml), lithium hydroxide monohydrate (16 mg, 0.373 mmol) was added, and the mixture was stirred for 20 hours at room temperature. 1 N hydrochloric acid (0.5 ml) and water were added to the reaction solution, and the mixture was extracted with methylene chloride. The organic layer was dried over anhydrous sodium sulfate and filtered, and then the filtrate was concentrated under reduced pressure. The resulting concentration residue was subjected to flash silica gel column chromatography, and the fraction obtained from an elution with methanol:methylene chloride (=1:10) was concentrated under reduced pressure. A mixed solution of ethyl acetate-hexane was added to the resulting concentration residue, and then the residue was collected by filtration to obtain the title compound (38 mg, 0.075 mmol, 24%) as a white powder.

¹H-NMR (400 MHz, CDCl₃) δ: 2.24 (3H, s), 4.24 (2H, s), 4.98-5.05 (2H, m), 5.96 (1H, s), 6.90-7.20 (4H, m), 7.67-7.80 (3H, m), 8.00 (1H, s), 8.85-8.95 (1H, m), 9.19 (1H, s).

IR(ATR)cm⁻¹: 1762, 1682, 1589, 1521, 1492, 1321, 1292, 1236, 1147.

MS (m/z): 509 (M⁺+H).

Anal. calcd for $C_{23}H_{19}F_3N_2O_6S \cdot 0.75H_2O$: C, 52.92; H, 3.96; F, 10.92; N, 5.37; S, 6.14.

Found: C, 53.20; H, 3.90; F, 10.69; N, 5.19; S, 6.03

Example 132

5-[(2,5-Difluorophenyl)[(4-fluorophenyl)sulfonyl]methyl]-N-(mercaptomethyl)-4-methylpyridine-2-carboxamide

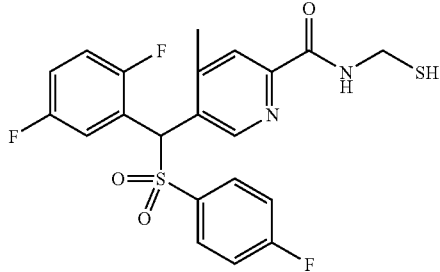

A solution of 5-[(2,5-difluorophenyl)[(4-fluorophenyl)sulfonyl]methyl]-N-(hydroxymethyl)-4-methylpyridine-2-carboxamide (170 mg, 0.377 mmol) obtained in Example 85, and Lowesson's Reagent (76 mg, 0.377 mmol) in toluene (5 ml) was heated to reflux for 30 minutes. The reaction solution was returned to room temperature, and was concentrated under reduced pressure. The resulting concentration residue was subjected to flash silica gel column chromatography, and the fraction obtained from an elution with 300 ethyl acetate/hexane was concentrated under reduced pressure, to obtain a solid. The obtained solid was washed with ethanol, and then was collected by filtration, to obtain the title compound mg, 0.152 mmol, 40%) as a white powder.

¹H-NMR (400 MHz, CDCl₃) δ: 2.21 (3H, s), 2.49 (1H, t, J=8.8 Hz), 4.55-4.65 (2H, m), 5.95 (1H, s), 6.90-7.20 (4H, m), 7.67-7.80 (3H, m), 7.96 (1H, s), 8.45-8.55 (1H, m), 9.16 (1H, s).

IR(ATR)cm⁻¹: 1673, 1589, 1508, 1492, 1315, 1286, 1238, 1211, 1147.

mp: 190-193° C.

EI-MS (m/z): 466 (M⁺).

Anal. calcd for $C_{21}H_{17}F_3N_2O_3S_2$: C, 54.07; H, 3.67; F, 12.22; N, 6.01; S, 13.75. Found: C, 54.05; H, 3.64; F, 12.13; N, 6.07; S, 13.78.

Example 133

5-[(2,5-Difluorophenyl)((4-fluorophenyl)sulfonyl)methyl]-N-(hydroxymethyl)-N,4-dimethylpyridine-2-carboxamide

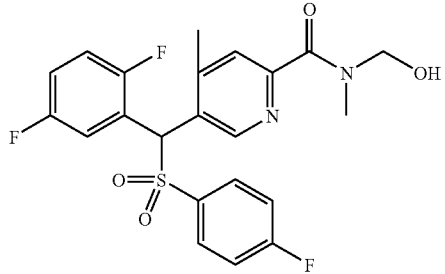

To a solution of 5-[(2,5-difluorophenyl) [(4-fluorophenyl)sulfonyl]methyl]-4-methylpyridine-2-carboxylic acid (405 mg, 0.961 mmol) obtained in Example 12, 1-hydroxybenzotriazole (130 mg, 0.961 mmol), 1-ethyl-3-(3-dimethylaminopropyl)carbodiimide hydrochloride (277 mg, 1.44 mmol), triethylamine (158 μl, 1.44 mmol) and anhydrous sodium sulfate in tetrahydrofuran (5 ml), a solution prepared by stirring methyl amine (2 M tetrahydrofuran solution: 1.4 ml) and a 37% aqueous solution of formalin (467 mg, 5.76 mmol) for 90 minutes at room temperature was added. The reaction solution was stirred for 90 minutes at room temperature, and then was subjected to filtration using silica gel. Elution with ethyl acetate was carried out, and the eluate was concentrated under reduced pressure. The resulting concentration residue was subjected to silica gel column chromatography, and the fraction obtained from an eluate of hexane:ethyl acetate (=1:2) was concentrated under reduced pressure to obtain a solid (73 mg). The resulting solid was washed with hexane:ethyl acetate (=1:2), and then was collected by filtration, to obtain the title compound (39 mg, 0.084 mmol, 8.7%) as a white powder.

¹H-NMR (400 MHz, CDCl₃) δ: 2.27 (3H, s), 3.25 (3H, s), 4.70-4.84 (2H, m), 5.67 (1H, t, J=8.0 Hz), 5.95 (1H, s), 6.90-7.19 (4H, m), 7.69-7.78 (4H, m), 9.12 (1H, s).

IR(ATR)cm⁻¹: 1635, 1589, 1490, 1326, 1295, 1230, 1149, 1039.

mp: 184-186° C.

MS m/z: 465 (M⁺+H).
Anal. Calcd for $C_{22}H_{19}F_3N_2O_4S$: C, 56.89; H, 4.12; F, 12.27; N, 6.03; S, 6.90. Found: C, 56.83; H, 4.03; F, 12.18; N, 5.90; S, 6.90.

Reference Example 17

5-Bromo-2-(difluoromethyl)pyridine

To a solution of 5-bromopyridine-2-carbaldehyde (372 mg, 2.00 mmol) in dichloromethane (5 ml), bis(2-methoxyethyl)aminosulfur trifluoride (0.553 ml, 3.00 mmol) was added in a nitrogen atmosphere at 0° C. The reaction mixture was stirred for 3 hours at room temperature, and saturated aqueous sodium hydrogencarbonate was added thereto. Water and dichloromethane were further added to take the organic layer, and the organic layer was dried over anhydrous sodium sulfate and filtered. Subsequently, the filtrate was concentrated under reduced pressure. The resulting residue was subjected to flash silica gel chromatography, and the fraction obtained from an elution with hexane:ethylacetate=49:1 was concentrated under reduced pressure to obtain the title compound (301 mg, 1.45 mmol, 72%) as a white solid.
¹H-NMR (400 MHz, CDCl₃) δ: 6.61 (1H, t, J=55.2 Hz), 7.55 (1H, d, J=8.3 Hz), 7.98 (1H, dd, J=8.3, 2.2 Hz), 8.72 (1H, d, J=2.2 Hz).
MS m/z: 208, 210 (M⁺+H).

Reference Example 18

Tert-butyl[6-(difluoromethyl)pyridin-3-yl]carbamate

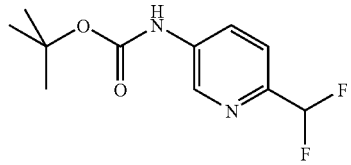

To a solution of 5-bromo-2-(difluoromethyl)pyridine (250 mg, 1.20 mmol) in diethyl ether (10 ml), a hexane solution of n-butyllithium (1.60 M, 0.825 ml, 1.32 mmol) was added in an argon atmosphere at −78° C. After stirring the mixture for 30 minutes at the same temperature, carbon dioxide was introduced. The reaction temperature was allowed to warm to 0° C., subsequently water and then 1 N aqueous sodium hydroxide (5 ml) were added to the reaction mixture, and the organic layer was separated. The organic layer was extracted twice with 1 N aqueous sodium hydroxide (15 ml), and then the obtained aqueous layer was combined and acidified with 1 N hydrochloric acid, and was extracted with dichloromethane. The obtained organic layer was dried over anhydrous sodium sulfate and filtered, and then the filtrate was concentrated under reduced pressure to obtain a brown solid (148 mg). The resulting solid (145 mg) was dissolved in a mixed solvent of 2-methyl-2-propanol (4 ml) and toluene (4 ml), and in a nitrogen atmosphere, triethylamine (0.233 ml, 1.68 mmol) and then diphenylphosphoric acid azide (0.269 ml, 1.26 mmol) were added at room temperature. The reaction mixture was heated to reflux for 18 hours, subsequently cooled to room temperature, and was concentrated under reduced pressure. The resulting residue was subjected to flash silica gel chromatography, and the fraction obtained from an elution with hexane:ethyl acetate=9:1 was concentrated under reduced pressure to obtain the title compound (82.4 mg, 0.337 mmol, 29%) as a pale yellow solid.
¹H-NMR (400 MHz, CDCl₃) δ: 1.53 (9H, s), 6.66 (1H, t, J=55.6 Hz), 6.62 (1H, brs), 7.58 (1H, d, J=8.6 Hz), 8.09-8.16 (1H, m), 8.46 (1H, d, J=2.5 Hz).
MS m/z: 245 (M⁺+H).

Reference Example 19

6-(Difluoromethyl)pyridine-3-amine

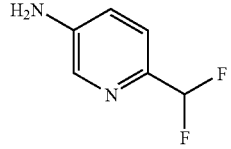

To a solution of tert-butyl[6-(difluoromethyl)pyridin-3-yl]carbamate (1.11 g, 4.54 mmol) in dichloromethane (8 ml), trifluoroacetic acid (8 ml) was added at room temperature. The reaction mixture was stirred for 5 hours at the same temperature, and then was concentrated under reduced pressure. Dichloromethane and saturated aqueous sodium hydrogencarbonate were added to the resulting residue. The organic layer was taken, and the organic layer was dried over anhydrous sodium sulfate and filtered. Subsequently, the filtrate was concentrated under reduced pressure. The resulting residue was subjected to flash silica gel chromatography, and the fraction obtained from an elution with hexane:ethyl acetate=2:1 was concentrated under reduced pressure to obtain the title compound (540 mg, 3.75 mmol, 82%) as a pale green oily substance.
¹H-NMR (400 MHz, CDCl₃) δ: 3.91 (2H, br s), 6.56 (1H, t, J=55.9 Hz), 7.04 (1H, dd, J=8.5, 2.7 Hz), 7.41 (1H, d, J=8.5 Hz), 8.07 (1H, d, J=2.7 Hz).
MS m/z: 145 (M⁺+H).

Reference Example 20

S-[6-(difluoromethyl)pyridin-3-yl]O-ethyl dithiocarbonate

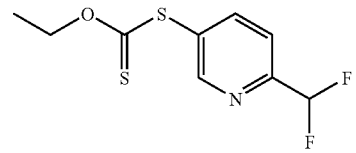

6-(Difluoromethyl)pyridine-3-amine (305 mg, 2.12 mmol) was dissolved in methanol (4 ml), and 1 N hydrochloric acid (4 ml) was added at −5° C. Subsequently, a solution of sodium nitrite mg, 3.17 mmol) in water (2 ml) was added dropwise thereto, and the mixture was stirred for 30 minutes at the same temperature. The obtained reaction mixture was added dropwise to a solution of O-ethyl potassium dithiocarbonate (678 mg, 4.23 mmol) in water (4 ml) at 60° C., subsequently the reaction temperature was heated to 80° C., and the mixture was stirred for 30 minutes. The reaction mixture was cooled to room temperature, subsequently the ethyl acetate and water were added, and the organic layer was collected by separation. The obtained organic layer was washed with saturated brine, subsequently dried over anhydrous sodium sulfate and filtered, and then the filtrate was concentrated under reduced pressure. The resulting residue was purified by preparative thin-layer silica gel chromatography (developing solvent:

hexane:ethyl acetate=19:1), to obtain the title compound (156 mg, 0.626 mmol, 30%) as a yellow oily substance.

$^1$H-NMR (400 MHz, CDCl$_3$) δ:1.37 (3H, t, J=7.1 Hz), 4.64 (2H, q, J=7.1 Hz), 6.67 (1H, t, J=7.1 Hz), 7.72 (1H, d, J=8.1 Hz), 7.98 (1H, dd, J=8.1, 2.2 Hz), 8.71 (1H, d, J=2.2 Hz).

Example 134

5-[[[6-(Difluoromethyl)pyridin-3-yl]thio](2,3,6-trifluorophenyl)methyl]-4-methylpyridine-2-carboxamide

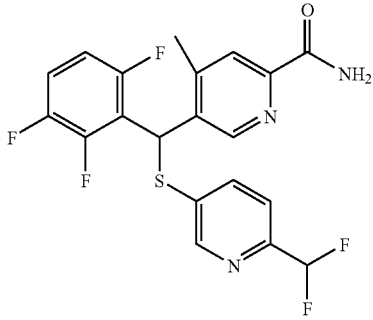

To a solution of S-[6-(difluoromethyl)pyridin-3-yl]O-ethyl dithiocarbonate (206 mg, 0.826 mmol) in ethanol (3 ml), 1 N aqueous sodium hydroxide (3 ml) was added, and the mixture was stirred for 1 hour at 60° C. The reaction mixture was cooled to room temperature, dichloromethane and water were added thereto, and the aqueous layer was separated. The obtained aqueous layer was acidified with 1 N hydrochloric acid, and was extracted with dichloromethane. The obtained organic layer was dried over anhydrous sodium sulfate and filtered, and then the filtrate was concentrated under reduced pressure.

To a solution of 5-[hydroxy(2,3,6-trifluorophenyl)methyl]-4-methylpyridine-2-carboxamide (355 mg, 1.20 mmol) obtained in Reference Example 14 in N,N-dimethylformamide (6 ml), methanesulfonyl chloride (0.186 ml, 2.40 mmol) and then triethylamine (0.502 ml, 3.60 mmol) were added in a nitrogen atmosphere at room temperature, and the mixture was stirred for 1 hour. Ethyl acetate, water and then saturated aqueous ammonium chloride were added to the reaction mixture, and the organic layer was separated. The obtained organic layer was washed with saturated brine, subsequently dried over anhydrous sodium sulfate and filtered, and the filtrate was concentrated under reduced pressure. The resulting residue was dissolved in N,N-dimethylformamide (12 ml), and the thiol previously obtained and potassium carbonate (199 mg, 1.44 mmol) were added thereto. The mixture was stirred for 2 hours in a nitrogen atmosphere at room temperature. Ethyl acetate and water were added to the reaction mixture, and the organic layer was collected by separation. The organic layer was washed with saturated aqueous ammonium chloride, and then with saturated brine. The obtained organic layer was dried over anhydrous sodium sulfate and filtered, and then the filtrate was concentrated under reduced pressure. The resulting residue was subjected to flash silica gel chromatography, and the fraction obtained from an elution with hexane:ethyl acetate=1:1 was concentrated under reduced pressure, to obtain the title compound (133 mg, 0.303 mmol, 37%) as a pale brown foamy substance.

$^1$H-NMR (400 MHz, CDCl$_3$) δ: 2.31 (3H, s), 5.55 (1H, br s), 5.93 (1H, s), 6.59 (1H, t, J=55.4 Hz) 6.81-6.88 (1H, m), 7.07-7.17 (1H, m), 7.54 (1H, d, J=8.3 Hz), 7.77 (1H, dd, J=8.3, 2.2 Hz), 7.81 (1H, br s), 8.00 (1H, s), 8.55 (1H, d, J=2.2 Hz), 9.08 (1H, s).

MS m/z: 440 (M$^+$+H).

Example 135

5-[[[6-(Difluoromethyl)pyridin-3-yl]sulfonyl](2,3,6-trifluorophenyl) methyl]-4-methylpyridine-2-carboxamide

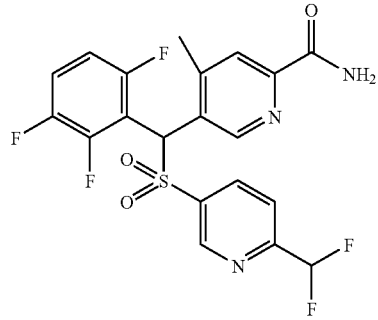

5-[[[6-(Difluoromethyl)pyridin-3-yl]thio](2,3,6-trifluorophenyl) methyl]-4-methylpyridine-2-carboxamide (132 mg, 0.300 mmol) was dissolved in ethyl acetate (3 ml), and methanol (2 ml), 31% aqueous hydrogen peroxide (3 ml) and hexaammonium heptamolybdate tetrahydrate (37.1 mg, 0.030 mmol) were added thereto. The mixture was stirred for 17 hours at room temperature. Ethyl acetate, water and then saturated aqueous sodium hydrogencarbonate were added to the reaction mixture, and the organic layer was separated. The obtained organic layer was washed with 10% aqueous sodium thiosulfate and then with saturated brine, subsequently dried over anhydrous sodium sulfate, and filtered, and then the filtrate was concentrated under reduced pressure. The resulting residue was subjected to flash silica gel chromatography, and the fraction obtained from an elution with dichloromethane:methanol=100:1 was concentrated under reduced pressure to obtain the title compound (118 mg, 0.250 mmol, 83%) as a white solid.

$^1$H-NMR (400 MHz, CDCl$_3$) δ: 2.20 (3H, s), 5.56 (1H, br s), 5.94 (1H, s), 6.68 (1H, t, J=54.9 Hz), 6.84-6.91 (1H, m), 7.20-7.27 (1H, m), 7.79 (1H, d, J=8.3 Hz), 7.85 (1H, br s) 8.03 (1H, s), 8.19 (1H, dd, J=8.3, 2.2 Hz), 8.93 (1H, d, J=2.2 Hz), 9.40 (1H, s).

MS m/z: 472 (M$^+$+H).

Example 136

5-[[[6-(Difluoromethyl)pyridin-3-yl]sulfonyl](2,3,6-trifluorophenyl)methyl]-N-(1-hydroxymethyl)-4-methylpyridine-2-carboxamide

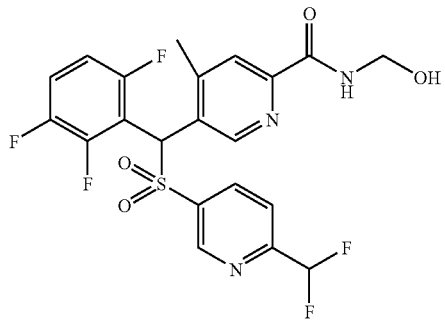

To a solution of 5-[[[6-(difluoromethyl)pyridin-3-yl]sulfonyl](2,3,6-trifluorophenyl) methyl]-4-methylpyridine-2-carboxamide (90.0 mg, 0.191 mmol) in ethylene glycol dimethyl ether (2 ml), an aqueous solution of formaldehyde (37%, 43.0 µl, 0.573 mmol) and 1 N aqueous sodium hydroxide (9.5 µl) were added at room temperature, and the mixture was stirred for 1 hour. Ethyl acetate was added to the reaction mixture, and the mixture was washed with saturated aqueous ammonium chloride. Subsequently, 1 N hydrochloric acid (5 ml) was added to the organic layer, and the mixture was stirred for 1 hour. After the organic layer was separated, the organic layer was washed with saturated aqueous sodium hydrogencarbonate and then with saturated brine, dried over anhydrous sodium sulfate, and filtered, and then the filtrate was concentrated under reduced pressure. The resulting residue was subjected to flash silica gel chromatography, and the fraction obtained from an elution with hexane:ethyl acetate=2:3 was concentrated under reduced pressure. The resulting residue was washed with a mixed solvent of 2-propanol and hexane, and then was collected by filtration, to obtain the title compound (77.0 mg, 0.154 mmol, 80%) as a white solid.

$^1$H-NMR (400 MHz, CDCl$_3$) δ: 2.21 (3H, s), 3.05 (1H, t, J=7.8 Hz), 4.98-5.05 (2H, m), 5.94 (1H, s), 6.68 (1H, t, J=54.9 Hz), 6.84-6.92 (1H, m), 7.20-7.27 (1H, m), 7.79 (1H, d, J=8.3 Hz), 8.01 (1H, s), 8.19 (1H, dd, J=8.3, 2.2 Hz), 8.86 (1H, t, J=6.9 Hz), 8.92 (1H, d, J=2.2 Hz), 9.40 (1H, s).

IR(ATR)cm$^{-1}$: 3442, 3383, 1676, 1523, 1491, 1338, 1153, 1084, 1055, 1036, 1014.

mp: 181-183° C.

Anal. Calcd for C$_2$—H$_{16}$F$_5$N$_3$O$_4$S: C, 50.30; H, 3.22; F, 18.94; N, 8.38; S, 6.39. Found: C, 50.07; H, 3.35; F, 19.03; N, 8.40; S, 6.50.

MS m/z: 502 (M$^+$+H).

Test Example 1

A Screening System Using Cells for Identifying a Material which Inhibits Production/Secretion of β-Amyloid Protein The activity of the compound inhibiting β-amyloid protein production was measured on E35 cells prepared by introducing APP751 gene, a gene of a human wild type β-amyloid protein precursor protein, to human glioma cells (H4 cells), by quantifying the amount of β-amyloid protein (Aβ) secreted to the culture medium by means of a sandwich type Enzyme-Linked Immunosorbent Assay (ELISA) method.

That is, E35 cells inoculated on a 96-well plate were cultured in an incubator at 37° C. which was maintained at equilibrium with 5% carbon dioxide, using Dulbecco's Modified Eagle's Medium containing inactivated 10% fetal bovine serum as the culture medium. After 24 hours from the inoculation, a test compound dissolved in a DMSO solution was added. The DMSO solution of the test compound was prepared at a concentration of 2000 times of the final concentration, such that the DMSO concentration in the culture medium would be 0.05%. After culturing for another 24 hours, the culture supernatant was recovered, and this was added to a 96-well plate for ELISA onto which a monoclonal antibody against Aβ, 25-1, was solid-phased. The plate was incubated at 4° C. for 16 to 20 hours. The plate was washed with phosphate buffer solution (pH 7.4), and then a biotinylated monoclonal antibody against Aβ, MA32-40, was added thereto. The plate was left to stand at 4° C. for 2 hours. The plate was washed again with phosphate buffer solution, and then alkaline phosphatase-conjugated streptavidin was added to conjugate streptavidin to biotin. Subsequently, the plate was washed with phosphate buffer solution. To this, Blue Phos (Kirkegaard & Perry Laboratories, Inc.) was added. After incubating the plate for an appropriate time, the reaction was terminated with an acid, and the absorbance for each well was measured. The amount of Aβ contained in the culture supernatant was determined from a calibration curve which was produced separately, and the amount was compared with that of control cells to which the compound was not added. Thus, the concentration at which 50% of the Aβ production is inhibited (EC50 value) was calculated. In addition, the 25-1 antibody and MA32-40 antibody used in ELISA were mouse monoclonal antibodies derived from the hybridoma cell clone lines, which were each produced and selected according to a standard method using Aβ25-35 and Aβ1-8 as antigens, respectively, and which specifically recognize their respective antigens.

The cytotoxic concentration was determined by the following test. H4 cells were cultured on a 96-well plate until the cells became semi-confluent, the test compound was added thereto, and the culturing was further continued. After 72 hours, the number of living cells was determined by using Alamar Blue (Biosource, Inc.) to develop color, and determining the colorant concentration. The concentration at which the number of living cells reached not more than 80% of the control cells which did not contain the compound, was called the cytotoxic concentration. Any compound showing a difference in the cytotoxic concentration for EC$_{50}$, was acknowledged as a compound having an activity for inhibiting the production of β-amyloid protein.

The results for assessing the compound (1) of the present invention according to the above assay method are shown in Table 1. The scores indicate ++++ for the case where EC$_{50}$ was 5 nM or less; +++ for the case where EC$_{50}$ was 5 to 50 nM; ++ for the case where EC$_{50}$ was 50 to 500 nM; and + for the case where EC$_{50}$ was 500 nM to 5 µM.

A control compound known to have an activity for inhibiting the secretion of β-amyloid protein, LY ((N)—((S)-2-hydroxy-3-methyl-butyryl)-1-(L-alaninyl)-(S)-1-amino-3-methyl-4,5,6,7-tetrahydro-2H-3-benzoazepin-2-one), was synthesized by the methods described in the Patent Documents to 5 cited in the present specification.

TABLE 1

| Test Example No. | Inhibitory Activity for Production of A((EC$_{50}$) |
|---|---|
| 4 | ++++ |
| 5 | ++ |
| 9 | ++++ |
| 13 | ++++ |
| 14 | ++ |
| 15 | ++++ |
| 16 | ++++ |
| 17 | ++++ |
| 18 | ++ |
| 19 | + |
| 21 | +++ |
| 22 | + |
| 24 | +++ |
| 28A | + |
| 28B | + |
| 30 | ++++ |
| 32 | +++ |
| 36A | +++ |
| 36B | + |
| 38 | +++ |
| 39 | ++++ |
| 43 | +++ |
| 47 | +++ |
| 55 | ++ |
| 59 | +++ |
| 63 | ++++ |
| 67 | ++++ |
| 71 | +++ |
| 73 | ++++ |
| 74 | ++++ |
| 75 | ++++ |
| 76 | + |
| 77 | + |
| 78 | +++ |

TABLE 1-continued

| Test Example No. | Inhibitory Activity for Production of A($EC_{50}$) |
|---|---|
| 79 | ++ |
| 83 | ++++ |
| 84 | ++++ |
| 85 | ++++ |
| 94 | ++++ |
| 101 | ++++ |
| 105 | ++++ |
| 106 | ++++ |
| 117 | ++++ |
| 118 | ++++ |
| 120 | ++++ |
| 123 | ++++ |
| 124 | +++ |
| Reference compound LY | +++ |

Test Example 2

Assessment of β-Amyloid Protein Production Inhibitory Action and Immunosuppressing Action in Vivo (Experimental Method)

As an example of the compound (1), the compounds described in Example 22, Example 85, Example 101, Example 106 or Example 118 (respectively, compound represented by the above formula (1-1), (1-2), (1-3), (1-4) or (1-5), which will be hereinafter referred respectively to compound (1-1), (1-2), (1-3), (1-4) or (1-5)), or the control compound LY, was suspended in a 0.5% aqueous solution of methylcellulose, and the suspension was orally administered in a single dose to male SD rats (about 5 weeks old). For the solvent control group, a 0.5% aqueous solution of methylcellulose was administered alone. After 3 hours of administration, the brain was excised, and the cerebrum was collected. The cerebrum was homogenized with a 42% aqueous solution of formic acid, and was centrifuged at 100,000×g for 60 minutes. The resulting supernatant was neutralized with 1 M Tris, and the Aβ concentration in these samples were measured using the sandwich type ELISA method as described in Test Example 1. Furthermore, the compound (1-1) to (1-5) or control compound LY was orally administered to male SD rats repeatedly for 7 days, and the rats were subjected to histopathological and serological examinations, so as to assess the immunosuppressing effect of the compound.

(Results)

With regard to the compound (1-1), (1-2), (1-3), (1-4) and (1-5), sufficient differences were recognized between the dose exhibiting a statistically significant decrease in the intracerebral amount of Aβ, and the dose exhibiting an immunosuppressing effect. On the other hand, for the control compound LY, no sufficient difference was recognized between the efficacious dose and the dose exhibiting toxicity.

The invention claimed is:
1. A compound of formula (2):

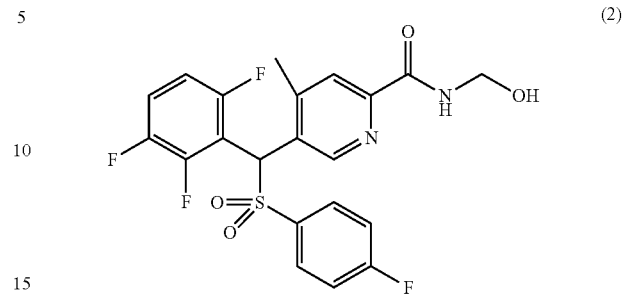

or a salt thereof.

2. A pharmaceutical composition, comprising:
the compound according to claim 1 or a pharmaceutically acceptable salt thereof; and
a pharmaceutically acceptable carrier.

3. A method for treating a disease which includes abnormal production of β-amyloid protein, abnormal secretion of β-amyloid protein or both abnormal production of β-amyloid protein and abnormal secretion of β-amyloid protein, comprising:
administering to a person in need thereof, an effective amount of the compound according to claim 1 or a pharmaceutically acceptable salt thereof;
wherein the disease is Alzheimer's disease or Down Syndrome.

4. A compound of formula (3):

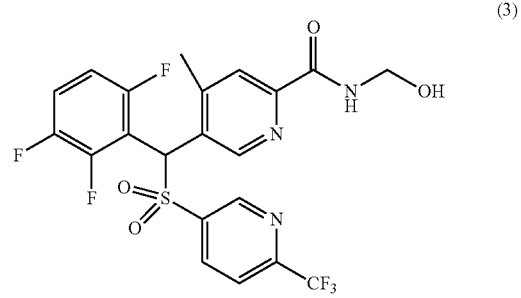

or a salt thereof.

5. A pharmaceutical composition, comprising:
the compound according to claim 4 or a pharmaceutically acceptable salt thereof; and
a pharmaceutically acceptable carrier.

6. A method for treating a disease which includes abnormal production of β-amyloid protein, abnormal secretion of β-amyloid protein or both abnormal production of β-amyloid protein and abnormal secretion of β-amyloid protein, comprising:
administering to a person in need thereof, an effective amount of the compound according to claim 4 or a pharmaceutically acceptable salt thereof;
wherein the disease is Alzheimer's disease or Down Syndrome.

* * * * *

UNITED STATES PATENT AND TRADEMARK OFFICE
CERTIFICATE OF CORRECTION

| | | |
|---|---|---|
| PATENT NO. | : 8,114,886 B2 | Page 1 of 1 |
| APPLICATION NO. | : 11/910500 | |
| DATED | : February 14, 2012 | |
| INVENTOR(S) | : Satoru Miyauchi et al. | |

It is certified that error appears in the above-identified patent and that said Letters Patent is hereby corrected as shown below:

On the title page, Item (86), the PCT information is incorrect. Item (86) should read:

-- (86) PCT No.:  PCT/JP2006/307464

§ 371 (c)(1),
(2), (4) Date: Oct. 5, 2007 --

Signed and Sealed this
Twenty-fourth Day of April, 2012

David J. Kappos
*Director of the United States Patent and Trademark Office*